United States Patent [19]
Katz et al.

[11] Patent Number: 6,060,234
[45] Date of Patent: May 9, 2000

[54] POLYKETIDE DERIVATIVES AND RECOMBINANT METHODS FOR MAKING SAME

[75] Inventors: Leonard Katz, Wheeling; Diane L. Stassi, Highland Park, both of Ill.; Richard G. Summers, Jr., Nashotah, Wis.; Xiaoan Ruan, Lake Bluff, Ill.; Ana Pereda-Lopez, Mundelein, Ill.; Stephan J. Kakavas, Buffalo Grove, Ill.

[73] Assignee: Abbott Laboratories, Abbott Park, Ill.

[21] Appl. No.: 08/858,003

[22] Filed: May 16, 1997

Related U.S. Application Data

[63] Continuation-in-part of application No. 07/642,734, Jan. 17, 1991, Pat. No. 5,824,513.

[51] Int. Cl.[7] .............................. C12Q 1/00; C12Q 1/18; C07H 17/08
[52] U.S. Cl. ................................ 435/4; 435/32; 514/29; 536/7.2
[58] Field of Search ........................... 435/4, 32; 536/7.2; 514/29

[56] References Cited

U.S. PATENT DOCUMENTS

| | | | |
|---|---|---|---|
| 3,869,445 | 3/1975 | Hallas et al. | 435/4 |
| 3,884,902 | 5/1975 | Hallas et al. | 435/4 |
| 4,740,502 | 4/1988 | Hannick et al. | 435/4 |
| 4,742,049 | 5/1988 | Baker et al. | 514/29 |
| 4,833,236 | 5/1989 | Morimoto et al. | 514/29 |
| 4,857,641 | 8/1989 | Hauske | 435/4 |
| 4,874,748 | 10/1989 | Katz et al. | 435/4 |
| 4,921,801 | 5/1990 | Rao et al. | 435/252.35 |
| 4,935,340 | 6/1990 | Baltz et al. | 435/4 |
| 5,081,023 | 1/1992 | Yaginuma et al. | 435/4 |
| 5,087,563 | 2/1992 | Beremand et al. | 435/4 |
| 5,110,728 | 5/1992 | Kridl et al. | 435/4 |
| 5,141,926 | 8/1992 | Weber et al. | 435/4 |
| 5,252,474 | 10/1993 | Gewain et al. | 435/4 |
| 5,672,491 | 9/1997 | Khosla et al. | 435/148 |
| 5,712,146 | 1/1998 | Khosla et al. | 435/148 |
| 5,744,350 | 4/1998 | Vinci et al. | 435/254.11 |
| 5,801,032 | 9/1998 | Stassi et al. | 435/254.11 |

FOREIGN PATENT DOCUMENTS 238323  3/1987  European Pat. Off. .

OTHER PUBLICATIONS

Schwecke, T., et al., Proceedings of the National Academy of Sciences, U.S.A., vol. 92, "The Biosynthetic Gene Cluster for the Polyketide Immunosuppressant Rapamycin", pp. 7839–7843 (1995).

Han, L. et al., Microbiology, vol. 140, "Cloning and Characterization of Polyketide Synthase Genes for Jadomycin B Biosynthesis in *Streptomyces Venezuelae* ISP5230", pp. 3379–3389 (1994).

MacNeil, D.J., et al., Annals of the New York Academy of Sciences, vol. 721, "Correlation of the Avermectin Polyketide Synthase Genes to the Avermectin Structure", pp. 123–132 (1994).

Hu, Z., et al., Molecular Microbiology, vol. 14, "Repeated Polyketide Synthase Modules Involved in the Biosynthesis of a Heptaene Macrolide by Streptomyces sp. FR–008", pp. 163–172 (1994).

(List continued on next page.)

*Primary Examiner*—Louise N. Leary
*Attorney, Agent, or Firm*—Dianne Casuto

[57] ABSTRACT

The invention provides novel erythromycin derivatives in which methyl groups on the macrolactone ring have been substituted with —H, —Et, and/or —OH. The invention also provides reagents such as isolated polynucleotides, vectors comprising the polynucleotides and host cells transformed with the vectors for making the novel compounds. Methods for making the compounds utilizing genetic engineering techniques are also disclosed.

29 Claims, 47 Drawing Sheets

OTHER PUBLICATIONS

Fernandez–Moreno, M.A., et al., The Journal of Biological Chemistry, vol. 269, "DNA Sequence and Functions of the actVI Region of the Actinorhodin Biosynthetic Gene Cluster of *Streptomyces Coelicolor* A3(2)*", pp. 24854–24863 (1994).

Kim, E.S., et al., Journal of Bacteriology, vol. 177, "Heterologous Expression of an Engineered Biosynthetic Pathway: Functional Dissection of Type II Polyketide Synthase Components in Streptomyces Species", pp. 1202–1207 (1994).

Brown, M.J.B., et al., Journal of the Chemical Society, Chemical Communications, vol. 15, "A Mutant Generated by Expression of an Engineered DEBS1 Protein from the Erythromycin–Producing Polyketide Synthase in *Streptomyce Coelicolor* Produces the Triket" (1995).

Kao, C.M., et al., Journal of the American Chemical Society, vol. 117, "Manipulation of Macrolide Ring Size by Directed Muutagenesis of a Modular Polyketide Synthase", pp. 9105–9106 (1996).

Kuhstoss, S., et al., Gene, vol. 183, "Production of a Novel Polyketide Through the Construction of a Hybrid Polyketide Synthase", pp. 231–236 (1996).

Kao, C.M., et al., Biochemistry, vol. 35, "Evidence for Two Catalytically Independent Clusters of Active Sites in a Functional Modular Polyketide Synthase", pp. 12363–12368 (1996).

Aigle, B., et al., Microbiology, vol. 142, "An Amplifiable and Deletable Locus of Streptomyces RP18110 Contains a Very Large Gene Homologous to Polyketide Synthase Genes", pp. 2815–2824 (1996).

Aparicio, et al., "Organization of the biosynthetic gene cluster for rapamycin in *Streptomyces hygroscopicus:* analysis of the enzymatic domains in the modular polyketide synthase", *Gene*, vol. 169 (1996), pp. 9–16.

Aparicio, et al., "Limited Proteolysis and Active–site Studies of the First Multienzyme Component of the Erythromycin–producing Polyketide Synthase", *The Journal of Biological Chemistry*, vol. 269 (1994), pp. 8524–8528.

Ashworth, et al., "On the biosynthetic origins of the hydrogen atoms in the macrotetrolide antibiotics: and their mode of assembly catalysed by a nonactin polyketide synthase", *Journal of the Chemical Society, Perkin Transactions*, vol. 1 (1989), p. 1461.

Baltz, et al. "Genetics of *streptomyces fradiae* and tylosin biosynthesis", *Annual Review of Microbiology*, vol. 42 (1988), pp. 547 & 558–574.

Bibb, et al., "Analysis of the Nucleotide sequence of the *streptomyces glaucescens* tcml genes provides key information about the enzymology of polyketide antibiotic biosynthesis", *The EMBO Journal*, vol. 8 (1989), pp. 2727–2736.

Caffrey, et al, "Identification of DEBS 1, DEBS 2 and DEBS 3, the multienzyme polypeptides of the erythromycin–producing polyketide synthase from *Saccharopolyspora erythraea*", *FEBS Letters*, vol. 304 (1992), pp. 225, 228.

Cane, et al., "Macrolide Biosynthesis. 4. Intact Incorporation of a Chain–Elongation Intermediate into Erythromycin", *J. Am. Chem. Soc.*, vol. 109 (1987), pp. 1255–1257.

Cortes, et al., "An unusually large multifunctional polypeptide in the erythromycin producing polyketide synthase of *saccharopolyspora erythraea*", *Nature*, vol. 348 (1990), pp. 176–178.

Cortes, et al., "Repositioning of a Domain in a Modular Polyketide Synthase to Promote Specific Chain Cleavage", *Science*, vol. 268 (1995), pp. 1487–1490.

Dhillon, et al., "Molecular characterization of a gene from *saccharopolyspora–erythraea* (*streptomyces–erythraeus*) which is involved in erythromycin biosynthesis", *Molecular Microbiology*, vol. 3 (1989), pp. 1405–1414.

Donadio, et al., "Organization of the enzymatic domains in the multifunctional polyketide synthase involved in erythromycin formation in *Saccharopolyspora etythraea*", *Gene*, vol. 111 (1992), pp. 51–60.

Donadio, et al., "Biosynthesis of the erythromycin macrolactone and a rational approach for producing hybrid macrolides" *Gene*, vol. 115 (1992), pp. 97–103.

Donadio, et al., "Modular Organization of Genes Required for Complex Polyketide Biosynthesis" *Science*, vol. 252 (1991), pp. 675–679.

Donadio, et al., "Genetic studies on erythromycin biosynthesis in *saccharopolyspora erythraea*", *Genetics and Molecular Biology of Industrial Microorganism*, (1989), pp. 53–59.

Harris, et al., "Initial planning", *Protein Purification Methods: A Practical Approach*, IRL Press, New York, NY; pp. 57–67.

Haydock, et al., "Divergent sequence motifs correlated with the substrate specificity of (methyl)malonyl–CoA:acyl carrier protein transacylase domains in modular polyketide synthases", *FEBS Letters*, vol. 374 (1995), pp. 246–248.

Haydock, et al., "Cloning and sequence analysis of genes involved in erythromycin biosynthesis in *Saccharopolyspora erythraea:* sequence similarities between EryG and a family of S–adenosylmethionine–dependent methyltransferases", *Mol. Gen. Genet.*, vol. 230 (1991), pp. 120–128.

Hopwood, et al., "'Hybrid' pathways for the production of secondary metabolites", *GIM 90: Proceedings of the 6th International Symposium on Genetics of Industrial Microorganisms*, vol. 1, pp. 259–270 (1991).

Hopwood, et al., "Molecular Genetics of Polyketides and its comparison to Fatty Acid Biosynthesis", *Annu. Rev. Genet.*, vol. 24 (1990), pp. 37–66.

Hopwood, et al., "Production of 'Hybrid' Antibiotics by Genetic Engineering", *Nature*, vol. 314 (1985), pp. 642–644.

Huber, et al., "Branched–chain fatty acids produced by mutants of *streptomyces fradiae*, putative precursors of the lactone ring of tylosin", *Antimicrobial Agents and Chemotherapy*, vol. 34 (1990), pp. 1535–1541.

Hutchinson, et al., "Polyketide synthase gene manipulation: A structure–function approach in engineering Novel antibiotics", *Annu. Rev. Microbio.*, vol. 49 (1995), pp. 201–238.

Kakinuma, et al., "Genetic studies of the biosynthesis of kalafungin, a benzoisochromanequinone antibiotic", *Tetrahedron*, vol. 47, pp. 6059–6068 (1991).

Kao, et al., "Engineered Biosynthesis of a Complete Macrolactone in a Heterologous Host", *Science*, vol. 265 (1994), pp. 509–512.

Kao, et al., "Engineered Biosynthesis of a Triketide Lactone from an Incomplete Modular Polyketide Synthase" *J. Am. Chem. Soc.*, vol. 116 (1994), pp. 11612–11613.

Kinoshita, et al., "Isolation of proposed intermediates in the biosynthesis of mycinamicins", *J. Chem. Soc. Chem. Commun.* (*1988*), pp. 943–945.

Kirst, et al., "New directions for macrolide antibiotics: Structural modifications and in vitro activity", *Antimicrobial Agents and Chemotherapy*, vol. 33 (1989), pp. 1413–1418.

Kuhstoss, et al., "Production of a novel polyketide through the construction of a hybrid polyketide synthase", *Gene,* vol. 183 (1996) pp. 231–236.

Leadlay, et al., "The erythromycin–producing polyketide synthase", *Biochemical Society Transactions,* vol. 21, (1993), pp. 218–221.

Li, et al., "Coloning and expression of spiramycin polyketide synthase genes and resistance genes from *S. Spiramyceticus* U–1941", *Chinese Journal of Biotechnology,* vol. 7, pp. 33–42.

Malpartida, et al., "Homology between Streptomyces Genes Coding for Synthesis of Different Polyketides Used to Clone Antibiotic Biosynthetic Genes", *Nature,* vol. 325 (1987), pp. 818–821.

Marsden, et al., "Stereospecific Acyl Transfers on the Erythromycin–Producing Polyketide Synthase", *Science,* vol. 263 (1994), pp. 378–380.

Motamedi, et al., "Structural organization of a multifunctional polyketide synthase involved in the biosynthesis of the macrolide immunosuppressant FK506", *Euro. j. Biohem.,* vol. 244 (1997), pp. 74–80.

Motamedi, et al., "FK506 Polyketide synthase is a large multifunctional polypeptide with 19 FAS–like domains", Merck Research Laboratories. (1994).

Oliynyk, et al., "A hybrid modular polyketide synthase obtained by domain swapping" *Chemistry & Biology,* vol. 3 (1996), pp. 833–839.

Omura, et al., "Biosynthetic origin of carbons 3 and 4 of leucomycin aglycone", *J. Antibiotics,* vol. 36 (1983), pp. 611–613.

Otten, et al., "Cloning and expression of daunorubicin biosynthesis genes from *Streptomyces peucetius* and *S. peucetius* subsp. *caesius*", *Journal of Bacteriology,* vol. 172 (1990), pp. 3427–3434.

Pieper, et al., "Cell–free synthesis of polyketides by recombinant erythromycin polyketide synthases", *Nature,* vol. 378 (1995), pp. 263–266.

Richardson, et al., "Cloning of spiramycin biosynthetic genes and their use in constructing *Streptomyces ambofaciens* mutants defective in spiramycin biosynthesis", *Journal of Bacteriology,* vol. 172 (1990), pp. 3790–3798.

Robinson, Polyketide synthase complexes: their structure and function in antibiotic biosynthesis, *Philosophical Transactions of the Royal Society of London, Series B: Biolocical Sciences,* vol. 332, pp. 107–114 (1991).

Salas, et al., "Genetic manipulation of antibiotic biosynthesis by actinomycetes", *BioTec–90,* (1990) pp. 47–52.

Sherman, et al., "Structure and deduced function of the granaticin–producing polyketide synthase gene cluster of *streptomyces violaceoruber* Tü22", *The EMBO Journal,* vol. 8 (1989), pp. 2727–2725.

Stanzak, et al., "Cloning and expression in *streptomyces lividans* of clustered erythromycin biosynthesis genes from *streptomyces erythreus*", *Bio/Technology,* vol. 4 (1986), pp. 229–232.

Stassi, et al., "Identification of a *Saccharopolyspora erythraea* gene required for the final hydroxylation step in erythromycin biosynthesis", *J. Bacteriology,* vol. 175 (1993), pp. 182–189.

Staunton, et al., "Evidence for a double–helical structure for modular polyketide synthases", *Nature Structural Biology,* vol. 3 (1996), pp. 188–192.

Summers, et al., "Malonyl–Coenzyme A:Acyl carrier protein acyltransferase of *streptomyces glaucescens:* A possible link between fatty acid and polyketide biosynthesis" *Biochemistry,* vol. 34 (1995), pp. 9389–9402.

Swan, et al., "Characterisation of a *Streptomyces antibioticus* gene encoding a type I polyketide synthase which has an unusual coding sequence", *Mol. Gen. Genet.,* vol. 242 (1994), pp. 358–362.

Tomich, "Streptomyces cloning: Possible construction of novel compounds and regulation of antibiotic biosynthetic genes", *Antimicrobial Agents and Chemotherapy,* vol. 32 (1988), pp. 1472–1476.

Tuan, et al.,"Cloning of genes involved in erythromycin biosynthesis from *saccharopolyspora erythraea* using a novel *actinomycete–escherichia coli* cosmid", *Gene,* vol. 90 (1990), pp. 21–29.

Vara, et al., "Cloning of genes governing the deoxysugar portion of the erythromycin biosynthesis pathway in *saccharopolyspora erythraea* (*streptomyces erythreus*)", *Journal of Bacteriology,* vol. 171 (1989), pp. 5872–5881.

Weber, et al., "Genetic analysis of erythromycin production in *streptomyces erythreus*", *Journal of Bacteriology,* vol. 164 (1985), pp. 425–433.

Weber, et al., "Organization of a cluster of erythromycin genes in *saccaropolyspora erythraea*", *Journal of Bacteriology,* vol. 172 (1990), pp. 2372–2383.

Weber, et al., "An erythromycin derieative produced by targeted gene disruption in *Saccharopolyspora erythraea*", *Science,* vol. 252 (1991), pp. 114–117.

Wiesmann, et al., "Polyketide synthesis in vitro on a modular polyketide synthase", *Current Biology,* vol. 2 (1995), pp. 583–589.

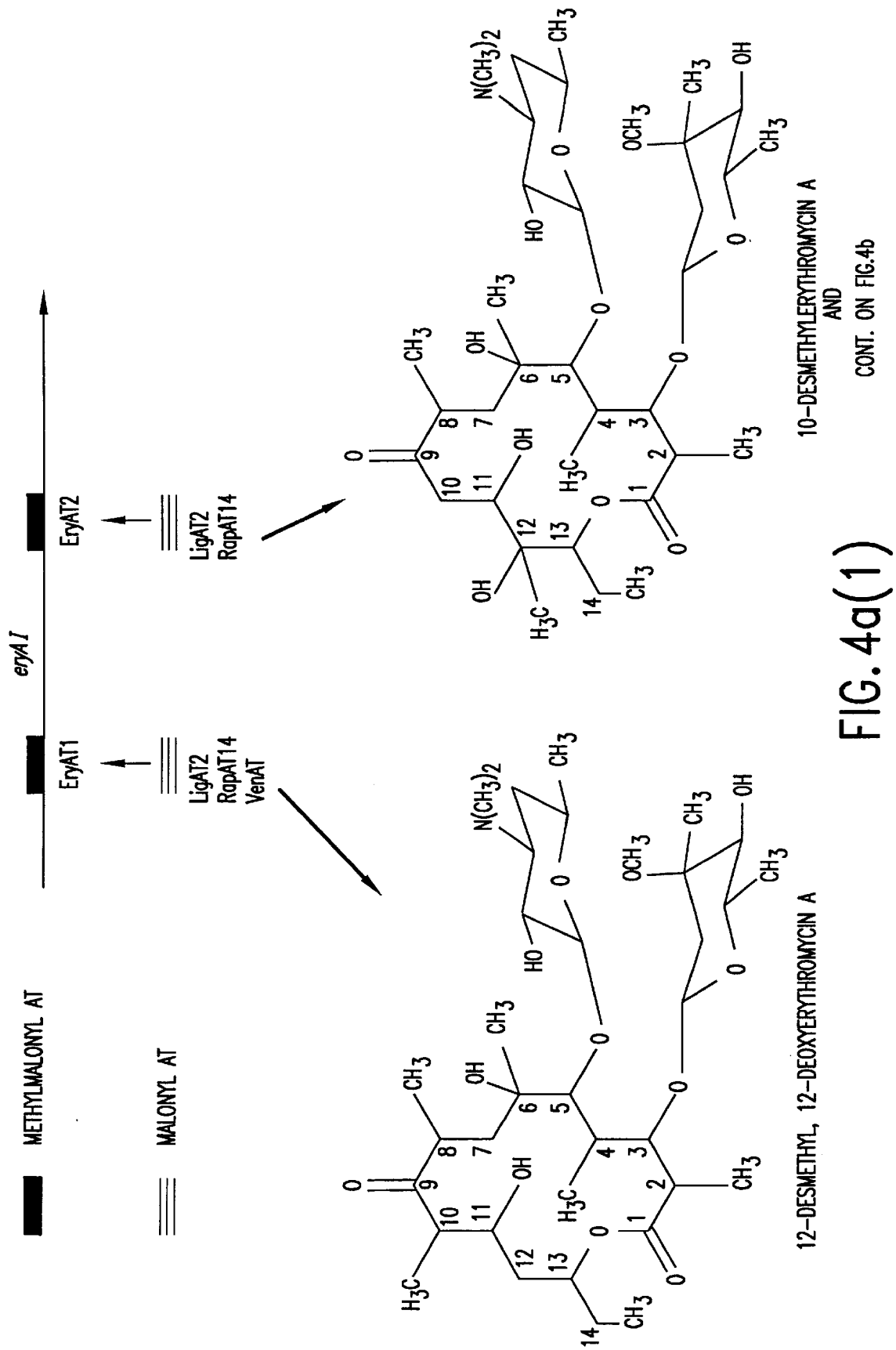
FIG. 4a(1)

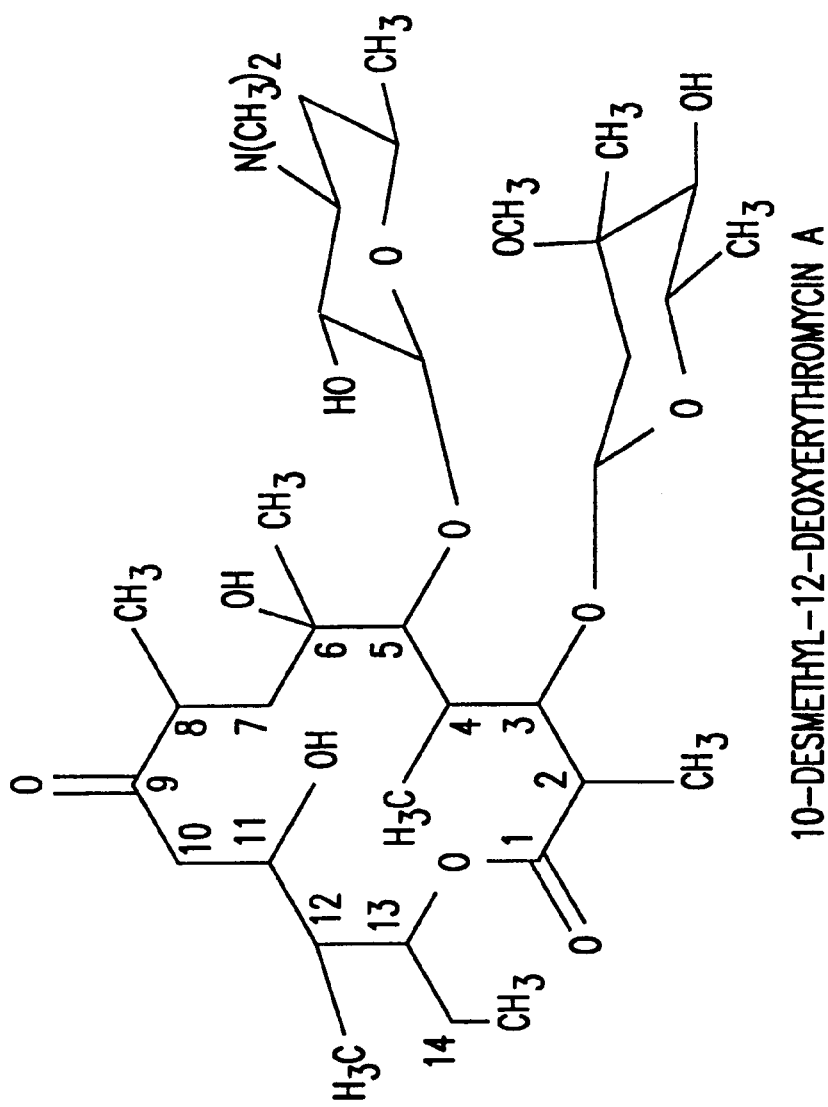
FIG. 4a(2)
10-DESMETHYL-12-DEOXYERYTHROMYCIN A

```
GGGCCGCTGGCGGTGATGTTCACCGGACAGGGCTCCCAACGCCCCGGCATGGGACGACAG  60
 G  P  L  A  V  M  F  T  G  Q  G  S  Q  R  P  G  M  G  R  Q   20
TTGTACGAGCACTTCCCCGTCTSCGCCCAGGCACTGGACGAGGTCTTCGCACTCGCCACC 120
 L  Y  E  H  F  P  V  F  A  Q  A  L  D  E  V  F  A  L  A  T   40
CCCGGACTACGCCGAGGTGATGTTCGACCCCGACCAGGCCGAAACACTCCAACGCACCGAC 180
 P  G  L  R  E  V  M  F  D  P  D  Q  A  E  T  L  Q  R  T  D   60
CACGCCCAGATCGCCCTGTTCGCCTTCGAAACCGCCCTCTACCGACTCTGGGAATCCTGG 240
 H  A  Q  I  A  L  F  A  F  E  T  A  L  Y  R  L  W  E  S  W   80
GGCCTGCGACCCGACATGGTCTGCGGACACTCGGTCGGAGAAATCACCGCAGCCCACGTC 300
 G  L  R  P  D  M  V  C  G  H  S  V  G  E  I  T  A  A  H  V  100
TCCGGCACCCTCACCCTCCCCGACGCCGTCCACCTCGTCACCACACGCGGCACCCTCATG 360
 S  G  T  L  T  L  P  D  A  V  H  L  V  T  T  R  G  T  L  M  120
CAAAACCTGCCCCCCGGCGGCGCCATGCTCGCCGTCGCCACCGACCCCCACACCCTCCAA 420
 Q  N  L  P  P  G  G  A  M  L  A  V  A  T  D  P  H  T  L  Q  140
CCCCACCTCGACAACCACCACGACACCATCTCCATCGCCGCCATCAACGGCCCCCACGCC 480
 P  H  L  D  N  H  H  D  T  I  S  I  A  A  I  N  G  P  H  A  160
ACCGTCCTCTCCGGCGACCGCACCACCCTCCACCACATCGCCACCCAACTCAACACCAAA 540
 T  V  L  S  G  D  R  T  T  L  H  H  I  A  T  Q  L  N  T  K  180
ACCAACTGGCTCAACGTCAGCCACGCCTTCCACTCCCCCCTCATGCAACCCATCCTCCAA 600
 T  N  W  L  N  V  S  H  A  F  H  S  P  L  M  Q  P  I  L  Q  200
CCCTTCACCACCACCCTCAACACCCTCACCCACCACCCCCACACACACCCCTCATCAGC 660
 P  F  T  T  T  L  N  T  L  T  H  H  P  P  H  T  P  L  I  S  220
ATGCTCACCGCCACACCCACCCACCCCGACACCACCCACTGGACCCAGCACATCACCGCA 720
 M  L  T  A  T  P  H  P  D  T  T  H  W  T  Q  H  I  T  A  240
CCCGTCCGCTACACCGACACCCTCCACCACCTCCACCACCACGGCATCACCACCTACCTC 780
 P  V  R  Y  T  D  T  L  H  H  L  H  H  H  G  I  T  T  Y  L  260
GAAATCGGCCCCGACACCACCCTCACCGCCCTCGCCCGCACCACCCTCCCCACCACCACC 840
 E  I  G  P  D  T  T  L  T  A  L  A  R  T  T  L  P  T  T  T  280
CACCTCATCCCCACCACCCGCCGCAACCACAACGAAGTCCGCAGCACGAACGAGGCGTTG 900
 H  L  I  P  T  T  R  R  N  H  N  E  V  R  S  T  N  E  A  L  300
GGCAGGGTGTTCAGCGTGGGCCACTCGGTGGACTGGCGGGCCCTCACTCCGACCGGGAGG 960
 G  R  V  F  S  V  G  H  S  V  D  W  R  A  L  T  P  T  G  R  320
CGTACCTCCCTGCCGACGTACCCCT                                    985
 R  T  S  L  P  T  Y  P                                      328
```

FIG.7

PCR OLIGOS:

N-TERMINAL OLIGO: 5' EcoRI Tag-CCTAG GCTGGCGGTGATGTTCA-3'
                              GGGCC
                        |ENGINEERED AvrII| |HOMOLOGOUS REGION|

C-TERMINAL OLIGO: 5' BamHI Tag-ATGCAT ACGTCGGCAGGGAGGTAC-3'
                               G  GG
                        |ENGINEERED NsiI| | HOMOLOGOUS REGION |

```
CCTAGGACGGCAGTCCTGCTCACCGGGCAGGGTTCCCAGCGTCAGGGCATGGGGCGCGAA   60
 P  R  T  A  V  L  L  T  G  Q  G  S  Q  R  Q  G  M  G  R  E    20
CTGTACGACCGGTCACCGGTGTTCGCCGCCTCGTTCGACGCGATCTGCGCTCAACTCGAC  120
 L  Y  D  R  S  P  V  F  A  A  S  F  D  A  I  C  A  Q  L  D    40
GGGCAACTGCCTCGTCCCCTCAAGGACGTTCTCTTCGCCCCCGAGGGGTCGGAGGACGCC  180
 G  Q  L  P  R  P  L  K  D  V  L  F  A  P  E  G  S  E  D  A    60
GCGCTCASCGACCGTACGGTGTTCACACAGGCGGCTCTGTTCGCCGTGGAGACCTCCCTG  240
 A  L  I  D  R  T  V  F  T  Q  A  A  L  F  A  V  E  T  S  L    80
TTCCGGCTGTTCGAGGCCCACGGCCTCGSCCCCGACTACCTCASCGGCCACTCCATCGGC  300
 F  R  L  F  E  A  H  G  L  V  P  D  Y  L  I  G  H  S  I  G   100
GAAGTGACCGCGGCCCGCCTGGCCGGGGTCCTCGATCTGGCGGACGCGTGCGTCCTGGTC  360
 E  V  T  A  A  H  L  A  G  V  L  D  L  A  D  A  C  V  L  V   120
GCCCACCGCGGCCGCCTGATGCAGTCGGCCCGGGCCGGCGGCGCGATGGCCGCGGTCCAG  420
 A  H  R  G  R  L  M  Q  S  A  R  A  G  G  A  M  A  A  V  Q   140
GCCAGCGAGGACGAGGTACGCGAGGCCCTCGCCGACCTTCGACGATGCCGGTTCCCGTGGCC  480
 A  S  E  D  E  V  R  E  A  L  A  T  F  D  D  A  V  A  V  A   160
GGAGTCAACGGCCCCGAACGCCACCGTCGTCTCCGGCGACGAGGACGCCGGTCGAGCGGCTG  540
 G  V  N  G  P  N  A  T  V  V  S  G  D  E  D  A  V  E  R  L   180
GTCGCGCGCTGGCGCGAGCAGGGCAGGCGGACGAAGCGGCTGCCGGTCAGCCACGCCTTC  600
 V  A  R  W  R  E  Q  G  R  R  T  K  R  L  P  V  S  H  A  F   200
CACTCGCCGCACATGGACGGGATCGTCGACGAGTTCGTCACCGCCGTCTCCGGGCTCACC  660
 H  S  P  H  M  I  G  I  V  D  E  F  V  T  A  V  S  G  L  T   220
TTCCGCTCCCCGACGLTCCCCGGTCGTCTCCAACGTCACCGGGACCCTCGCCACCGTCGAC  720
 F  R  S  P  T  I  P  V  V  S  N  V  T  G  T  L  A  T  V  D   240
CACCTGACCTCGCCCCGCGTACTGGGCACGCCACATCCGCGAGGCCGTGCGCTTCGCCGAC  780
 Q  L  T  S  P  A  Y  W  A  R  H  I  R  E  A  V  R  F  A  D   260
GGGGTGCGGTACCTGGAGGGCGAGGGCGTCACCGAATGGCTGGAGCTCGGGCCCGACGGC  840
 G  V  R  Y  L  E  G  E  G  V  T  E  W  L  E  L  G  P  D  G   230
GTTCTCGTCGCCCTGGTCGAGGACTGCCTGGCGAAGGAGGCGGGATCGCTCGCGTCCGCC  900
 V  L  V  A  L  V  E  D  C  L  A  K  E  A  G  S  L  A  S  A   300
CTGCGCAAGGGGGCGAGCGAGCCCCACACCGTGGGCGCGGCCATGGCCCGCGCGGTGCTG  960
 L  R  K  G  A  S  E  P  H  T  V  G  A  A  M  A  R  A  V  L   320
CGCGGATCCGGCCCCGACTGGGCGGCGGTGTTCCCCGGCGCACGGCGGGTCGACCTTCCG 1020
 R  G  S  G  P  D  W  A  A  V  F  P  G  A  R  R  V  D  L  P   340
ACGTATGCAT                                                   1030
 T  Y  A                                                      343
```

```
GCCGACCGTGTCGTGTTCGTGTTCCCCGGCCAGGGCTCGCAGTGGGCCGGAATGGCCGAG  60
A  D  R  V  V  F  V  F  P  G  Q  G  S  Q  W  A  G  M  A  E   20
GGGCTGCTGGAGCGGTCCGGCGCGTTCCGGAGTGCGGCCGACTCGTGCGACGCCGCGCTG  120
G  L  L  E  R  S  G  A  F  R  S  A  A  D  S  C  D  A  A  L   40
CGGCCGTACCTCGGCTGCTCGGTGCTGAGCGTGCTGCGCGGGGAACCGGACGCGCCCTCG  180
R  P  Y  L  G  W  S  V  L  S  V  L  R  G  E  P  D  A  P  S   60
CTCGACCGGGTCGACGTCGTGCAGCCGGTGCTGTTCACGATGATGGTCTCGCTCGCGGCG  240
L  D  R  V  D  V  V  Q  P  V  L  F  T  M  M  V  S  L  A  A   80
GTCTGGCGTGCGCTGGGCGTGGAACCGGCGGCGGTCGTCGGGCACTCGCAGGGTGAGATC  300
V  W  R  A  L  G  V  E  P  A  A  V  V  G  H  S  Q  G  E  I   100
GCCGCTGCCCATGTCGCCGGTGCGCTGTCGCTGGACGACTCGGCCCGGATCGTCGCCCTG  360
A  A  A  H  V  A  G  A  L  S  L  D  D  S  A  R  I  V  A  L   120
CGCAGTCGGGCGTGGCTCGGACTGGCGGGCAAGGGCGGCATGGTGGCGGTGCCGATGCCG  420
R  S  R  A  W  L  G  L  A  G  K  G  G  M  V  A  V  P  M  P   140
GCGGAGGAGCTGCGGCCGCGGCTGGTGACGTGGGGGGACCGTCTGGCCGTCGCCGCCGTC  480
A  E  E  L  R  P  R  L  V  T  W  G  D  R  L  A  V  A  A  V   160
AACAGCCCCGGTTCCTGCGCCGTCGCAGGCGACCCGGAGGCGCTGGCCGAACTGGTGGCG  540
N  S  P  G  S  C  A  V  A  G  D  P  E  A  L  A  E  L  V  A   180
CTGCTGACCGGTGAGGGGGTGCACGCCCGGCCGATCCCCGGCGTCGACACGGCGGGCCAC  600
L  L  T  G  E  G  V  H  A  R  P  I  P  G  V  D  T  A  G  H   200
TCGCCCGCAGGTGGACGCGTTGCGGGCTCATCTGCTGGAGGTGCTGGCCCCGGTCGCCCCC  660
S  P  Q  V  D  A  L  R  A  H  L  L  E  V  L  A  P  V  A  P   220
CGACCGGCCGACATCCCGTTCTACTCGACGGTGACCGGCGGGCTGCTGGACGGCACCGAG  720
R  P  A  D  T  P  F  Y  S  T  V  T  G  G  L  L  D  G  T  E   240
CTGGACGCGACGTACTGGTACCGCAACATGCGCGAGCCCGTCGAGTTCGAGCGGGCCACA  780
L  D  A  T  Y  W  Y  R  N  M  R  E  P  V  E  F  E  R  A  T   260
CGGGCGCTGATCGCCGACGGGCACGACGTCTTCCTGGAGACGAGCCCGCATCCCATGCTG  840
R  A  L  I  A  D  G  H  D  V  F  L  E  T  S  P  H  P  M  L   280
GCCGTGGCGCTGGAGCAGACCGTCACCGACGCCGGCACCGACGCGGCGGTGCTCGGGACC  900
A  V  A  L  E  Q  T  V  T  D  A  G  T  D  A  A  V  L  G  T   300
CTGCGCCGCCGCCACGGCGGTCCTCGCGCGCTGGCCCTGGCCGTCTGCCGCGCCTTCGCG  960
L  R  R  R  H  G  G  P  R  A  L  A  L  A  V  C  R  A  F  A   320
CACGGCGTGGAGGTGGACCCCGAGGCGGTCTTCGGTCCGGGCGCACGGCCCGTGGAGTTG  1020
H  G  V  E  V  D  P  E  A  V  F  G  P  G  A  R  P  V  E  L   340
CCCACCTATCCG                                                 1032
P  T  Y  P                                                    344
```

FIG. 34

PROTEIN SEQUENCE        S   A   P   R   K   P

ORIGINAL SEQUENCE       TCCGCGCCGCGCAAGCCG
                                 ↓ ↓ ↓
ALTERED SEQUENCE        TCCGCGCCTAGGAAGCCG
                                └────┘
                                AvrII SITE

PCR OLIGOS FOR 5'-FLANK AvrII SITE

┌──► 5'- FLANK SEQUENCE
N-TERMINAL OLIGO 5'-GAGAGAGGAACCAACGCGCACGTGATCGTCGAAGAGGCACCAGC
   (SEQ. ID. NO. 21)                     └────┘
                                         PmII SITE

┌──► 5'-FLANK SEQUENCE
C-TERMINAL OLIGO 5'-GAGAGAGGATCCGACCTAGGCGCGGAGGTCACCGGCGCGACGGCG
   (SEQ. ID. NO. 22)         └────┘ └────┘
                             BamHI SITE AvrII SITE

PCR OLIGOS FOR NidAT5 FRAGMENT

┌──► BEGINNING OF NidAT5
N-TERMINAL OLIGO 5'-GAGAGACCTAGGAAGCCGGTGTTCGTGTTCCCCGGCCAGGGCT
   (SEQ. ID. NO. 23)        └────┘
                            AvrII SITE

┌──► 3' END OF NidAT5
C-TERMINAL OLIGO 5'-GAGAGAGGATCCGAGGCCGGCCGTGCGCCCGGACCGAAGACCGCCTC
   (SEQ. ID. NO. 24)         └────┘  └────┘
                             BamHI SITE FseI SITE

FIG.36

```
CGCGCGCCTGCCTTCGTCTTTCCCGGGCAGGGCGCCCAGTGGGCCGGACTGGGAGCGCGG 60
 R  A  P  A  F  V  F  P  G  Q  G  A  Q  W  A  G  L  G  A  R   20
CTCCTCGCGGACTCCCCCGTCTTCCGCGCCAGGGCCGAGGCATGCGCGCGGGCGCTGGAG 120
 L  L  A  D  S  P  V  F  R  A  R  A  E  A  C  A  R  A  L  E   40
CCTCACCTCGACTGGTCGGTCCTCGACGTGCTGGCCGGCGCCCCGGGCACCCCTCCCATC 180
 P  H  L  D  W  S  V  L  D  V  L  A  G  A  P  G  T  P  P  I   60
GACCGGGCCGACGTGGTGCAGCCGGTGCTGTTCACCACGATGGTCTCGCTGGCCGCCCTC 240
 D  R  A  D  V  V  Q  P  V  L  F  T  T  M  V  S  L  A  A  L   80
TGGGAGGCCCACGGGGTGCGGCCGGCCGCGGTCGTGGGCCACTCCCAGGGCGAGGTGGCC 300
 W  E  A  H  G  V  R  P  A  A  V  V  G  H  S  Q  G  E  V  A   100
GCGGCCTGCGTGGCCGGTGCCCTGTCGCTGGACGACGCTGCCCTGGTGATCGCCGGACGC 360
 A  A  C  V  A  G  A  L  S  L  D  D  A  A  L  V  I  A  G  R   120
AGCAGGCTGTGGGGGCGGCTGGCCGGGAACGGCGGGATGCTCGCGGTGATGGCTCCGGCC 420
 S  R  L  W  G  R  L  A  G  N  G  G  M  L  A  V  M  A  P  A   140
GAGCGGATCCGTGAGCTGCTCGAACCATGGCGGCAGCGGATTTCGGTGGCGGCGGTCAAT 480
 E  R  I  R  E  L  L  E  P  W  R  Q  R  I  S  V  A  A  V  N   160
GGCCCCGCCTCGGTCACCGTCTCCGGTGACGCGCTCGCGCTGGAGGAGTTCGGCGCGCGG 540
 G  P  A  S  V  T  V  S  G  D  A  L  A  L  E  E  F  G  A  R   180
CTCTCCGCCGAGGGGGTGCTGCGCTGGCCGCTGCCGGGCGTCGACTTCGCCGGCCACTCG 600
 L  S  A  E  G  V  L  R  W  P  L  P  G  V  D  F  A  G  H  S   200
CCGCAGGTGGAGGAGTTCC GC5CTGAGCTCCTGGACCTGCTCTCCGGCGTACGGCCGGC 660
 P  Q  V  E  E  F  R  A  E  L  L  D  L  L  S  G  V  R  P  A   220
CCTTCGCGGATACCTTTCTTCTCCACCGTGACGGCCGGGTCCTTGCGGCCGGCGACCAGCTG 720
 P  S  R  I  P  F  P  S  T  V  T  A  G  P  C  G  G  D  Q  L   240
GACGGGGCGTACTGGTACCGCAACACGCGCGAACCCGTGGAGTTCGACGCCACGGTCCGG 780
 D  G  A  Y  W  Y  R  N  T  R  E  P  V  E  F  D  A  T  V  R   260
GCGCTGCTGCGTGCGGGCCATCACACGTTCATCGAGGTCGGTCCGCATCCGCTGCTCAAC 840
 A  L  L  R  A  G  H  H  T  F  I  E  V  G  P  H  P  L  L  N   280
GCCGCGATCGACGAGATCGCAGCGGACGAGGGGGTAGCGGCCACGGCCCTGCATACGCTC 900
 A  A  I  D  E  I  A  A  D  E  G  V  A  A  T  A  L  H  T  L   300
CAGCGGGGCGCTGGCGGCCTTGACCGCGTGCGCAACGCGGTGGGCGCCGCTTTCGCGCAC 960
 Q  R  G  A  G  G  L  D  R  V  R  N  A  V  G  A  A  F  A  H   320
GGTGTCCGGGTCGACTGGAACGCCCTGTTCGAGGGCACCGGTGCGCGCAGGGTGCCGCTT 1020
 G  V  R  V  D  W  N  A  L  F  E  G  T  G  A  R  R  V  P  L   340
CCCTCGTACGCCTTC                                              1035
 P  S  Y  A  F                                                345
```

FIG. 41

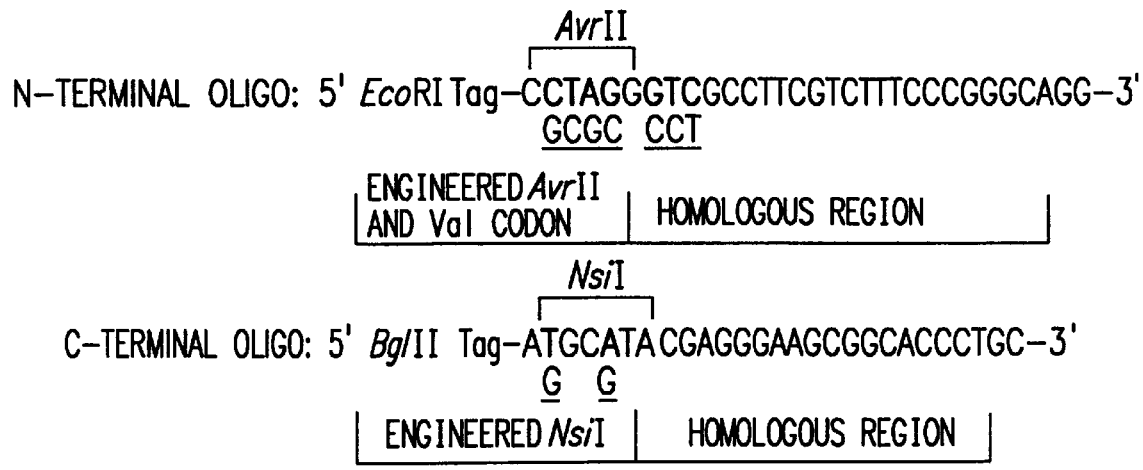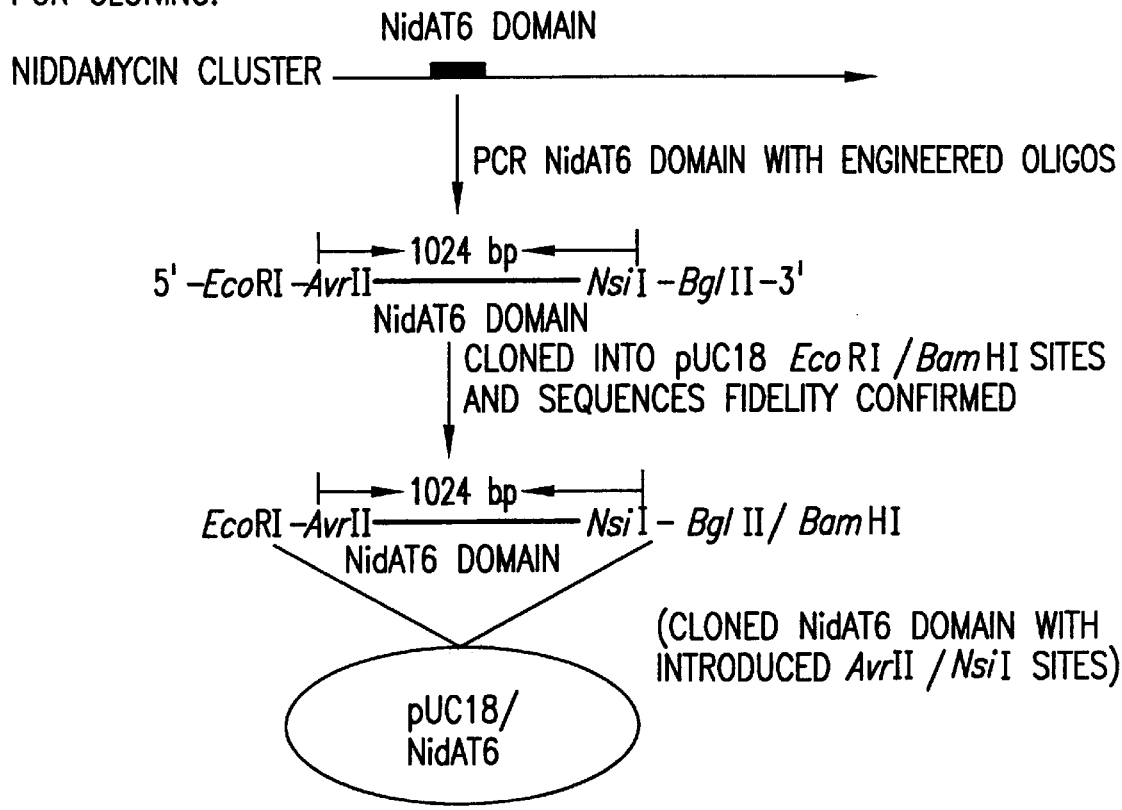
FIG. 42

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
        (A) LENGTH: 925 base pairs
        (B) TYPE: nucleic acid
        (C) STRANDEDNESS: double
        (D) TOPOLOGY: linear (xi) SEQUENCE DESCRIPTION: SEQ ID NO:1:

```
GGGCCGCTGG CGGTGATGTT CACCGGACAG GGCTCCCAAC GCCCCGGCAT GGGACGACAG    60

TTGTACGAGC ACTTCCCCGT CTTCGCCCAG GCACTGGACG AGGTCTTCGC ACTCGCCACC   120

CCCGGACTAC GCGAGGTGAT GTTCGACCCC GACCAGGCCG AAACACTCCA ACGCACCGAC   180

CACGCCCAGA TCGCCCTGTT CGCCTTCGAA ACCGCCCTCT ACCGACTCTG GGAATCCTGG   240

GGCCTGCGAC CCGACATGGT CTGCGGACAC TCGGTCGGAG AAATCACCGC AGCCCACGTC   300

TCCGGCACCC TCACCCTCCC CGACGCCGTC CACCTCGTCA CCACACGCGG CACCCTCATG   360

CAAAACCTGC CCCCGGCGG CGCCATGCTC GCCGTCGCCA CCGACCCCCA CACCCTCCAA    420

CCCCACCTCG ACAACCACCA CGACACCATC TCCATCGCCG CCATCAACGG CCCCCACGCC   480

ACCGTCCTCT CCGGCGACCG CACCACCCTC CACCACATCG CCACCCAACT CAACACCAAA   540

CCCTTCACCA CCACCCTCAA CACCCTCACC CACCACCCCC CACACACACC CCTCATCAGC   600

ATGCTCACCG CCACACCCAC CCACCCCGAC ACCACCCACT GGACCCAGCA CATCACCGCA   660

CCCGTCCGCT ACACCGACAC CCTCCACCAC CTCCACCACC ACGGCATCAC CACCTACCTC   720

GAAATCGGCC CCGACACCAC CCTCACCGCC CTCGCCCGCA CCACCCTCCC CACCACCACC   780

CACCTCATCC CCACCACCCG CCGCAACCAC AACGAAGTCC GCAGCACGAA CGAGGCGTTG   840

GGCAGGGTGT TCAGCGTGGG CCACTCGGTG GACTGGCGGG CCCTCACTCC GACCGGGAGG   900

CGTACCTCCC TGCCGACGTA CCCCT                                        925
```

(2) INFORMATION FOR SEQ ID NO:2:

(i) SEQUENCE CHARACTERISTICS:
        (A) LENGTH: 1030 base pairs
        (B) TYPE: nucleic acid
        (C) STRANDEDNESS: double
        (D) TOPOLOGY: linear (xi) SEQUENCE DESCRIPTION: SEQ ID NO:2:

```
CCTAGGACGG CAGTCCTGCT CACCGGGCAG GGTTCCCAGC GTCAGGGCAT GGGGCGCGAA    60

CTGTACGACC GGTCACCGGT GTTCGCCGCC TCGTTCGACG CGATCTGCGC TCAACTCGAC   120

GGGCAACTGC CTCGTCCCCT CAAGGACGTT CTCTTCGCCC CCGAGGGGTC GGAGGACGCC   180

GCGCTCATCG ACCGTACGGT GTTCACACAG GCGGCTCTGT TCGCCGTGGA GACCTCCCTG   240

TTCCGGCTGT TCGAGGCCCA CGGCCTCGTC CCCGACTACC TCATCGGCCA CTCCATCGGC   300
```

```
GAAGTGACCG CGGCCCACCT GGCCGGGGTC CTCGATCTGG CGGACGCGTG CGTCCTGGTC        360

GCCCACCGCG GCCGCCTGAT GCAGTCGGCC CGGGCCGGCG GCGCGATGGC CGCGGTCCAG        420

GCGAGCGAGG ACGAGGTACG CGAGGCCCTC GCGACCTTCG ACGATGCGGT TGCCGTGGCC        480

GGAGTCAACG GCCCGAACGC CACCGTCGTC TCCGGCGACG AGGACGCGGT CGAGCGGCTG        540

GTCGCGCGCT GGCGCGAGCA GGGCAGGCGG ACGAAGCGGC TGCCGGTCAG CCACGCCTTC        600

CACTCGCCGC ACATGGACGG GATCGTCGAC GAGTTCGTCA CCGCCGTCTC CGGGCTCACC        660

TTCCGCTCCC CGACGATCCC GGTCGTCTCC AACGTCACCG GGACCCTCGC CACCGTCGAC        720

CAGCTGACCT CGCCCGCGTA CTGGGCACGC CACATCCGCG AGGCCGTGCG CTTCGCCGAC        780

GGGGTGCGGT ACCTGGAGGG CGAGGGCGTC ACCGAATGGC TGGAGCTCGG GCCCGACGGC        840

GTTCTCGTCG CCCTGGTCGA GGACTGCCTG GCGAAGGAGG CGGGATCGCT CGCGTCCGCC        900

CTGCGCAAGG GGGCGAGCGA GCCCCACACC GTGGGCGCGG CCATGGCCCG CGCGGTGCTG        960

CGCGGATCCG GCCCCGACTG GGCGGCGGTG TTCCCCGGCG CACGGCGGGT CGACCTTCCG       1020

ACGTATGCAT                                                              1030
```

(2) INFORMATION FOR SEQ ID NO:3:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:3:

```
ATCTACACST CSGGCACSAC SGGCAAGCCS AAGGG                                     35
```

(2) INFORMATION FOR SEQ ID NO:4:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:4:

```
CTSAAGGCSG GCGGCGCSTA CGTSCCSATC GACCC                                     35
```

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:5:

```
CGCGAATTCC TAGGCTGGCG GTGATGTTCA                                           30
```

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:6:

```
GCCGGATCCA TGCATACGTC GGCAGGGAGG TAC                                       33
```

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:7:

GCTCGAATTC GCTGGTCGCG GTGCACCT                                      28

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:8:

GACGGATCCG GCCCTAGGCT GCGCCCGGCT CG                                 32

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:9:

TTGGGATCCT ATGCATTCCA GCGCGAGCGC                                    30

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:10:

GAGAAGCTTG GCGCGACTTG CCCGCT                                        26

(2) INFORMATION FOR SEQ ID NO:11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:11:

TTTTTTAAGC TTGGTACCTG CTCACCGGCA ACACCG                             36

(2) INFORMATION FOR SEQ ID NO:12:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:12:

TTTTTTGGAT CCCTGCAGCC TAGGGTCGGA GGCACTGCCG GT                      42

(2) INFORMATION FOR SEQ ID NO:13:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:13:

TTTTTTCTGC AGTATGCATT CCAGGGCAAG CGGTTCT                                37

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:14:

TTTTTTGAAT TCACGCGTTG CCCGCGGCGT AGGCGC                                 36

(2) INFORMATION FOR SEQ ID NO:15:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:15:

GATCGAATTC CCTAGGACGG CAGTCCTGCT CACC                                   34

(2) INFORMATION FOR SEQ ID NO:16:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:16:

GATCGGATCC ATGCATACGT CGGAAGGTCG ACCCG                                  35

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:17:

TTCGAAGAAT TCCCTAGGGT TGCCTTCCTG TTCGAC                                 36

(2) INFORMATION FOR SEQ ID NO:18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:18:

TTCGAAAAGC TTATGCATAG ACCGGCAGAT CCACCG                                 36

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:19:

CGGTSAAGTC SAACATCGG                                                19

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:20:

GCRATCTCRC CCTGCGARTG                                               20

(2) INFORMATION FOR SEQ ID NO:21:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:21:

GAGAGAGGAA CCAACGCGCA CGTGATCGTC GAAGAGGCAC CAGC                     44

(2) INFORMATION FOR SEQ ID NO:22:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:22:

GAGAGAGGAT CCGACCTAGG CGCGGAGGTC ACCGGCGCGA CGGCG                    45

(2) INFORMATION FOR SEQ ID NO:23:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:23:

GAGAGACCTA GGAAGCCGGT GTTCGTGTTC CCCGGCCAGG GCT                      43

(2) INFORMATION FOR SEQ ID NO:24:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:24:

GAGAGAGGAT CCGAGGCCGG CCGTGCGCCC GGACCGAAGA CCGCCTC                  47

(2) INFORMATION FOR SEQ ID NO:25:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:25:

GAGAGAATTC CCTAGGGTCG CCTTCGTCTT TCCCGGGCAG G                    41

(2) INFORMATION FOR SEQ ID NO:26:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:26:

TTGAGATCTT ATGCATACGA GGGAAGCGGC ACCCTGC                         37

(2) INFORMATION FOR SEQ ID NO:27:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:27:

TTGAGATCTT ATGCATACGA GGGAAGCGGC ACCCTGC                         37

(2) INFORMATION FOR SEQ ID NO:28:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:28:

TTGAGATCTT ATGCATACGA GGGAAGCGGC ACCCTGC                         37

(2) INFORMATION FOR SEQ ID NO:29:

(i) SEQUENCE CHARACTERISTICS:
        (A) LENGTH: 1010 base pairs
        (B) TYPE: nucleic acid
        (C) STRANDEDNESS: double
        (D) TOPOLOGY: linear (xi) SEQUENCE DESCRIPTION: SEQ ID NO:29:

GCCGACCGTG TCGTGTTCGT GTTCCCCGGC CAGGGCTCGC AGTGGGCCGG AATGGCCGAG    60

GGGCTGCTGG AGCGGTCCGG CGCGTTCCGG AGTGCGGCCG ACTCGTGCGA CGCCGCGCTG   120

CGGCCGTACC TCGGCTGGTC GGTGCTGAGC GTGCTGCGCG GGAACCGGA CGCGCCCTCG    180

CTCGACCGGG TCGACGTCGT GCAGCCGGTG CTGTTCACGA TGATGGTCTC GCTCGCGGCG   240

GTCTGGCGTG CGCTGGGGGT GGAACCGGCG GCGGTCGTCG GCACTCGCA GGGTGAGATC    300

GCCGCTGCCC ATGTCGCCGG TGCGCTGTCG CTGGACGACT CGGCCCGGAT CGTCGCCCTG   360

CGCAGTCGGG CGTGGCTCGG ACTGGCGGGC AAGGGCGGCA TGGTGGCGGT GCCGATGCCG   420

GCGGAGGAGC TGCGGCCGCG GCTGGTGACG TGGGGGGACC GTCTGGCCGT CGCCGCCGTC   480

-continued

```
AACAGCCCCG GTTCCTGCGC CGTCGCAGGC GACCCGGAGG CGCTGGCCGA ACTGGTGGCG    540

CTGCTGACCG GTGAGGGGGT GCACGCCCGG CCGATCCCCG GCGTCGACAC GGCGGGCCAC    600

TCGCCGCAGG TGGACGCGTT GCGGGCTCAT CTGCTGGAGG TGCTGGCCCC GGTCGCCCCC    660

CGACCGGCCG ACATCCCGTT CTACTCGACG GTGACCGGCG GGCTGCTGGA CGGCACCGAG    720

CTGGACGCGA CGTACTGGTA CCGCAACATG CGCGAGCCCG TCGAGTTCGA GCGGGCCACA    780

CGGGCGCTGA TCGCCGACGG GCACGACGTC TTCCTGGAGA CGAGCCCGCA TCCCATGCTG    840

GCCGTGGCGC TGGAGCAGAC GGTCACCGAC GCCGGCACCG ACGCGGCGGT GCTCGGGACC    900

CTGCGCCGCC GCCACGGCGG TCCTCGCGCG CTGGCCCTGG CCGTCTGCCG CGCCTTCGCG    960

AGGCGGTCTT CGGTCCGGGC GCACGGCCCG TGGAGTTGCC CACCTATCCG             1010
```

(2) INFORMATION FOR SEQ ID NO:30:

(i) SEQUENCE CHARACTERISTICS:
        (A) LENGTH: 1035 base pairs
        (B) TYPE: nucleic acid
        (C) STRANDEDNESS: double
        (D) TOPOLOGY: linear (xi) SEQUENCE DESCRIPTION: SEQ ID NO:30:

```
CGCGCGCCTG CCTTCGTCTT TCCCGGGCAG GGCGCCCAGT GGGCCGGACT GGGAGCGCGG     60

CTCCTCGCGG ACTCCCCCGT CTTCCGCGCC AGGGCCGAGG CATGCGCGCG GGCGCTGGAG    120

CCTCACCTCG ACTGGTCGGT CCTCGACGTG CTGGCCGGCG CCCCGGGCAC CCCTCCCATC    180

GACCGGGCCG ACGTGGTGCA GCCGGTGCTG TTCACCACGA TGGTCTCGCT GGCCGCCCTC    240

TGGGAGGCCC ACGGGGTGCG GCCGGCCGCG GTCGTGGGCC ACTCCCAGGG CGAGGTGGCC    300

GCGGCCTGCG TGGCCGGTGC CCTGTCGCTG GACGACGCTG CCCTGGTGAT CGCCGGACGC    360

AGCAGGCTGT GGGGGCGGCT GGCCGGGAAC GGCGGGATGC TCGCGGTGAT GGCTCCGGCC    420

GAGCGGATCC GTGAGCTGCT CGAACCATGG CGGCAGCGGA TTTCGGTGGC GGCGGTCAAT    480

GGCCCCGCCT CGGTCACCGT CTCCGGTGAC GCGCTCGCGC TGGAGGAGTT CGGCGCGCGG    540

CTCTCCGCCG AGGGGGTGCT GCGCTGGCCG CTGCCGGGCG TCGACTTCGC CGGCCACTCG    600

CCGCAGGTGG AGGAGTTCCG CGCTGAGCTC CTGGACCTGC TCTCCGGCGT ACGGCCGGCT    660

CCTTCGCGGA TACCTTTCTT CTCCACCGTG ACGGCGGGTC CTTGCGGCGG CGACCAGCTG    720

GACGGGGCGT ACTGGTACCG CAACACGCGC GAACCCGTGG AGTTCGACGC CACGGTCCGG    780

GCGCTGCTGC GTGCGGGCCA TCACACGTTC ATCGAGGTCG GTCCGCATCC GCTGCTCAAC    840

GCCGCGATCG ACGAGATCGC AGCGGACGAG GGGGTAGCGG CCACGGCCCT GCATACGCTC    900

CAGCGGGGCG CTGGCGGCCT TGACCGCGTG CGCAACGCGG TGGGCGCCGC TTTCGCGCAC    960

GGTGTCCGGG TCGACTGGAA CGCCCTGTTC GAGGGCACCG GTGCGCGCAG GGTGCCGCTT   1020

CCCTCGTACG CCTTC                                                    1035
```

(2) INFORMATION FOR SEQ ID NO:31:

(i) SEQUENCE CHARACTERISTICS:
        (A) LENGTH: 328 amino acids
        (B) TYPE: amino acid
        (C) STRANDEDNESS: single
        (D) TOPOLOGY: linear (ii) MOLECULE TYPE: None -continued (xi) SEQUENCE DESCRIPTION: SEQ ID NO:31:

Gly Pro Leu Ala Val Met Phe Thr Gly Gln Gly Ser Gln Arg Pro Gly
1               5                   10                  15

Met Gly Arg Gln Leu Tyr Glu His Phe Pro Val Phe Ala Gln Ala Leu
                20                  25                  30

Asp Glu Val Phe Ala Leu Ala Thr Pro Gly Leu Arg Glu Val Met Phe
            35                  40                  45

Asp Pro Asp Gln Ala Glu Thr Leu Gln Arg Thr Asp His Ala Gln Ile
        50                  55                  60

Ala Leu Phe Ala Phe Glu Thr Ala Leu Tyr Arg Leu Trp Glu Ser Trp
65                  70                  75                  80

Gly Leu Arg Pro Asp Met Val Cys Gly His Ser Val Gly Glu Ile Thr
                85                  90                  95

Ala Ala His Val Ser Gly Thr Leu Thr Leu Pro Asp Ala Val His Leu
                100                 105                 110

Val Thr Thr Arg Gly Thr Leu Met Gln Asn Leu Pro Pro Gly Gly Ala
            115                 120                 125

Met Leu Ala Val Ala Thr Asp Pro His Thr Leu Gln Pro His Leu Asp
130                 135                 140

Asn His His Asp Thr Ile Ser Ile Ala Ala Ile Asn Gly Pro His Ala
145                 150                 155                 160

Thr Val Leu Ser Gly Asp Arg Thr Thr Leu His His Ile Ala Thr Gln
                165                 170                 175

Leu Asn Thr Lys Thr Asn Trp Leu Asn Val Ser His Ala Phe His Ser
                180                 185                 190

Pro Leu Met Gln Pro Ile Leu Gln Pro Phe Thr Thr Leu Asn Thr
            195                 200                 205

Leu Thr His His Pro Pro His Thr Pro Leu Ile Ser Met Leu Thr Ala
        210                 215                 220

Thr Pro Thr His Pro Asp Thr Thr His Trp Thr Gln His Ile Thr Ala
225                 230                 235                 240

Pro Val Arg Tyr Thr Asp Thr Leu His Leu His His His Gly Ile
                245                 250                 255

Thr Thr Tyr Leu Glu Ile Gly Pro Asp Thr Thr Leu Thr Ala Leu Ala
            260                 265                 270

Arg Thr Thr Leu Pro Thr Thr Thr His Leu Ile Pro Thr Thr Arg Arg
        275                 280                 285

Asn His Asn Glu Val Arg Ser Thr Asn Glu Ala Leu Gly Arg Val Phe
        290                 295                 300

Ser Val Gly His Ser Val Asp Trp Arg Ala Leu Thr Pro Thr Gly Arg
305                 310                 315                 320

Arg Thr Ser Leu Pro Thr Tyr Pro
                325

(2) INFORMATION FOR SEQ ID NO:32:

(i) SEQUENCE CHARACTERISTICS:
        (A) LENGTH: 343 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:32:

```
Pro Arg Thr Ala Val Leu Leu Thr Gly Gln Gly Ser Gln Arg Gln Gly
 1               5                  10                  15

Met Gly Arg Glu Leu Tyr Asp Arg Ser Pro Val Phe Ala Ala Ser Phe
            20                  25                  30

Asp Ala Ile Cys Ala Gln Leu Asp Gly Gln Leu Pro Arg Pro Leu Lys
        35                  40                  45

Asp Val Leu Phe Ala Pro Glu Gly Ser Glu Asp Ala Ala Leu Ile Asp
    50                  55                  60

Arg Thr Val Phe Thr Gln Ala Ala Leu Phe Ala Val Glu Thr Ser Leu
65                  70                  75                  80

Phe Arg Leu Phe Glu Ala His Gly Leu Val Pro Asp Tyr Leu Ile Gly
                85                  90                  95

His Ser Ile Gly Glu Val Thr Ala Ala His Leu Ala Gly Val Leu Asp
            100                 105                 110

Leu Ala Asp Ala Cys Val Leu Val Ala His Arg Gly Arg Leu Met Gln
        115                 120                 125

Ser Ala Arg Ala Gly Gly Ala Met Ala Ala Val Gln Ala Ser Glu Asp
    130                 135                 140

Glu Val Arg Glu Ala Leu Ala Thr Phe Asp Asp Ala Val Ala Val Ala
145                 150                 155                 160

Gly Val Asn Gly Pro Asn Ala Thr Val Val Ser Gly Asp Glu Asp Ala
                165                 170                 175

Val Glu Arg Leu Val Ala Arg Trp Arg Glu Gln Gly Arg Arg Thr Lys
            180                 185                 190

Arg Leu Pro Val Ser His Ala Phe His Ser Pro His Met Asp Gly Ile
        195                 200                 205

Val Asp Glu Phe Val Thr Ala Val Ser Gly Leu Thr Phe Arg Ser Pro
    210                 215                 220

Thr Ile Pro Val Val Ser Asn Val Thr Gly Thr Leu Ala Thr Val Asp
225                 230                 235                 240

Gln Leu Thr Ser Pro Ala Tyr Trp Ala Arg His Ile Arg Glu Ala Val
                245                 250                 255

Arg Phe Ala Asp Gly Val Arg Tyr Leu Glu Gly Glu Gly Val Thr Glu
            260                 265                 270

Trp Leu Glu Leu Gly Pro Asp Gly Val Leu Ala Leu Val Glu Asp
        275                 280                 285

Cys Leu Ala Lys Glu Ala Gly Ser Leu Ala Ser Ala Leu Arg Lys Gly
290                 295                 300

Ala Ser Glu Pro His Thr Val Gly Ala Ala Met Ala Arg Ala Val Leu
305                 310                 315                 320

Arg Gly Ser Gly Pro Asp Trp Ala Val Phe Pro Gly Ala Arg Arg
                325                 330                 335

Val Asp Leu Pro Thr Tyr Ala
            340
```

(2) INFORMATION FOR SEQ ID NO:33:

(i) SEQUENCE CHARACTERISTICS:
        (A) LENGTH: 344 amino acids
        (B) TYPE: amino acid (C) STRANDEDNESS: single
(D) TOPOLOGY: linear (ii) MOLECULE TYPE: None (xi) SEQUENCE DESCRIPTION: SEQ ID NO:33:

| Ala | Asp | Arg | Val | Val | Phe | Val | Phe | Pro | Gly | Gln | Gly | Ser | Gln | Trp | Ala |
|---|---|---|---|---|---|---|---|---|---|---|---|---|---|---|---|
| 1 | | | | 5 | | | | | 10 | | | | | 15 | |

| Gly | Met | Ala | Glu | Gly | Leu | Leu | Glu | Arg | Ser | Gly | Ala | Phe | Arg | Ser | Ala |
|---|---|---|---|---|---|---|---|---|---|---|---|---|---|---|---|
| | | | 20 | | | | | 25 | | | | | 30 | | |

| Ala | Asp | Ser | Cys | Asp | Ala | Ala | Leu | Arg | Pro | Tyr | Leu | Gly | Trp | Ser | Val |
|---|---|---|---|---|---|---|---|---|---|---|---|---|---|---|---|
| | | 35 | | | | | 40 | | | | | 45 | | | |

| Leu | Ser | Val | Leu | Arg | Gly | Glu | Pro | Asp | Ala | Pro | Ser | Leu | Asp | Arg | Val |
|---|---|---|---|---|---|---|---|---|---|---|---|---|---|---|---|
| 50 | | | | | 55 | | | | | 60 | | | | | |

| Asp | Val | Val | Gln | Pro | Val | Leu | Phe | Thr | Met | Met | Val | Ser | Leu | Ala | Ala |
|---|---|---|---|---|---|---|---|---|---|---|---|---|---|---|---|
| 65 | | | | 70 | | | | | 75 | | | | | 80 | |

| Val | Trp | Arg | Ala | Leu | Gly | Val | Glu | Pro | Ala | Ala | Val | Val | Gly | His | Ser |
|---|---|---|---|---|---|---|---|---|---|---|---|---|---|---|---|
| | | | | 85 | | | | | 90 | | | | | 95 | |

| Gln | Gly | Glu | Ile | Ala | Ala | Ala | His | Val | Ala | Gly | Ala | Leu | Ser | Leu | Asp |
|---|---|---|---|---|---|---|---|---|---|---|---|---|---|---|---|
| | | | 100 | | | | | 105 | | | | | 110 | | |

| Asp | Ser | Ala | Arg | Ile | Val | Ala | Leu | Arg | Ser | Arg | Ala | Trp | Leu | Gly | Leu |
|---|---|---|---|---|---|---|---|---|---|---|---|---|---|---|---|
| | | 115 | | | | | 120 | | | | | 125 | | | |

| Ala | Gly | Lys | Gly | Gly | Met | Val | Ala | Val | Pro | Met | Pro | Ala | Glu | Glu | Leu |
|---|---|---|---|---|---|---|---|---|---|---|---|---|---|---|---|
| | | 130 | | | | | 135 | | | | | 140 | | | |

| Arg | Pro | Arg | Leu | Val | Thr | Trp | Gly | Asp | Arg | Leu | Ala | Val | Ala | Ala | Val |
|---|---|---|---|---|---|---|---|---|---|---|---|---|---|---|---|
| 145 | | | | | 150 | | | | | 155 | | | | | 160 |

| Asn | Ser | Pro | Gly | Ser | Cys | Ala | Val | Ala | Gly | Asp | Pro | Glu | Ala | Leu | Ala |
|---|---|---|---|---|---|---|---|---|---|---|---|---|---|---|---|
| | | | | 165 | | | | | 170 | | | | | 175 | |

| Glu | Leu | Val | Ala | Leu | Leu | Thr | Gly | Glu | Gly | Val | His | Ala | Arg | Pro | Ile |
|---|---|---|---|---|---|---|---|---|---|---|---|---|---|---|---|
| | | | 180 | | | | | 185 | | | | | 190 | | |

| Pro | Gly | Val | Asp | Thr | Ala | Gly | His | Ser | Pro | Gln | Val | Asp | Ala | Leu | Arg |
|---|---|---|---|---|---|---|---|---|---|---|---|---|---|---|---|
| | | 195 | | | | | 200 | | | | | 205 | | | |

| Ala | His | Leu | Leu | Glu | Val | Leu | Ala | Pro | Val | Ala | Pro | Arg | Pro | Ala | Asp |
|---|---|---|---|---|---|---|---|---|---|---|---|---|---|---|---|
| | 210 | | | | | 215 | | | | | 220 | | | | |

| Ile | Pro | Phe | Tyr | Ser | Thr | Val | Thr | Gly | Gly | Leu | Leu | Asp | Gly | Thr | Glu |
|---|---|---|---|---|---|---|---|---|---|---|---|---|---|---|---|
| 225 | | | | | 230 | | | | | 235 | | | | | 240 |

| Leu | Asp | Ala | Thr | Tyr | Trp | Tyr | Arg | Asn | Met | Arg | Glu | Pro | Val | Glu | Phe |
|---|---|---|---|---|---|---|---|---|---|---|---|---|---|---|---|
| | | | | 245 | | | | | 250 | | | | | 255 | |

| Glu | Arg | Ala | Thr | Arg | Ala | Leu | Ile | Ala | Asp | Gly | His | Asp | Val | Phe | Leu |
|---|---|---|---|---|---|---|---|---|---|---|---|---|---|---|---|
| | | | 260 | | | | | 265 | | | | | 270 | | |

| Glu | Thr | Ser | Pro | His | Pro | Met | Leu | Ala | Val | Ala | Leu | Glu | Gln | Thr | Val |
|---|---|---|---|---|---|---|---|---|---|---|---|---|---|---|---|
| | | 275 | | | | | 280 | | | | | 285 | | | |

| Thr | Asp | Ala | Gly | Thr | Asp | Ala | Ala | Val | Leu | Gly | Thr | Leu | Arg | Arg | Arg |
|---|---|---|---|---|---|---|---|---|---|---|---|---|---|---|---|
| | 290 | | | | | 295 | | | | | 300 | | | | |

| His | Gly | Gly | Pro | Arg | Ala | Leu | Ala | Leu | Ala | Val | Cys | Arg | Ala | Phe | Ala |
|---|---|---|---|---|---|---|---|---|---|---|---|---|---|---|---|
| 305 | | | | | 310 | | | | | 315 | | | | | 320 |

| His | Gly | Val | Glu | Val | Asp | Pro | Glu | Ala | Val | Phe | Gly | Pro | Gly | Ala | Arg |
|---|---|---|---|---|---|---|---|---|---|---|---|---|---|---|---|
| | | | | 325 | | | | | 330 | | | | | 335 | |

| Pro | Val | Glu | Leu | Pro | Thr | Tyr | Pro |
|---|---|---|---|---|---|---|---|
| | | | 340 | | | | |

(2) INFORMATION FOR SEQ ID NO:34:

(i) SEQUENCE CHARACTERISTICS:
        (A) LENGTH: 345 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:34:

```
Arg Ala Pro Ala Phe Val Phe Pro Gly Gln Gly Ala Gln Trp Ala Gly
  1               5                  10                  15

Leu Gly Ala Arg Leu Leu Ala Asp Ser Pro Val Phe Arg Ala Arg Ala
                 20                  25                  30

Glu Ala Cys Ala Arg Ala Leu Glu Pro His Leu Asp Trp Ser Val Leu
             35                  40                  45

Asp Val Leu Ala Gly Ala Pro Gly Thr Pro Pro Ile Asp Arg Ala Asp
         50                  55                  60

Val Val Gln Pro Val Leu Phe Thr Thr Met Val Ser Leu Ala Ala Leu
 65                  70                  75                  80

Trp Glu Ala His Gly Val Arg Pro Ala Ala Val Val Gly His Ser Gln
                 85                  90                  95

Gly Glu Val Ala Ala Ala Cys Val Ala Gly Ala Leu Ser Leu Asp Asp
                100                 105                 110

Ala Ala Leu Val Ile Ala Gly Arg Ser Arg Leu Trp Gly Arg Leu Ala
            115                 120                 125

Gly Asn Gly Gly Met Leu Ala Val Met Ala Pro Ala Glu Arg Ile Arg
        130                 135                 140

Glu Leu Leu Glu Pro Trp Arg Gln Arg Ile Ser Val Ala Ala Val Asn
145                 150                 155                 160

Gly Pro Ala Ser Val Thr Val Ser Gly Asp Ala Leu Ala Leu Glu Glu
                165                 170                 175

Phe Gly Ala Arg Leu Ser Ala Glu Gly Val Leu Arg Trp Pro Leu Pro
                180                 185                 190

Gly Val Asp Phe Ala Gly His Ser Pro Gln Val Glu Glu Phe Arg Ala
            195                 200                 205

Glu Leu Leu Asp Leu Leu Ser Gly Val Arg Pro Ala Pro Ser Arg Ile
210                 215                 220

Pro Phe Phe Ser Thr Val Thr Ala Gly Pro Cys Gly Gly Asp Gln Leu
225                 230                 235                 240

Asp Gly Ala Tyr Trp Tyr Arg Asn Thr Arg Glu Pro Val Glu Phe Asp
                245                 250                 255

Ala Thr Val Arg Ala Leu Leu Arg Ala Gly His His Thr Phe Ile Glu
                260                 265                 270

Val Gly Pro His Pro Leu Leu Asn Ala Ala Ile Asp Glu Ile Ala Ala
            275                 280                 285

Asp Glu Gly Val Ala Ala Thr Ala Leu His Thr Leu Gln Arg Gly Ala
        290                 295                 300

Gly Gly Leu Asp Arg Val Arg Asn Ala Val Gly Ala Ala Phe Ala His
305                 310                 315                 320

Gly Val Arg Val Asp Trp Asn Ala Leu Phe Glu Gly Thr Gly Ala Arg
                325                 330                 335

Arg Val Pro Leu Pro Ser Tyr Ala Phe
                340                 345
```

POLYKETIDE DERIVATIVES AND RECOMBINANT METHODS FOR MAKING SAME

This application is a continuation-in-part of U.S. application Ser. No. 07/642,734, filed Jan. 17, 1991, now U.S. Pat. No. 5,824,513.

TECHNICAL FIELD

The present invention relates to novel polynucleotide sequences, proteins encoded therefrom which are involved in the biosynthesis of polyketides, methods for directing the biosynthesis of novel polyketides using those polynucleotide sequences and novel derivatives produced therefrom. In particular, the invention relates to the production of novel polyketide derivatives through manipulation of the genes encoding polyketide synthases.

BACKGROUND OF THE INVENTION

Polyketides are a large class of natural products that includes many important antibiotic, antifungal, anticancer, antihelminthic, and immunosuppressant compounds such as erythromycins, tetracyclines, amphotericins, daunorubicins, avermectins, and rapamycins. Their synthesis proceeds by an ordered condensation of acyl esters to generate carbon chains of varying length and substitution pattern that are later converted to mature polyketides. This process has long been recognized as resembling fatty acid biosynthesis, but with important differences. Unlike a fatty acid synthase, a typical polyketide synthase is programmed to make many choices during carbon chain assembly: for example, the choice of "starter" and "extender" units, which are often selected from acetate, propionate or butyrate residues in a defined sequence by the polyketide synthase. The choice of using a full cycle of reduction-dehydration-reduction after some condensation steps, omitting it completely, or using one of two incomplete cycles (reduction alone or reduction followed by dehydration) is additionally programmed, and determines the pattern of keto or hydroxyl groups and the degree of saturation at different points in the chain. Finally, the stereochemistry for the substituents at many of the carbon atoms is programmed by the polyketide synthase.

Streptomyces and the closely related Saccharopolyspora genera are producers of a prodigious diversity of polyketide metabolites. Because of the commercial significance of these compounds, a great amount of effort has been expended in the study of Streptomyces and Saccharopolyspora genetics. Consequently. much is known about these organisms and several cloning vectors and techniques exist for their transformation.

Although many polyketides have been identified, there remains the need to obtain novel polyketide structures with enhanced properties. Current methods of obtaining such molecules include screening of natural isolates and chemical modification of existing polyketides, both of which are costly and time consuming. Current screening methods are based on gross properties of the molecules. i.e. antibacterial. antifungal activity, etc., and both a priori knowledge of the structure of the molecules obtained or predetermination of enhanced properties are virtually impossible. Chemical modification of preexisting structures has been successfully employed to obtain novel polyketides, but still suffers from practical limitations to the type of compounds obtainable, largely connected to the poor yield of multistep synthesis and available chemistry to effect modifications. Modifications which are particularly difficult to achieve are those involving additions or deletions of carbon side chains. Accordingly, there exists a considerable need to obtain molecules wherein such changes can be specified and performed in a cost effective manner and with high yield.

The present invention solves these problems by providing reagents (specifically, polynucleotides, vectors comprising the polynucleotides and host cells comprising the vectors) and methods to generate novel polyketides by de novo biosynthesis rather than by chemical modification.

SUMMARY OF THE INVENTION

In one aspect, the present invention provides compounds of the formula:

X

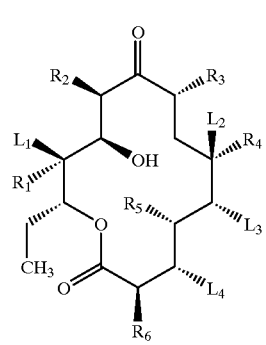

wherein $R_1$, $R_2$, $R_3$, $R_4$, $R_5$, and $R_6$ are independently selected from Q wherein Q is selected from the group consisting of (a) —H, (b) —Me, (c) —Et, and (d) —OH; $L_1$ and $L_2$ are independently —H or —OH: $L_3$ is D-desosamine or —OH; and $L_4$ is L-mycarose, L-cladinose or —OH with the proviso that when $R_1$–$R_5$ are —Me, $R_6$ is other than —H or —Me. Preferred compounds of the invention are those in Q is selected from the group consisting of (a), (b) and (c) above or (a), (b) and (d) above or (a), (c) and (d) above or (b), (c) and (d) above or (a) and (b) above or (a) and (c) above or (a) and (d) above or (b) and (c) above or (c) and (d) above and $L_1$, $L_2$, $L_3$ and $L_4$ are as defined above. Other preferred compounds include those in which $R_1$, $R_2$, $R_3$, $R_4$, $R_5$ and $R_6$ are all —H or —Et or —OH and $L_1$, $L_2$, $L_3$ and $L_4$ are as defined above. Still other preferred compounds include didesmethyl, tridesmethyl, tetradesmethyl, pentadesmethyl and hexadesmethyl derivatives of the compounds of formula X and particularly, di- tri-, tetra-, penta- and hexadesmethyl derivatives of erythromycins A and B. Other especially preferred compounds of formula X include 6,10-didesmethyl-6-ethylerythromycin A, 10,12-didesmethyl-12-deoxy-12-ethylerythromycin A, 10,12-didesmethyl-12-deoxy-10-hydroxyerythromycin A, 6,10,12-tridesmethyl-6,12-diethylerythromycin A, 6,10,12-tridesmethyl-6-deoxy-6,12-diethylerythromycin A, 10-desmethylerythronolide B, 10-desmethyl-6-deoxyerythronolide B, 12-desmethylerythronolide B, 12-desmethyl-6-deoxyerythronolide B, 12-desmethyl-12-ethylerythronolide B, 6-desmethyl-6-deoxy-6-ethylerythronolide B, 10-desmethylerythromycin A, 10-desmethyl-12-deoxyerythromycin A, 10-desmethyl-6,12-dideoxyerythromycin A, 12-desmethylerythromycin A, 12-desmethyl-12-deoxyerythromycin A, 12-desmethyl-6,12-dideoxyerythromycin A, 6-desmethyl-6-ethylerythromycin A, 12-desmethyl-12-ethylerythromycin A, 12-desmethyl-12-deoxy-12-ethylerythromycin A, 10-desmethyl-10-hydroxyerythromycin A, 12-desmethyl-12-epihydroxyerythromycin A, 10,12- didesmethylerythromycin A, 10,12-didesmethyl-12-deoxyerythromycin A, 10,12-didesmethyl-6,12-dideoxyerythromycin A, 10-desmethylerythronolide B, 10-desmethyl-6-deoxyerythronolide B, 12-desmethylerythronolide B, 12-desmethyl-6-deoxyerythronolide B, 10-desmethylerythromycin A, 10-desmethyl-12-deoxyerythromycin A, 10-desmethyl-6,12-dideoxyerythromycin A, 12-desmethylerythromycin A, 12-desmethyl-12-deoxyerythromycin A, 12-desmethyl-6,12-dideoxyerythromycin A, 10,12-didesmethylerythromycin A, 10,12-didesmethyl-12-deoxyerythromycin A, and 10,12-didesmethyl-6,12-dideoxyerythromycin A. Most preferred compounds include 10-desmethylerythromycin A, 10-desmethyl-12-deoxyerythromycin A, and 12-desmethyl-12-deoxyerythromycin A.

In another aspect, the present invention provides an isolated polynucleotide sequence or fragment thereof which encodes an enzymatically active acyltransferase domain from a PKS selected from *Streptomyces hygroscopicus*, *Streptomyces venezuelae*, and *Streptomyces caelestis*. Preferably, the polynucleotide sequence is SEQ ID NO: 1, SEQ ID NO:2, SEQ ID NO:29 or SEQ ID NO:30. In another preferred embodiment, the polynucleotide sequence encodes an acyltransferase domain selected from the group consisting of SEQ ID NO:31, SEQ ID NO:32, SEQ ID NO:33 and SEQ ID NO:34.

The present invention also provides a vector comprising a polynucleotide sequence or fragment thereof which encodes which encodes an enzymatically active acyltransferase domain from Streptomyces. Preferably, the polynucleotide sequence is selected from those described above and the Streptomyces is *Streptomyces hygroscopicus, Streptomyces venezuelae*, or *Streptomyces caelestis*. A particularly preferred vector is pCS5. Other vectors of the invention include pUC18/LigAT2, pEryAT1/LigAT2, pEryAT2/LigAT2, pUC18/venAT, pEryAT1/venAT, pUC19/rapAT14, pEryAT1/rapAT14, pEryAT2/rapAT14, pUC/5'-flank/ethAT, pUC/ethAT/C-6, pEAT4, pUC18/NidAT6, and pEryAT2/NidAT6.

In another aspect, the invention provides host cells transformed with a vector as described above. The host cell may be a bacterial cell and preferably is selected from the group consisting of *E. coli* and Bacillus species. Alternatively, the host cell is a polyketide-producing microorganism. A preferred polyketide-producing host cell is selected from the group consisting of Saccharopolyspora species, Nocardia species, Micromonospora species, Arthrobacter species, Streptomyces species, Actinomadura species, and Dactylosporangium. species. An even more preferred polyketide-producing host cell is selected from the group consisting of *Saccharopolyspora hirsuta, Micromonospora rosaria, Micromonospora megalomicea, Streptomyces antibioticus, Streptomyces mycarofaciens, Streptomyces avermitilis, Streptomyces hygroscopicus, Streptomyces caelestis, Streptomyces tsukubaensis, Streptomyces fradiae, Streptomyces platensis, Streptomyces violaceoniger, Streptomyces ambofaciens, Streptomyces griseoplanus*, and *Streptomyces venezuelae*. Of these host cells, *Saccharopolyspora erythraea, Streptomyces hygroscopicus, Streptomyces venezuelae*, and *Streptomyces caelestis* are most preferred.

The invention also provides a method for altering the substrate specificity of a polyketide synthase in a first polyketide-producing microorganism comprising the steps of (a) isolating a first and second genomic DNA segment, each comprising a polyketide synthase wherein the first genomic DNA segment is from the first polyketide-producing microorganism and the second genomic DNA segment is from the first polyketide-producing microorganism or a second polyketide-producing microorganism;

(b) identifying one or more discrete fragments of the first genomic DNA segment, each of which encodes an acyltransferase domain;

(c) identifying one or more discrete fragments of the second genomic DNA segment, each of which encodes a related domain to the acyltransferase domain of the first genomic DNA segment; and (d) transforming a cell of the first polyketide-producing microorganism with one or more of the fragments from step (c) under conditions suitable for the occurrence of a homologous recombination event, leading to the replacement of one or more of the fragments from the first genomic DNA segment with one or more of the fragments from step (c). In one embodiment, the first polyketide-producing microorganism is *Saccharopolyspora erythraea* and the second polyketide-producing microorganism is Streptomyces. Preferred Streptomyces are selected from the group consisting of *Streptomyces antibioticus, Streptomyces mycarofaciens, Streptomyces avermitilis, Streptomyces hygroscopicus, Streptomyces caelestis, Streptomyces tsukubaenisis, Streptomyces fradiae, Streptomyces platensis, Streptonzyces violaceoniger, Streptomyces ambofaciens*, and *Streptomyces venezuelae*. Even more preferred Streptomyces are *Streptomyces caelestis, Streptomyces hygroscopicus*, or *Streptomyces venezuelae*. In a second embodiment, the first polyketide-producing microorganism is a Streptomyces as described above and the second polyketide-producing microorganism is *Saccharopolyspora erythraea*. Also in a preferred embodiment, the related domain is selected from the group consisting of SEQ ID NO:31, SEQ ID NO:32, SEQ ID NO:33, and SEQ ID NO:34.

BRIEF DESCRIPTION OF THE DRAWINGS

The present invention will be more readily appreciated in connection with the accompanying drawings.

FIG. 4a is a schematic representation of gene replacements of EryAT1 with LigAT2 or venAT and EryAT2 with LigAT2 in *Sac. erythraea*.

FIG. 7 represents the nucleotide sequence (SEQ ID NO:1, top strand) and corresponding amino acid sequence (SEQ ID NO:31, bottom strand) of LigAT, the malonyl AT domain from module 2 of the Ligase-PKS cluster of *S. hygroscopicus* ATCC 29253.

FIG. 18 represents the nucleotide sequence (SEQ ID NO:2, top strand) and corresponding amino acid sequence (SEQ ID NO:32, bottom strand) of venAT, the malonate AT domain from the PKS cluster (hereinafter designated pven4) from *S. venezuelae* ATCC 15439.

FIG. 34 represents the nucleotide sequence (SEQ ID NO:29, top strand) and corresponding amino acid sequence (SEQ ID NO:33, bottom strand) of NidAT5, the ethyl AT domain from module 5 of the PKS cluster of *Streptomyces caelesns* NRRL-2821.

FIG. 36 is a diagram showing the nucleotide changes made to create an AvrII site at the 5' end of NidAT5.

FIG. 41 represents the nucleotide sequence (SEQ ID NO:30, top strand) and corresponding amino acid sequence (SEQ ID NO:34, bottom strand) of NidAT6, the AT domain in module 6 of the niddamycin PKS cluster.

FIG. 42 is a diagrammatic representation of the strategy to clone the NidAT6 domain.

DETAILED DESCRIPTION OF THE INVENTION

Figure 1A:
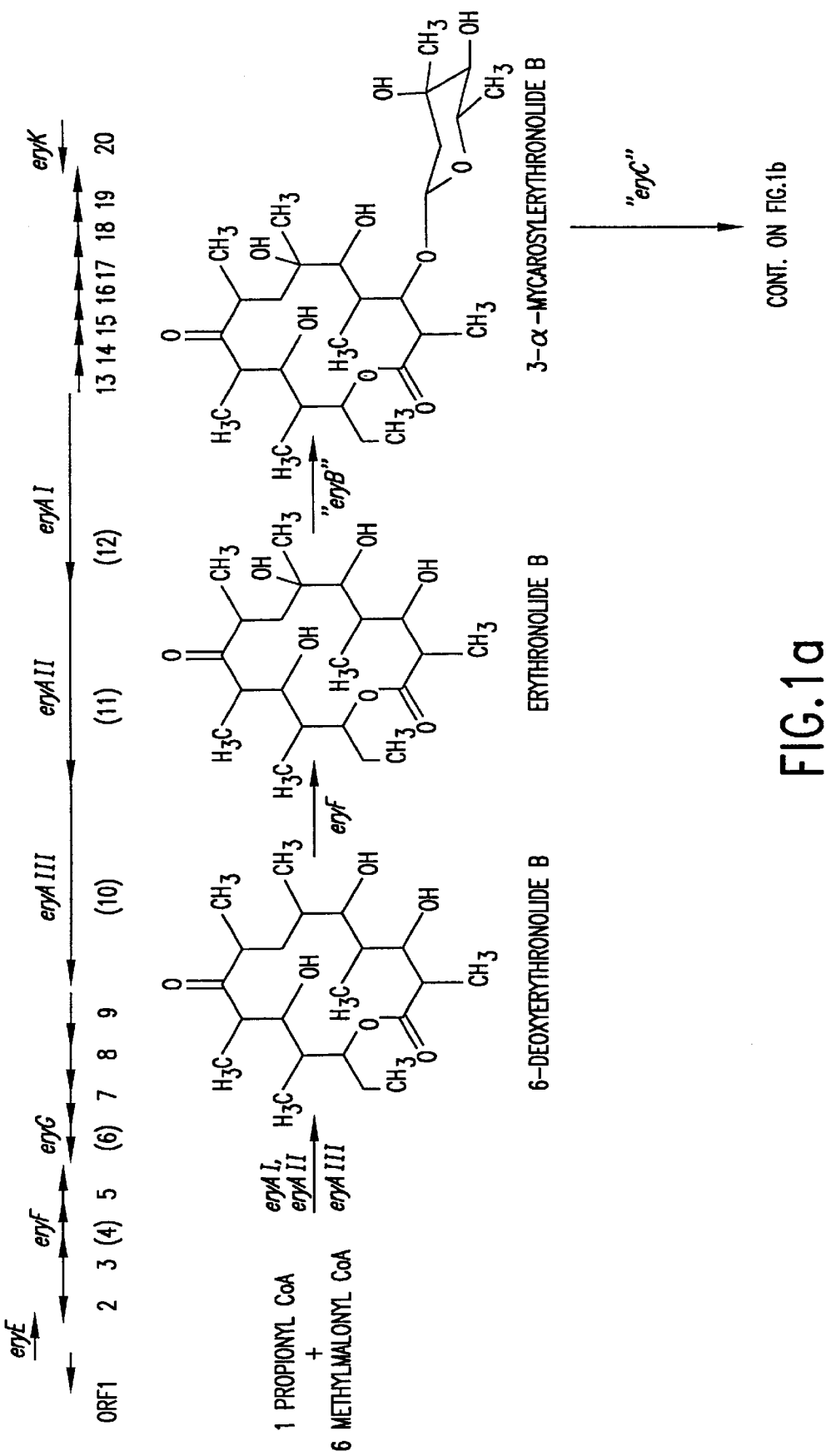
FIG. 1 is a proposed metabolic pathway for the biosynthesis of erythromycin A in *Sac. erythraea*.

I. Definitions:

For the purposes of the present invention as disclosed and claimed herein, the following terms are defined:

The term "polyketide" as used herein refers to a large and diverse class of natural products including but not limited to antibiotic, anticancer, antihelminthic, antifungal, pigment, and immunosuppressant compounds. Antibiotics include but are not limited to anthracyclines, tetracyclines, polyethers, polyenes, ansamycins, and macrolides of various types such as avermectins, erythromycins, and niddamycins. The term polyketide is also intended to refer to compounds of this class that can be used as intermediates in chemical syntheses. For example, erythromycin A is a polyketide that is isolated and used in the synthesis of the antibiotic clarithromycin. Polyketides used as intermediates do not themselves necessarily have any biological or therapeutic activity.

The term "polyketide-producing microorganism" as used herein includes but is not limited to bacteria from the order Actinomycetales, Myxococcales or other Eubacteriales that can produce a polyketide. Examples of actinomycetes and myxobacteria that produce polyketides include but are not limited to *Saccharopolyspora erythraea, Saccharopolyspora hirsuta, Micromonospora rosaria, Micromonospora megalomicea, Sorangium cellulosum, Streptomyces antibioticus, Streptomyces mycarofaciens, Streptomyces avermitilis, Streptomyces hygroscopicus, Streptomyces caelestis, Streptomyces tsukubaensis, Streptomyces fradiae, Streptomyces platensis, Streptomyces violaceoniger, Streptomyces ambofaciens, Streptomyces venezuelae* and various other Streptomyces, Actinomadura, Dactylosporangium and Amycolotopsis strains that produce polyketides. Yeast and fungi that produce polyketides are also considered "polyketide-producing microorganisms". Examples of fungi that produce polyketides include but are not limited to members of the genus Aspergillus.

The term "polyketide synthase" (PKS) as used herein refers to a complex of enzyme activities responsible for the biosynthesis of polyketides. The enzymatic activities contained within a PKS include but are not limited to β-ketoreductase (KR), dehydratase (DH), enoylreductase (ER), β-ketoacyl ACP synthase (KS), acyl carrier protein (ACP), acyltransferase (AT) and thioesterase (TE). The polypeptide fragment responsible for each enzymatic activity is referred to as a "domain". A "module" refers to a group or set of domains which carry out one condensation step in the process of polyketide formation and may or may not include domains which effect processing of the β-carbonyl group in the growing polyketide.

The term "Type I PKS" as used herein refers to a PKS which is a large multifunctional protein and is exemplified by DEBS (see below). The term "Type II PKS" refers to a PKS having several separate, largely monofunctional enzymes, and is exemplified by the PKSs responsible for the biosynthesis of actinorhodin and tetracenomycin (C.R. Hutchinson and I. Fujii, *Annu. Rev. Microbiol.* 49:201–238 (1995)).

The term "cognate domains" as used herein refers to the members of a specific set of domains which constitute a naturally occurring single module.

The term "related domain" or "heterologous domain" as used herein refers to a PKS domain which is functionally similar to a second PKS domain. By "functionally similar" it is meant that each domain catalyzes a particular type of reaction but acts upon a different substrate. For example, the AT domain of module I of *Sac. erythraea* (eryAT1) and the AT domain of module 14 of *S. hygroscopicus* (rapAT14) both catalyze the transfer of an extender unit to a corresponding ACP domain. In the case of *Sac. erythraea*, however, eryAT1 utilizes methylmalonyl CoA as a substrate whereas in *S. hygroscopicus*, rapAT14 utilizes malonyl CoA. Thus, eryAT1 and rapAT14 are considered to be "related" or "heterologous" domains.

The term "condensation" as used herein refers to the addition of an extender unit to the nascent polyketide chain and requires the action of KS, AT and ACP domains of the PKS.

The term "starter" as used herein refers to a coenzyme A thioester of a carboxylic acid which is used by a polyketide synthase as the first building block of the polyketide.

The term "extender" as used herein refers to a coenzyme A thioester of a dicarboxylic acid that is incorporated into a polyketide by a polyketide synthase at positions other than the first position.

The term "DEBS" as used herein refers to the enzyme 6-deoxyerythronolide B synthase, the PKS that builds the polyketide-derived macrolactone 6-deoxyerythronolide B (6-DEB).

The term "eryA" as used herein refers to the genes which encode the DEBS.

The term "homologous recombination" as used herein refers to crossing over between DNA strands containing identical sequences.

The term "isolated" as used herein means that the material is removed from its original environment (e.g. the natural environment where the material is naturally occurring). For example, a naturally occurring polynucleotide or polypeptide present in a living animal is not isolated, but the same polynucleotide or polypeptide, which is separated from some or all of the coexisting materials in the natural system, is isolated. Such polynucleotides could be part of a vector and/or such polynucleotides or polypeptides could be part of a composition, and still be isolated in that the vector or composition is not part of the natural environment.

The term "restriction fragment" as used herein refers to any linear DNA generated by the action of one or more restriction enzymes.

The term "transformation" as used herein refers to the introduction of DNA into a recipient microorganism, irrespective of the method used for the insertion into the microorganism.

The term "replicon" as used herein means any genetic element, such as a plasmid, chromosome or virus, that behaves as an autonomous unit of polynucleotide replication within a cell. A "vector" is a replicon in which another polynucleotide fragment is attached, such as to bring about the replication and/or expression of the attached fragment.

The terms "recombinant polynucleotide" or "recombinant polypeptide" as used herein means at least a polynucleotide or polypeptide which by virtue of its origin or manipulation is not associated with all or a portion of the polynucleotide or polypeptide with which it is associated in nature and/or is linked to a polynucleotide or polypeptide other than that to which it is linked in nature.

The term "host cell" as used herein, refers to both prokaryotic and eukaryotic cells which are used as recipients of the recombinant polynucleotides and vectors provided herein.

The term "open reading frame" or "ORF" as used herein refers to a region of a polynucleotide sequence which encodes a polypeptide, this region may represent a portion of a coding sequence or a total coding sequence.

II. The Invention

In its broadest sense, the present invention entails novel polyketides with therapeutic activity (e.g. antimicrobial, anticancer, antifungal, immunosuppressant and/or antihelminthic activity) and immediate compounds of such polyketides. The invention also provides a method for producing novel polyketides in vivo by selectively altering the genetic information of an organism that naturally produces a polyketide. The present invention further provides isolated and purified polynucleotides that encode PKS domains (i.e. polypeptides) from polyketide-producing mnicroorganisms, fragments thereof, vectors containing those polynucleotides, and host cells transformed with those vectors. These polynucleotides, fragments thereof, and vectors comprising the polynucleotides can be used as reagents in the above described method. Portions of the polynucleotide sequences disclosed herein are also useful as primers for the amplification of DNA or as probes to identify related domains from other polyketide-producing microorganisms.

III. Polynucleotides

The present invention provides isolated and purified polynucleotides that encode PKS domains (i.e. polypeptides) and fragments thereof which are involved in the production of polyketides. Polynucleotides included within the scope of the invention may be in the form of RNA, DNA, cDNA, genomic DNA and synthetic DNA. The DNA may be double-stranded or single-stranded, and if single-stranded may be the coding (sense) strand or non-coding (anti-sense) strand. The coding sequence which encodes a polypeptide may be identical to a coding sequence provided herein or may be a different coding sequence which, as a result of the redundancy or degeneracy of the genetic code, encodes the same polypeptide as the DNA provided herein.

Polynucleotides may include only the coding sequence for a particular polypeptide or for a polypeptide which is functionally equivalent to the polypeptide sequences provided herein. Additionally, the invention includes variant polynucleotides containing modifications such as polynucleotide deletions, substitutions or additions; and any polypeptide modification resulting from the variant polynucleotide sequence. A polynucleotide of the present invention also may have a coding sequence which is a naturally occurring allelic variant of the coding sequence provided herein.

Probes and primers constructed according to the polynucleotide sequences provided herein are also contemplated as within the scope of the present invention and can be used in various methods to provide various types of analysis. For example, primer sequences may be designed according to polynucleotide sequences which encode particular domains and then used to amplify polynucleotide sequences of the same or other related domains using well-known amplification techniques such as the polymerase chain reaction (PCR) and the ligase chain reaction (LCR). (PCR has been disclosed in U.S. Pat. Nos. 4,683,195 and 4,683,202, and LCR, in EP-A-320 308 to K. Backman published Jun. 16, 1989 and EP-A439 182 to K. Backman et al., published Jul. 31, 1991, all of which are incorporated herein by reference). Generation of primers for use in other amplification techniques or in variations of these amplification techniques, (such as nested PCR) is also contemplated within the scope of the invention and is considered within the knowledge of the routine practitioner.

Probes and primers may be designed from conserved nucleotide regions of a polynucleotide of interest or from non-conserved nucleotide regions of a polynucleotide of interest. Generally, nucleic acid probes are developed from non-conserved or unique regions when maximum specificity is desired, and nucleic acid probes are developed from conserved regions when assaying for nucleotide regions of related members of a multigene family or in related species. Probes can also be labeled with radioisotopes or other detection labels for screening of recombinant libraries.

Various methods for synthesizing primers and probes are well-known in the art as are methods for attaching labels to primers or probes. For example, it is a matter of routine to synthesize desired nucleic acid primers or probes using conventional nucleotide phosphoramidite chemistry and instruments available from Applied Biosystems, Inc., (Foster City, Calif.), Dupont (Wilmington, Del.), or Milligen (Bedford Mass.). Many methods have been described for labeling oligonucleotides such as the primers or probes of the present invention. Commercially available probe labeling kits include those from Amersham Life Science (Arlington Heights, Ill.), Promega (Madison. Wis.), Enzo Biochemical (New York, N.Y.) and Clontech (Palo Alto, Calif.).

IV. Vectors and Host Cells

The present invention provides vectors which include polynucleotides of the present invention and host cells which are genetically engineered with vectors of the present invention.

a. Vectors and Expression Systems

The present invention includes recombinant constructs comprising one or more of the sequences as broadly described above. The constructs comprise a vector, such as a plasmid or viral vector, into which a sequence of the invention has been inserted, in a forward or reverse orientation. Such vectors include chromosomal, nonchromosomal and synthetic DNA sequences from prokaryotic or eukaryotic sources. Large numbers of suitable plasmids and vectors are known to those of skill in the art, and are commercially available. Vectors which are particularly useful for cloning and expression in intermediate hosts include but are not limited to: (a) Bacterial: $pBR_{322}$ (ATCC 37017); pGEM (Promega Biotec, Madison, Wis.), pUC, pSPORT1 and pProEx1 (Life Technologies, Gaithersburg, Md.); pQE70, pQE60, pQE-9 (Qiagen); pBs, phagescript, psiX174, pBluescript SK, pBsKS, pNH8a, pNH16a, pNH18a, pNH46a (Stratagene®, La Jolla, Calif.); pTrc99A, pKK223-3, pKK233-3, $pDR_{540}$, pRIT5, and pGEX4T (Pharmacia®, Piscataway, N.J.); and (b) Eukaryotic: pWLneo, pSV2cat, pOG44, pXT1, pSG (Stratagene®); pSVK3, pBPV, pMSG, pSVL (Pharmacia®); pcDNA3.1 (Invitrogen, Carlsbad, Calif.). Other appropriate cloning and expression vectors for use with prokaryotic and eukaryotic hosts are described by Maniatis et al., *Molecular Cloning: A Laboratory Manual*, Second Edition, (Cold Spring Harbor Press, N.Y., 1982), which is hereby incorporated by reference. Generally however, any plasmid or vector may be used as long as it is replicable and viable in a host.

In another embodiment, the construct is an expression vector which also comprises regulatory sequences operably linked to the sequence of interest, to direct mRNA synthesis and polypeptide production. Regulatory sequences known to operate in prokaryotic and/or eukaryotic cells include inducible and non-inducible promoters for regulating mRNA transcription, ribosome binding sites for translation initiation, stop codons for translation termination and transcription terminators and/or polyadenylation signals. In addition, an expression vector may include appropriate sequences for amplifying expression.

Promoter regions may be selected from any desired gene. Particular named bacterial promoters include lacZ, gpt. lambda $P_R$, lambda $P_L$, trc, trp, ermE and its derivatives such as ermEP1ΔTGG. also known in the art as ermE*, (Bibb, M. J., et al., *Molecular Microbiology*, 14(3): 533–545 (1994)), melCI, and actII (C. M. Kao, et al., *Science*, 265: 509–512 (1994)). Eukaryotic promoters include cytomegalovirus (CMV) immediate early, herpes simplex virus (HSV) thymidine kinase, early and late SV40, LTRs from retroviruses, mouse metallothionein-I, prion protein and neuronal specific enolase (NSE). Selection of the appropriate promoter is well within the level of ordinary skill in the art. In addition, a recombinant expression vector will include an origin of replication and selectable marker (such as a gene conferring resistance to an antibiotic (eg. neomycin, chloramphenicol, ampicillin, or thiostrepton) or a reporter gene (eg. luciferase)) which permit selection of stably transformed or transfected host cells.

In any expression vector, a heterologous structural sequence (i.e. a polynucleotide of the present invention) is assembled in appropriate phase with translation initiation and termination sequences. Optionally, the heterologous sequence will encode a fusion protein including an N-terminal identification peptide imparting desired characteristics, e.g., stabilization or simplified purification of expressed recombinant product Eukaryotic expression vectors will also generally comprise an origin of replication, a suitable promoter operably linked to a sequence of interest and also any necessary translation enhancing sequence, polyadenylation site, transcriptional termination sequences, and 5' flanking nontranscribed sequences. DNA sequences derived from the SV40 viral genome, for example, SV40 origin, early promoter, enhancer, and polyadenylation sites may be used to provide the required genetic elements. Such vectors may also include an enhancer sequence to increase transcription of a gene. Enhancers are cis-acting elements of DNA, usually about from 10 to 300 bp, that act on a promoter to increase its transcription rate. Examples include the SV40 enhancer on the late side of the replication origin (bp 100 to 270), a cytomegalovirus early promoter enhancer, a polyoma enhancer on the late side of the replication origin, and adenovirus enhancers.

i. Vector construction

The appropriate DNA sequence may be inserted into a vector by a variety of procedures. Generally, site-specific DNA cleavage is performed by treating the DNA with suitable restriction enzymes under conditions which are generally specified by the manufacturer of these commercially available enzymes. Usually, about 1 microgram ($\mu$g) of plasmid or DNA sequence is cleaved by 1 unit of enzyme in about 20 microliters ($\mu$L) of buffer solution by incubation at 37° C. for 1 to 2 hours. After incubation with the restriction enzyme, protein can be removed by phenol/chloroform extraction and the DNA recovered by precipitation with ethanol. The cleaved fragments may be separated using polyacrylamide or agarose gel electrophoresis, according to methods known by the routine practitioner. (See Maniatis et al., supra).

Ligations are performed using standard buffer and temperature conditions and with a ligase (such as T4 DNA ligase) and ATP. Sticky end ligations require less ATP and less ligase than blunt end ligations. Vector fragments may be treated with bacterial alkaline phosphatase (BAP) or calf intestinal alkaline phosphatase (CIAP) to remove the 5'-phosphate and thus prevent religation of the vector. Ligation mixtures are transformed into suitable cloning hosts such as *E. coli* and successful transformants selected by methods including antibiotic resistance, and then screened for the correct construct.

ii. Transformation/Transfection

Transformation or transfection of an appropriate host with a construct of the invention, such that the host produces recombinant polypeptides, may also be performed in a variety of ways. For example, a construct may be introduced into a host cell by calcium chloride or polyethylene glycol transformation, lithium chloride or calcium phosphate transfection, DEAE-Dextran mediated transfection, or electroporation. These and other methods for transforming/transfecting host cells are well known to routine practitioners (see L. Davis et al., "Basic Methods in Molecular Biology", 2nd edition, Appleton and Lang, Paramount Publishing, East Norwalk, Conn. (1994) and D. A. Hopwood et al., Genetic Manipulation of Streptomyces: a laboratory manual, The John Innes Foundation, Norwich, England (1985)).

b. Host Cells

In one embodiment, the present invention provides host cells containing recombinant constructs as described below. In one aspect, a host cell may be an "intermediate" host which is used to produce polynucleotides of the invention on a large-scale basis (for the purpose of cloning and/or verifying recombinant polynucleotide sequences, for example) or as a means to maintain such polynucleotide sequences over time (i.e. as maintenance or storage strains). A "production" host is a host cell which is used to produce novel polyketides. The host cell (either intermediate or production) can be a higher eukaryotic cell, such as a mammalian cell, or a lower eukaryotic cell, such as a yeast cell, or a prokaryotic cell, such as a bacterial cell. Lower eukaryotic and prokaryotic cells are preferred intermediate and production hosts.

Representative examples of appropriate hosts include bacterial cells, such as *E. coli, Bacillus subtilis, Saccharopolyspora erythraea, Streptomyces caelestis, Streptomyces hygroscopicus, Streptomyces venezuelae*; and various other species within the genera Arthrobacter, Micromonospora, Nocardia, Pseudomonas, Streptomyces, Staphylococcus, and Saccharopolyspora, although others (of eukaryotic origin) may also be employed. Additional representative examples of host cells are polyketide-producing microorganisms (as defined above). The selection of an appropriate host is deemed to be within the scope of those skilled in the art from the teachings provided herein.

Host cells are genetically engineered (transduced, transformed, transfected, conjugated, or electroporated) with the vectors of this invention which may be a cloning vector or an expression vector. The engineered host cells can be cultured in conventional nutrient media modified as appropriate for activating promoters, selecting transformants, or as a source of a biosynthetic substrate. The culture conditions, such as temperature, pH and the like, are those previously used with the host cell selected for expression, and will be apparent to the ordinarily skilled artisan.

V. Novel Polyketides and Methods of Making Novel Polyketides

The invention also provides novel polyketides, intermediate compounds thereof, and methods for producing novel polyketides. The methods utilize the polyketide biosynthetic genes from *Sac. erythraea* (i.e. the eryA genes) as well as those from other known polyketide-producing microorganisms and/or putative polyketide-producing microorganisms (i.e. those having nucleotide sequences which hybridize to known PKS sequences but whose polyketide products are unknown).

Figure 1B:
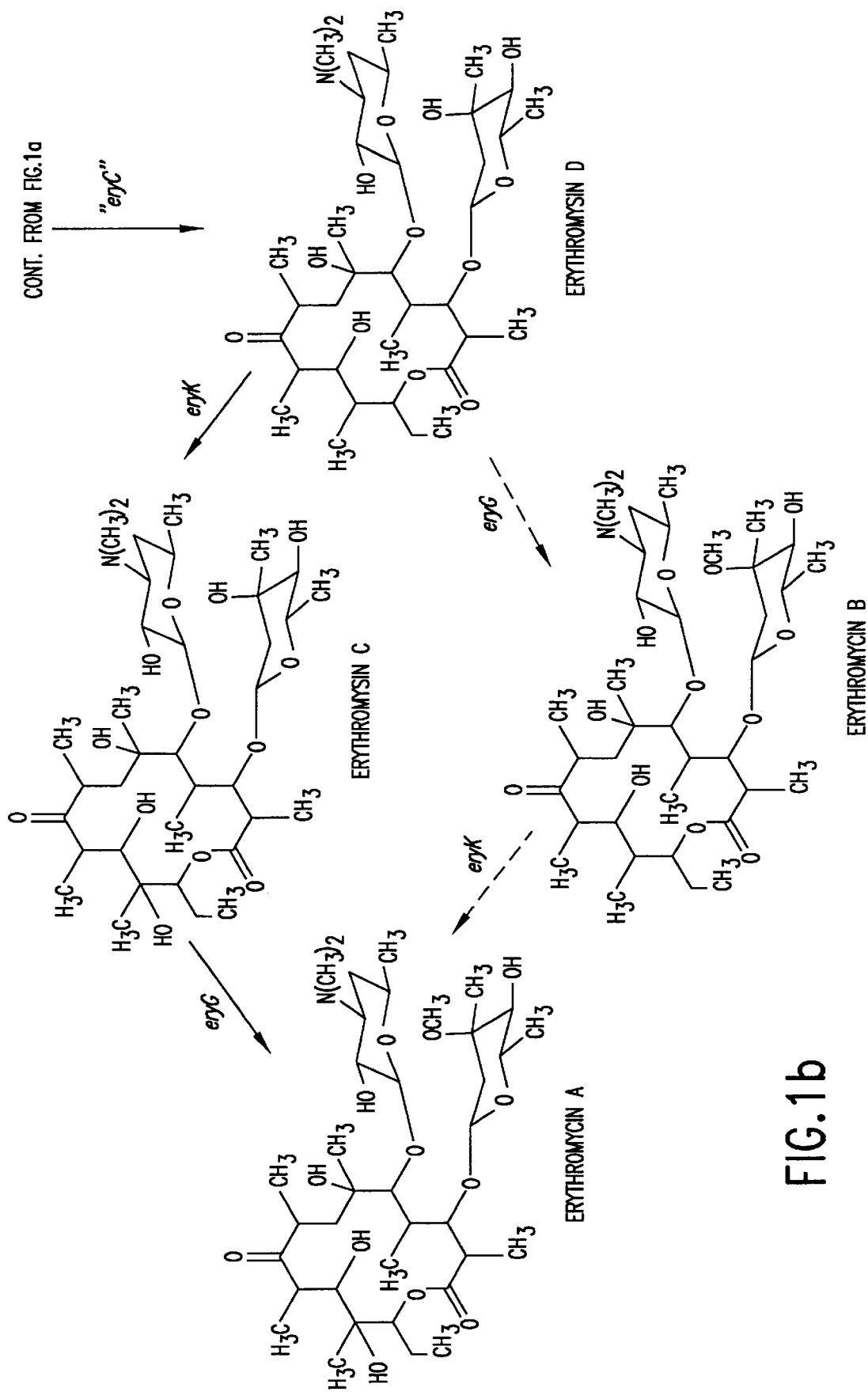
Figure 2:
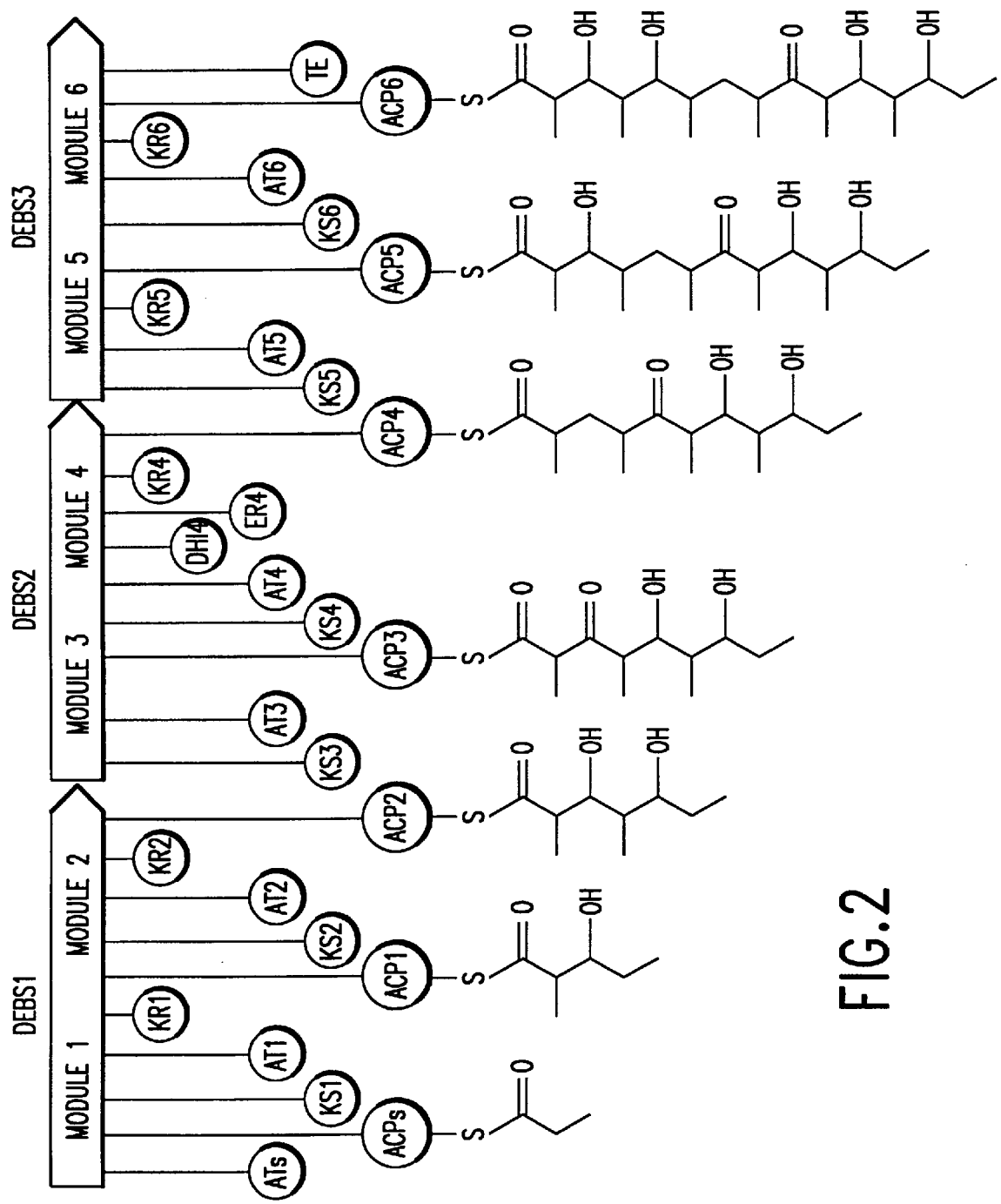
FIG. 2 is a schematic representation of the erythromycin PKS.

The organization of eryA and the DEBS encoded therefrom (see FIG. 1 and FIG. 2) have been described in co-pending U.S. application Ser. No. 07/642,734, filed Jan. 17, 1991, which is incorporated herein by reference in its entirety. As FIG. 2 shows, DEBS is organized in modules, with each module being responsible for one condensation step through the action of the resident KS, AT and ACP domains within that module wherein an extender unit, methylmalonyl CoA, is added first to the starter unit, propionyl CoA, and then successively to the growing acyl chain. The precise succession of the elongation steps is dictated by the order of the six modules: module 1 determines the first condensation; module 2, the second; module 3, the third, and so on until the sixth condensation step has occurred. In addition, the choice of extender unit that is incorporated into a growing polyketide chain at each condensation is determined, in whole or in part, by the AT domain within each module. In the case of DEBS, the extender unit incorporated is always methylmalonate. Thus, as 6-deoxyerythronolide B grows through successive condensations, two carbons are added to the nascent chain and every other carbon, starting with the carbon corresponding to C-12 in the ring, carries a methyl group as a side chain.

As also seen in FIG. 2, the processing of the growing carbon chain after each condensation is determined by the information within each module. Thus, β-ketoreduction of the β-keto group generated by the condensation event takes place after each condensation step except the third, as determined by the presence of an active KR domain in each module except module 3, whereas dehydration and enoyl-reduction take place after the fourth condensation step. as determined by the presence of the DH and ER domains in module 4. Once the polyketide chain is fully synthesized, it is released from the PKS through the action of the TE domain present at the end of module 6 and cyclizes to form the macrocyclic lactone 6-deoxyerythronolide B which is subsequently acted upon by a series of other enzymes, whose genes reside in the erythromycin cluster of the *Sac. erythraea* chromosome (see FIG. 1). As shown in FIG. 1, erythromycin carries methyl side chains at position 2, 4, 6, 8, 10 and 12, through the incorporation of methylmalonate as the extender unit at each step of synthesis of the polyketide moiety.

In the present invention, novel polyketide molecules of a desired structure are produced by introducing specific genetic alterations into a PKS-encoding sequence in the genome of a polyketide-producing microorganism. Alteration of one or more genes or fragments thereof may be generated through manipulation of genes residing exclusively within a species (i.e. intraspecies alterations), and include not only manipulations of genes within a single PKS cluster but also between different PKS clusters residing within a single strain (as is seen in *S. hygroscopicus*). Several examples of intraspecies alterations showing the manipulation of genes exclusively within a single PKS (namely, eryA) are described in U.S. application Ser. No. 07/624,734 cited supra. Alternatively, a gene or fragment thereof may be exchanged with a heterologous gene or gene fragment encoding one or more related domains from the PKS of a different polyketide-producing microorganism (interspecies alterations). Several examples of novel polyketides produced from exchange of heterologous genes are provided herein.

Whether the genetic manipulations are performed intraspecies or interspecies, three types of alterations to a PKS sequence may be carried out: (i) those which affect a module but do not cause the arrest of chain growth (Type I alterations); (ii) those which affect a single function in a module thereby causing the arrest of chain growth (Type II alterations); and (iii) those which affect an entire module (Type III alterations). In one embodiment, Type I alterations are produced by inactivation of domains that specify the functional groups and/or degree of oxidation found at specific ring positions in the native polyketide. Such domains typically include β-ketoreductases, dehydratases and enoyl-reductases. For example, an allele corresponding to β-ketoreductase of module 5 may be mutated by deleting a substantial portion of the DNA encoding the β-ketoreductase (thereby producing an inactive domain) and used to replace the wild-type allele in the native strain. Such a transfer results in the production of the novel polyketide 5-oxo-5,6-dideoxy-3- -mycarosyl erythronolide B.

In an alternative embodiment, Type I alterations are generated by replacing at least one domain in a particular PKS with at least one related domain from the same or a second PKS. Such related domains may exist between different polyketide-producing microorganisms (such as for example, the AT domains of *Sac. erythraea, S. venezuelae, S. hygroscopicus,* and *S. caelestis*) or within a single species (as for example, the LigAT2 and rapAT1 domains in *S. hygroscopicus*).

Ways to identify polyketide synthases, their domains and the functional similarity of domains are well-known to those of ordinary skill in the art. For example, the PKS region of the chromosome of a polyketide or putative polyketide-producing microorganism may be identified by hybridizing with nucleic acid probes under conditions of low or high stringency. Hybridization under high stringency conditions is generally performed in a buffer consisting of 15 mM sodium chloride and 1.5 mM trisodium citrate (0.1×SSC) with an incubation temperature of about 65° C. (see for example, Maniatis. et al. supra). To detect more distantly related PKS genes. hybridization is performed under low stringency conditions which include lower temperature incubations and/or the presence of increased amounts of sodium chloride and trisodium citrate (Maniatis, et al. supra). Once identified, the chromosomal region may be isolated, cloned into a suitable vector and sequenced, using conventional methods or commercial sequencing kits such as Sequenase (US Biochemical Corp, Cleveland, Ohio). Methods for isolating and cloning chromosomal DNA are also well known in the art (Maniatis, et al. supra). An amino acid sequence may then be deduced from the DNA sequence and a comparison made of the unknown amino acid sequence to that of one or more polypeptides involved in polyketide biosynthesis. Two amino acid sequences showing at least about 20% and more preferably about 25% identity and having conserved active site residues or motifs are considered to specify functionally similar or equivalent PKS domains. Having identified such domains, the number and composition of modules as well as the arrangement of modules within particular ORFs can be determined.

In the case where the newly defined PKS produces a polyketide of known structure, the β-carbonyl processing and types of side chain moieties and their positioning on the polyketide backbone can be correlated to specific domains within modules. Because modules are established linearly within ORFs, this correlation also allows one to determine the order of modular activity (i.e. which module catalyzes which condensation step) in the PKS. For example, the β-carbonyl processing and types of side chain moieties in the polyketide generates a pattern of chemical groups that can be correlated to a pattern of domains within an ORF. Based on the specific type of side chain moiety at a given carbon, one can then predict the particular substrate utilized by that module's AT domain.

In the case where the polyketide structure is unknown, theoretically, comparative sequence analysis alone may be used to predict the substrate specificity of an AT domain. To accomplish this, at least two and preferably, three or more sequences known or predicted to specify a particular substrate can be compared to determine one or more conserved or consensus motifs unique to that family of ATs. An unknown AT having such motifs can then be assigned to a particular family.

Figure 3:
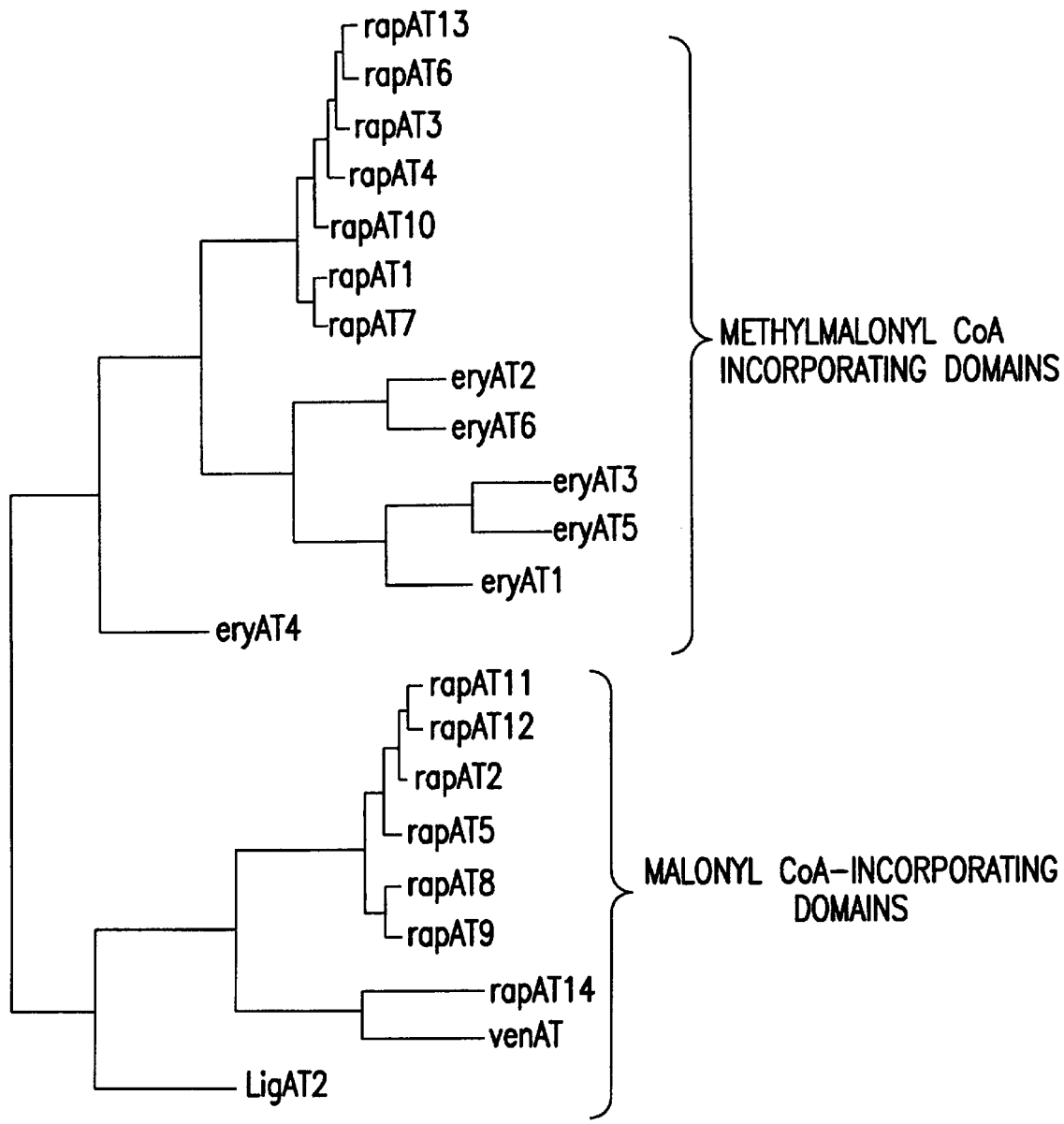
FIG. 3 is a Growtree analysis of AT domains from *Streptomyces hygroscopicus* (*S. hygroscopicus*; LigAT2 and rapAT1-14), *Streptomyces venezuelae* (*S. venezuelae*; venAT) and *Saccharopolyspora erythraea* (*Sac. erythraea*; eryAT1-6).

Alternatively, comparative analyses can be performed using computer programs which group AT domains based on primary amino acid sequence similarity or phylogenetic relationships. For example, comparative analyses were made of the amino acid sequences of the AT domains in DEBS with corresponding AT domains in the PKS for rapamycin to determine whether the extender unit used by a particular AT domain, (either malonate or methylmalonate), correlated with the degree of sequence identity between these domains. Rapamycin is a large polyketide that is assembled through 14 condensation events; the rapamycin PKS possesses 14 AT domains whose sequences were deduced from known nucleotide sequences (Aparicio et al. Gene 169:9–16 (1996)). Amino acid sequence comparisons of the 14 AT domains of the rapamycin PKS with each other and with the 6 AT domains from DEBS, showed that the AT domains fell into two distinct groupings in which the rapamycin AT domains from modules 1, 3, 4, 6, 7, 10 and 13 clustered with the 6 erythromycin AT domains and the rapamycin AT domains in modules 2, 5, 8, 9, 11, 12 and 14 formed a separate cluster (Haydock et al. *FEBS Letts.* 374:246–248 (1995)). Examination of the polyketide structure of rapamycin indicated that methyl side chains were at positions on the lactone ring corresponding to condensation steps 1, 3, 4, 6, 7, 10 and 13, which suggested that methylmalonate was used as the extender unit during synthesis of these sections of the acyl chain; protons at the positions of the lactone ring corresponding to condensations steps 2, 5, 8, 9, 11, 12 and 14 suggested that malonate was utilized as the extender unit during synthesis of these sections. Two additional AT domains described herein, ligAT2 and venAT, were also found to cluster with the putative malonate AT domains from the rapamycin PKS (FIG. 3). Having predicted that AT domains from rap modules 2, 5, 8, 9, 11, 12 or 14, as well as ligAT2 and venAT, specify malonate as extender units, the DNA encoding such domains could be isolated, cloned and used to replace the DNA encoding one or more AT domains in a PKS such as DEBS, in order to generate novel polyketides.

The techniques for determining the amino acid sequence "similarity" are well-known in the art. In general, when two or more polypeptides are aligned with one another, their sequence similarity refers to the amino acids at corresponding positions within each polypeptide sequence that are identical or possess similar chemical and/or physical properties such as charge or hydrophobicity. A so-termed "percent similarity" then can be determined between the compared polypeptide sequences. In general, the term "identity" refers to an exact nucleotide to nucleotide or amino acid to amino acid correspondence at a given position of two polynucleotides or polypeptide sequences, respectively. Two amino acid sequences (or for that matter, two or more polynucleotide sequences) can be compared by determining their "percent identity." The programs available in the Wisconsin Sequence Analysis Package, Version 8 (available from Genetics Computer Group (GCG), Madison, Wis.), for example, the GAP program, are capable of calculating both the identity between two polynucleotides and the identity and similarity between two polypeptide sequences, respectively. Other programs for calculating and displaying similarity between sequences are known in the art. For example, the Growtree program (GCG, Madison, Wis.) creates a phylogenetic tree wherein the most closely related sequences are clustered and joined by the shortest lines. This tree is derived from a matrix created by the program Distances (GCG, Madison, Wis.) which calculates pairwise relationships within a group of aligned sequences.

In a preferred embodiment, novel polyketide molecules of desired structure are produced by the replacement of at least one AT domain-encoding fragment of DNA of the *Sac. erythraea* chromosome with at least one heterologous AT domain-encoding fragment of DNA from another PKS cluster to yield novel polyketide compounds which are derivatives of 6-deoxyerythronolide B, erythronolide B, 3-α-L-mycarosylerythronolide B, or erythromycins A, B, C and D. Such derivatives are compounds wherein methyl (—Me)

side chains at one or more positions of the macrocylic lactone ring are replaced by substituents independently selected from the group consisting of (a) —H; (b) ethyl group (—Et); (c) hydroxyl group (—OH) and (d) allyl group (—Al). In a particularly preferred embodiment, a method is provided for the genetic modification of erythromycin-producing microorganisms which enables them to produce the novel compounds 12-desmethyl-12-deoxyerythromycin A, 10-desmethylerythromycin A. 10-desmethyl-12-deoxyerythromycin A. or 6-desmethyl-6-ethylerythromycin A. The compounds 12-desmethyl-12-deoxyerythromycin A, 10-desmethylerythromycin A, 10-desmethyl-12-deoxyerythromycin A. and 6-desmethyl-6-ethylerythromycin A are represented by the structural formulae:

(I)

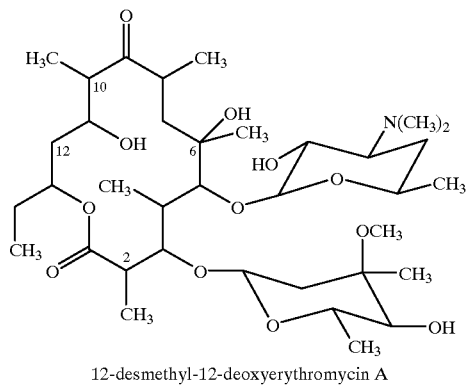

12-desmethyl-12-deoxyerythromycin A (II)

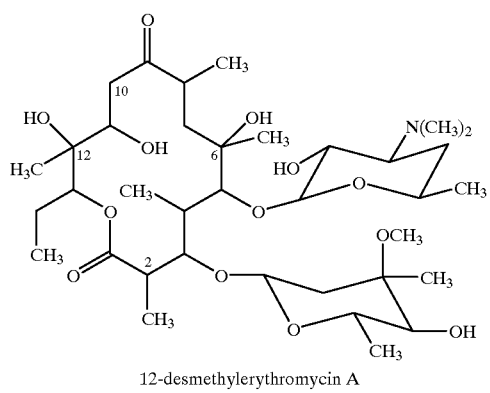

12-desmethylerythromycin A (III)

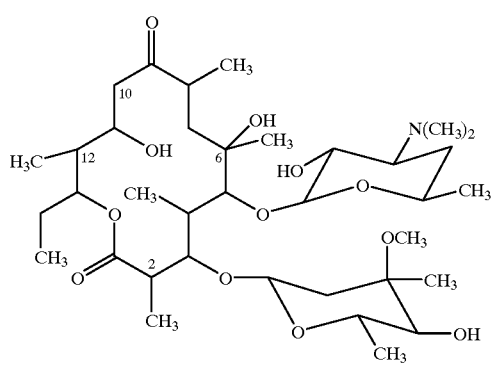

10-desmethyl-12-deoxyerythromycin A

-continued (IV)

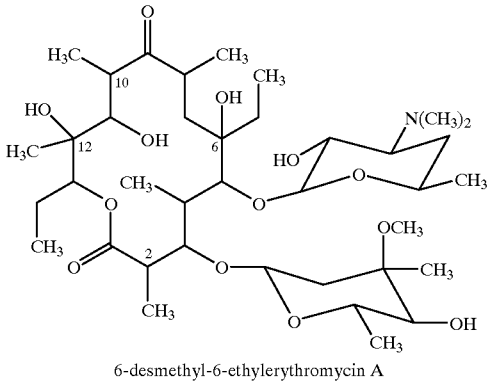

6-desmethyl-6-ethylerythromycin A

Figure 4B:
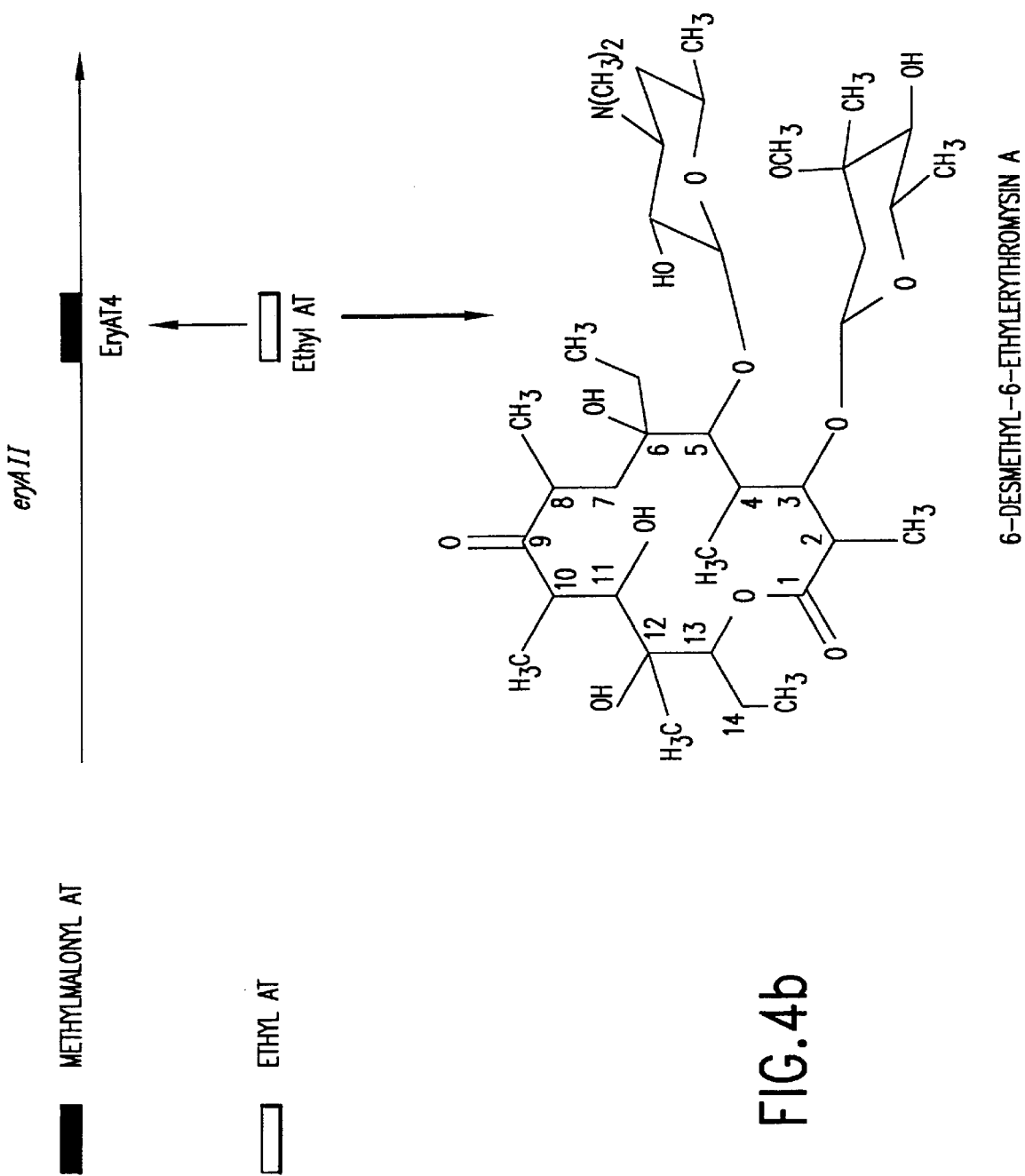
FIG. 4b is a schematic representation of gene replacements of EryAT4 with an ethyl AT (NidAT5) in *Sac. erythraea*.

The general scheme for producing such polyketides is outlined in FIG. 4a and FIG. 4b. In the preferred embodiment, heterologous DNA fragments encoding related AT domains are introduced into the Sac. erythraea chromosome by a two-step method termed gene replacement.

In the first step of gene replacement, an integration vector is constructed through a multi-step cloning approach that places a heterologous gene or fragment thereof between two segments of DNA having sequences which are identical to those that immediately border (on each side) the resident polynucleotide sequence to be replaced. Construction of such a vector may be achieved by any means known to those of ordinary skill in art. For example, nucleotide sequences which flank the gene to be replaced can be generated by PCR amplification using chromosomal DNA as template and primers which hybridize to the chromosomal sequences immediately upstream and downstream of the flanking sequences of interest. The length of the flanking sequences is not critical to the practice of the invention but preferably is about 20–5000 base pairs (bp), more preferably about 100–5000 bp. and even more preferably about 500–5000 bp. A most preferred length of flanking sequence is about 750–1500 bp. Primers used for such amplifications may also comprise convenient restriction sites to facilitate cloning of the amplified sequences into suitable preparative vectors, to facilitate insertion of the heterologous sequence of interest between the flanking sequences and/or to facilitate subcloning of the entire group of sequences (5'-flanking region/heterologous polynucleotide sequence of interest/flanking region-3') into suitable vectors for integration. The desired heterologous polynucleotide sequences may be generated in a like manner.

The integration vectors are constructed to also comprise a fragment of DNA containing at least one origin of replication that is functional in an intermediate host but is non-functional or poorly functional in the production host. The vectors further comprise one or more fragments of DNA conferring resistance to an antibiotic, of which at least one functions in the intermediate host and at least one functions in the production host. Preferred integration vectors comprise the ColE1 and pIJ101 origins of replication, as found in plasmid pCS5 (J. Vara et al., J. Bacteriol. 171:5872–5881 (1989)). A particularly preferred vector carries a DNA fragment conferring resistance to thiostrepton and ampicillin. However, those skilled in the art understand that the particular antibiotic resistance genes and origins of replication identified above are necessary only inasmuch as they allow for the generation and selection of the desired recombinant plasmids and host cells. Other markers and origins of replication may also be used in the practice of the invention.

When the resident domains of a PKS are functional components of large multifunctional polypeptides, care must be taken in the construction of the integration plasmid so that the heterologous DNA fragment encoding the heterologous AT domain is positioned in the correct orientation and reading frame to its flanking DNA segments so that upon translation from the beginning of the coding sequence, an enzymatically functional protein is produced. The correct positioning becomes immediately apparent from knowledge of the nucleotide sequences of the host PKS genes and the heterologous genes used for gene replacement.

Figure 5:
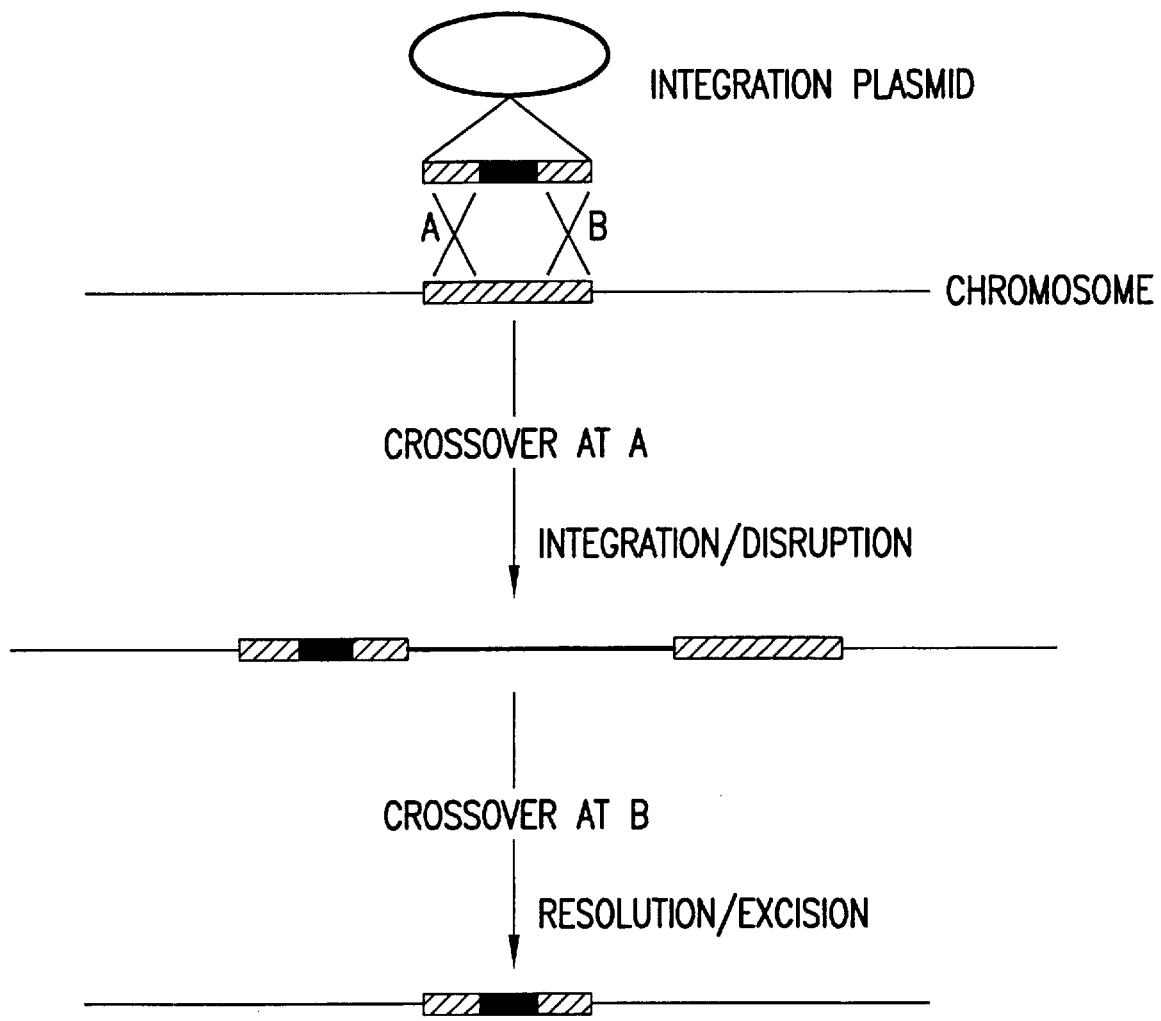
FIG. 5 is a diagrammatic representation of gene replacement by homologous recombination.

In the second step, each of the integration vectors carrying a related gene or fragment thereof is independently introduced into a host strain and recombination between each of the genomic fragments in the integration plasmid and its corresponding homologous fragment in the host strain chromosome is allowed to occur. This procedure results in the exchange of the resident AT-encoding DNA in the chromosome for its heterologous counterpart. The general scheme for gene replacement by homologous recombination is outlined in FIG. 5. Procedures to introduce DNA into polyketide-producing microorganisms and to facilitate homologous recombination are described herein. However, those skilled in the art understand that alternative procedures for introducing DNA into a polyketide-producing microorganism, such as electroporation, transduction, or conjugation. are well known and may also be used in the practice of the invention. Procedures for cultivating polyketide-producing microorganisms, as well as methods to recover novel polyketides produced from modified strains, to purify such compounds and to confirm the identity of those compounds (such as by mass spectrometry or NMR) are well-known to those of ordinary skill in the art.

Although the present invention is described in the Examples that follow in terms of preferred embodiments, they are not to be regarded as limiting the scope of the invention. The descriptions that follow serve to illustrate the principles and methodologies involved in creating novel derivatives of erythromycin. Whereas the examples below describe the replacement of the Sac. erythraea AT1, AT2, and AT4encoding DNA fragments with a heterologous DNA fragment which encodes either an AT domain that specifies incorporation of malonate (malonate-AT) or an AT domain that specifies incorporation of ethylmalonate (ethylmalonate-AT), those skilled in the art understand that one or more fragments of heterologous DNA encoding malonate, ethylmalonate, allylmalonate, and/or hydroxymalonate (tartronate)-AT domains can be used to replace the other AT-encoding DNA fragments of the erythromycin PKS in Sac. erythraea to result in the production of other novel erythromycin derivatives. For example, novel erythromycins produced when resident AT-encoding DNA fragments in the erythromycin PKS (eryPKS) are independently replaced with heterologous DNA fragments specifying malonate and/or ethylmalonate as the extender unit are shown in Table 1.

In particular, those skilled in the art understand that following the methods described herein for replacement of a single resident AT-encoding DNA fragment in the eryPKS, replacements of two resident AT-encoding DNA fragments with heterologous DNA fragments (specifying malonate, ethylmalonate, allylmalonate, and/or hydroxymalonate—AT domains) in stepwise fashion are also possible and result in the formation of novel disubstituted erythromycins. Similarly, trisubstituted erythromycins, tetrasubstituted erythromycins, pentasubstituted erythromycins and hexasubstituted erythromycins can also be made by replacement of three, four, five and six resident AT-encoding DNA fragments in the eryPKS, respectively, with heterologous AT-encoding DNA fragments as described herein. Therefore, all substitutions of AT-encoding DNA fragments in the eryPKS with heterologous AT-encoding DNA fragments (yielding all varieties of proton, ethyl, allyl, and hydroxyl substituted erythromycin derivatives) are within the scope of the present invention. Examples of compounds produced by such replacements include but are not limited to those shown in Table 1 below.

TABLE 1

Structures from Changes at Side Chain Positions

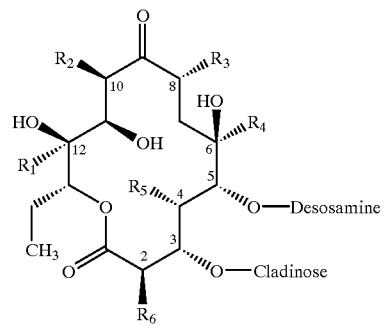

| $R_1$ | $R_2$ | $R_3$ | $R_4$ | $R_5$ | $R_6$ | Name |
|---|---|---|---|---|---|---|
| A. Single Changes ||||||||
| H | Me | Me | Me | Me | Me | 12-Desmethylerythromycin A |
| Et | Me | Me | Me | Me | Me | 12-Desmethyl-12-ethylerythromycin A |
| Me | H | Me | Me | Me | Me | 10-Desmethylerythromycin A |
| Me | Et | Me | Me | Me | Me | 10-Desmethyl-10-ethylerythromycin A |
| Me | Me | H | Me | Me | Me | 8-Desmethylerythromycin A |
| Me | Me | Et | Me | Me | Me | 8-Desmethyl-8-ethylerythromycin A |
| Me | Me | Me | H | Me | Me | 6-Desmethylerythromycin A |

TABLE 1-continued

Structures from Changes at Side Chain Positions

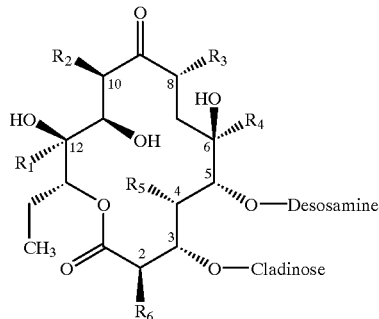

| $R_1$ | $R_2$ | $R_3$ | $R_4$ | $R_5$ | $R_6$ | Name |
|---|---|---|---|---|---|---|
| Me | Me | Me | Et | Me | Me | 6-Desmethyl-6-ethylerythromycin A |
| Me | Me | Me | Me | H | Me | 4-Desmethylerythromycin A |
| Me | Me | Me | Me | Et | Me | 4-Desmethyl-4-ethylerythromycin A |
| Me | Me | Me | Me | Me | H | 2-Desmethylerythromycin A |
| Me | Me | Me | Me | Me | Et | 2-Desmethyl-2-ethylerythromycin A |
| B. Two Changes | | | | | | |
| H | Me | Me | Me | Me | Et | 2,12-Didesmethyl-2-ethylerythromycin A |
| H | Me | Me | Me | Et | Me | 4,12-Didesmethyl-4-ethylerythromycin A |
| H | Me | Me | Et | Me | Me | 6,12-Didesmethyl-6-ethylerythromycin A |
| H | Me | Et | Me | Me | Me | 8,12-Didesmethyl-8-ethylerythromycin A |
| H | Et | Me | Me | ME | Me | 10,12-Didesmethyl-10-ethylerythromycin A |
| H | Me | Me | Me | Me | H | 2,12-Didesmethylerythromycin A |
| H | Me | Me | Me | H | Me | 4,12-Didesmethylerythromycin A |
| H | Me | Me | H | Me | Me | 6,12-Didesmethylerythromycin A |
| H | Me | H | Me | Me | Me | 8,12-Didesmethylerythromycin A |
| H | H | Me | Me | Me | Me | 10,12-Didesmethylerythromycin A |
| Me | H | Me | Me | Me | Et | 2,10-Didesmethyl-2-ethylerythromycin A |
| Me | H | Me | Me | Et | Me | 4,10-Didesmethyl-4-ethylerythromycin A |
| Me | H | Me | Et | Me | Me | 6,10-Didesmethyl-6-ethylerythromycin A |
| Me | H | Et | Me | Me | Me | 8,10-Didesmethyl-8-ethylerythromycin A |
| Me | H | Me | Me | Me | H | 2,10-Didesmethylerythromycin A |
| Me | H | Me | Me | H | Me | 4,10-Didesmethylerythromycin A |
| Me | H | Me | H | Me | Me | 6,10-Didesmethylerythromycin A |
| Me | H | H | Me | Me | Me | 8,10-Didesmethylerythromycin A |
| Me | Me | H | Me | Me | Et | 2,8-Didesmethyl-2-ethylerythromycin A |
| Me | Me | H | Me | Et | Me | 4,8-Didesmethyl-4-ethylerythromycin A |
| Me | Me | H | Et | Me | Me | 6,8-Didesmethyl-6-ethylerythromycin A |
| Me | Me | H | Me | Me | H | 2,8-Didesmethylerythromycin A |
| Me | Me | H | Me | H | Me | 4,8-Didesmethylerythromycin A |
| Me | Me | H | H | Me | Me | 6,8-Didesmethylerythromycin A |
| Me | Me | Me | H | Me | Et | 2,6-Didesmethyl-2-ethylerythromycin A |
| Me | Me | Me | H | Et | Me | 4,6-Didesmethyl-4-ethylerythromycin A |
| Me | Me | Me | H | Me | H | 2,6-Didesmethylerythromycin A |
| Me | Me | Me | H | H | Me | 4,6-Didesmethylerythromycin A |
| Me | Me | Me | Me | H | Et | 2,4,-Didesmethyl-2-ethylerythromycin A |
| Me | Me | Me | Me | H | H | 2,4,-Didesmethylerythromycin A |
| Et | Me | Me | Me | Me | Et | 2,12-Didesmethyl-2,12-diethylerythromycin A |
| Et | Me | Me | Me | Et | Me | 4,12-Didesmethyl-4,12-diethylerythromycin A |
| Et | Me | Me | Et | Me | Me | 6,12-Didesmethyl-6,12-diethylerythromycin A |
| Et | Me | Et | Me | Me | Me | 8,12-Didesmethyl-8,12-diethylerythromycin A |
| Et | Et | Me | Me | Me | Me | 10,12-Didesmethyl-10,12-diethylerythromycin A |
| Et | Me | Me | Me | Me | H | 2,12-Didesmethyl-12-ethylerythromycin A |
| Et | Me | Me | Me | H | Me | 4,12-Didesmethyl-12-ethylerythromycin A |
| Et | Me | Me | H | Me | Me | 6,12-Didesmethyl-12-ethylerythromycin A |
| Et | Me | H | Me | Me | Me | 8,12-Didesmethyl-12-ethylerythromycin A |
| Et | H | Me | Me | Me | Me | 10,12-Didesmethyl-12-ethylerythromycin A |
| Me | Et | Me | Me | Me | Et | 2,10-Didesmethyl-2,10-diethylerythromycin A |
| Me | Et | Me | Me | Et | Me | 4,10-Didesmethyl-4,10-diethylerythromycin A |
| Me | Et | Me | Et | Me | Me | 6,10-Didesmethyl-6,10-diethylerythromycin A |
| Me | Et | Et | Me | Me | Me | 8,10-Didesmethyl-8,10-diethylerythromycin A |
| Me | Et | Me | Me | Me | H | 2,10-Didesmethyl-10-ethylerythromycin A |
| Me | Et | Me | Me | H | Me | 4,10-Didesmethyl-10-ethylerythromycin A |
| Me | Et | Me | H | Me | Me | 6,10-Didesmethyl-10-ethylerythromycin A |
| Me | Et | H | Me | Me | Me | 8,10-Didesmethyl-10-ethylerythromycin A |
| Me | Me | Et | Me | Me | Et | 2,8-Didesmethyl-2,8-diethylerythromycin A |
| Me | Me | Et | Me | Et | Me | 4,8-Didesmethyl-4,8-diethylerythromycin A |
| Me | Me | Et | Et | Me | Me | 6,8-Didesmethyl-6,8-diethylerythromycin A |

TABLE 1-continued

Structures from Changes at Side Chain Positions

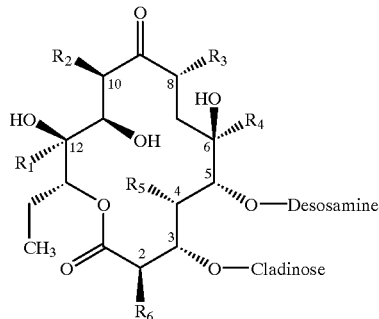

| $R_1$ | $R_2$ | $R_3$ | $R_4$ | $R_5$ | $R_6$ | Name |
|---|---|---|---|---|---|---|
| Me | Me | Et | Me | Me | H | 2,8-Didesmethyl-8-ethylerythromycin A |
| Me | Me | Et | Me | H | Me | 4,8-Didesmethyl-8-ethylerythromycin |
| Me | Me | Et | H | Me | Me | 6,8-Didesmethyl-8-ethylerythromycin |
| Me | Me | Me | Et | Me | Et | 2,6-Didesmethyl-2,6-diethylerythromycin A |
| Me | Me | Me | Et | Et | Me | 4,6-Didesmethyl-4,6-diethylerythromycin A |
| Me | Me | Me | Et | Me | H | 2,6-Didesmethyl-6-ethylerythromycin A |
| Me | Me | Me | Et | H | Me | 4,6-Didesmethyl-6-ethylerythromycin |
| Me | Me | Me | Me | Et | Et | 2,4-Didesmethyl-2,4-diethylerythromycin A |
| Me | Me | Me | Me | Et | H | 2,4-Didesmethyl-4-ethylerythromycin A |
| | | | | | | C. Three Changes |
| H | H | Me | Me | Me | Et | 2,10,12-Tridesmethyl-2-Ethylerythromycin A |
| H | H | Me | Me | Me | H | 2,10,12-Tridesmethylerythromycin A |
| H | H | Me | Me | Et | Me | 4,10,12-Tridesmethyl-4-Ethylerythromycin A |
| H | H | Me | Me | H | Me | 4,10,12-Tridesmethylerythromycin A |
| H | H | Me | Et | Me | Me | 6,10,12-Tridesmethyl-6-Ethylerythromycin A |
| H | H | Me | H | Me | Me | 6,10,12-Tridesmethylerythromycin A |
| H | H | Et | Me | Me | Me | 8,10,12-Tridesmethyl-8-ethylerythromycin A |
| H | H | H | Me | Me | Me | 8,10,12-Tridesmethylerythromycin A |
| Et | H | Me | Me | Me | Et | 2,10,12-Tridesmethyl-2,12,-diethylerythromycin A |
| Et | H | Me | Me | Me | H | 2,10,12-Tridesmethyl-12-ethylerythromycin A |
| Et | H | Me | Me | Et | Me | 4,10,12-Tridesmethyl-4,12-diethylerythromycin A |
| Et | H | Me | Me | H | Me | 4,10,12-Tridesmethyl-12-ethylerythromycin A |
| Et | H | Me | Et | Me | Me | 6,10,12-Tridesmethyl-6,12-diethylerythromycin A |
| Et | H | Me | H | Me | Me | 6,10,12-Tridesmethyl-12-ethylerythromycin A |
| Et | H | Et | Me | Me | Me | 8,10,12-Tridesmethyl-8,12-diethylerythromycin A |
| Et | H | H | Me | Me | Me | 8,10,12-Tridesmethyl-12-ethylerythromycin A |
| H | Et | Me | Me | Me | Et | 2,10,12-Tridesmethyl-2,10-diethylerythromycin A |
| H | Et | Me | Me | Me | H | 2,10,12-Tridesmethyl-10-ethylerythromycin A |
| H | Et | Me | Me | Et | Me | 4,10,12-Tridesmethyl-4,10-diethylerythromycin A |
| H | Et | Me | Me | H | Me | 4,10,12-Tridesmethyl-10-ethylerythromycin A |
| H | Et | Me | Et | Me | Me | 6,10,12-Tridesmethyl-6,10-diethylerythromycin A |
| H | Et | Me | H | Me | Me | 6,10,12-Tridesmethyl-10-ethylerythromycin A |
| H | Et | Et | Me | Me | Me | 8,10,12-Tridesmethyl-8,10-diethylerythromycin A |
| H | Et | H | Me | Me | Me | 8,10,12-Tridesmethyl-10-ethylerythromycin A |
| Et | Et | Me | Me | Me | Et | 2,10,12-Tridesmethyl-2,10,12-triethylerythromycin A |
| Et | Et | Me | Me | Me | H | 2,10,12-Tridesmethyl-10,12-diethylerythromycin A |
| Et | Et | Me | Me | Et | Me | 4,10,12-Tridesmethyl-4,10,12-triethylerythromycin A |
| Et | Et | Me | Me | H | Me | 4,10,12-Tridesmethyl-10,12,-diethylerythromycin A |
| Et | Et | Me | Et | Me | Me | 6,10,12-Tridesmethyl-6,10,12-triethylerythromycin A |
| Et | Et | Me | H | Me | Me | 6,10,12-Tridesmethyl-10,12-diethylerythromycin A |
| Et | Et | Et | Me | Me | Me | 8,10,12-Tridesmethyl-8,10,12-triethylerythromycin A |
| Et | Et | H | Me | Me | Me | 8,10,12-Tridesmethyl-10,12-diethylerythromycin A |
| H | Me | H | Me | Me | Et | 2,8,12-Tridesmethyl-2-ethylerythromycin A |
| H | Me | H | Me | Me | H | 2,8,12-Tridesmethylerythromycin A |
| H | Me | H | Me | Et | Me | 4,8,12-Tridesmethyl-4-ethylerythromycin A |
| H | Me | H | Me | H | Me | 4,8,12-Tridesmethylerythromycin A |
| H | Me | H | Et | Me | Me | 6,8,12-Tridesmethyl-6-ethylerythromycin A |
| H | Me | H | H | Me | Me | 6,8,12-Tridesmethylerythromycin A |
| Et | Me | H | Me | Me | Et | 2,8,12-Tridesmethyl-2,12-diethylerythromycin A |
| Et | Me | H | Me | Me | H | 2,8,12-Tridesmethyl-12-ethylerythromycin A |
| Et | Me | H | Me | Et | Me | 4,8,12-Tridesmethyl-4,12-diethylerythromycin A |
| Et | Me | H | Me | H | Me | 4,8,12-Tridesmethyl-12-ethylerythromycin A |
| Et | Me | H | Et | Me | Me | 6,8,12-Tridesmethyl-6,12-diethylerythromycin A |
| Et | Me | H | H | Me | Me | 6,8,12-Tridesmethyl-12-ethylerythromycin A |
| H | Me | Et | Me | Me | Et | 2,8,12-Tridesmethyl-2,8-diethylerythromycin A |
| H | Me | Et | Me | Me | H | 2,8,12-Tridesmethyl-8-ethylerythromycin A |
| H | Me | Et | Me | Et | Me | 4,8,12-Tridesmethyl-4,8-diethylerythromycin A |

TABLE 1-continued

Structures from Changes at Side Chain Positions

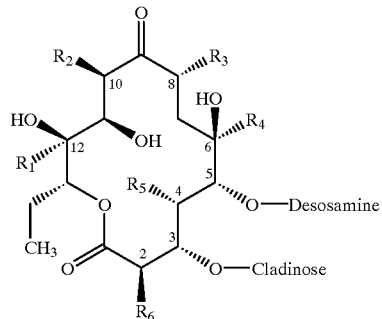

| $R_1$ | $R_2$ | $R_3$ | $R_4$ | $R_5$ | $R_6$ | Name |
|---|---|---|---|---|---|---|
| H | Me | Et | Me | H | Me | 4,8,12-Tridesmethyl-8-ethylerythromycin A |
| H | Me | Et | Et | Me | Me | 6,8,12-Tridesmethyl-6,8-diethylerythromycin A |
| H | Me | Et | H | Me | Me | 6,8,12-Tridesmethyl-8-ethylerythromycin A |
| Et | Me | Et | Me | Me | Et | 2,8,12-Tridesmethyl-2,8,12-triethylerythromycin A |
| Et | Me | Et | Me | Me | H | 2,8,12-Tridesmethyl-8,12-diethylerythromycin A |
| Et | Me | Et | Me | Et | Me | 4,8,12-Tridesmethyl-4,8,12-triethylerythromycin A |
| Et | Me | Et | Me | H | Me | 4,8,12-Tridesmethyl-8,12-diethylerythromycin A |
| Et | Me | Et | Et | Me | Me | 6,8,12-Tridesmethyl-6,8,12-triethylerythromycin A |
| Et | Me | Et | H | Me | Me | 6,8,12-Tridesmethyl-8,12-diethylerythromycin A |
| H | Me | Me | H | Me | Et | 2,6,12-Tridesmethyl-2-ethylerythromycin A |
| H | Me | Me | H | Me | H | 2,6,12-Tridesmethylerythromycin A |
| H | Me | Me | H | Et | Me | 4,6,12-Tridesmethyl-4-ethylerythromycin A |
| H | Me | Me | H | H | Me | 4,6,12-Tridesmethylerythromycin A |
| Et | Me | Me | H | Me | Et | 2,6,12-Tridesmethyl-2,12-diethylerythromycin A |
| Et | Me | Me | H | Me | H | 2,6,12-Tridesmethyl-12-ethylerythromycin A |
| Et | Me | Me | H | Et | Me | 4,6,12-Tridesmethyl-4,12-diethylerythromycin A |
| Et | Me | Me | H | H | Me | 4,6,12-Tridesmethyl-12-ethylerythromycin A |
| H | Me | Me | Et | Me | Et | 2,6,12-Tridesmethyl-2,6-diethylerythromycin A |
| H | Me | Me | Et | Me | H | 2,6,12-Tridesmethyl-6-ethylerythromycin A |
| H | Me | Me | Et | Et | Me | 4,6,12-Tridesmethyl-4,6-diethylerythromycin A |
| H | Me | Me | Et | H | Me | 4,6,12-Tridesmethyl-6-ethylerythromycin A |
| Et | Me | Me | Et | Me | Et | 2,6,12-Tridesmethyl-2,6,12-triethylerythromycin A |
| Et | Me | Me | Et | Me | H | 2,6,12-Tridesmethyl-6,12-diethylerythromycin A |
| Et | Me | Me | Et | Et | Me | 4,6,12-Tridesmethyl-4,6,12-triethylerythromycin A |
| Et | Me | Me | Et | H | Me | 4,6,12-Tridesmethyl-6,12-diethylerythromycin A |
| H | Me | Me | Me | H | Et | 2,4,12-Tridesmethyl-2-ethylerythromycin A |
| H | Me | Me | Me | H | H | 2,4,12-Tridesmethylerythromycin A |
| Et | Me | Me | Me | H | Et | 2,4,12-Tridesmethyl-2,12-diethylerythromycin A |
| Et | Me | Me | Me | H | H | 2,4,12-Tridesmethyl-12-ethylerythromycin A |
| H | Me | Me | Me | Et | Et | 2,4,12-Tridesmethyl-2,4-diethylerythromycin A |
| H | Me | Me | Me | Et | H | 2,4,12-Tridesmethyl-4-ethylerythromycin A |
| Et | Me | Me | Me | Et | Et | 2,4,12-Tridesmethyl-2,4,12-triethylerythromycin A |
| Et | Me | Me | Me | Et | H | 2,4,12-Tridesmethyl-2,12-diethylerythromycin A |
| Me | H | H | Me | Me | Et | 2,8,10-Tridesmethyl-2-ethylerythromycin A |
| Me | H | H | Me | Me | H | 2,8,10-Tridesmethylerythromycin A |
| Me | H | H | Me | Et | Me | 4,8,10-Tridesmethyl-4-ethylerythromycin A |
| Me | H | H | Me | H | Me | 4,8,10-Tridesmethylerythromycin A |
| Me | H | H | Et | Me | Me | 6,8,10-Tridesmethyl-6-ethylerythromycin A |
| Me | H | H | H | Me | Me | 6,8,10-Tridesmethylerythromycin A |
| Me | Et | H | Me | Me | Et | 2,8,10-Tridesmethyl-2,10-diethylerythromycin A |
| Me | Et | H | Me | Me | H | 2,8,10-Tridesmethyl-10-ethylerythromycin A |
| Me | Et | H | Me | Et | Me | 4,8,10-Tridesmethyl-4,10-diethylerythromycin A |
| Me | Et | H | Me | H | Me | 4,8,10-Tridesmethyl-10-ethylerythromycin A |
| Me | Et | H | Et | Me | Me | 6,8,10-Tridesmethyl-6,10-diethylerythromycin A |
| Me | Et | H | H | Me | Me | 6,8,10-Tridesmethyl-10-ethylerythromycin A |
| Me | H | Et | Me | Me | Et | 2,8,10-Tridesmethyl-2,8-diethylerythromycin A |
| Me | H | Et | Me | Me | H | 2,8,10-Tridesmethyl-8-ethylerythromycin A |
| Me | H | Et | Me | Et | Me | 4,8,10-Tridesmethyl-4,8-diethylerythromycin A |
| Me | H | Et | Me | H | Me | 4,8,10-Tridesmethyl-8-ethylerythromycin A |
| Me | H | Et | Et | Me | Me | 6,8,10-Tridesmethyl-6,8-diethylerythromycin A |
| Me | H | Et | H | Me | Me | 6,8,10-Tridesmethyl-8-ethylerythromycin A |
| Me | Et | Et | Me | Me | Et | 2,8,10-Tridesmethyl-2,8,10-triethylerythromycin A |
| Me | Et | Et | Me | Me | H | 2,8,10-Tridesmethyl-8,10-diethylerythromycin A |
| Me | Et | Et | Me | Et | Me | 4,8,10-Tridesmethyl-4,8,10-triethylerythromycin A |
| Me | Et | Et | Me | H | Me | 4,8,10-Tridesmethyl-8-10-diethylerythromycin A |
| Me | Et | Et | Et | Me | Me | 6,8,10-Tridesmethyl-6,8,10-triethylerythromycin A |
| Me | Et | Et | H | Me | Me | 6,8,10-Tridesmethyl-8,10-diethylerythromycin A |
| Me | H | Me | H | Me | Et | 2,6,10-Tridesmethyl-2-ethylerythromycin A |

TABLE 1-continued

Structures from Changes at Side Chain Positions

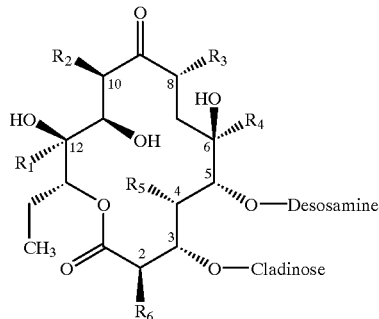

| $R_1$ | $R_2$ | $R_3$ | $R_4$ | $R_5$ | $R_6$ | Name |
|---|---|---|---|---|---|---|
| Me | H | Me | H | Me | H | 2,6,10-Tridesmethylerythromycin A |
| Me | H | Me | H | Et | Me | 4,6,10-Tridesmethyl-4-ethylerythromycin A |
| Me | H | Me | H | H | Me | 4,6,10-Tridesmethylerythromycin A |
| Me | Et | Me | H | Me | Et | 2,6,10-Tridesmethyl-2,1--diethylerythromycin A |
| Me | Et | Me | H | Me | H | 2,6,10-Tridesmethyl-10-ethylerythromycin A |
| Me | Et | Me | H | Et | Me | 4,6,10-Tridesmethyl-4,10-diethylerythromycin A |
| Me | Et | Me | H | H | Me | 4,6,10-Tridesmethyl-10-ethylerythromycin A |
| Me | H | Me | Et | Me | Et | 2,6,10-Tridesmethyl-2,6-diethylerythromcin A |
| Me | H | Me | Et | Me | H | 2,6,10-Tridesmethyl-6-ethylerythromycin A |
| Me | H | Me | Et | Et | Me | 4,6,10-Tridesmethyl-4,6,diethylerythromycin A |
| Me | H | Me | Et | H | Me | 4,6,10-Tridesmethyl-6-ethylerythromycin A |
| Me | Et | Me | Et | Me | Et | 2,6,10-Tridesmethyl-2,6,10-triethylerythromycin A |
| Me | Et | Me | Et | Me | H | 2,6,10-Tridesmethyl-6,10-diethylerythromycin A |
| Me | Et | Me | Et | Et | Me | 4,6,10-Tridesmethyl-4,6,10-triethylerythromycin A |
| Me | Et | Me | Et | H | Me | 4,6,10-Tridesmethyl-6,10-diethylerythromycin A |
| Me | H | Me | Me | H | Et | 2,4,10-Tridesmethyl-2-ethylerythromycin A |
| Me | H | Me | Me | H | H | 2,4,10-Tridesmethylerythromycin A |
| Me | Et | Me | Me | H | Et | 2,4,10-Tridesmethyl-2,10-diethylerythromycin A |
| Me | Et | Me | Me | H | H | 2,4,10-Tridesmethyl-10-ethylerythromycin A |
| Me | H | Me | Me | Et | Et | 2,4,10-Tridesmethyl-2,4-diethylerythromycin A |
| Me | H | Me | Me | Et | H | 2,4,10-Tridesmethyl-4-ethylerythromycin A |
| Me | Et | Me | Me | Et | Et | 2,4,10-Tridesmethyl-2,4,10-triethylerythromycin A |
| Me | Et | Me | Me | Et | H | 2,4,10-Tridesmethyl-4,10-diethylerythromycin A |
| Me | Me | H | H | Me | Et | 2,6,8-Tridesmethyl-2-ethylerythromycin A |
| Me | Me | H | H | Me | H | 2,6,8-Tridesmethylerythromycin A |
| Me | Me | H | H | Et | Me | 4,6,8-Tridesmethyl-4-ethylerythromycin A |
| Me | Me | H | H | H | Me | 4,6,8-Tridesmethylerythromycin A |
| Me | Me | Et | H | Me | Et | 2,6,8-Tridesmethyl-2,8-diethylerythromycin A |
| Me | Me | Et | H | Me | H | 2,6,8-Tridesmethyl-8-ethylerythromycin A |
| Me | Me | Et | H | Et | Me | 4,6,8-Tridesmethyl-4,8-diethylerythromycin A |
| Me | Me | Et | H | H | Me | 4,6,8-Tridesmethyl-8-ethylerythromycin A |
| Me | Me | H | Et | Me | Et | 2,6,8-Tridesmethyl-2,6-diethylerythromycin A |
| Me | Me | H | Et | Me | H | 2,6,8-Tridesmethyl-6-ethylerythromycin A |
| Me | Me | H | Et | Et | Me | 4,6,8-Tridesmethyl-4,6-diethylerythromycin A |
| Me | Me | H | Et | H | Me | 4,6,8-Tridesmethyl-6-ethylerythromycin A |
| Me | Me | Et | Et | Me | Et | 2,6,8-Tridesmethyl-2,6,8-triethylerythromycin A |
| Me | Me | Et | Et | Me | H | 2,6,8-Tridesmethyl-6,8-diethylerythromycin A |
| Me | Me | Et | Et | Et | Me | 4,6,8-Tridesmethyl-4,6,8-triethylerythromycin A |
| Me | Me | Et | Et | H | Me | 4,6,8-Tridesmethyl-6,8-triethylerythromycin A |
| Me | Me | H | Me | H | Et | 2,4,8-Tridesmethyl-2-ethylerythromycin A |
| Me | Me | H | Me | H | H | 2,4,8-Tridesmethylerythromycin A |
| Me | Me | Et | Me | H | Et | 2,4,8-Tridesmethyl-2,8-diethylerythromycin A |
| Me | Me | Et | Me | H | H | 2,4,8-Tridesmethyl-8-ethylerythromycin A |
| Me | Me | H | Me | Et | Et | 2,4,8-Tridesmethyl-2,4-diiethylerythromycin A |
| Me | Me | H | Me | Et | H | 2,4,8-Tridesmethyl-4-ethylerythromycin A |
| Me | Me | Et | Me | Et | Et | 2,4,8-Tridesmethyl-2,4,8-triethylerythromycin A |
| Me | Me | Et | Me | Et | H | 2,4,8-Tridesmethyl-4,8-diethylerythromycin A |
| Me | Me | Me | H | H | Et | 2,4,6-Tridesmethyl-2-ethylerythromycin A |
| Me | Me | Me | H | H | H | 2,4,6-Tridesmethylerythromycin A |
| Me | Me | Me | Et | H | Et | 2,4,6-Tridesmethyl-2,6-diethylerythromycin A |
| Me | Me | Me | Et | H | H | 2,4,6-Tridesmethyl-6-ethyl erythromycin A |
| Me | Me | Me | H | Et | Et | 2,4,6-Tridesmethyl-2,4-diethyl erythromycin A |
| Me | Me | Me | H | Et | H | 2,4,6-Tridesmethyl-4-ethyl erythromycin A |
| Me | Me | Me | Et | Et | Et | 2,4,6-Tridesmethyl-2,4,6-triethyl erythromycin A |
| Me | Me | Me | Et | Et | H | 2,4,6-Tridesmethyl-4,6-diethyl erythromycin A |

TABLE 1-continued

Structures from Changes at Side Chain Positions

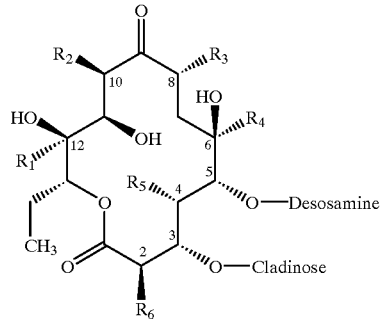

| R₁ | R₂ | R₃ | R₄ | R₅ | R₆ | Name |
|---|---|---|---|---|---|---|
| | | | | | | D. Four Changes |
| H | H | H | Me | Me | Et | 2,8,10,12-Tetradesmethyl-2-ethylerythromycin A |
| H | H | H | Me | Me | H | 2,8,10,12-Tetradesmethylerythromycin A |
| H | H | H | Me | Et | Me | 4,8,10,12-Tetradesmethyl-4-ethylerythromycin A |
| H | H | H | Me | H | Me | 4,8,10,12-Tetradesmethylerythromycin A |
| H | H | H | Et | Me | Me | 6,8,10,12-Tetradesmethyl-6-ethylerythromycin A |
| H | H | H | H | Me | Me | 6,8,10,12-Tetradesmethylerythromycin A |
| H | Et | H | Me | Me | Et | 2,6,10,12-Tetradesmethyl-2,10-diethylerythromycin A |
| H | Et | H | Me | Me | H | 2,6,10,12-Tetradesmethyl-10-ethylerythromycin A |
| H | Et | H | Me | Et | Me | 4,8,10,12-Tetradesmethyl-4,10-diethylerythromycin A |
| H | Et | H | Me | H | Me | 4,8,10,12-Tetradesmethyl-10-ethylerythromycin A |
| H | Et | H | Et | Me | Me | 6,8,10,12-Tetradesmethyl-6,10-diethylerythromycin A |
| H | Et | H | H | Me | Me | 6,8,10,12-Tetradesmethyl-10-ethylerythromycin A |
| H | H | Et | Me | Me | Et | 2,8,10,12-Tetradesmethyl-2,8-diethylerythromycin A |
| H | H | Et | Me | Me | H | 2,8,10,12-Tetradesmethyl-8-ethylerythromycin A |
| H | H | Et | Me | Et | Me | 4,8,10,12-Tetradesmethyl-4,8-diethylerythromycin A |
| H | H | Et | Me | H | Me | 4,8,10,12-Tetradesmethyl-8-ethylerythromycin A |
| H | H | Et | Et | Me | Me | 6,8,10,12-Tetradesmethyl-6,8-diethylerythromycin A |
| H | H | Et | H | Me | Me | 6,8,10,12-Tetradesmethyl-8-ethylerythromycin A |
| H | Et | Et | Me | Me | Et | 2,6,10,12-Tetradesmethyl-2,8,10-triethylerythromycin A |
| H | Et | Et | Me | Me | H | 2,6,10,12-Tetradesmethyl-8,10-diethylerythromycin A |
| H | Et | Et | Me | Et | Me | 4,8,10,12-Tetradesmethyl-4,8,10-triethylerythromycin A |
| H | Et | Et | Me | H | Me | 4,8,10,12-Tetradesmethyl-8,10-diethylerythromycin A |
| H | Et | Et | Et | Me | Me | 6,8,10,12-Tetradesmethyl-6,8,10-triethylerythromycin A |
| H | Et | Et | H | Me | Me | 6,8,10,12-Tetradesmethyl-8,10-diethylerythromycin A |
| Et | H | H | Me | Me | Et | 2,8,10,12-Tetradesmethyl-2,12-diethylerythromycin A |
| Et | H | H | Me | Me | H | 2,8,10,12-Tetradesmethyl-12-ethylerythromycin A |
| Et | H | H | Me | Et | Me | 4,8,10,12-Tetradesmethyl-4,12-diethylerythromycin A |
| Et | H | H | Me | H | Me | 4,8,10,12-Tetradesmethyl-12-ethylerythromycin A |
| Et | H | H | Et | Me | Me | 6,8,10,12-Tetradesmethyl-6,12-diethylerythromycin A |
| Et | H | H | H | Me | Me | 6,8,10,12-Tetradesmethyl-12-ethylerythromycin A |
| Et | Et | H | Me | Me | Et | 2,6,10,12-Tetradesmethyl-2,10,12-triethylerythromycin A |
| Et | Et | H | Me | Me | H | 2,6,10,12-Tetradesmethyl-10,12-diethylerythromycin A |
| Et | Et | H | Me | Et | Me | 4,8,10,12-Tetradesmethyl-4,10,12-triethylerythromycin A |
| Et | Et | H | Me | H | Me | 4,8,10,12-Tetradesmethyl-10,12-diethylerythromycin A |
| Et | Et | H | Et | Me | Me | 6,8,10,12-Tetradesmethyl-6,10,12-triethylerythromycin A |
| Et | Et | H | H | Me | Me | 6,8,10,12-Tetradesmethyl-10,12-diethylerythromycin A |
| Et | H | Et | Me | Me | Et | 2,8,10,12-Tetradesmethyl-2,8,12-triethylerythromycin A |
| Et | H | Et | Me | Me | H | 2,8,10,12-Tetradesmethyl-8,12-diethylerythromycin A |
| Et | H | Et | Me | Et | Me | 4,8,10,12-Tetradesmethyl-4,8,12-triethylerythromycin A |
| Et | H | Et | Me | H | Me | 4,8,10,12-Tetradesmethyl-8,12-diethylerythromycin A |
| Et | H | Et | Et | Me | Me | 6,8,10,12-Tetradesmethyl-6,8,12-triethylerythromycin A |
| Et | H | Et | H | Me | Me | 6,8,10,12-Tetradesmethyl-8,12-diethylerythromycin A |
| Et | Et | Et | Me | Me | Et | 2,6,10,12-Tetradesmethyl-2,8,10,12-tetraethylerythromycin A |
| Et | Et | Et | Me | Me | H | 2,6,10,12-Tetradesmethyl-8,10,12-triethylerythromycin A |
| Et | Et | Et | Me | Et | Me | 4,8,10,12-Tetradesmethyl-4,8,10,12-tetraethylerythromycin A |
| Et | Et | Et | Me | H | Me | 4,8,10,12-Tetradesmethyl-8,10,12-triethylerythromycin |
| Et | Et | Et | Et | Me | Me | 6,8,10,12-Tetradesmethyl-6,8,10,12-tetraethylerythromycin A |
| Et | Et | Et | H | Me | Me | 6,8,10,12-Tetradesmethyl-8,10,12-triethylerythromycin |
| H | H | Me | H | Me | Et | 2,6,10,12-Tetradesmethyl-2-ethylerythromycin A |
| H | H | Me | H | Me | H | 2,6,10,12-Tetradesmethylerythromycin A |
| H | H | Me | H | Et | Me | 4,6,10,12-Tetradesmethyl-4-ethylerythromycin A |
| H | H | Me | H | H | Me | 4,6,10,12-Tetradesmethylerythromycin A |
| H | Et | Me | H | Me | Et | 2,6,10,12-Tetradesmethyl-2,10-diethylerythromycin A |
| H | Et | Me | H | Me | H | 2,6,10,12-Tetradesmethyl-10-ethylerythromycin A |
| H | Et | Me | H | Et | Me | 4,6,10,12-Tetradesmethyl-4,10-diethylerythromycin A |
| H | Et | Me | H | H | Me | 4,6,10,12-Tetradesmethyl-10-ethylerythromycin A |

TABLE 1-continued

Structures from Changes at Side Chain Positions

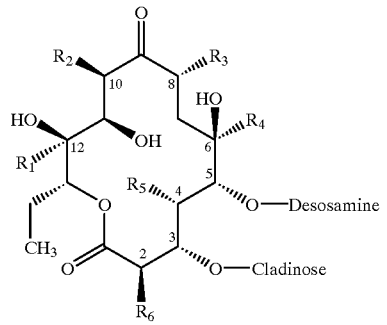

| $R_1$ | $R_2$ | $R_3$ | $R_4$ | $R_5$ | $R_6$ | Name |
|---|---|---|---|---|---|---|
| H | H | Me | Et | Me | Et | 2,6,10,12-Tetradesmethyl-2,6-diethylerythromycin A |
| H | H | Me | Et | Me | H | 2,6,10,12-Tetradesmethyl-6-ethylerythromycin A |
| H | H | Me | Et | Et | Me | 4,6,10,12-Tetradesmethyl-4,6-diethylerythromycin A |
| H | H | Me | Et | H | Me | 4,6,10,12-Tetradesmethyl-6-ethylerythromycin A |
| H | Et | Me | Et | Me | Et | 2,6,10,12-Tetradesmethyl-2,6,10-triethylerythromycin A |
| H | Et | Me | Et | Me | H | 2,6,10,12-Tetradesmethyl-6,10-diethylerythromycin A |
| H | Et | Me | Et | Et | Me | 4,6,10,12-Tetradesmethyhyl-4,6,10-triethylerythromycin A |
| H | Et | Me | Et | H | Me | 4,6,10,12-Tetradesmethyl-6,10-diethylerythromycin A |
| Et | H | Me | H | Me | Et | 2,6,10,12-Tetradesmethyl-2,12-diethylerythromycin A |
| Et | H | Me | H | Me | H | 2,6,10,12-Tetradesmethyl-12-ethylerythromycin A |
| Et | H | Me | H | Et | Me | 4,6,10,12-Tetradesmethyl-4,12-diethylerythromycin A |
| Et | H | Me | H | H | Me | 4,6,10,12-Tetradesmethyl-12-ethylerythromycin A |
| Et | Et | Me | H | Me | Et | 2,6,10,12-Tetradesmethyl-2,10,12-triethylerythromycin A |
| Et | Et | Me | H | Me | H | 2,6,10,12-Tetradesmethyl-10,12-diethylerythromycin A |
| Et | Et | Me | H | Et | Me | 4,6,10,12-Tetradesmethyl-4,10,12-triethylerythromycin A |
| Et | Et | Me | H | H | Me | 4,6,10,12-Tetradesmethyl-10,12-diethylerythromycin A |
| Et | H | Me | Et | Me | Et | 2,6,10,12-Tetradesmethyl-2,6,12-triethylerythromycin A |
| Et | H | Me | Et | Me | H | 2,6,10,12-Tetradesmethyl-6,12--diethylerythromycin A |
| Et | H | Me | Et | Et | Me | 4,6,10,12-Tetradesmethyl-4,6,12-triethylerythromycin A |
| Et | H | Me | Et | H | Me | 4,6,10,12-Tetradesmethyl-6,12--diethylerythromycin A |
| Et | Et | Me | Et | Me | Et | 2,6,10,12-Tetradesmethyl-2,6,10,12-tetraethylerythromycin A |
| Et | Et | Me | Et | Me | H | 2,6,10,12-Tetradesmethyl-6,10,12-triethylerythromycin A |
| Et | Et | Me | Et | Et | Me | 4,6,10,12-Tetradesmethyl-4,6,10,12-tetraethylerythromycin A |
| Et | Et | Me | Et | H | Me | 4,6,10,12-Tetradesmethyl-6,10,12-triethylerythromycin A |
| H | H | Me | Me | H | Et | 2,4,10,12-Tetradesmethyl-2-ethylerythroinycin A |
| H | H | Me | Me | H | H | 2,4,10,12-Tetradesmethylerythromycin A |
| H | Et | Me | Me | H | Et | 2,4,10,12-Tetradesmethyl-2,10-diethylerythromycin A |
| H | Et | Me | Me | H | H | 2,4,10,12-Tetradesmethyl-10-ethylerythromycin A |
| H | H | Me | Me | Et | Et | 2,4,10,12-Tetradesmethyl-2,4-diethylerythromycin A |
| H | H | Me | Me | Et | H | 2,4,10,12-Tetradesmethyl-4-ethylerythromycin A |
| H | Et | Me | Me | Et | Et | 2,4,10,12-Tetradesmethyl-2,4,10-triethylerythromycin A |
| H | Et | Me | Me | Et | H | 2,4,10,12-Tetradesmethyl-4,10-diethylerythromycin A |
| Et | H | Me | Me | H | Et | 2,4,10,12-Tetradesmethyl-2,12-diethylerythromycin A |
| Et | H | Me | Me | H | H | 2,4,10,12-Tetradesmethyl-12-ethylerythromycin A |
| Et | Et | Me | Me | H | Et | 2,4,10,12-Tetradesmethyl-2,10,12-triethylerythromycin A |
| Et | Et | Me | Me | H | H | 2,4,10,12-Tetradesmethyl-10,12-diethylerythromycin A |
| Et | H | Me | Me | Et | Et | 2,4,10,12-Tetradesmethyl-2,4,12-triethylerythromycin A |
| Et | H | Me | Me | Et | H | 2,4,10,12-Tetradesmethyl-4,12-diethylerythromycin A |
| Et | Et | Me | Me | Et | Et | 2,4,10,12-Tetradesmethyl-2,4,10,12-tetraethylerythromycin A |
| Et | Et | Me | Me | Et | H | 2,4,10,12-Tetradesmethyl-4,10,12-triethylerythromycin A |
| H | Me | H | H | Me | Et | 2,6,8,12-Tetradesmethyl-2-ethylerythromycin A |
| H | Me | H | H | Me | H | 2,6,8,12-Tetradesmethylerythromycin A |
| H | Me | H | H | Et | Me | 4,6,8,12-Tetradesmethyl-4--ethylerythromycin A |
| H | Me | H | H | H | Me | 4,6,8,12-Tetradesmethylerythromycin A |
| H | Me | Et | H | Me | Et | 2,6,8,12-Tetradesmethyl-2,8-diethylerythromycin A |
| H | Me | Et | H | Me | H | 2,6,8,12-Tetradesmethyl-8--ethylerythromycin A |
| H | Me | Et | H | Et | Me | 4,6,8,12-Tetradesmethyl-4,,8-diethylerythromycin A |
| H | Me | Et | H | H | Me | 4,6,8,12-Tetradesmethyl-8-ethylerythromycin A |
| H | Me | H | Et | Me | Et | 2,6,8,12-Tetradesmethyl-2,6-diethylerythromycin A |
| H | Me | H | Et | Me | H | 2,6,8,12-Tetradesmethyl-6-ethylerythromycin A |
| H | Me | H | Et | Et | Me | 4,6,8,12-Tetradesmethyl-4,6-diethylerythromycin A |
| H | Me | H | Et | H | Me | 4,6,8,12-Tetradesmethyl-6-ethylerythromycin A |
| H | Me | Et | Et | Me | Et | 2,6,8,12-Tetradesmethyl-2,6,8-triethylerythromycin A |
| H | Me | Et | Et | Me | H | 2,6,8,12-Tetradesmethyl-6,8-diethylerythromycin A |
| H | Me | Et | Et | Et | Me | 4,6,8,12-Tetradesmethyl-4,6,8-triethylerythromycin A |
| H | Me | Et | Et | H | Me | 4,6,8,12-Tetradesmethyl-6,8-diethylerythromycin A |
| Et | Me | H | H | Me | Et | 2,6,8,12-Tetradesmethyl-2,12-diethylerythromycin A |
| Et | Me | H | H | Me | H | 2,6,8,12-Tetradesmethyl-12-ethylerythromycin A |

TABLE 1-continued

Structures from Changes at Side Chain Positions

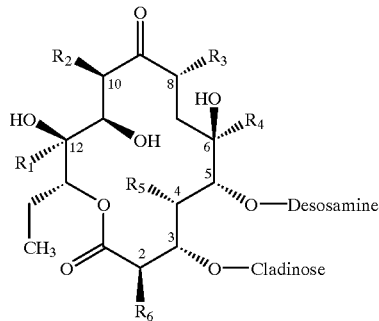

| $R_1$ | $R_2$ | $R_3$ | $R_4$ | $R_5$ | $R_6$ | Name |
|---|---|---|---|---|---|---|
| Et | Me | H | H | Et | Me | 4,6,8,12-Tetradesmethyl-4,12-diethylerythromycin A |
| Et | Me | H | H | H | Me | 4,6,8,12-Tetradesmethyl-12-ethylerythromycin A |
| Et | Me | Et | H | Me | Et | 2,6,8,12-Tetradesmethyl-2,8,12-triethylerythromycin A |
| Et | Me | Et | H | Me | H | 2,6,8,12-Tetradesmethyl-8,12-diethylerythromycin A |
| Et | Me | Et | H | H | Et | 4,6,8,12-Tetradesmethyl-4,8,12-triethylerythromycin A |
| Et | Me | Et | H | H | Me | 4,6,8,12-Tetradesmethyl-8,12-diethylerythromycin A |
| Et | Me | H | Et | Me | Et | 2,6,8,12-Tetradesmethyl-2,6,12-triethylerythromycin A |
| Et | Me | H | Et | Me | H | 2,6,8,12-Tetradesmethyl-6,12-diethylerythromycin A |
| Et | Me | H | Et | H | Et | 4,6,8,12-Tetradesmethyl-4,6,12-triethylerythromycin A |
| Et | Me | H | Et | H | Me | 4,6,8,12-Tetradesmethyl-6,12-diethylerythromycin A |
| Et | Me | Et | Et | Me | Et | 2,6,8,12-Tetradesmethyl-2,6,8,12-tetraethylerythromycin A |
| Et | Me | Et | Et | Me | H | 2,6,8,12-Tetradesmethyl-6,8,12-triethylerythromycin A |
| Et | Me | Et | Et | H | Me | 4,6,8,12-Tetradesmethyl-4,6,8,12-tetraethylerythromycin A |
| Et | Me | Et | Et | H | Me | 4,6,8,12-Tetradesmethyl-6,8,12-triethylerythromycin A |
| H | Me | Me | H | H | Et | 2,4,6,12-Tetradesmethyl-2-ethylerythromycin A |
| H | Me | Me | H | H | H | 2,4,6,12-Tetradesmethylerythromycin A |
| H | Me | Me | Et | H | Et | 2,4,6,12-Tetradesmethyl-2,6-diethylerythromycin A |
| H | Me | Me | Et | H | H | 2,4,6,12-Tetradesmethyl-6-ethylerythromycin A |
| H | Me | Me | H | Et | Et | 2,4,6,12-Tetradesmethyl-2,4-diethylerythromycin A |
| H | Me | Me | H | Et | H | 2,4,6,12-Tetradesmethyl-4-ethylerythromycin A |
| H | Me | Me | Et | Et | Et | 2,4,6,12-Tetradesmethyl-2,4,6-triethylerythromycin A |
| H | Me | Me | Et | Et | H | 2,4,6,12-Tetradesmethyl-4,6-diethylerythromycin A |
| Et | Me | Me | H | H | Et | 2,4,6,12-Tetradesmethyl-2,12-diethylerythromycin A |
| Et | Me | Me | H | H | H | 2,4,6,12-Tetradesmethyl-12-ethylerythromycin A |
| Et | Me | Me | Et | H | Et | 2,4,6,12-Tetradesmethyl-2,6,12-triethylerythromycin A |
| Et | Me | Me | Et | H | H | 2,4,6,12-Tetradesmethyl-6,12-diethylerythromycin A |
| Et | Me | Me | H | Et | Et | 2,4,6,12-Tetradesmethyl-2,4,12-triethylerythromycin A |
| Et | Me | Me | H | Et | H | 2,4,6,12-Tetradesmethyl--diethylerythromycin A |
| Et | Me | Me | Et | Et | Et | 2,4,6,12-Tetradesmethyl-2,4,6,12-tetraethylerythromycin A |
| Et | Me | Me | Et | Et | H | 2,4,6,12-Tetradesmethyl-4,6,12-triethylerythromycin A |
| Me | H | H | H | Me | Et | 2,6,8,10-Tetradesmethyl-2-ethylerythromycin A |
| Me | H | H | H | Me | H | 2,6,8,10-Tetradesmethylerythromycin A |
| Me | H | H | H | Et | Me | 4,6,8,10-Tetradesmethyl-4-ethylerythromycin A |
| Me | H | H | H | H | Me | 4,6,8,10-Tetradesmethylerythromycin A |
| Me | H | Et | H | Me | Et | 2,6,8,10-Tetradesmethyl-2,8-diethylerythromycin A |
| Me | H | Et | H | Me | H | 2,6,8,10-Tetradesmethyl-8-ethylerythromycin A |
| Me | H | Et | H | Et | Me | 4,6,8,10-Tetradesmethyl-4,8-diethylerythromycin A |
| Me | H | Et | H | H | Me | 4,6,8,10-Tetradesmethyl-8-ethylerythromycin A |
| Me | H | H | Et | Me | Et | 2,6,8,10-Tetradesmethyl-2,6-diethylerythromycin A |
| Me | H | H | Et | Me | H | 2,6,8,10-Tetradesmethyl-6-ethylerythromycin A |
| Me | H | H | Et | Et | Me | 4,6,8,10-Tetradesmethyl-4,6-diethylerythromycin A |
| Me | H | H | Et | H | Me | 4,6,8,10-Tetradesmethyl-6-ethylerythromycin A |
| Me | H | Et | Et | Me | Et | 2,6,8,10-Tetradesmethyl-2,6,8-triethylerythromycin A |
| Me | H | Et | Et | Me | H | 2,6,8,10-Tetradesmethyl-6,8-diethylerythromycin A |
| Me | H | Et | Et | Et | Me | 4,6,8,10-Tetradesmethyl-4,6,8-triethylerythromycin A |
| Me | H | Et | Et | H | Me | 4,6,8,10-Tetradesmethyl-6,8-diethylerythromycin A |
| Me | Et | H | H | Me | Et | 2,6,8,10-Tetradesmethyl-2,10-diethylerythromycin A |
| Me | Et | H | H | Me | H | 2,6,8,10-Tetradesmethyl-10-ethylerythromycin A |
| Me | Et | H | H | Et | Me | 4,6,8,10-Tetradesmethyl-4,10-diethylerythromycin A |
| Me | Et | H | H | H | Me | 4,6,8,10-Tetradesmethyl-10-ethylerythromycin A |
| Me | Et | Et | H | Me | Et | 2,6,8,10-Tetradesmethyl-2,8,10-triethylerythromycin A |
| Me | Et | Et | H | Me | H | 2,6,8,10-Tetradesmethyl-8,10-diethylerythromycin A |
| Me | Et | Et | H | Et | Me | 4,6,8,10-Tetradesmethyl-4,8,10-triethylerythromycin A |
| Me | Et | Et | H | H | Me | 4,6,8,10-Tetradesmethyl-8,10-diethylerythromycin A |
| Me | Et | H | Et | Me | Et | 2,6,8,10-Tetradesmethyl-2,6,10-triethylerythromycin A |
| Me | Et | H | Et | Me | H | 2,6,8,10-Tetradesmethyl-6,10-diethylerythromycin A |
| Me | Et | H | Et | Et | Me | 4,6,8,10-Tetradesmethyl-4,6,10-triethylerythromycin A |
| Me | Et | H | Et | H | Me | 4,6,8,10-Tetradesmethyl-6,10-diethylerythromycin A |

TABLE 1-continued

Structures from Changes at Side Chain Positions

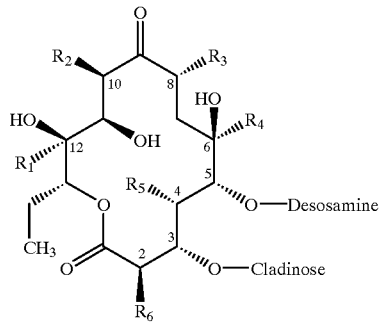

| $R_1$ | $R_2$ | $R_3$ | $R_4$ | $R_5$ | $R_6$ | Name |
|---|---|---|---|---|---|---|
| Me | Et | Et | Et | Me | Et | 2,6,8,10-Tetradesmethyl-2,6,8,10-tetraethylerythromycin A |
| Me | Et | Et | Et | Me | H | 2,6,8,10-Tetradesmethyl-6,8,10-triethylerythromycin A |
| Me | Et | Et | Et | Et | Me | 4,6,8,10-Tetradesmethyl-4,6,8,10-tetraethylerythromycin A |
| Me | Et | Et | Et | H | Me | 4,6,8,10-Tetradesmethyl-6,8,10-triethylerythromycin A |
| Me | H | H | Me | H | Et | 2,4,8,10-Tetradesmethyl-2-ethylerythromycin A |
| Me | H | H | Me | H | H | 2,4,8,10-Tetradesmethylerythromycin A |
| Me | H | Et | Me | H | Et | 2,4,8,10-Tetradesmethyl-2,8-diethylerythromycin A |
| Me | H | Et | Me | H | H | 2,4,8,10-Tetradesmethyl-8-ethylerythromycin A |
| Me | H | H | Me | Et | Et | 2,4,8,10-Tetradesmethyl-2,4-diethylerythromycin A |
| Me | H | H | Me | Et | H | 2,4,8,10-Tetradesmethyl-4-ethylerythromycin A |
| Me | H | Et | Me | Et | Et | 2,4,8,10-Tetradesmethyl-2,4,8-triethylerythromycin A |
| Me | H | Et | Me | Et | H | 2,4,8,10-Tetradesmethyl-4,8-diethylerythromycin A |
| Me | Et | H | Me | H | Et | 2,4,8,10-Tetradesmethyl-2,10-diethyletythromycin A |
| Me | Et | H | Me | H | H | 2,4,8,10-Tetradesmethyl-10-ethylerythromycin A |
| Me | Et | Et | Me | H | Et | 2,4,8,10-Tetradesmethyl-2,8,10-triethylerythromycin A |
| Me | Et | Et | Me | H | H | 2,4,8,10-Tetradesmethyl-8,10-diethylerythromycin A |
| Me | Et | H | Me | Et | Et | 2,4,8,10-Tetradesmethyl-2,4,10-triethylerythromycin A |
| Me | Et | H | Me | Et | H | 2,4,8,10-Tetradesmethyl-2,4,10-diethylerythromycin A |
| Me | Et | Et | Me | Et | Et | 2,4,8,10-Tetradesmethyl-2,4,8,10-tetraethylerythromycin A |
| Me | Et | Et | Me | Et | H | 2,4,8,10-Tetradesmethyl-4,8,10-triethylerythromycin A |
| Me | Me | H | H | H | Et | 2,4,6,8-Tetradesmethyl-2-ethylerythromycin A |
| Me | Me | H | H | H | H | 2,4,6,8-Tetradesmethylerythromycin A |
| Me | Me | H | Et | H | Et | 2,4,6,8-Tetradesmethyl-2,6,-diethylerythromycin A |
| Me | Me | H | Et | H | H | 2,4,6,8-Tetradesmethyl-6-ethylerythromycin A |
| Me | Me | H | H | Et | Et | 2,4,6,8-Tetradesmethyl-2,4-diethylerythromycin A |
| Me | Me | H | H | Et | H | 2,4,6,8-Tetradesmethyl-4-ethylerythromycin A |
| Me | Me | H | Et | Et | Et | 2,4,6,8-Tetradesmethyl-2,4,6-triethylerythromycin A |
| Me | Me | H | Et | Et | H | 2,4,6,8-Tetradesmethyl-4,6-diethylerythromycin A |
| Me | Me | Et | H | H | Et | 2,4,6,8-Tetradesmethyl-2,8-diethylerythromycin A |
| Me | Me | Et | H | H | H | 2,4,6,8-Tetradesmethyl-8-ethylerythromycin A |
| Me | Me | Et | Et | H | Et | 2,4,6,8-Tetradesmethyl-2,6,8-triethylerythromycin A |
| Me | Me | Et | Et | H | H | 2,4,6,8-Tetradesmethyl-6,8-diethylerythromycin A |
| Me | Me | Et | H | Et | Et | 2,4,6,8-Tetradesmethyl-2,4,8-triethylerythromycin A |
| Me | Me | Et | H | Et | H | 2,4,6,8-Tetradesmethyl-4,8-diethylerythromycin A |
| Me | Me | Et | Et | Et | Et | 2,4,6,8-Tetradesmethyl-2,4,6,8-tetraethylerythromycin A |
| Me | Me | Et | Et | Et | H | 2,4,6,8-Tetradesmethyl-4,6,8-triethylerythromycin A |
| | | | | | | E. Five Changes |
| H | H | H | H | H | Me | 4,6,8,10,12-Pentadesmethylerythromycin A |
| Et | H | H | H | H | Me | 4,6,8,10,12-Pentadesmethyl-12-ethylerythromycin A |
| H | Et | H | H | H | Me | 4,6,8,10,12-Pentadesmethyl-10-ethylerythromycin A |
| H | H | Et | H | H | Me | 4,6,8,10,12-Pentadesmethyl-8-ethylerythromycin A |
| H | H | H | Et | H | Me | 4,6,8,10,12-Pentadesmethyl-6-ethylerythromycin A |
| H | H | H | H | Et | Me | 4,6,8,10,12-Pentadesmethyl-4-ethylerythromycin A |
| Et | Et | H | H | H | Me | 4,6,8,10,12-Pentadesmethyl-10,12-diethylerythromycin A |
| Et | H | Et | H | H | Me | 4,6,8,10,12-Pentadesmethyl-8,12-diethylerythromycin A |
| Et | H | H | Et | H | Me | 4,6,8,10,12-Pentadesmethyl-6,12-diethylerythromycin A |
| Et | H | H | H | Et | Me | 4,6,8,10,12-Pentadesmethyl-4,12-diethylerythromycin A |
| H | Et | Et | H | H | Me | 4,6,8,10,12-Pentadesmethyl-8,10-diethylerythromycin A |
| H | Et | H | Et | H | Me | 4,6,8,10,12-Pentadesmethyl-6,10-diethylerythromycin A |
| H | Et | H | H | Et | Me | 4,6,8,10,12-Pentadesmethyl-4,10-diethylerythromycin A |
| H | H | Et | Et | H | Me | 4,6,8,10,12-Pentadesmethyl-6,8-diethylerythromycin A |
| H | H | Et | H | Et | Me | 4,6,8,10,12-Pentadesmethyl-4,8-diethylerythromycin A |
| H | H | H | Et | Et | Me | 4,6,8,10,12-Pentadesmethyl-4,6-diethylerythromycin A |
| Et | Et | Et | H | H | Me | 4,6,8,10,12-Pentadesmethyl-8,10,12-triethylerythromycin A |
| Et | Et | H | Et | H | Me | 4,6,8,10,12-Pentadesmethyl-6,10,12-triethylerythromycin A |
| Et | Et | H | H | Et | Me | 4,6,8,10,12-Pentadesmethyl-4,10,12-triethylerythromycin A |
| Et | H | Et | Et | H | Me | 4,6,8,10,12-Pentadesmethyl-6,8,12-triethylerythromycin A |

TABLE 1-continued

Structures from Changes at Side Chain Positions

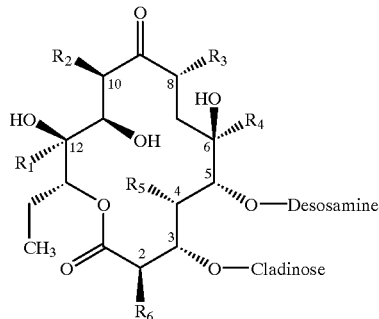

| $R_1$ | $R_2$ | $R_3$ | $R_4$ | $R_5$ | $R_6$ | Name |
|---|---|---|---|---|---|---|
| Et | H | Et | H | Et | Me | 4,6,8,10,12-Pentadesmethyl-4,8,12-triethylerythromycin A |
| Et | H | H | Et | Et | Me | 4,6,8,10,12-Pentadesmethyl-4,6,12-triethylerythromycin A |
| H | Et | Et | Et | H | Me | 4,6,8,10,12-Pentadesmethyl-6,8,10-triethylerythromycin A |
| H | Et | Et | H | Et | Me | 4,6,8,10,12-Pentadesmethyl-4,8,10-triethylerythromycin A |
| H | Et | H | Et | Et | Me | 4,6,8,10,12-Pentadesmethyl-4,6,10-triethylerythromycin A |
| H | H | Et | Et | Et | Me | 4,6,8,10,12-Pentadesmethyl-4,6,8-triethylerythromycin A |
| Et | Et | Et | Et | H | Me | 4,6,8,10,12-Pentadesmethyl-6,8,10,12-tetraethylerythromycin A |
| Et | Et | Et | H | Et | Me | 4,6,8,10,12-Pentadesmethyl-4,8,10,12-tetraethylerythromycin A |
| Et | Et | H | Et | Et | Me | 4,6,8,10,12-Pentadesmethyl-4,6,10,12-tetraethylerythromycin A |
| Et | H | Et | Et | Et | Me | 4,6,8,10,12-Pentadesmethyl-4,6,8,12-tetraethylerythromycin A |
| H | Et | Et | Et | Et | Me | 4,6,8,10,12-Pentadesmethyl-4,6,8,10-tetraethylerythromycin A |
| Et | Et | Et | Et | Et | Me | 4,6,8,10,12-Pentadesmethyl-4,6,8,10,12-pentaethylerythromycin A |
| H | H | H | H | Me | H | 2,6,8,10,12-Pentadesmethylerythromycin A |
| Et | H | H | H | Me | H | 2,6,8,10,12-Pentadesmethyl-12-ethylerythromycin A |
| H | Et | H | H | Me | H | 2,6,8,10,12-Pentadesmethyl-10-ethylerythromycin A |
| H | H | Et | H | Me | H | 2,6,8,10,12-Pentadesmethyl-8-ethylerythromycin A |
| H | H | H | Et | Me | H | 2,6,8,10,12-Pentadesmethyl-6-ethylerythromycin A |
| H | H | H | H | Me | Et | 2,6,8,10,12-Pentadesmethyl-2-ethylerythromycin A |
| Et | Et | H | H | Me | H | 2,6,8,10,12-Pentadesmethyl-10,12-diethylerythromycin A |
| Et | H | Et | H | Me | H | 2,6,8,10,12-Pentadesmethyl-8,12-diethylerythromycin A |
| Et | H | H | Et | Me | H | 2,6,8,10,12-Pentadesmethyl-4,12-diethylerythromycin A |
| Et | H | H | H | Me | Et | 2,6,8,10,12-Pentadesmethyl-2,12-diethylerythromycin A |
| H | Et | Et | H | Me | H | 2,6,8,10,12-Pentadesmethyl-8,10-diethylerythromycin A |
| H | Et | H | Et | Me | H | 2,6,8,10,12-Pentadesmethyl-6,10-diethylerythromycin A |
| H | Et | H | H | Me | Et | 2,6,8,10,12-Pentadesmethyl-2,10-diethylerythromycin A |
| H | H | Et | Et | Me | H | 2,6,8,10,12-Pentadesmethyl-6,8-diethylerythromycin A |
| H | H | Et | H | Me | Et | 2,6,8,10,12-Pentadesmethyl-2,8-diethylerythromycin A |
| H | H | H | Et | Me | Et | 2,6,8,10,12-Pentadesmethyl-2,6-diethylerythromycin A |
| Et | Et | Et | H | Me | H | 2,6,8,10,12-Pentadesmethyl-8,10,12-triethylerythromycin A |
| Et | Et | H | Et | Me | H | 2,6,8,10,12-Pentadesmethyl-6,10,12-triethylerythromycin A |
| Et | Et | H | H | Me | Et | 2,6,8,10,12-Pentadesmethyl-2,10,12-triethylerythromycin A |
| Et | H | Et | Et | Me | H | 2,6,8,10,12-Pentadesmethyl-6,8,12-triethylerythromycin A |
| Et | H | Et | H | Me | Et | 2,6,8,10,12-Pentadesmethyl-2,8,12-triethylerythromycin A |
| Et | H | H | Et | Me | Et | 2,6,8,10,12-Pentadesmethyl-2,6,12-triethylerythromycin A |
| H | Et | Et | Et | Me | H | 2,6,8,10,12-Pentadesmethyl-6,8,10-triethylerythromycin A |
| H | Ft | Et | H | Me | Et | 2,6,8,10,12-Pentadesmethyl-2,8,10-triethylerythromycin A |
| H | Et | H | Et | Me | Et | 2,6,8,10,12-Pentadesmethyl-2,6,10-triethylerythromycin A |
| H | H | Et | Et | Me | Et | 2,6,8,10,12-Pentadesmethyl-2,6,8-triethylerythromycin A |
| Et | Et | Et | Et | Me | H | 2,6,8,10,12-Pentadesmethyl-6,8,10,12-tetraethylerythromycin A |
| Et | Et | Et | H | Me | Et | 2,6,8,10,12-Pentadesmethyl-2,8,10,12-tetraethylerythromycin A |
| Et | Et | H | Et | Me | Et | 2,6,8,10,12-Pentadesmethyl-2,6,10,12-tetraethylerythromycin A |
| Et | H | Et | Et | Me | Et | 2,6,8,10,12-Pentadesmethyl-2,6,,8,12-tetraethylerythromycin A |
| H | Et | Et | Et | Me | Et | 2,6,8,10,12-Pentadesmethyl-2,6,8,10-tetraethylerythromycin A |
| Et | Et | Et | Et | Me | Et | 2,6,8,10,12-Pentadesmethyl-2,6,,8,10,12-pentaethylerythromycin A |
| H | H | H | Me | H | H | 2,4,8,10,12-Pentadesmethylerythromycin A |
| Et | H | H | Me | H | H | 2,4,8,10,12-Pentadesmethyl-12-ethylerythromycin A |
| H | Et | H | Me | H | H | 2,4,8,10,12-Pentadesmethyl-10-ethylerythromycin A |
| H | H | Et | Me | H | H | 2,4,8,10,12-Pentadesmethyl-8-ethylerythromycin A |
| H | H | H | Me | Et | H | 2,4,8,10,12-Pentadesmethyl-4-ethylerythromycin A |
| H | H | H | Me | H | Et | 2,4,8,10,12-Pentadesmethyl-2-ethylerythromycin A |
| Et | Et | H | Me | H | H | 2,4,8,10,12-Pentadesmethyl-10,12-diethylerythromycin A |
| Et | H | Et | Me | H | H | 2,4,8,10,12-Pentadesmethyl-8,12-diethylerythromycin A |
| Et | H | H | Me | Et | H | 2,4,8,10,12-Pentadesmethyl-4,12-diethylerythromycin A |
| Et | H | H | Me | H | Et | 2,4,8,10,12-Pentadesmethyl-2,12-diethylerythromycin A |
| H | Et | Et | Me | H | H | 2,4,8,10,12-Pentadesmethyl-8,10-diethylerythromycin A |
| H | Et | H | Me | Et | H | 2,4,8,10,12-Pentadesmethyl-4,10-diethylerythromycin A |
| H | Et | H | Me | H | Et | 2,4,8,10,12-Pentadesmethyl-2,10-diethylerythromycin A |
| H | H | Et | Me | Et | H | 2,4,8,10,12-Pentadesmethyl-4,8-diethylerythromycin A |

TABLE 1-continued

Structures from Changes at Side Chain Positions

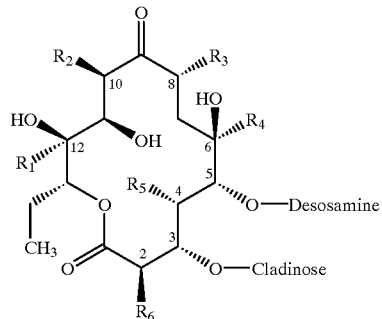

| R₁ | R₂ | R₃ | R₄ | R₅ | R₆ | Name |
|---|---|---|---|---|---|---|
| H | H | Et | Me | H | Et | 2,4,8,10,12-Pentadesmethyl-2,8-diethylerythromycin A |
| H | H | H | Me | Et | Et | 2,4,8,10,12-Pentadesmethyl-2,4-diethylerythromycin A |
| Et | Et | Et | Me | H | H | 2,4,8,10,12-Pentadesmethyl-8,10,12-triethylerythromycin A |
| Et | Et | H | Me | Et | H | 2,4,8,10,12-Pentadesmethyl-4,10,12-triethylerythromycin A |
| Et | Et | H | Me | H | Et | 2,4,8,10,12-Pentadesmethyl-2,10,12-triethylerythromycin A |
| Et | H | Et | Me | Et | H | 2,4,8,10,12-Pentadesmethyl-4,8,12-triethylerythromycin A |
| Et | H | Et | Me | H | Et | 2,4,8,10,12-Pentadesmethyl-2,8,12-triethylerythromycin A |
| Et | H | H | Me | Et | Et | 2,4,8,10,12-Pentadesmethyl-2,4,12-triethylerythromycin A |
| H | Et | Et | Me | Et | H | 2,4,8,10,12-Pentadesmethyl-4,8,10-triethylerythromycin A |
| H | Et | Et | Me | H | Et | 2,4,8,10,12-Pentadesmethyl-2,8,10-triethylerythromycin A |
| H | Et | H | Me | Et | Et | 2,4,8,10,12-Pentadesmethyl-2,4,10-triethylerythromycin A |
| H | H | Et | Me | Et | Et | 2,4,8,10,12-Pentadesmethyl-2,4,8-triethylerythromycin A |
| Et | Et | Et | Me | Et | H | 2,4,8,10,12-Pentadesmethyl-4,8,10,12-tetraethylerythromycin A |
| Et | Et | Et | Me | H | Et | 2,4,8,10,12-Pentadesmethyl-2,8,10,12-tetraethylerythromycin A |
| Et | Et | H | Me | Et | Et | 2,4,8,10,12-Pentadesmethyl-2,4,10,12-tetraethylerythromycin A |
| Et | H | Et | Me | Et | Et | 2,4,8,10,12-Pentadesmethyl-2,4,8,12-tetraethylerythromycin A |
| H | Et | Et | Me | Et | Et | 2,4,8,10,12-Pentadesmethyl-2,4,8,10-tetraethylerythromycin A |
| Et | Et | Et | Me | Et | Et | 2,4,8,10,12-Pentadesmethyl-2,4,8,10,12-pentaethylerytthromycin A |
| H | H | Me | H | H | H | 2,4,6,10,12-Pentadesmethylerythromycin |
| Et | H | Me | H | H | H | 2,4,6,10,12-Pentadesmethyl-12-ethylerythromycin A |
| H | Et | Me | H | H | H | 2,4,6,10,12-Pentadesmethyl-10-ethylerythromycin A |
| H | H | Me | Et | H | H | 2,4,6,10,12-Pentadesmethyl-6-ethylerythromycin A |
| H | H | Me | H | Et | H | 2,4,6,10,12-Pentadesmethyl-4-ethylerythromycin A |
| H | H | Me | H | H | Et | 2,4,6,10,12-Pentadesmethyl-2-ethylerythromycin A |
| Et | Et | Me | H | H | H | 2,4,6,10,12-Pentadesmethyl-10,12-diethylerythromycin A |
| Et | H | Me | Et | H | H | 2,4,6,10,12-Pentadesmethyl-6,12-diethylerythromycin A |
| Et | H | Me | H | Et | H | 2,4,6,10,12-Pentadesmethyl-4,12-diethylerythromycin A |
| Et | H | Me | H | H | Et | 2,4,6,10,12-Pentadesmethyl-2,12-diethylerythromycin A |
| H | Et | Me | Et | H | H | 2,4,6,10,12-Pentadesmethyl-6,10-diethylerythromycin A |
| H | Et | Me | H | Et | H | 2,4,6,10,12-Pentadesmethyl-4,10-diethylerythromycin A |
| H | Et | Me | H | H | Et | 2,4,6,10,12-Pentadesmethyl-2,10-diethylerythromycin A |
| H | H | Me | Et | Et | H | 2,4,6,10,12-Pentadesmethyl-4,6-diethylerythromycin A |
| H | H | Me | Et | H | Et | 2,4,6,10,12-Pentadesmethyl-2,6-diethylerythromycin A |
| H | H | Me | H | Et | Et | 2,4,6,10,12-Pentadesmethyl-2,4-diethylerythromycin A |
| Et | Et | Me | Et | H | H | 2,4,6,10,12-Pentadesmethyl-6,10,12-triethylerythromycin A |
| Et | Et | Me | H | Et | H | 2,4,6,10,12-Pentadesmethyl-4,10,12-triethylerythromycin A |
| Et | Et | Me | H | H | Et | 2,4,6,10,12-Pentadesmethyl-2,10,12-triethylerythromycin A |
| Et | H | Me | Et | Et | H | 2,4,6,10,12-Pentadesmethyl-4,6,12-triethylerythromycin A |
| Et | H | Me | Et | H | Et | 2,4,6,10,12-Pentadesmethyl-2,6,12-triethylerythromycin A |
| Et | H | Me | H | Et | Et | 2,4,6,10,12-Pentadesmethyl-2,4,12-triethylerythromycin A |
| H | Et | Me | Et | Et | H | 2,4,6,10,12-Pentadesmethyl-4,6,10-triethylerythromycin A |
| H | Et | Me | Et | H | Et | 2,4,6,10,12-Pentadesmethyl-2,6,10-triethylerythromycin A |
| H | Et | Me | H | Et | Et | 2,4,6,10,12-Pentadesmethyl-2,4,10-triethylerythromycin A |
| H | H | Me | Et | Et | Et | 2,4,6,10,12-Pentadesmethyl-2,4,6-triethylerythromycin A |
| Et | Et | Me | Et | Et | H | 2,4,6,10,12-Pentadesmethyl-4,6,10,12-tetraethylerythromycin A |
| Et | Et | Me | Et | H | Et | 2,4,6,10,12-Pentadesmethyl-2,6,10,12-tetraethylerythromycin A |
| Et | Et | Me | H | Et | Et | 2,4,6,10,12-Pentadesmethyl-2,4,10,12-tetraethylerythromycin A |
| Et | H | Me | Et | Et | Et | 2,4,6,10,12-Pentadesmethyl-2,4,6,12-tetraethylerythromycin A |
| H | Et | Me | Et | Et | Et | 2,4,6,10,12-Pentadesmethyl-2,4,6,10-tetraethylerythromycin A |
| Et | Et | Me | Et | Et | Et | 2,4,6,10,12-Pentadesmethyl-2,4,6,10,12-pentaethylerythromycin A |
| H | Me | H | H | H | H | 2,4,6,8,12-Pentadesmethylerythromycin A |
| Et | Me | H | H | H | H | 2,4,6,8,12-Pentadesmethyl-12-ethylerythromycin A |
| H | Me | Et | H | H | H | 2,4,6,8,12-Pentadesmethyl-8-ethylerythromycin A |
| H | Me | H | Et | H | H | 2,4,6,8,12-Pentadesmethyl-6-ethylerythromycin A |
| H | Me | H | H | Et | H | 2,4,6,8,12-Pentadesmethyl-4-ethylerythromycin A |
| H | Me | H | H | H | Et | 2,4,6,8,12-Pentadesmethyl-2-ethylerythromycin A |
| Et | Me | Et | H | H | H | 2,4,6,8,12-Pentadesmethyl-8,12-diethylerythromycin A |
| Et | Me | H | Et | H | H | 2,4,6,8,12-Pentadesmethyl-6,12-diethylerythromycin A |

TABLE 1-continued

Structures from Changes at Side Chain Positions

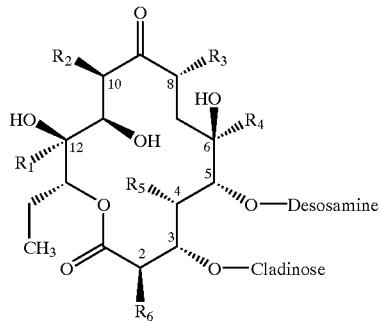

| $R_1$ | $R_2$ | $R_3$ | $R_4$ | $R_5$ | $R_6$ | Name |
|---|---|---|---|---|---|---|
| Et | Me | H | H | Et | H | 2,4,6,8,12-Pentadesmethyl-4,12-diethylerythromycin A |
| Et | Me | H | H | H | Et | 2,4,6,8,12-Pentadesmethyl-2,12-diethylerythromycin A |
| H | Me | Et | Et | H | H | 2,4,6,8,12-Pentadesmethyl-6,8-diethylerythromycin A |
| H | Me | Et | H | Et | H | 2,4,6,8,12-Pentadesmethyl-4,8-diethylerythromycin A |
| H | Me | Et | H | H | Et | 2,4,6,8,12-Pentadesmethyl-2,8-diethylerythromycin A |
| H | Me | H | Et | Et | H | 2,4,6,8,12-Pentadesmethyl-4,6-diethylerythromycin A |
| H | Me | H | Et | H | Et | 2,4,6,8,12-Pentadesmethyl-2,6-diethylerythromycin A |
| H | Me | H | H | Et | Et | 2,4,6,8,12-Pentadesmethyl-2,4-diethylerythromycin A |
| Et | Me | Et | Et | H | H | 2,4,6,8,12-Pentadesmethyl-6,8,12-triethylerythromycin A |
| Et | Me | Et | H | Et | H | 2,4,6,8,12-Pentadesmethyl-4,8,12-triethylerythromycin A |
| Et | Me | Et | H | H | Et | 2,4,6,8,12-Pentadesmethyl-2,8,12-triethylerythromycin A |
| Et | Me | H | Et | Et | H | 2,4,6,8,12-Pentadesmethyl-4,6,12-triethylerythromycin A |
| Et | Me | H | Et | H | Et | 2,4,6,8,12-Pentadesmethyl-2,6,12-triethylerythromycin A |
| Et | Me | H | H | Et | Et | 2,4,6,8,12-Pentadesmethyl-2,4,12-triethylerythromycin A |
| H | Me | Et | Et | Et | H | 2,4,6,8,12-Pentadesmethyl-4,6,8-triethylerythromycin A |
| H | Me | Et | Et | H | Et | 2,4,6,8,12-Pentadesmethyl-2,6,8-triethylerythromycin A |
| H | Me | Et | H | Et | Et | 2,4,6,8,12-Pentadesmethyl-2,4,8-triethylerythromycin A |
| H | Me | H | Et | Et | Et | 2,4,6,8,12-Pentadesmethyl-2,4,6-triethylerythromycin A |
| Et | Me | Et | Et | Et | H | 2,4,6,8,12-Pentadesmethyl-4,6,8-triethylerythromycin A |
| Et | Me | Et | Et | H | Et | 2,4,6,8,12-Pentadesmethyl-2,6,8,12-tetraethylerythromycin A |
| Et | Me | Et | H | Et | Et | 2,4,6,8,12-Pentadesmethyl-2,4,8,12-tetraethylerythromycin A |
| Et | Me | H | Et | Et | Et | 2,4,6,8,12-Pentadesmethyl-2,4,6,12-tetraethylerythromycin A |
| H | Me | Et | Et | Et | Et | 2,4,6,8,12-Pentadesmethyl-2,4,6,8-tetraethylerythromycin A |
| Et | Me | Et | Et | Et | Et | 2,4,6,8,12-Pentadesmethyl-2,4,6,8,12-pentaethylerythromycin A |
| Me | H | H | H | H | H | 2,4,6,8,10-Pentadesmethylerythromycin A |
| Me | Et | H | H | H | H | 2,4,6,8,10-Pentadesmethyl-10-ethylerythromycin A |
| Me | H | Et | H | H | H | 2,4,6,8,10-Pentadesmethyl-8-ethylerythromycin A |
| Me | H | H | Et | H | H | 2,4,6,8,10-Pentadesmethyl-6-ethylerythromycin A |
| Me | H | H | H | Et | H | 2,4,6,8,10-Pentadesmethyl-4-ethylerythromycin A |
| Me | H | H | H | H | Et | 2,4,6,8,10-Pentadesmethyl-2-ethylerythromycin A |
| Me | Et | Et | H | H | H | 2,4,6,8,10-Pentadesmethyl-8,10 diethylerythromycin A |
| Me | Et | H | Et | H | H | 2,4,6,8,10-Pentadesmethyl-6,10 diethylerythromycin A |
| Me | Et | H | H | Et | H | 2,4,6,8,10-Pentadesmethyl-4,10 diethylerythromycin A |
| Me | Et | H | H | H | Et | 2,4,6,8,10-Pentadesmethyl-2,10 diethylerythromycin A |
| Me | H | Et | Et | H | H | 2,4,6,8,10-Pentadesmethyl-6,8-diethylerythromycin A |
| Me | H | Et | H | Et | H | 2,4,6,8,10-Pentadesmethyl-4,8-diethylerythromycin A |
| Me | H | Et | H | H | Et | 2,4,6,8,10-Pentadesmethyl-2,8-diethylerythromycin A |
| Me | H | H | Et | Et | H | 2,4,6,8,10-Pentadesmethyl-4,6-diethylerythromycin A |
| Me | H | H | Et | H | Et | 2,4,6,8,10-Pentadesmethyl-2,6-diethylerythromycin A |
| Me | H | H | H | Et | Et | 2,4,6,8,10-Pentadesmethyl-2,4-diethylerythromycin A |
| Me | Et | Et | Et | H | H | 2,4,6,8,10-Pentadesmethyl-6,8,10-triethylerythromycin A |
| Me | Et | Et | H | Et | H | 2,4,6,8,10-Pentadesmethyl-4,8,10-triethylerythromycin A |
| Me | Et | Et | H | H | Et | 2,4,6,8,10-Pentadesmethyl-2,8,10-triethylerythromycin A |
| Me | Et | H | Et | Et | H | 2,4,6,8,10-Pentadesmethyl-4,6,10-triethylerythromycin A |
| Me | Et | H | Et | H | Et | 2,4,6,8,10-Pentadesmethyl-2,6,10-triethylerythromycin A |
| Me | Et | H | H | Et | Et | 2,4,6,8,10-Pentadesmethyl-2,4,10-triethylerythromycin A |
| Me | H | Et | Et | Et | H | 2,4,6,8,10-Pentadesmethyl-4,6,8-triethylerythromycin A |
| Me | H | Et | Et | H | Et | 2,4,6,8,10-Pentadesmethyl-2,6,8-triethylerythromycin A |
| Me | H | Et | H | Et | Et | 2,4,6,8,10-Pentadesmethyl-2,4,8-triethylerythromycin A |
| Me | H | H | Et | Et | Et | 2,4,6,8,10-Pentadesmethyl-2,4,6-triethylerythromycin A |
| Me | Et | Et | Et | Et | H | 2,4,6,8,10-Pentadesmethyl-4,6,8,10-tetraethylerythromycin A |
| Me | Et | Et | Et | H | Et | 2,4,6,8,10-Pentadesmethyl-2,6,8,10-tetraethylerythromycin A |
| Me | Et | Et | H | Et | Et | 2,4,6,8,10-Pentadesmethyl-2,4,8,10-tetraethylerythromycin A |
| Me | Et | H | Et | Et | Et | 2,4,6,8,10-Pentadesmethyl-2,4,6,10-tetraethylerythromycin A |
| Me | H | Et | Et | Et | Et | 2,4,6,8,10-Pentadesmethyl-2,4,6,8-tetraethylerythromycin A |
| Me | Et | Et | Et | Et | Et | 2,4,6,8,10-Pentadesmethyl-2,4,6,8,10-pentaethylerythromycin A |

TABLE 1-continued

Structures from Changes at Side Chain Positions

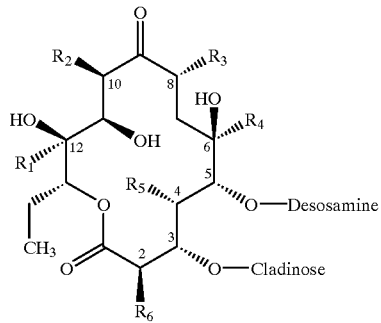

| $R_1$ | $R_2$ | $R_3$ | $R_4$ | $R_5$ | $R_6$ | Name |
|---|---|---|---|---|---|---|
| | | | | | | F. Six Changes |
| H | H | H | H | H | H | 2,4,6,8,10,12-Hexadesmethylerythromycin A |
| Et | H | H | H | H | H | 2,4,6,8,10,12-Hexadesmethyl-12-ethylerythromycin A |
| H | Et | H | H | H | H | 2,4,6,8,10,12-Hexadesmethyl-10-ethylerythromycin A |
| H | H | Et | H | H | H | 2,4,6,8,10,12-Hexadesmethyl-8-ethylerythromycin A |
| H | H | H | Et | H | H | 2,4,6,8,10,12-Hexadesmethyl-6-ethylerythromycin A |
| H | H | H | H | Et | H | 2,4,6,8.10,12-Hexadesmethyl-4-ethylerythromycin A |
| H | H | H | H | H | Et | 2,4,6,8.10,12-Hexadesmethyl-2-ethylerythromycin A |
| Et | Et | H | H | H | H | 2,4,6,8,10,12-Hexadesmethyl-10,12-diethylerythromycin A |
| Et | H | Et | H | H | H | 2,4,6,8,10,12-Hexadesmethyl-8,12-diethylerythromycin A |
| Et | H | H | Et | H | H | 2,4,6,8,10,12-Hexadesmethyl-6,12-diethylerythromycin A |
| Et | H | H | H | Et | H | 2,4,6,8,10,12-Hexadesmethyl-4,12-diethylerythromycin A |
| Et | H | H | H | H | Et | 2,4,6,8,10,12-Hexadesmethyl-2,12-diethylerythromycin A |
| H | Et | Et | H | H | H | 2,4,6,8,10,12-Hexadesmethyl-8,10-diethylerythromycin A |
| H | Et | H | Et | H | H | 2,4,6,8,10,12-Hexadesmethyl-6,10-diethylerythromycin A |
| H | Et | H | H | Et | H | 2,4,6,8,10,12-Hexadesmethyl-4,10-diethylerythromycin A |
| H | Et | H | H | H | Et | 2,4,6,8,10,12-Hexadesmethyl-2,10-diethylerythromycin A |
| H | H | Et | Et | H | H | 2,4,6,8,10,12-Hexadesmethyl-6,8-diethylerythromycin A |
| H | H | Et | H | Et | H | 2,4,6,8,10,12-Hexadesmethyl-4,8-diethylerythromycin A |
| H | H | Et | H | H | Et | 2,4,6,8,10,12-Hexadesmethyl-2,8-diethylerythromycin A |
| H | H | H | Et | Et | H | 2,4,6,8,10,12-Hexadesmethyl-4,6-diethylerythromycin A |
| H | H | H | Et | H | Et | 2,4,6,8,10,12-Hexadesmethyl-2,6-diethylerythromycin A |
| H | H | H | H | Et | Et | 2,4,6,8,10,12-Hexadesmethyl-2,4-diethylerythromycin A |
| Et | Et | Et | H | H | H | 2,4,6,8,10,12-Hexadesmethyl-8,10,12-triethylerythromycin A |
| Et | Et | H | Et | H | H | 2,4,6,8,10,12-Hexadesmethyl-6,10,12-triethylerythromycin A |
| Et | Et | H | H | Et | H | 2,4,6,8,10,12-Hexadesmethyl-4,10,12-triethylerythromycin A |
| Et | Et | H | H | H | Et | 2,4,6,8,10,12-Hexadesmethyl-2,10,12-triethylerythromycin A |
| Et | H | Et | Et | H | H | 2,4,6,8,10,12-Hexadesmethyl-6,8,12-triethylerythromycin A |
| Et | H | Et | H | Et | H | 2,4,6,8,10,12-Hexadesmethyl-4,8,12-triethylerythromycin A |
| Et | H | Et | H | H | Et | 2,4,6,8,10,12-Hexadesmethyl-2,8,12-triethylerythromycin A |
| Et | H | H | Et | Et | H | 2,4,6,8,10,12-Hexadesmethyl-4,6,12-triethylerythromycin A |
| Et | H | H | Et | H | Et | 2,4,6,8,10,12-Hexadesmethyl-2,6,12-triethylerythromycin A |
| Et | H | H | H | Et | Et | 2,4,6,8,10,12-Hexadesmethyl-2,4,12-triethylerythromycin A |
| H | Et | Et | Et | H | H | 2,4,6,8,10,12-Hexadesmethyl-6,8,10-triethylerythromycin A |
| H | Et | Et | H | Et | H | 2,4,6,8,10,12-Hexadesmethyl-4,8,10-triethylerythromycin A |
| H | Et | Et | H | H | Et | 2,4,6,8,10,12-Hexadesmethyl-2,8,10-triethylerythromycin A |
| H | Et | H | Et | Et | H | 2,4,6,8,10,12-Hexadesmethyl-4,6,10-triethylerythromycin A |
| H | Et | H | Et | H | Et | 2,4,6,8,10,12-Hexadesmethyl-2,6,10-triethylerythromycin A |
| H | Et | H | H | Et | Et | 2,4,6,8,10,12-Hexadesmethyl-2,4,10-triethylerythromycin A |
| H | H | Et | Et | Et | H | 2,4,6,8,10,12-Hexadesmethyl-4,6,8-triethylerythromycin A |
| H | H | Et | Et | H | Et | 2,4,6,8,10,12-Hexadesmethyl-2,6,8-triethylerythromycin A |
| H | H | Et | H | Et | Et | 2,4,6,8,10,12-Hexadesmethyl-2,4,8-triethylerythromycin A |
| H | H | H | Et | Et | Et | 2,4,6,8,10,12-Hexadesmethyl-2,4,6-triethylerythromycin A |
| Et | Et | Et | Et | H | H | 2,4,6,8,10,12-Hexadesmethyl-6,8,10,12-tetraethylerythromycin A |
| Et | Et | Et | H | Et | H | 2,4,6,8,10,12-Hexadesmethyl-4,8,10,12-tetraethylerythromycin A |
| Et | Et | Et | H | H | Et | 2,4,6,8,10,12-Hexadesmethyl-2,8,10,12-tetraethylerythromycin A |
| Et | Et | H | Et | Et | H | 2,4,6,8,10,12-Hexadesmethyl-4,6,10,12-tetraethylerythromycin A |
| Et | Et | H | Et | H | Et | 2,4,6,8,10,12-Hexadesmethyl-2,6,10,12-tetraethylerythromycin A |
| Et | Et | H | H | Et | Et | 2,4,6,8,10,12-Hexadesmethyl-2,4,10,12-tetraethylerythromycin A |
| Et | H | Et | Et | Et | H | 2,4,6,8,10,12-Hexadesmethyl-4,6,8,12-tetraethylerythromycin A |
| Et | H | Et | Et | H | Et | 2,4,6,8,10,12-Hexadesmethyl-2,6,8,12-tetraethylerythromycin A |
| Et | H | Et | H | Et | Et | 2,4,6,8,10,12-Hexadesmethyl-2,4,8,12-tetraethylerythromycin A |
| Et | H | H | Et | Et | Et | 2,4,6,8,10,12-Hexadesmethyl-2,4,6,12-tetraethylerythromycin A |
| H | Et | Et | Et | Et | H | 2,4,6,8,10,12-Hexadesmethyl-4,6,8,10-tetraethylerythromycin A |
| H | Et | Et | Et | H | Et | 2,4,6,8,10,12-Hexadesmethyl-2,6,8,10-tetraethylerythromycin A |
| H | Et | Et | H | Et | Et | 2,4,6,8,10,12-Hexadesmethyl-2,4,8,10-tetraethylerythromycin A |
| H | Et | H | Et | Et | Et | 2,4,6,8,10,12-Hexadesmethyl-2,4,6,10-tetraethylerythromycin A |

TABLE 1-continued

Structures from Changes at Side Chain Positions

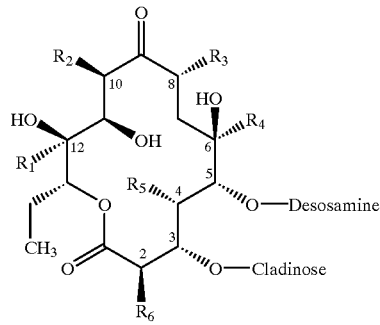

| $R_1$ | $R_2$ | $R_3$ | $R_4$ | $R_5$ | $R_6$ | Name |
|---|---|---|---|---|---|---|
| H  | H  | Et | Et | Et | Et | 2,4,6,8,10,12-Hexadesmethyl-2,4,6,8-tetraethylerythromycin A |
| Et | Et | Et | Et | Et | H  | 2,4,6,8,10,12-Hexadesmethyl-4,6,8,10,12-pentaethylerythromycin A |
| Et | Et | Et | Et | H  | Et | 2,4,6,8,10,12-Hexadesmethyl-2,6,8,10,12-pentaethylerythromycin A |
| Et | Et | Et | H  | Et | Et | 2,4,6,8,10,12-Hexadesmethyl-2,4,8,10,12-pentaethylerythromycin A |
| Et | Et | H  | Et | Et | Et | 2,4,6,8,10,12-Hexadesmethyl-2,4,6,10,12-pentaethylerythromycin A |
| Et | H  | Et | Et | Et | Et | 2,4,6,8,10,12-Hexadesmethyl-2,4,6,,8,12-pentaethylerythromycin A |
| H  | Et | Et | Et | Et | Et | 2,4,6,8,10,12-Hexadesmethyl-2,4,6,8,10-pentaethylerythromycin A |
| Et | Et | Et | Et | Et | Et | 2,4,6,8,10,12-Hexadesmethyl-2,4,6,8,10,12-hexaethylerythromycin A |

Although in the Examples that follow the AT-encoding DNA fragments from *S. hygroscopicuis* ATCC 29253, *S. venezuelae* ATCC 15439, and *S. caelestis* NRRL-2821 were used to replace resident AT-encoding DNA fragments in the eryPKS to yield desmethyl, desmethylethyl, and desmethylhydroxyerythromycins, it is understood that many malonate, ethylmalonate, and hydroxymalonate AT-encoding DNA fragments can be used in place of or in addition to the heterologous malonate, ethylmalonate, and hydroxymalonate-AT DNA fragments described herein to produce the same desmethyl, desmethylethyl, and desmethylhydroxyerythromycin compounds. Examples of DNA fragments encoding malonate-AT domains that can be used in place of or in addition to those specifically described in the Examples below include but are not limited to the DNA fragments encoding AT domains from modules 2, 5, 8, 9, 11, or 12 of the rapamycin PKS genes from *S. hygroscopicus*, the AT domain from module 2 of the PKS responsible the synthesis of methymycin or pikromycin by *S. venezuelae*, the AT domains from modules 3 and 7 of the PKS responsible for the synthesis of tylosin by *S. fradiae*, or the AT domains from modules 1, 2, 3 and 7 of the PKS responsible for the synthesis of spiramycin by *S. ambofaciens*. Examples of DNA fragments encoding ethylmalonate-AT domains that can be used in place of or in addition to those specifically described in the Examples below include but are not limited to the DNA fragments encoding the AT domain from module 5 of the spiramycin PKS genes from *S. ambofaciens*, the AT domain from module 5 of the tylosin PKS genes from *S. fradiae*, and the AT domain from module 5 of the maridomycin PKS genes of *S. hygroscopicus*. Examples of DNA fragments encoding hydroxymalonate-AT domains that can be used in place of or in addition to those specifically described in the Examples below include but are not limited to the DNA fragments encoding the AT domain from module 6 of the spiramycin PKS genes from *S. ambofaciens*, the AT domain from module 6 of the maridomycin PKS genes from *S. hygroscopicus*, and the AT domain from module 6 of the leucomycin PKS genes from *Streptoverticillium kitasatoensis*. Thus the use of any and all DNA fragments encoding malonate, ethylmalonate, and hydroxymalonate-ATs to replace any of the resident DNA fragments encoding methylmalonate-ATs in the eryPKS genes to result in the production of novel derivatives of erythromycin are considered within the scope of the present invention.

Furthermore, those of ordinary skill understand that following the methods described herein for replacement of resident AT-encoding DNA fragments in the eryPKS, the DNA fragment encoding malonate-ATs in *S. hygroscopicus*, *S. venezuelae*, or *S. caelestis*, and ethylmalonate or hydroxymalonate-ATs in *S. caelestis* may be replaced with those AT-encoding DNA fragments from the eryPKS which utilize methylmalonyl CoA as a substrate. As with the eryPKS, all combinations are contemplated, leading to the production of, for example, 13-methylrapamycin, 15-methylrapamycin, 33-methylrapamycin, 13,15-dimethylrapamycin, 13,15,33-trimethylrapamycin, and 10-methylpikromycin.

The methods of the present invention are widely applicable to all erythromycin-producing microorganisms, of which a non-exhaustive list includes Saccharopolyspora species, *Streptomyces griseoplanus*, Nocardia sp., Micromonospora sp., Arthrobacter sp. and *Streptomyces antibioticus*. Of these, *Sac. erythraea* is the most preferred. Other hosts, which normally do not produce erythromycin but into which the erythromycin biosynthesis genes can be introduced by cloning, can also be employed. Such strains include but are not limited to *Streptomyces coelicolor* and *Streptomyces lividans* or *Bacillus subtilis*, as examples. In each of the other erythromycin-producing strains, replacement of the resident AT domains in the erythromycin PKS is conducted by double homologous recombination using cloned eryPKS sequences on both sides of the AT domain to be replaced to effect the switching of the resident AT with a heterologous AT as illustrated in the Examples that follow.

Many other variations of the methods that are illustrated in the Examples that follow will occur to those skilled in the art. For example, whereas the plasmids pUC18, pUC19, pGEM3Zf, and pCS5 were employed in the present invention for the cloning of the LigAT2, venT, rapAT14, NidAT5, or NidAT6-encoding DNA fragments and construction of the integration vectors, other plasmids, phage, or phagemids including but not limited to pBR322, pACYC184, M13mp18, M13mp19, pGEM7Zf and the like can be used in their place to allow the same constructions to be made. Furthermore, many alternative strategies can be followed for the cloning of the heterologous AT-encoding DNA fragments into integration vectors that enable homologous recombination to occur in corresponding regions of the eryPKS. Examples of alternative strategies include the use of longer or shorter fragments of DNA corresponding to either the AT domains or the flanking sequences, using different restriction sites for the cloning of the AT domains or the adjacent flankina sequences, or changing the sequence of a resident AT-encoding DNA fragment so that it expresses a domain which recognizes malonyl CoA as a substrate rather than methylmalonyl CoA. All such variations are within the scope of the present invention. Similarly, employing alternative strategies to introduce DNA into *Sac. erythraea* or other erythromycin-producing hosts for the purpose of effecting gene exchange to result in the production of novel erythromycins, such as conjugation, transduction or electroporation are also included within the scope of the present invention.

Those skilled in the art also understand that erythromycins B, C and D are naturally occurring forms of erythromycin and therefore would be produced as novel derivatives in *Sac. erythraea* by the modifications disclosed herein. Production of these forms may be further enhanced by inactivation of ezyK (Stassi, D. et al. *J. Bacteriology*, 175: 182–189, (1993)) to yield erythromycin B derivatives, eryG (S. F. Haydock et al. *Mol. Gen. Genet.* 230:120–128(1991)) to yield erythromycin C derivatives and eryK and eryG to yield erythromycin D derivatives. Furthermore, in *Sac. erythraea*, 6-deoxy forms of the novel erythromycins A, B, C and D can be generated by inactivation of eryF (J. M. Weber et al. *Science* 252:114–117(1991)) (in addition to those specified above), which encodes the hydroxylase responsible for hydroxylating the C-6 position. In addition, conversion of 6-deoxy forms of the novel erythromycins A, B, C and D to their corresponding erythromycin A, B, C, and D derivatives may be accomplished by cloning additional copies or by employing other means of overexpression of the eryF gene in the production host. Similarly, conversion of novel forms of erythromycins B, C and D to novel forms of erythromycin A may be achieved by expressing or overexpressing eryK and/or eryG in the production host. The methodologies for generating erythromycins B, C and D and 6-deoxyerythromycins A, B, C and D are well known to those of ordinary skill in the art.

Those skilled in the art also understand that erythronolide B and 3-α-mycarosylerythronolide B are naturally occurring intermediates in the biosynthesis of erythromycin and therefore would be produced as novel intermediates in *Sac. erythraea* by the modifications disclosed herein. Production of these forms may be further enhanced by inactivation of any of the eryB genes to yield erythronolide B or eryC genes to yield 3-α-L-mycarosylerythronolide B (Weber et al. *J. Bacteriol.* 172:2372–2383 (1990)) and Haydock et al. *Mol. Gen. Genet.* 230:120–128 (1991)). Furthermore, 6-deoxy forms of these novel intermediates can be generated by inactivation of eryF as described above. The methodologies for generating erythronolide B and 3-α-mycarosylerythronolide B, as well as their 6-deoxy derivatives, are well known to those of ordinary skill in the art.

Bacterial Strains, Plasmid Vectors, and Growth Media

The erythromycin-producing microorganism used to practice the following examples of the invention was *Sac. erythraea* ER720 (J. P. DeWitt, *J. Bacteriol.* 164: 969 (1985)). The host strain for the growth of *E. coli* derived plasmids was DH5α from GIBCO BRL, Gaithersburg, Md.). The *S. hygroscopicus* strain that carries the Lig-PKS cluster is available from the American Type Culture Collection, Bethesda, Md. under the accession number ATCC 29253. The *S. venezuelae* strain that carries the venAT domain described herein is available from the American Type Culture Collection, Bethesda, Md. under the accession number ATCC 15439.

*E. coli* bacteria carrying pUC18/venAT has been deposited at the Agricultural Research Culture Collection (NRRL), 1815 N. University Street, Peoria, Ill. 61604 U.S.A., as of Dec. 23. 1996, under the terms of the Budapest Treaty and will be maintained for a period of thirty (30) years from the date of deposit, or for five (5) years after the last request for the deposit, or for the enforceable period of the U.S. patent, whichever is longer. The deposit and any other deposited material described herein are provided for convenience only, and are not required to practice the present invention in view of the teachings provided herein. The DNA sequence in all of the deposited material is incorporated herein by reference. *E. coli* bacteria carrying pUC18/venAT was accorded NRRL Deposit No B-21652.

Plasmid pUC18 and pUC19 can be obtained from GIBCO BRL. Plasmid pCS5, a multifunctional vector for integrative transformation of *Sac. erythraea* is described in Vara, et al., *J. Bacteriology*, 171:5872–5881 (1989) and is referred to therein as pWHM3. Cosmid pNJ1 is described in Tuan, et al., *Gene*, 90: 21–29 (1990).

*Sac. erythraea* was grown for protoplast formation and routine liquid culture in 50 mL of SGGP medium (Yamamoto, et al., *J. Antibiotic*. 39:1304 (1986)), supplemented with 10 μg of thiostrepton/mL for plasmid selection where appropriate.

Reagents and General Methods

Commercially available reagents were used to make compounds, plasmids and genetic variants of the present invention, including butyric acid, ampicillin, thiostrepton, restriction endonucleases, T4-DNA ligase, and calf intestine alkaline phosphatase. The nucleotide sequence of the eryA genes from *Sac. erythraea* has been deposited in the GenBank database under the accession numbers M63676 and M63677 and are publicly available.

Standard molecular biology procedures (Maniatis et al., supra) were used for the construction and characterization of replacement plasmids. Plasmid DNA was routinely isolated by the alkaline lysis method (H. C. Birnboim and J. Doly, 1979 Nucleic Acids Res. 7: 1513) or with QIAprep Spin Plasmid kit (Qiagen, Inc., Chatsworth, Calif.) according to the manufacturers instructions. Restriction fragments were recovered from 0.8–1% agarose gels with Prep-A-Gene (BioRad). The products of ligation for each step of the plasmid constructions were used to transform the intermediate host, *E. coli* DH5α (GIBCO BRL), which was cultured in the presence of ampicillin to select for host cells carrying recombinant plasmids. Selection for insert DNA with X-gal was used where appropriate. Typically, LB plates contain 30 mL of LB agar (Maniatis et al., supra). Plasmid DNAs were isolated from individual transformants that had been grown in liquid culture and characterized with respect to known restriction sites. DNA sequence determination was by cycle sequencing (fmol DNA Sequencing System. Promega Corp. Madison. Wis.) according to the manufacturer's instructions.

SCM medium consist of 20 g Soytone, 15 g Soluble Starch, 10.5 g MOPS, 1.5 g Yeast Extract and 0.1 g $CaCl_2$ per liter of distilled $H_2O$. SGGP medium is described in Yamamoto, et al., 1986, J. Antibiotic. 39:1304. $P_M$ buffer (per liter) is 200 g sucrose, 0.25 g $K_2SO_4$ in 890 mL $H_2O$, with the addition after sterilization of 100 mL 0.25 M TES, pH 7.2, 2 mL trace elements solution (Hopwood, et al., 1985, Genetic Manipulation of Streptomyces A Laboratory Manual, The John Innes Foundation), 0.08 mL 2.5 M $CaCl_2$, 10 mL 0.5% $KH_2PO_4$, 2 mL 2.5 M $MgCl_2$.

Integrative transformation of Sac. erythraea protoplasts, and routine growth and sporulation were carried out according to procedures described in Donadio, et al., 1991, Science 115:97; Weber and Losick, 1988, Gene 68:173; and Yamamoto, et al., 1986, J. Antibiotic. 39:1304.

Oligo primers used in the PCR amplifications and described in the Examples below are as follows:

For large scale preparation of erythromycin derivatives, fermentation beers are typically adjusted to pH 9 with $NH_4OH$ and then extracted two times with an equal volume of $CH_2Cl_2$. The pooled extract is then concentrated to a wet oil (approx. 1 g per liter of fermentation beer). Concentrated extracts are digested in methanol and chromatographed over a column of Sephadex® LH-20 (Pharmacia Biotech, Uppsala, Sweden) in the same solvent. Fractions are tested for bioactivity against Staphylococcus aureus, and active fractions are combined and concentrated. When additional column chromatography is desired to reduce sample weight, the concentrated sample is digested in a solvent system consisting of n-heptane, chloroform, ethanol (10:10:1, v/v/v) and chromatographed over a column of Sephadex® LH-20 in the same system. Fractions are then analyzed by $^1H$ NMR, focusing on the characteristic erythromycin resonances

| Sequence | ID |
|---|---|
| 5'-ATCTACACSTCSGGCACSACSGGCAAGCCSAAGGG-3' | SEQ ID NO:3 |
| 5'-CTSAAGGCSGGCGGCGCSTACGTSCCSATCGACCC)-3' | SEQ ID NO:4 |
| 5'-CGCGAATTCCTAGGCTGGCGGTGATGTTCA-3' | SEQ ID NO:5 |
| 5'-GCCGGATCCATGCATACGTCGGCAGGGAGGTAC-3' | SEQ ID NO:6 |
| 5'-GCTCGAATTCGCTGGTCGCGGTGCACCT-3' | SEQ ID NO:7 |
| 5'-GACGGATCCGGCCCTAGGCTGCGCCCGGCTCG-3' | SEQ ID NO:8 |
| 5'-TTGGGATCCTATGCATTCCAGCGCGAGCGC-3' | SEQ ID NO:9 |
| 5'-GAGAAGCTTGGCGCGACTTGCCCGCT-3' | SEQ ID NO:10 |
| 5'-TTTTTTAAGCTTGGTACCTGCTCACCGGCAACACCG-3' | SEQ ID NO:11 |
| 5'-TTTTTTGGATCCCTGCAGCCTAGGGTCGGAGGCACTGCCGGT-3' | SEQ ID NO:12 |
| 5'-TTTTTTCTGCAGTATGCATTCCAGGGCAAGCGGTTCT-3' | SEQ ID NO:13 |
| 5'-TTTTTTGAATTCACGCGTTGCCCGCGGCGTAGGCGC-3' | SEQ ID NO:14 |
| 5'-GATCGAATTCCCTAGGACGGCAGTCCTGCTCACC-3' | SEQ ID NO:15 |
| 5'-GATCGGATCCATGCATACGTCGGAAGGTCGACCCG-3' | SEQ ID NO:16 |
| 5'-TTCGAAGAATTCCCTAGGGTTGCCTTCCTGTTCGAC-3' | SEQ ID NO:17 |
| 5'-TTCGAAAAGCTTATGCATAGACCGGCAGATCCACCG-3' | SEQ ID NO:18 |
| 5'-CGGTSAAGTCSAACATCGG-3' | SEQ ID NO:19 |
| 5'-GCRATCTCRCCCTGCGARTG-3' | SEQ ID NO:20 |
| 5'-GAGAGAGGAACCAACGCGCACGTGATCGTCGAAGAGGCACCAGC-3' | SEQ ID NO:21 |
| 5'-GAGAGAGGATCCGACCTAGGCGCGGAGGTCACCGGCGCGACGGCG-3' | SEQ ID NO:22 |
| 5'-GAGAGACCTAGGAAGCCGGTGTTCGTGTTCCCCGGCCAGGGCT-3' | SEQ ID NO:23 |
| 5'-GAGAGAGGATCCGAGGCCGGCCGTGCGCCCGGACCGAAGACCGCCTC-3' | SEQ ID NO:24 |
| 5'-GAGAGAATTCCCTAGGGTCGCCTTCGTCTTTCCCGGGCAGG-3' | SEQ ID NO:25 |
| 5'-TTGAGATCTTATGCATACGAGGGAAGCGGCACCCTGC-3' | SEQ ID NO:26 |

Mass spectrometry was routinely performed with a Finnigan-MAT7000 mass spectrometer equipped with an atmospheric pressure chemical ionization source (APCI). Electrospray mass spectrometry (ESI-MS) was performed with a Finnigan-MAT752-7000 mass spectrometer equipped with a Finnigan atmospheric pressure ionization (API) source. HPLC separation was carried out on a Hewlett-Packard 1050 liquid chromatograph using a Prodigy ODS (2) column (5 μm, 50×2 mm) and a gradient elution of 5 mM ammonium acetate and methanol. The flow rate was 0.3 mL/min.

around δ=5.0 (H-13), δ=4.9 (H-1"), and δ=4.4 (H-1') (Everett and Tyler, J. Chem. Soc. Perkin Trans. I, pg. 2599 (1985)) and pooled according to purity. Alternatively, column chromatography is replaced with an extraction sequence. In this case, the initial pooled $CH_2Cl_2$ extract is concentrated to approximately 400 mL. This is extracted twice with equal volumes of 0.05 M aqueous potassium phosphate with the pH chosen between pH 4.5–6. The aqueous phase is then pooled, adjusted to pH 8–9, and extracted twice with equal volumes of ethyl acetate. Finally, the ethyl acetate extracts are pooled and concentrated. When additional reduction in sample weight is desired, the extraction sequence is repeated on a 10–50 fold smaller scale, typically yielding about 500 mgs of partially pure material.

High resolution separation of erythromycin derivatives is obtained by one or more rounds of countercurrent chromatography (Hostettmann and Marston, Anal. Chim. Acta, 236:63–76 (1990)). When the weight of the partially pure sample from column chromatography or the extraction sequence is less than 5 g, but greater than 0.5 g, it is digested in 7 mL of the upper phase of a solvent system (3:7:5, v/v/v) consisting of n-hexane, ethyl acetate, 0.02 M aqueous potassium phosphate, with a pH chosen between 6.5–8.0, and chromatographed on a custom droplet countercurrent chromatography (DCCC) instrument [100 vertical columns, 0.4 cm dia.×24 cm length; Hostettmann and Marston, Anal. Chim. Acta, 236:63–76 (1990)] in the same system with the upper phase as the mobile phase. Flow rates of approximately 120–200 mL/hr are employed. As before, fractions are analyzed by NMR and bioactivity, and pooled according to purity. When the weight of the partially pure sample is approximately 0.5 g or less, countercurrent chromatography is carried out on an Ito multi-layered horizontal Coil Planet Centrifuge (P.C. Inc., Potomac, Md.) using either the system consisting of n-hexane, ethyl acetate. 0.02 M aqueous potassium phosphate, with the pH chosen between 6.5–8.0, (3:7:5, v/v/v) employed above, or similar systems in which the ratio of hexane to EtOAc and/or the pH are varied. The chromatography is developed either isocratically, or with a gradient starting, for example, with the upper phase of a solvent system consisting of n-hexane, ethyl acetate, 0.02 M aqueous potassium phosphate, with the pH chosen between 6.5–8.0, (7:3:5, v/v/v) and finishing with the upper phase of a solvent system consisting of n-hexane, ethyl acetate, 0.02 M aqueous potassium phosphate, at the same pH, (1:1:1, v/v/v). In all cases, flow rates of approximately 120 mL/hr are employed. As before, fractions are analyzed by NMR and bioactivity, and pooled according to purity. Once sufficient purity is achieved, $^1$H and $^{13}$C NMR spectra are measured with a General Electric GN500 spectrometer and structural assignments are made with the aid of with the aid of correlational spectroscopy (COSY), heteronuclear multiple quantum correlation (HMQC), heteronuclear multiple bond correlation (HMBC), and distortionless enhancement by polarization transfer (DEPT) experiments.

The foregoing can be better understood by reference to the following examples, which are provided as non-limiting illustrations of the practice of the instant invention.

EXAMPLE 1

Cloning of the LigAT2 Domain from *Streptomyces hygroscopicus* ATCC 29253

A genomic library of *Streptomyces hygroscopicus* ATCC 29253 DNA was constructed in the bifunctional cosmid pNJ1 (Tuan, et al., Gene 90: 21–29 (1990)) using standard methods of recombinant DNA technology. Briefly, cosmid vector was prepared by digesting approximately 5 μg of pNJI with EcoRI, dephosphorylating with calf intestinal alkaline phosphatase (CIAP) and then digesting with BglII to generate one arm and also digesting 5 μg of pNJI with HindIII, dephosphorylating with CIAP and then digesting with BglII to generate the other. Insert DNA was prepared by partially digesting approximately 25 μg of high molecular weight *S. hygroscopicus* chromosomal DNA with Sau IIIA according to the procedure outlined in Maniatis, et al. supra. Sau IIIA fragments of approximately 35 kb were recovered from a 0.5% low melting point agarose gel by melting the appropriate gel slice to 65° C., adding 3 volumes of TE buffer, gently extracting 2× with phenol and once with chloroform and ethanol precipitating the aqueous phase. For the ligation, approximately 3 μg of this chromosomal DNA was mixed with approximately 0.5 μg of each cosmid arm and EtOH precipitated. The precipitate was resuspended in 7 μL of water to which was added 2 μL of 5× ligation buffer and 1 μL of T4 DNA ligase. The mixture was incubated overnight at 16° C. GigapackII XL (Stratagene®) was used for packaging 2 μL of the ligation mix according to the manufacture's instructions. The host bacterium was *E. coli* ER1772 from New England Biolabs (Beverly, Mass.). Twenty-six colonies were examined by restriction analysis and all were found to contain insert DNA. Individual colonies were picked into thirty-four 96-well plates to give a 99.99% probability that the library represented all *S. hygroscopicus* sequences. Further restriction analysis demonstrated the average insert size to be about 30 kb.

The library was screened with a 1.45 kb SstI-MscI DNA fragment encompassing the ketosynthase (KS) domain from module 5 of the erythromycin PKS gene eryAIII (Donadio and Katz, 1992, Gene, 111: 51–60). The DNA fragment was labeled with $^{32}$P using the Megaprime DNA labeling system (Amersham Life Science, Arlington Heights, Ill.). Colonies (3600) were transferred from 96-well plates to Hybond-N nylon membranes (Amersham Life Science, Arlington Heights, Ill.) and probed according to procedures outlined in Maniatis, et al. supra. Hybridization was performed at 65° C. and a stringency wash carried out with 0×SSC at 65° C. About 60 cosmid clones were chosen which gave the strongest signals with this PKS probe.

Figure 6:
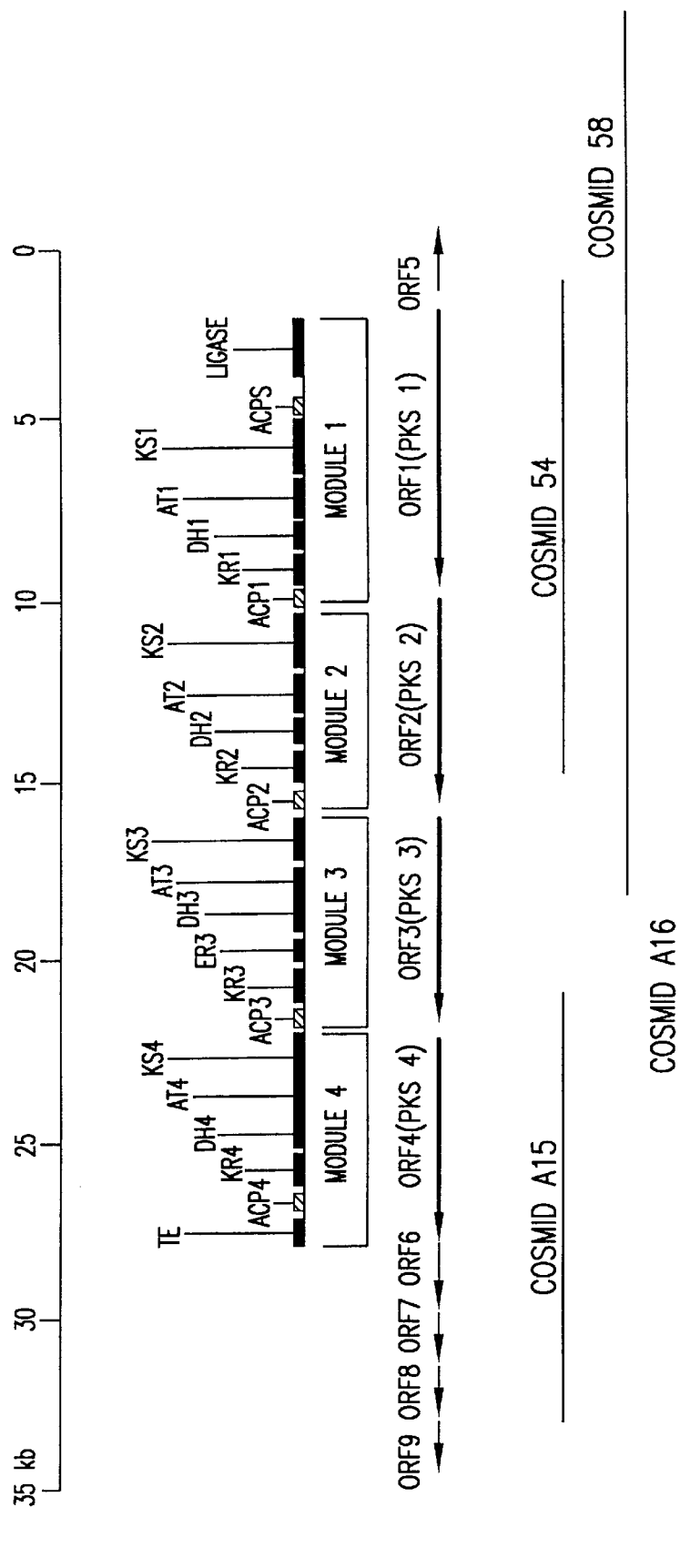
FIG. 6 is a schematic representation of the genetic organization of the Ligase-PKS cluster from *S. hygroscopicus* ATCC 29253.

We also decided to screen Southern digests of these clones with a second probe in order to identify potential genetically linked peptide synthetases in this strain. The probe was designed from conserved motifs of nonribosomal peptide synthetases (Borchert et al., 1992, FEMS Microbiology Letters, 92: 175–180) and consisted of a mixture of two degenerative 35-mers, SEQ ID NO:3 and SEQ ID NO:4. The mixed probe was labeled using DNA 5' End Labeling System (Promega Corp., Madison, Wis.). The 60 cosmid clones were digested with SmaI and run on 0.9% agarose gels. Southern analysis was performed according to Maniatis, et al. supra, except that hybridization was overnight at 55° C. and the stringency wash was with 0.5×SSC at 55° C. Two cosmids, 54 and 58, were identified using this second probe. Thirteen additional cosmids were subsequently isolated by re-probing the cosmid library with a 1 kb fragment from the left of the insert of cosmid 58. Two of these thirteen cosmids, designated A15 and A16, were then further analyzed by restriction analysis and DNA sequencing. Restriction and sequence analysis of a 32.8 kb continuous segment of DNA from A16 revealed a type I PKS cluster with four PKS modules. A genetic map of the cluster is shown in FIG. 6. Since an unusual CoA ligase-like domain was found in ORF1 (PKS1), the cluster was named "Lig-PKS".

The nucleotide sequence of the LigAT2 domain from Lig-PKS (top strand) and its corresponding amnino acid sequence (bottom strand) are shown in FIG. 7 (SEQ ID NO:1 and SEQ ID NO:31 respectively). When SEQ ID NO:31 was compared with the 14 AT domains in the rapamycin PKS (Growtree Program, GCG, Madison Wis.), it was found to cluster with malonate-specifying rapamycin domains (see Growtree analysis of FIG. 3). Therefore, it was predicted that the LigAT2 specifies malonate as its cognate extender unit during synthesis of the polyketide encoded by Lig-PKS.

EXAMPLE 2
Construction of Plasmid pUC18/LiaAT2

Figure 8:
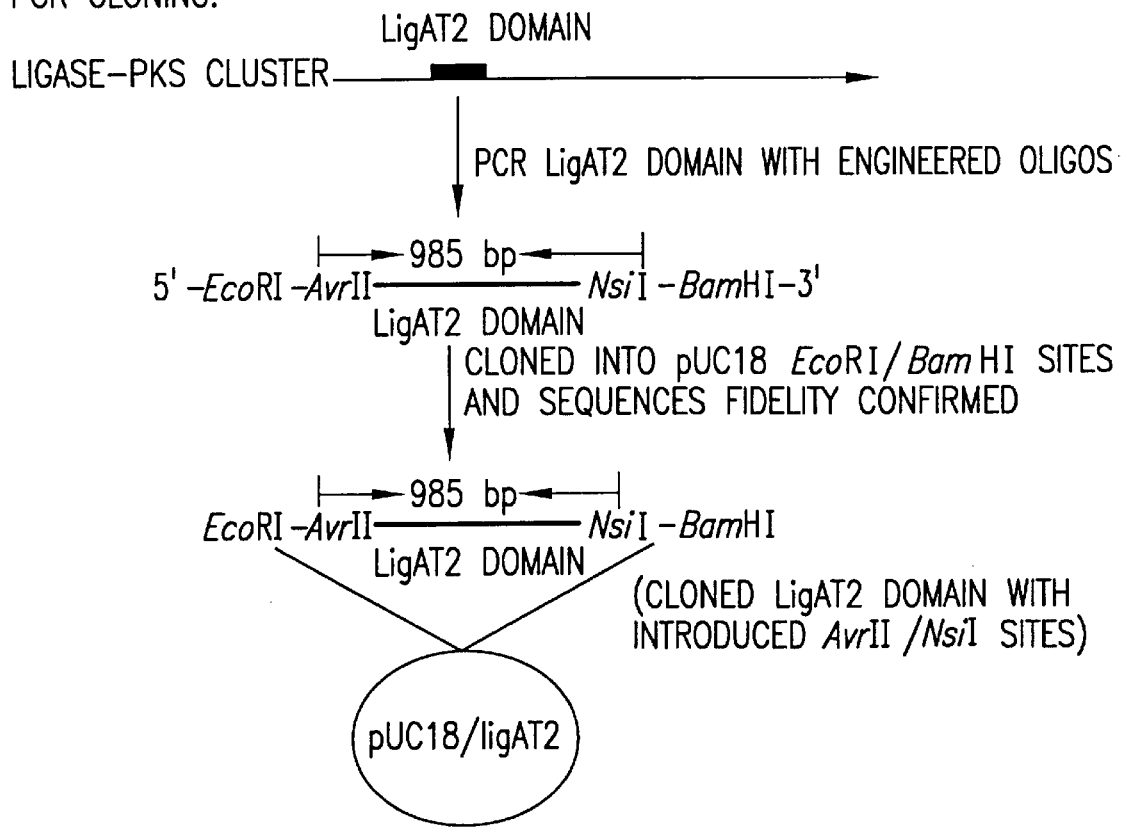
FIG. 8 is a diagrammatic representation of the strategy to clone the LigAT2 domain.

Two PCR oligonucleotides (SEQ ID NO:5 and SEQ ID NO:6) were designed to subclone the 985 bp DNA segment encoding the LigAT2 domain from the Lig-PKS cluster and to introduce two unique restriction sites, AvrII and NsiI. for cassette cloning. The unique restriction sites AvrII and NsiI required for cassette cloning of the AT-encoding DNA were chosen based on multiple sequence alignment using the programs PILEUP and PRETTY (GCG, Madison Wis.) which compared the amino acid sequences of LigAT2, venAT, rapAT2, rapAT5, rapAT8, rapAT9, rapAT11, rapAT12, rapAT14, eryAT1, eryAT2, eryAT3, eryAT4, eryAT5, eryAT6. and a monofunctional AT from *Streptomyces glaucescens* (R. G. Summers et al., *Biochemistry* 34:9389–9402 (1995)). The selection and positioning of the restriction enzyme sites were based on the following considerations: (i) extent of amnino acid sequence conservation among the various ATs, with the sites being positioned outside, but near the regions of greatest conservation, (ii) absence of the sites from the heterologous AT-encoding DNA and the eryAT flanking DNA and (iii) impact of the amino acid sequence changes resulting from translation of these sites on the heterologous AT amino acid sequence. This necessitated nucleotide changes, shown in bold in FIG. 8, at the beginning and near the end of the LigAT2-encoding DNA sequence. (In FIG. 8, the underlined nucleotides are the wild-type sequence.) In addition, two other restriction sites, EcoRI and BarnHI, were also introduced at the 5' ends of the N-terminal and C-terminal oligonucleotides, respectively, for convenient subcloning of the PCR-generated product. The approximately 1 kb LigAT2 domain was amplified from Cosmid 58 as follows: The 100 μL PCR reaction mixture contained 10 μL of 10×PCR buffer (Bethesda Research Laboratories), 2 μL of 10 mM dNTP mixture, 2–4 μL of 50 mM MgCl$_2$ 100 pM of each oligo, 10–50 ng of template DNA and water to 100 μL. Cycling conditions were as follows: One cycle at 96° C./6 min, 80° C./1 min (add 5 U Taq DNA Polymerase during this 1 min) and 72° C./2 min; 30 cycles at 95° C./1 min, 65° C./1 min and 72° C./2 min with a 5 min extension at 72° C. for the last cycle. The entire reaction was then run on a 1% agarose gel and the desired fragment was isolated with Prep-A-Gene (BioRad, Hercules, Calif.). The PCR product was digested with EcoRI and BamHI and subcloned into the EcoRI and BamHI sites of pUC18. The ligation mixture was transformed into *E. coli* DH5α (GIBCO BRL) according to the manufacturer's instructions and transformants were selected on LB plates containing 150 μg/mL ampicillin and 50 μL of a 2% solution of X-gal for blue/white selection. Clones were confirmed by restriction analysis and the fidelity of the insert was confirmed by DNA sequencing. The final plasmid construct was named pUC18/LigAT2.

Figure 9:
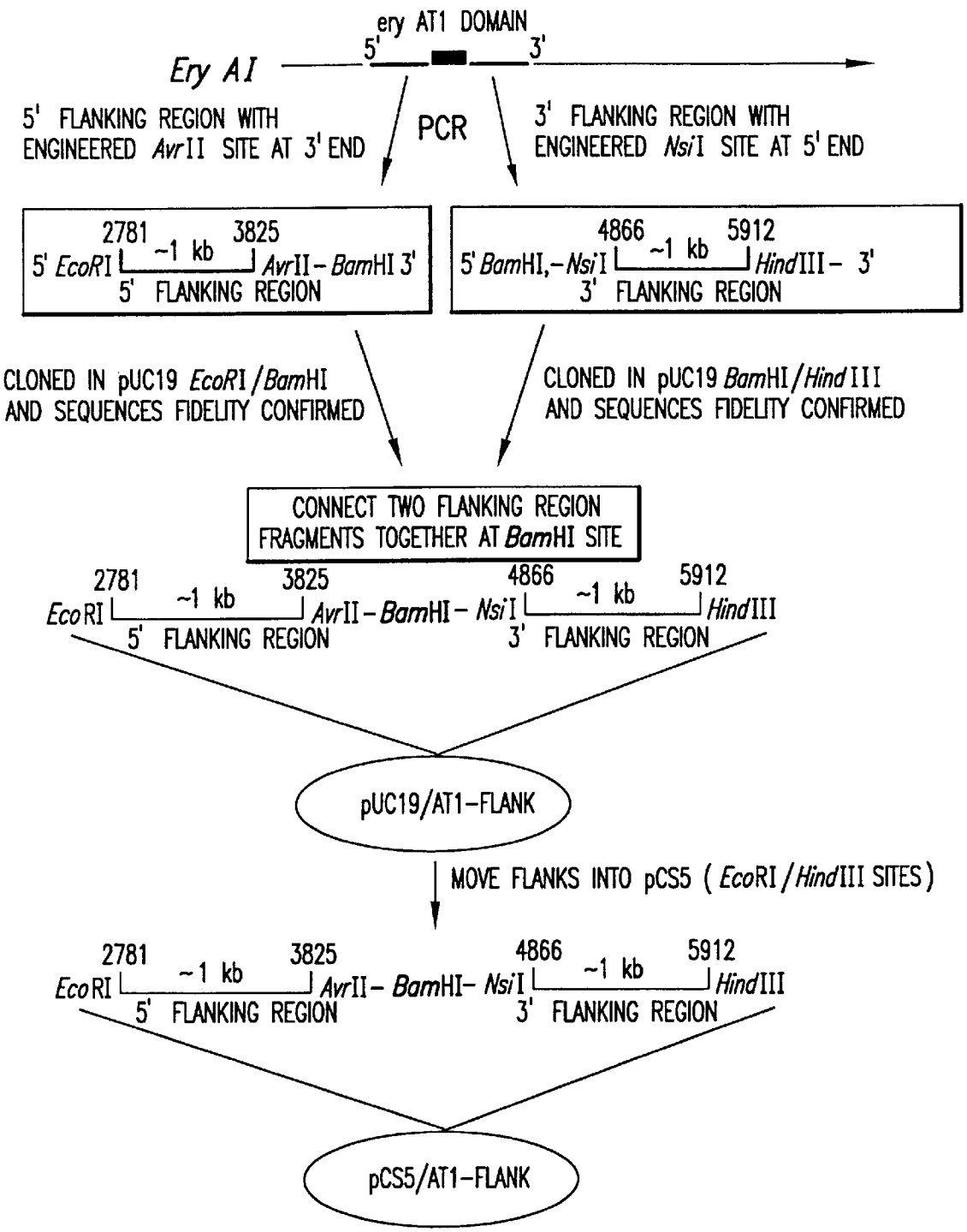
FIG. 9 is a flow diagram depicting the cloning of the EryAT1 flanking regions in plasmnid pCS5.
Figure 10:
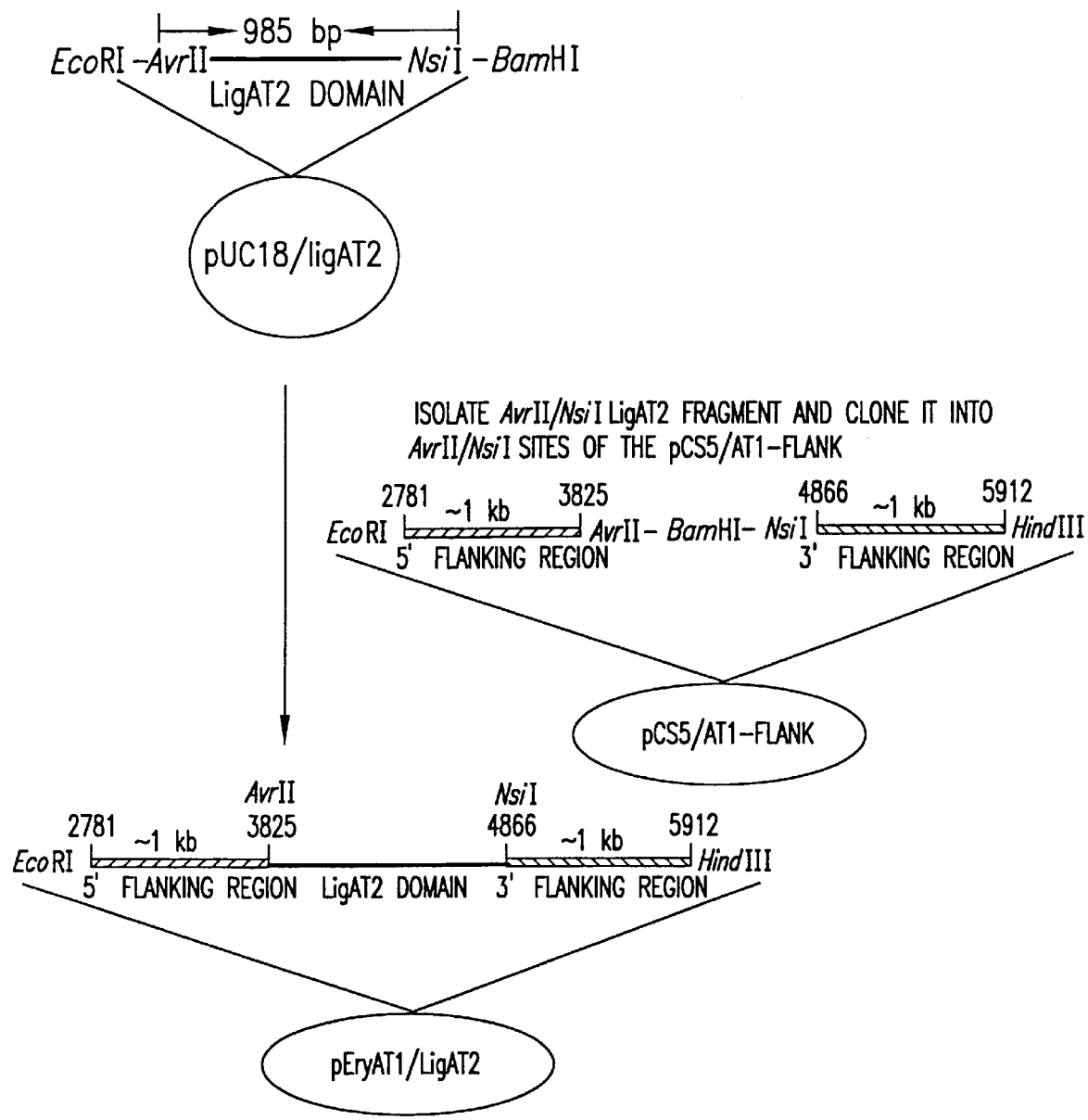
FIG. 10 is a flow diagram depicting construction of pEryAT1/LigAT2.

EXAMPLE 3
Construction of Plasmid pEryAT1/LigAT2 pEryAT1/LigAT2 was constructed using standard methods of recombinant DNA technology according to the schematic outlines of FIGS. 9 and 10. To construct a gene-replacement vector specific for the eryAT1 domain, the two DNA regions immediately adjacent to eryAT1-encoding DNA were cloned and positioned adjacent to the LigAT2-encoding DNA as described in Example 2. The 5' and 3' boundaries of eryAT1 were designated as 3825 and 4866, and correspond to the deposited eryAI sequence (GenBank accession number M63676). To subclone the DNA fragment upstream of the eryAT1 domain encoding region from the *Sac. erythraea* chromosome, two PCR oligonucleotides (SEQ ID NO:7 and SEQ ID NO:8) were designed so that an EcoRI site was added at the 5' end of the region and AvrII-BamHI restriction sites were introduced at the 3' end. The 5'-flanking region (about 1 kb) was PCR generated as described in EXAMPLE 2 using plasmid pAIEN22 DNA as template. (This plasmid is a pUC19 derivative containing 22 kb of *Sac. erythraea* DNA from an EcoRI site upstream of eryAI to an NheI site in eryAII cloned into EcoRI and XbaI cut pUC19). The PCR product was subcloned into EcoRI and BanHI sites of pUC19 and the ligated DNA transformed into *E. coli* DH5α ((GIBCO BRL) according to the manufacturer's instructions. Clones were selected on LB plates containing 150 μg/mL ampicillin and 50 μL of a 2% solution of X-gal for blue/white selection. Clones were confirmed by restriction analysis and the fidelity of the insert was confirmed by DNA sequencing. The resulting construct was named pUC19/AT1/5'-flank.

For subcloning the 3'-flanking region of the eryAT1 from *Sac. erythraea* chromosome, two PCR oligonucleotides (SEQ ID NO:9 and SEQ ID NO:10) were designed so that BamHI-NsiI restriction sites were introduced into the 5' end of the region and a HindIII restriction site was added to the 3' end. The 3'-flanking region (about 1 kb) was also generated by PCR using pAIEN22 as template as described above. The PCR fragment was subcloned into the BamHI and HindIII sites of pUC19 and the ligated DNA transformed into *E. coli* DH5α as above. Clones were selected on LB plates containing 150 μg/mL ampicillin and 50 μL of a 2% solution of X-gal for blue/white selection. Clones were confirmed by restriction analysis and the fidelity of the insert was confirmed by DNA sequencing. This intermediate construct was named pUC19/AT1/3'-flank. The two flanking regions were joined by first isolating the 1 kb BamHI-HindIII fragment (3'-flank) from pUC19/AT1/3'-flank and then ligating this fragment to pUC19/AT1/5'-flank cut with BamHI and HindIII. Ligated DNA was transformed into *E. coli* DH5α and clones isolated as described. The resulting plasmid was named pUC19/AT1-flank. The 2.1 kb EcoRI and HindIII fragment from pUC19/AT1-flank was then isolated and ligated to pCS5 cut with the same enzymes to generate pCS5/AT1-flank. The final step in the construction of pEryAT1/LigAT2 was to ligate the 1 kb LigAT2 fragment having AvrII and NsiI ends to pCS5/AT1-flank cut with the same enzymes to give the gene replacement/integration plasmid pEryAT1/LigAT2. All ligation mixtures were transformed into the intermediate host *E. coli* DH5α and clones selected as previously described.

EXAMPLE 4
Construction of *Sac. erythraea* ER720 EryAT1/Lig2AT2

An example of a 12-desmethyl-12-deoxyerythromycin A producing microorganism was prepared by replacing the DNA fragment encoding the methylmalonyl acyltransferase domain in module 1 of the erythromycin PKS (EryAT1) of *Sac. erythraea* ER720 with a newly discovered DNA fragment encoding a malonyl acyltransferase domain (LigAT2) from *S. hygroscopicus* ATCC 29253. This was accomplished with the recombinant plasmid. pEryAT1/LigAT2, prepared as described in Example 3. Transformation of *Sac. erythraea* ER720 and resolution of the integration event were carried out according to the following method. *Sac. erythraea* ER720 cells were grown in 50 mL of SGGP medium (per 1 liter aqueous solution: 4 g peptone, 4 g yeast extract, 4 g casamino acids, 2 g glycine, 0.5 g MgSO$_4$.7 H$_2$O, 10 g glucose, 20 mL of 500 mM KH$_2$PO$_4$) for 3 days at 32° C. and then washed in 10 mL of 10.3% sucrose. The cells were resuspended in 10 mL of P$_M$ buffer containing 1 mg/mL lysozyme and incubated at 30° C. for 15–30 minutes until most of the mycelial segments were converted into spherical protoplasts. ($P_M$ buffer per 1 liter aqueous solution: 200 g sucrose, 0.25 g $K_2SO_4$ in 890 mL $H_2O$, with the addition after sterilization of 100 mL 0.25 M TES, pH 7.2, 2 mL trace elements solution (Hopwood, et al., 1985, Genetic Manipulation of Streptomyces A Laboratory Manual, The John Innes Foundation), 0.08 mL 2.5 M $CaCl_2$, 10 mL 0.5% $KH_2PO_4$, 2 mL 2.5 M $MgCl_2$.) The protoplasts were washed once with $P_M$ and then resuspended in 3 mL of the same buffer containing 10% DMSO for storage in 200 µL aliquots at −80° C.

Transformation was accomplished by quickly thawing an aliquot of protoplasts, centrifuging for 15 seconds in a microfuge, decanting the supernatant, and resuspending the protoplasts in the $P_M$ remaining in the tube. Ten µL of DNA solution was added (3 µL of pEryAT1/LigAT2 DNA from Example 3 at about 1 µg/µL in 7 µL of $P_M$ buffer) and mixed with the protoplasts by gently tapping the tube. Two tenths of a mL of 25% PEG 8000 in T buffer (Hopwood, et al., 1985, Genetic Manipulation of Streptomyces A Laboratory Manual, The John Innes Institute) was then added, mixed by pipetting the solution 3 times and the suspension immediately spread on a dried R3M plate. The plate was incubated at 30° C. for 20 hours and overlaid with 2 mL of water containing 100 µg/mL thiostrepton, dried briefly and incubated 4 more days at 30° C.

To select stable transformants (integrants) colonies arising on the transformation plates were re-streaked onto R3M plates containing thiostrepton (20 µg/mL). Two colonies were confirmed to be thiostrepton resistant and one of these was inoculated into SGGP containing thiostrepton (10 µg/mL) to isolate chromosomal DNA for Southern analysis. Integration of the plasmid DNA into the ER720 chromosome was further confirmed by Southern hybridization (data not shown). Hybridization was at 65° C. and the stringency wash was with 0.1×SSC at 65° C.

Figure 11:
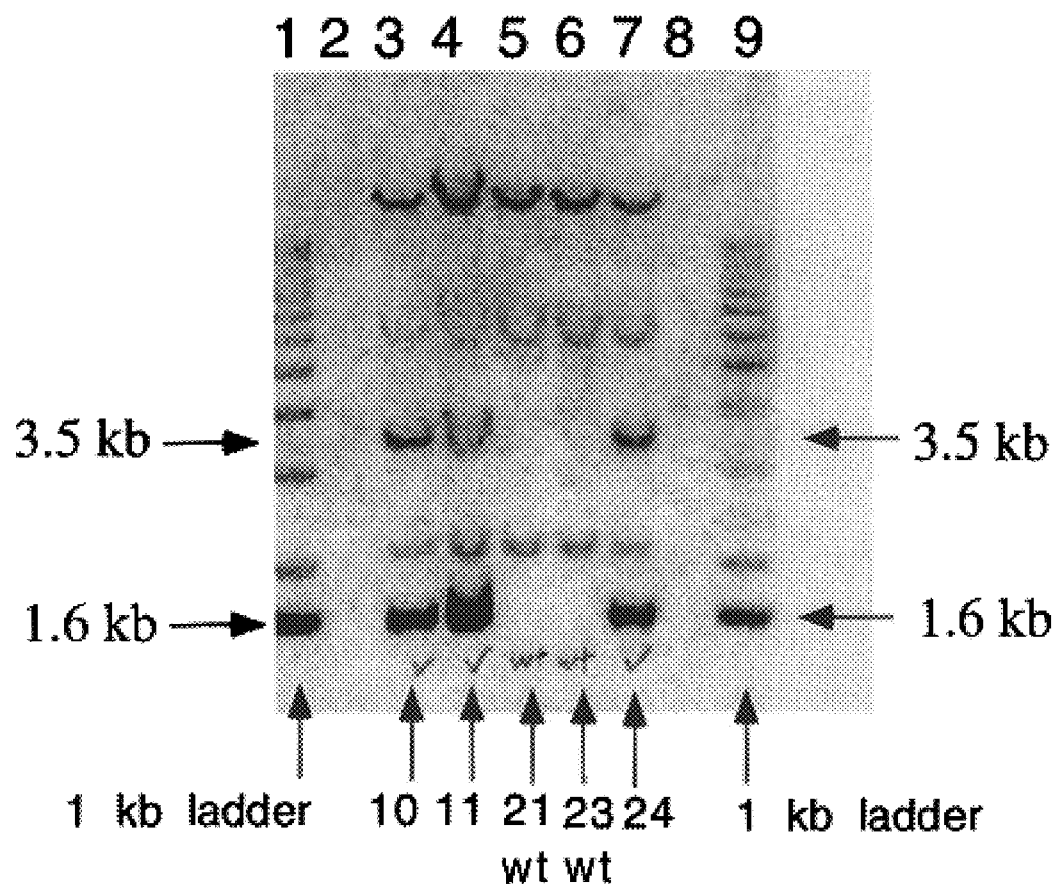
FIG. 11 is a computer generated PhosphorImage of a Southern analysis of chromosomal DNA from *Sac. ezythraea* ER720 EryAT1/LigAT2 resolvants cut with SphI and probed with an approximately 3 kb EcoRI/HindIII fragment from pEryAT1/LigAT2. As shown in lanes 3, 4 and 7 the probe hybridized with fragments of 3.5 and 1.6 kb, indicating that LigAT2 had replaced EryAT1 in the chromosomes of these resolvants (clone #10, #11 and #24 respectively). Lanes 5 and 6: chromosomal DNA from *Sac. erythraea* ER720 resolvants to wild-type (wt); lanes 1 and 9: molecular weight markers (1 kb ladder).

The confirmed integrant was grown in SGGP without antibiotic for four days and then plated onto non-selective R3M plates for sporulation. Spores were plated on R3M plates to obtain individual colonies, which were then screened for sensitivity to thiostrepton, indicating loss of the plasmid sequence from the chromosome. Five thiostrepton sensitive colonies were selected and 3 of these were confirmed by Southern hybridization to have the EryAT1 replaced by LigAT2 (FIG. 11). Hybridization was at 65° C. and the stringency wash was with 0.12×SSC at 65° C. The strain was named Sac. erythraea ER720 EryAT1/LigAT2.

EXAMPLE 5
Analysis of Compounds Produced by Sac. erythraea ER720 EryAT1/LigAT2

Compounds produced by the recombinant Sac. erythraea strain, ER720 EryAT1/LigAT2, whose construction is described in Example 4, were characterized by TLC, bioautography, mass spectrometry and NMR analysis.

Figure 12:
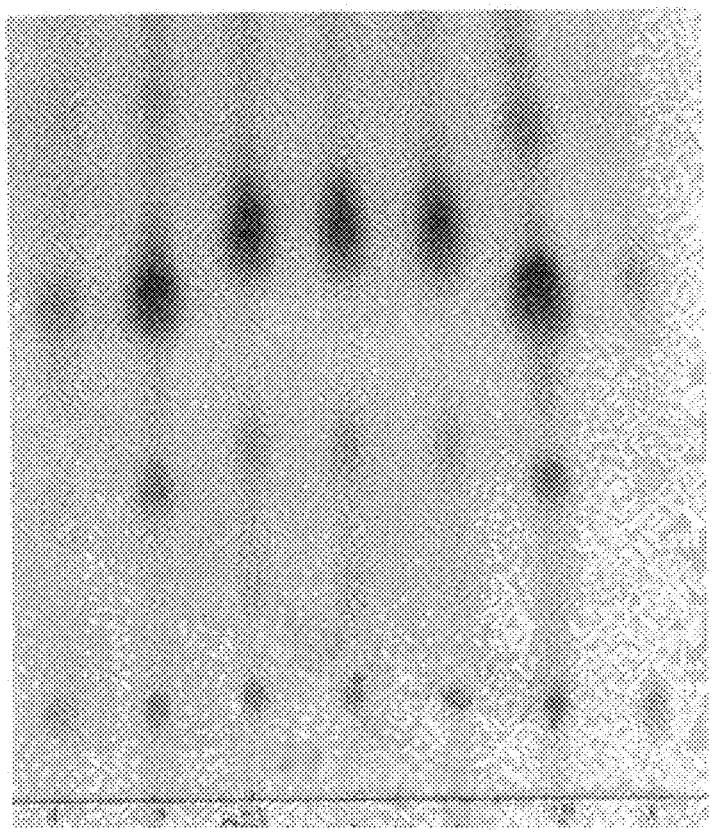
FIG. 12 is a computer reproduction of a TLC plate on which the products produced by *Sac. erythraea* ER720 EryAT1/LigAT2 were run. Lanes 1 and 7: erythromycin A standard (5 µg); lanes 2 and 6: compounds produced by wild-type *Sac. erythraea* ER720; lanes 3, 4 and 5: compounds produced by *Sac. erythraea* ER720 EryAT1/LigAT2 resolvants to mutant-type, clones #10, #11 and #24 respectively.

For TLC analysis cells were grown in either SGGP or SCM medium (20 g Soytone, 15 g Soluble Starch, 10.5 g MOPS, 1.5 g Yeast Extract and 0.1 g $CaCl_2$ per liter of distilled $H_2O$) for 4–5 days at 30° C. 1.5 mL of culture was centrifuged for 1 minute in a microfuge to remove cells. One mL of the resulting supernatant was removed to another microfuge tube and the pH adjusted to 9.0 by the addition of 6 µL of $NH_4OH$. Then 0.5 mL of ethyl acetate was added, the tube was vortexed for 10 sec and then centrifuged for approximately 5 min to achieve phase separation. The organic phase was removed to another tube, and the aqueous phase was re-extracted with 0.5 mL of ethyl acetate. The second organic phase was combined with the first and dried in a Speed Vac. The residue was taken up in 10 µL of ethyl acetate and 5 µL was spotted onto a Merck 60F-254 silica gel TLC plate. The plate was run in isopropyl ether:methanol:$NH_4OH$ (75:35:2). Erythromycin derivatives were visualized by spraying the plates with anisaldehyde:sulfuric acid:ethanol (1:1:9). Using this reagent, a novel compound predicted to be 12-desmethyl-12-deoxyerythromycin A, appeared as a blue spot running slightly faster than erythromycin A (FIG. 12).

To detect biological activity, a TLC-bioautography assay was performed. In this assay, one microliter of the extracted sample from above was spotted onto a TLC plate which was run as described above. The plate was then air-dried and placed in a sterile bio-assay dish (245×245×25 mm). The plate was then covered with 100 mL of antibiotic medium 11 (DIFCO-BACTO) containing Staphylococcus aureus as an indicator strain and incubated overnight at 37° C. As with the positive controls, a clear zone of inhibition developed around the sample spot indicating that the novel compound had bioactivity.

To determnine whether the novel spot seen on TLC had the molecular mass corresponding to the predicted 12-desmethyl-12-deoxyerythromycin A, an ethyl acetate extract was further analyzed by mass spectrometry. The mass spectrometry samples were isolated by TLC basically as described above except that plates were not sprayed with the anisaldehyde reagent. The region of the novel spot was instead scraped from the TLC plate and the silica resin re-extracted with ethyl acetate-methanol (1:1) and then twice with ethyl acetate. The combined solvent phases were then dried in a Speed Vac. Mass spectrometric analysis revealed the novel compound to have a mass of 704, which corresponds to the molecular ion plus a proton ($M+H^+$) of 12-desmethyl-12-deoxyerythromycin A.

To acquire milligram quantities of highly purified material for performance of NMR analysis, the culture was grown in a 42-liter LH Fermentation Series 2000 fermentor. SCM medium was used for growth of inoculum and for the fermentation. Seed for the fermentation was grown in two steps. In the first step, frozen vegetative inoculum was used to seed 100 mL of SCM medium in a 500 mL Erlenmeyer flask. For the second step, 2-liter Erlenmeyer flasks containing 600 mL of SCM medium were seeded at 5% from the first passage growth. Each step was incubated for 3 days at 32° C. on a rotary shaker operated at 225 rpm.

Thirty liters of SCM medium were prepared in the 42-liter fermentor and sterilized at 121° C. and 15 psi for 1 hour. Antifoam (XFO-371, Ivanhoe Chemical Co., Mundelein, Ill.) was added initially at 0.01% and then was available on demand. The fermentor was inoculated with 1.5 liters of the second passage seed growth. The temperature was controlled at 32° C. The agitation rate was 260 rpm and the air flow was 1.3 vol/vol/min. The head pressure was maintained at 6 psi. During fermentation pH was controlled at 7.3 with 5 M propionic acid. The fermentation was terminated at 111 hours, and the fermentation beer was adjusted to pH 8. This was followed by two extractions with equal volumes of $CH_2Cl_2$. The pooled $CH_2Cl_2$ extract was then concentrated to approximately 400 mL and extracted twice with equal volumes of 0.05 M aqueous potassium phosphate pH 5.5. The aqueous phase was pooled and adjusted to pH 8, and then extracted twice with equal volumes of ethyl acetate. The ethyl acetate extracts were pooled and concentrated to yield 5 ml oil. The extraction sequence described above was then repeated to yield 600 mg of oil after concentration. Next, the sample was split and each half was digested in 2.5 ml each of the upper and lower phases of a solvent system consisting of n-hexane, ethyl acetate, 0.02 M aqueous potassium phosphate, pH 8, (1:1:1, v/v/v). These were then chromatographed on the Coil Planet Centrifuge using the upper phase as the mobile phase. Fractions were analyzed by bioassay against *Staphylococcus aureus* and $^1$H NMR. Two macrolide containing peaks of bioactivity were observed in both samples, and the later eluting peaks from each sample, which contained most of the bioactivity, were pooled and concentrated. The concentrated material was then digested in 2.5 mL each of the upper and lower phases of a solvent system consisting of n-hexane, ethyl acetate, 0.02 M aqueous potassium phosphate, pH 6.5, (6:4:5, v/v/v), and was chromatographed on the Coil Planet Centrifuge using the upper phase as the mobile phase. Fractions were analyzed by bioassay and $^1$H NMR. Two macrolide containing peaks of bioactivity were observed and the later eluting species was readily characterized by its $^1$H and $^{13}$C NMR spectra as 12-desmethyl-12-deoxyerythromycin A. Parameters from the $^1$H NMR spectra are listed in Table 2. The assignments were made with the aid of correlational spectroscopy (COSY), heteronuclear multiple quantum correlation (HMQC), heteronuclear multiple bond correlation (HMBC), and distortionless enhancement by polarization transfer (DEPT) experiments. Mass spectral data of this sample was also consistent with the structural assignment. Electrospray ionization (ESI) of this sample revealed an M+H$^+$ ion at M/Z 704, which is in full accord with erythromycin A lacking both a methyl group and a hydroxyl group.

TABLE 2

$^1$H NMR chemical shift ($\delta$) assignments for 12-desmethyl-12-deoxyerythromycin A in CDCl$_3$

| | | | |
|---|---|---|---|
| 2-H | 2.74 | 1'-H | 4.47 |
| 3-H | 4.15 | 2'-H | 3.25 |
| 4-H | 2.01 | 3'-H | 2.49 |
| 5-H | 3.58 | 4'-H$_a$ | 1.67 |
| 7-H$_a$ | 1.91 | 4'-H$_b$ | 1.23 |
| 7-H$_b$ | 1.66 | 5'-H | 3.54 |
| 8-H | 2.86 | 6'-H$_3$ | 1.23 |
| 10-H | 2.70 | N(CH$_3$)$_2$ | 2.30 |
| 11-H | 4.05 | 1"-H | 4.85 |
| 12-H$_a$ | 1.71 | 2"-H$_a$ | 2.40 |
| 12-H$_b$ | 1.46 | 2"-H$_b$ | 1.59 |
| 13-H | 5.06 | 4"-H | 3.03 |
| 14-H$_2$ | 1.59 | 5"-H | 4.04 |
| 15-H$_3$ | 0.89 | 6"-H$_3$ | 1.30 |
| 2-CH$_3$ | 1.19 | 3"-CH$_3$ | 1.25 |
| 4-CH$_3$ | 1.13 | OCH$_3$ | 3.33 |
| 6-CH$_3$ | 1.38 | | |
| 8-CH$_3$ | 1.19 | | |
| 10-CH$_3$ | 1.11 | | |

Figure 13:
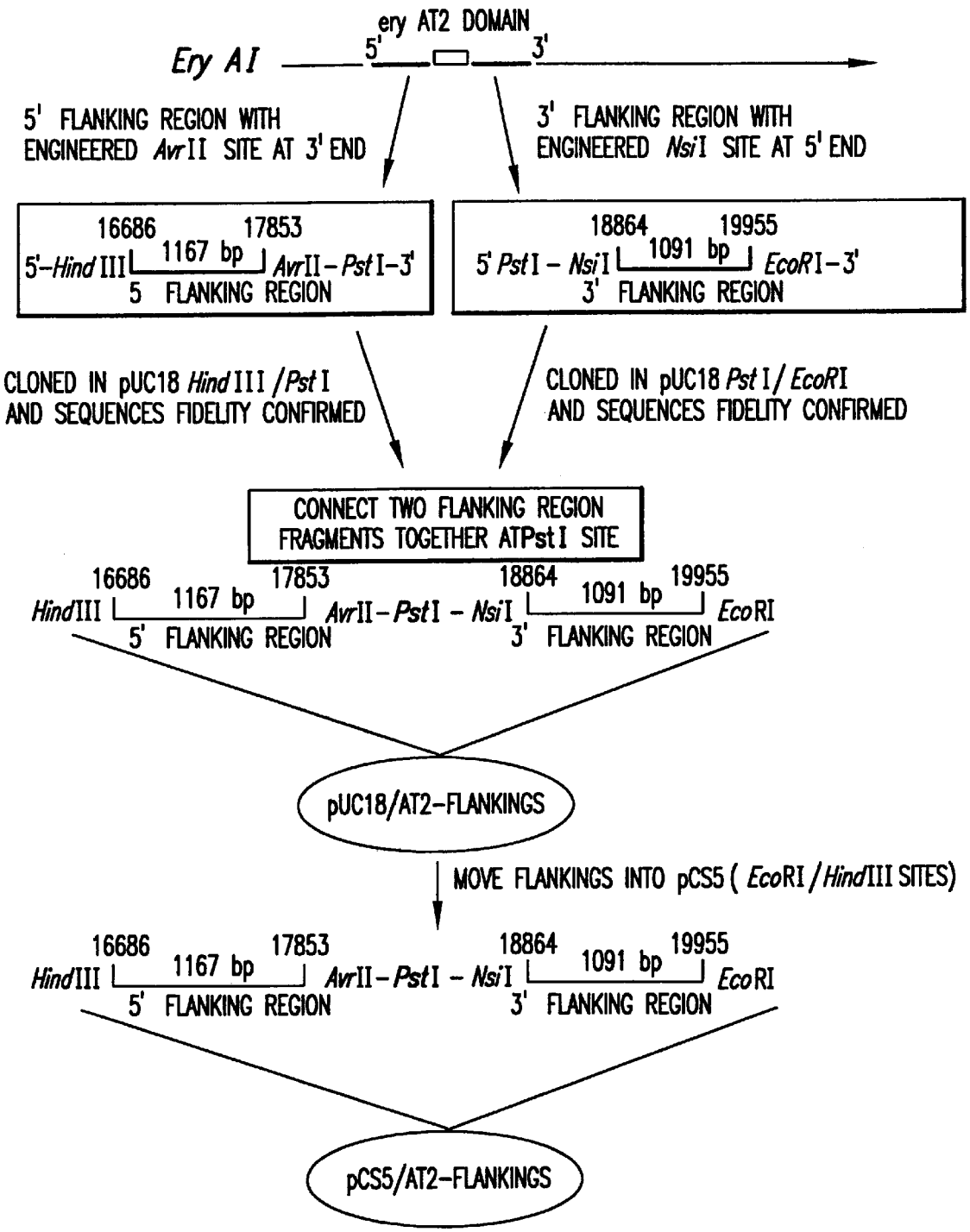
FIG. 13 is a flow diagram depicting the cloning of the EryAT2 flanking regions in plasmid pCS5.
Figure 14:
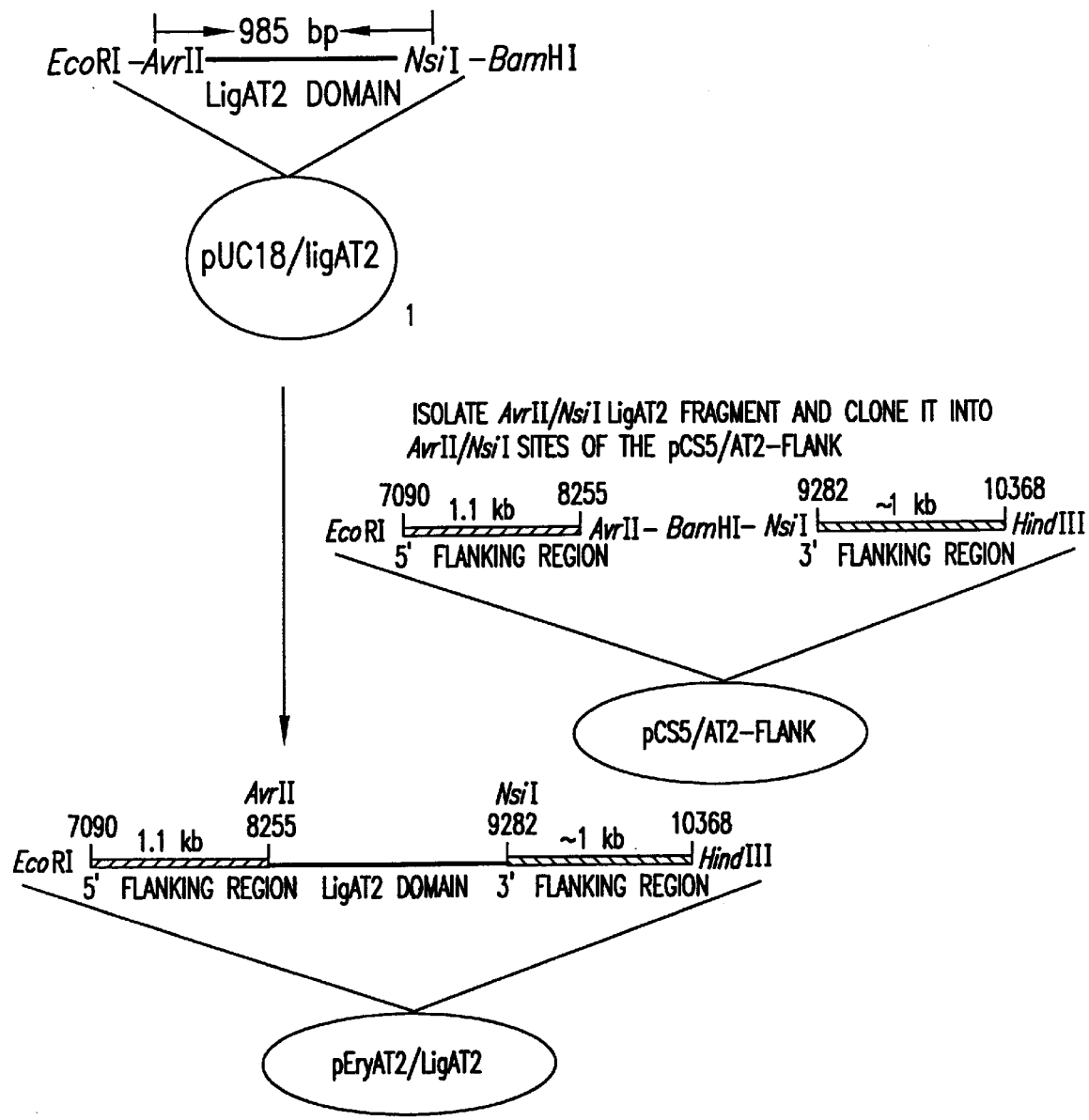
FIG. 14 is a flow diagram depicting construction of pEryAT2/LigAT2.

EXAMPLE 6
Construction of Plasmid pEryAT2/LigAT2 pEryAT2/LigAT2 was constructed using standard methods of recombinant DNA technology. To make a gene-replacement vector specific for the eryAT2 domain, two DNA regions flanking eryAT2 were cloned and positioned adjacent to the DNA encoding the domain to be inserted in order to effect homologous recombination. Boundaries of the AT2 domain were chosen as described in Example 2. The 5' and 3' boundaries of eryAT2 are designated as 8255 and 9282, respectively, and correspond to deposited eryAI sequence (GenBank accession number M63676). To subclone the DNA fragment upstream of the eryAT2 DNA, two PCR oligonucleotides (SEQ ID NO:11 and SEQ ID NO:12) were designed so that a HindIII site was added at the 5' end of the region and AvrII-PstI restriction sites were introduced at the 3' end. For subcloning the 3'-flanking region of eryAT2, two PCR oligonucleotides (SEQ ID NO: 13 and SEQ ID NO:14) were designed so that PstI-NsiI restriction sites were introduced at the 5' end of the region and an EcoRI site at the 3' end. Both the 5'-flanking and 3'-flanking regions (about 1 kb each) were PCR generated as described in Example 3. In the case of the 5'-flanking region, the PCR product was subsequently subcloned into HindIII and PstI sites of pUC18 whereas the PCR product of the 3'-flanking region was subcloned into the PstI and EcoRI sites of pUC18. Ligations, transformations and confirmations of selected clones were performed as in Example 3. The resulting construct containing the AT2 5'-flanking region was designated pUC18/AT 2/5'-flank and the construction containing the AT2 3'-flanking region was designated pUC18/AT2/3'-flank. The two flanking regions were then joined by first isolating the 1 kb PstI and EcoRI fragment (3'-flank) from pUC18/AT2/3'-flank, and ligating this fragment to pUC18/AT2/5'-flank cut with PstI and EcoRI. The ligation was transformed into *E. coli* DH5α and clones isolated as described. The resulting plasmid was named pUC18/AT2-flank (FIG. 13). The 2.2 kb EcoRI and HindIII fragment from pUC18/AT2-flank was then isolated and ligated to pCS5 cut with the same enzymes to generate pCS5/AT2-flank. The final step in the construction of pEryAT2/LigAT2 was to ligate the LigAT2 encoding DNA fragment from pUC18/LigAT2 having AvrII U and NsiI ends (described in Example 2) to pCS5/AT2-flank cut with the same enzymes to give the gene replacement, integration plasmid pEryAT2/LigAT2 (FIG. 14). All ligations were transformed into the intermediate host *E. coli* DH5α and clones selected as previously described.

EXAMPLE 7
Construction of *Sac. erythraea* ER720 EryAT2/LigAT2

An example of a 10-desmethylerythromycin A and 10-desmethyl-12-deoxyerythromycin A producing microorganism was prepared by replacing the methylmalonyl acyltransferase domain of module 2 of the erythromycin PKS (EryAT2) of *Sac. erythraea* ER720 with a newly discovered malonyl acyltransferase domain (LigAT2) from *S. hygroscopicus* ATCC 29253. This was accomplished with the recombinant plasmid, pEryAT2/LigAT2, prepared as described in Example 6. Transformation of ER720 and resolution of the integration event were carried out according to the procedures described in Example 4 using 10 μL of a DNA solution consisting of 3 μL of pEryAT2/LigAT2 DNA from Example 6 at about 1 μg/μL in 7 μL of P$_M$ buffer. Three colonies were confirmed to be thiostrepton resistant and were inoculated into SGGP containing thiostrepton (10 μg/mL) to isolate chromosomal DNA for Southern analysis. Integration of the plasmid DNA into ER720 chromosome was further confirmed by Southern hybridization (data not shown). Hybridization was at 65° C. and the stringency wash was with 0.1×SSC at 65° C.

Figure 15:
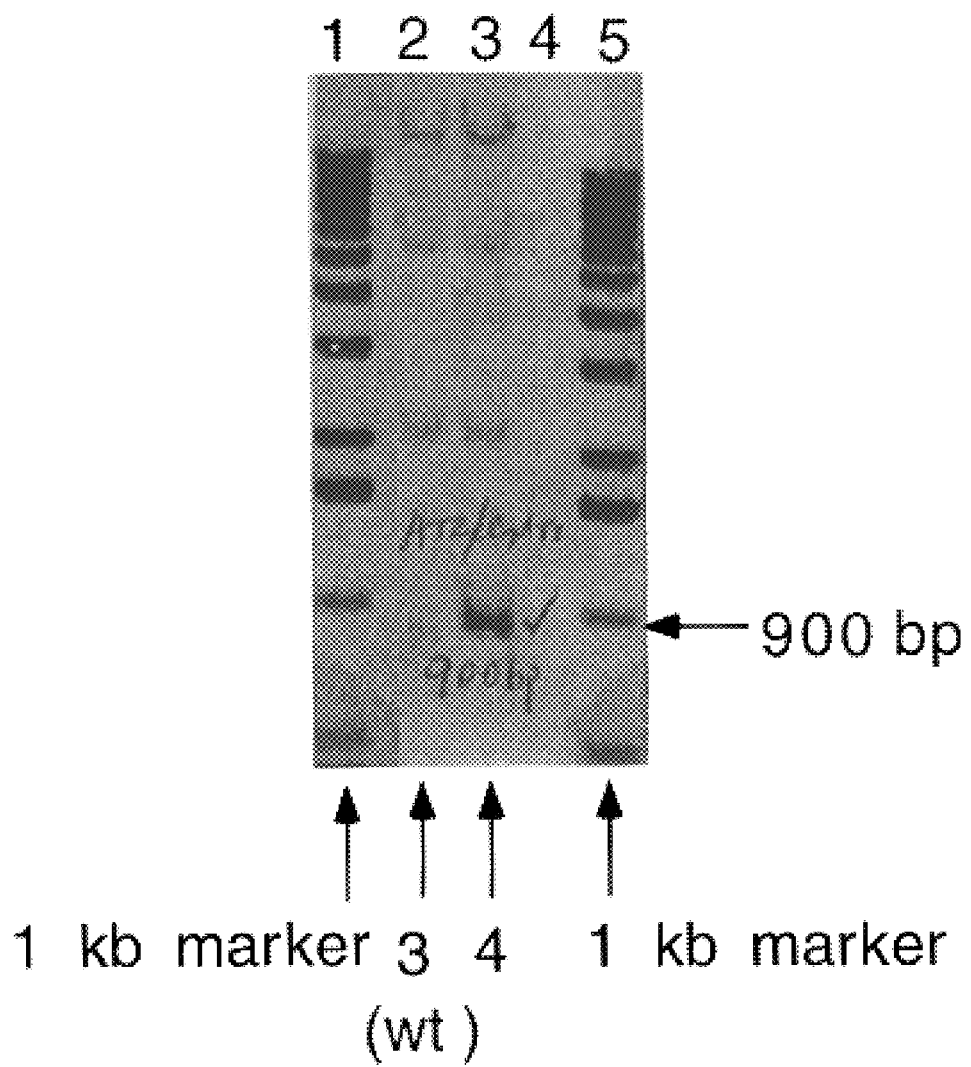
FIG. 15 is a computer generated Phosphorimage of a Southern analysis of chromosomal DNA from *Sac. erythraea* ER720 EryAT2/LigAT2, cut with SphI and probed with an approximately 1 kb LigAT2 sequence. As seen in lane 3, an approximately 900 base pair fragment hybridized with the probe, indicating that LigAT2 had replaced EryAT2 in this resolvant. Lane 2: chromosomal DNA from wild-type (wt) *Sac. erythraea* ER720; lanes 1 and 5: molecular weight markers (1 kb ladder).

The confirmed integrant was rown in SGGP without antibiotic for four days and then plated onto non-selective R3M plates for sporulation. Spores were plated on R3M plates to obtain individual colonies, which were then screened for sensitivity to thiostrepton, indicating loss of the plasmid sequence from the chromosome. Two thiostrepton sensitive colonies were selected and one of these was confirmed by Southern hybridization to have the EryAT2 replaced by LigAT2 (FIG. 15). Hybridization was at 65° C. and the stringency wash was with 0.1×SSC at 65° C. The strain was named *Sac. erythraea* ER720 EryAT2/LigAT2.

EXAMPLE 8
Analysis of Compounds Produced by Sac. erythraea ER720 EryAT2/LigAT2

Compounds produced by the recombinant Sac. erythraea strain, ER720 EryAT2/LigAT2, whose construction is described in Example 7, were characterized by TLC, bioautography and mass spectrometry.

Figure 16:
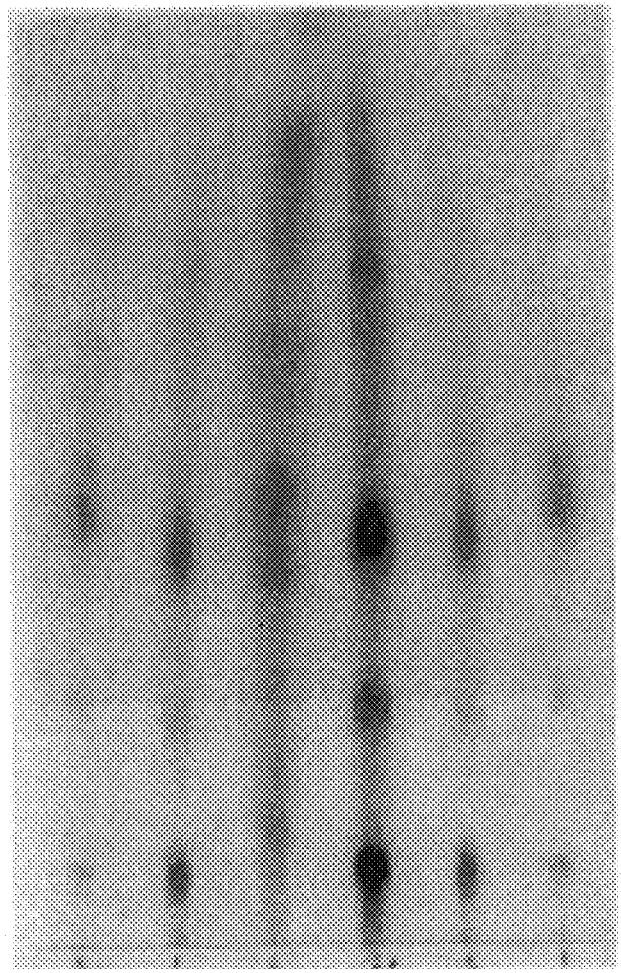
FIG. 16 is a computer reproduction of a TLC plate on which the products produced by *Sac. erythraea* ER720 EryAT2/LigAT2 were run. Lanes 1 and 6: erythromycin B standard (5 µg); lanes 2 and 5: erythromycin A standard (5 µg); lane 4: compounds produced by wild-type *Sac. erythraea* ER720; lane 3: compounds produced by *Sac. erythraea* ER720 EryAT2/LigAT2 resolvant, clone #2-4.

For small scale analysis, the cells were grown in either SGGP or SCM medium for 4–5 days at 30° C. 15 mL of culture was centrifuged for 10 minute in a Sorval GLC4 General Laboratory Centrifuge at setting 10 to remove cells. Ten mL of the resulting supernatant was pH adjusted to 9.0 by the addition of 60 μL of NH$_4$OH. Then 5 mL of ethyl acetate was added, the tube was shaken vigorously for 3 minutes and then centrifuged for approximately 5 min to achieve phase separation. The organic phase was removed to another tube, and the aqueous phase was re-extracted with 5 mL of ethyl acetate. The second organic phase was combined with the first and dried in a Speed Vac. The residue was taken up in 20 μL of ethyl acetate and 10 μL was spotted onto a Merck 60F-254 silica gel TLC plate. The plate was run in isopropyl ether:methanol:NH$_4$OH (75:35:2). Erythromycin derivatives were visualized by spraying the plates with anisaldehyde:sulfuric acid:ethanol (1:1:9). Using this reagent, two novel compounds predicted to be 10-desmethylerythromycin A and 10-desmethyl-12-deoxyerythromycin A, appeared as blue spots with the lower spot running slightly slower than erythromycin A and upper spot running slightly faster than erythromycin A (FIG. 16).

Figure 17:
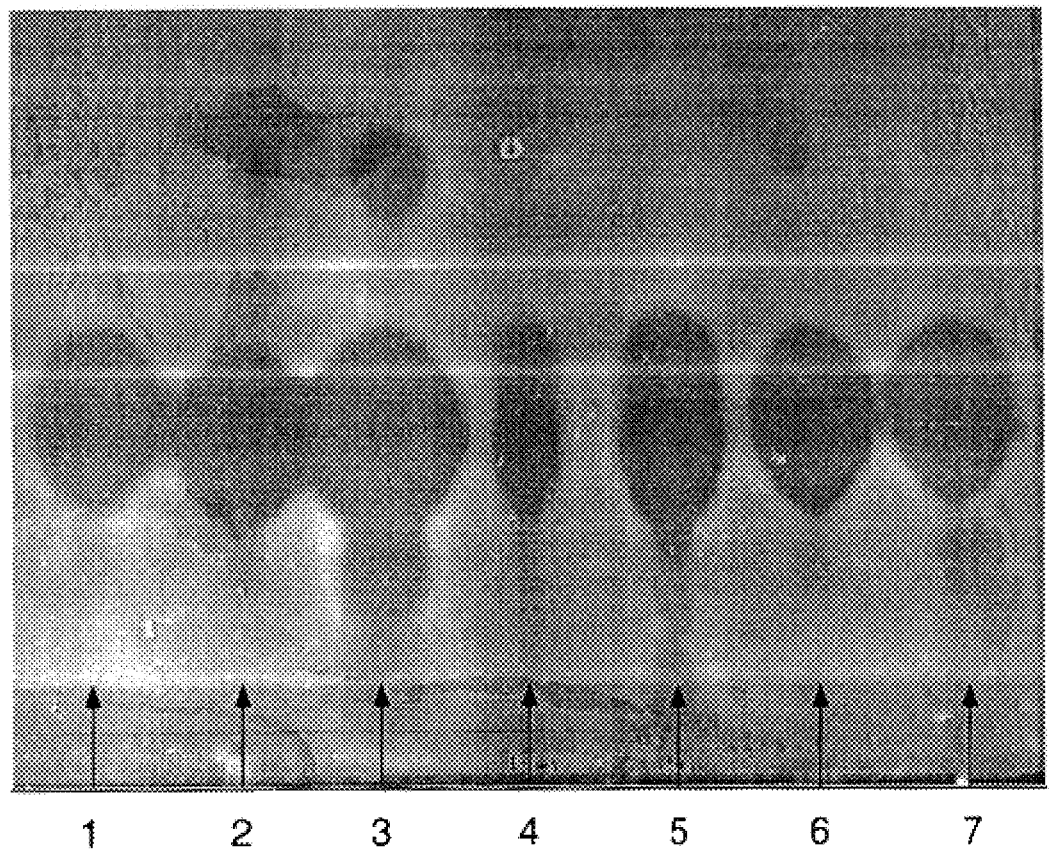
FIG. 17 is a computer reproduction of a Xerox image of a bioautography plate of products made by *Sac. erythraea* ER720 EryAT2/LigAT2 against *S. aureus*. Lanes 1 and 7: erythromycin B standard (1 µg); lanes 2 and 6: erythromycin A standard; lane 3: compounds produced by wild-type *Sac. erythraea* ER720; lane 4: extract from an 0.1 mL culture of *Sac. erythraea* ER720 EryAT2/LigAT2 resolvant clone #2-4: lane 5: extract from an 0.5 mL culture of *Sac. erythraea* ER720 EryAT2/LigAT2 resolvant clone #2-4.

To detect biological activity, a TLC-bioautography assay was performed. In this assay, 0.2 to 1 microliter of the extracted sample from above was spotted onto a TLC plate which was run as described. The plate was then air-dried and placed in a sterile bio-assay dish (245×245×25 mm). The plate was then covered with 100 mL of antibiotic medium 11 (DIFCO-BACTO) containing Staphylococcus aureus as an indicator strain. The inhibition zones were developed by overnight incubation of the plate at 37° C. As shown in FIG. 17 (TLC-bioautography), the two novel spots (compounds) each have bioactivity against Staphylococcus aureus.

To determine whether the novel spots seen on TLC had the molecular masses corresponding to the predicted 10-desmethylerythromycin A and 10-desmethyl-12-deoxyerythromycin A, an ethyl acetate extract was further analyzed by mass spectrometry. The mass spectrometry samples were isolated by TLC similarly to the method described above except that plates were not sprayed with the anisaldehyde reagent. Instead, two regions which contain the novel spots were scraped from the TLC plate and the silica resin re-extracted with ethyl acetate-methanol (1:1) and then twice with ethyl acetate. The combined solvent phases were then dried in a Speed Vac. In addition to the samples described above, a crude ethyl acetate extract was also analyzed by LC-MS, in which the sample components were first separated by liquid chromatography and then analyzed by mass spectrometry. Mass spectrometric analysis revealed the two novel compounds to have masses of 720 and 704, which correspond to the molecular ion plus a proton (M+H$^+$) of 10-desmethylerythromycin A and 10-desmethyl-12-deoxyerythromycin A, respectively.

EXAMPLE 9
Cloning of the venAT Domain from Streptomyces venezuelae

A genomic library of Streptomyces venezuelae ATCC 15439 DNA was constructed in the bifunctional cosmid pNJ1 (Tuan, et al., Gene 90: 21–29 (1990)) using standard methods of recombinant DNA technology. A cosmid from this library, pVen17, was characterized by Southern analysis and SstI fragments of approximately 3.5, 3.8, and 4.0 kb were found to hybridize to a 1.37 kb SmaI fragment that encompasses the ketosynthase (KS) domain from module 2 of the erythromycin PKS gene eryAI (Donadio et al., Science 252: 675–679 (1991)). The 4.0 kb SstI fragment was then subcloned into pUC19 to give pVen4.0. The nucleotide sequence of pVen4.0 insert DNA was determined from single strand DNA templates prepared from M13mp18 and M13mp19 (Yanisch-Perron, et al., Gene, 33:103 (1985)) subclones using Sequenase version 2.0 with 7-deaza-dGTP (United States Biochemnical, Cleveland, Ohio) and 5'-[α-$^{32}$P] or 5'-[α-$^{33}$P]-dCTP (NEN Research Products, Boston, Mass.). Because pVen4.0 did not contain the entire AT domain, the nucleotide sequence was extended using pVen17 DNA as the template. The nucleotide sequence of the venAT domain (SEQ ID NO:2) and its corresponding amino acid sequence (SEQ ID NO:32) is shown in FIG. 18 (top and bottom strands respectively).

Figure 19:
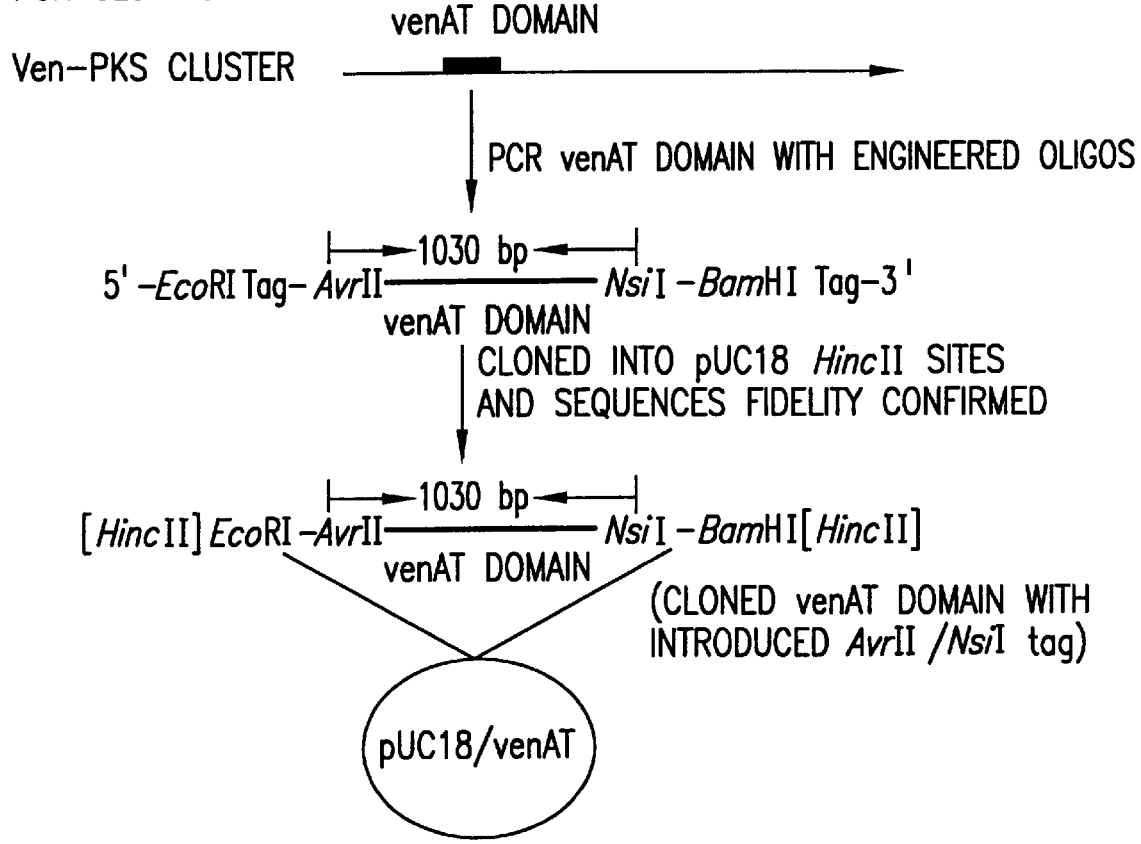
FIG. 19 is a diagrammatic representation of the strategy to clone the venAT domain.
Figure 23:
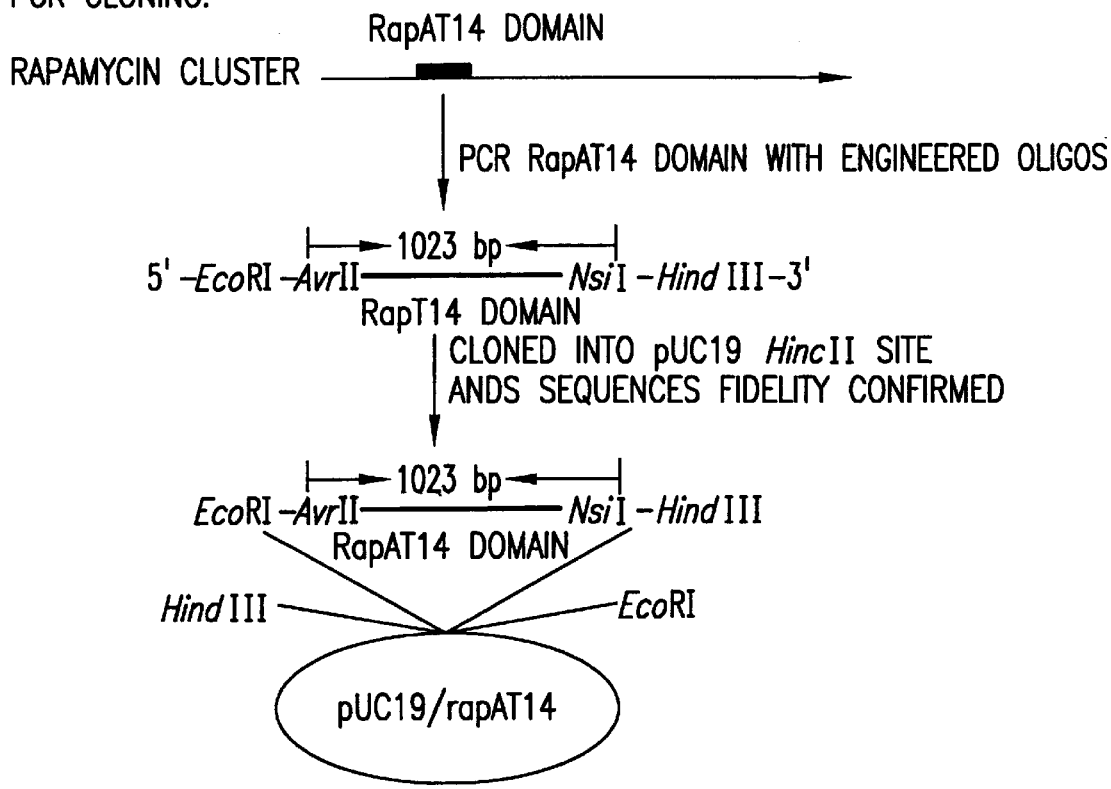
FIG. 23 is a diagrammatic representation of the strategy to clone the rapAT14 domain.
Figure 24:
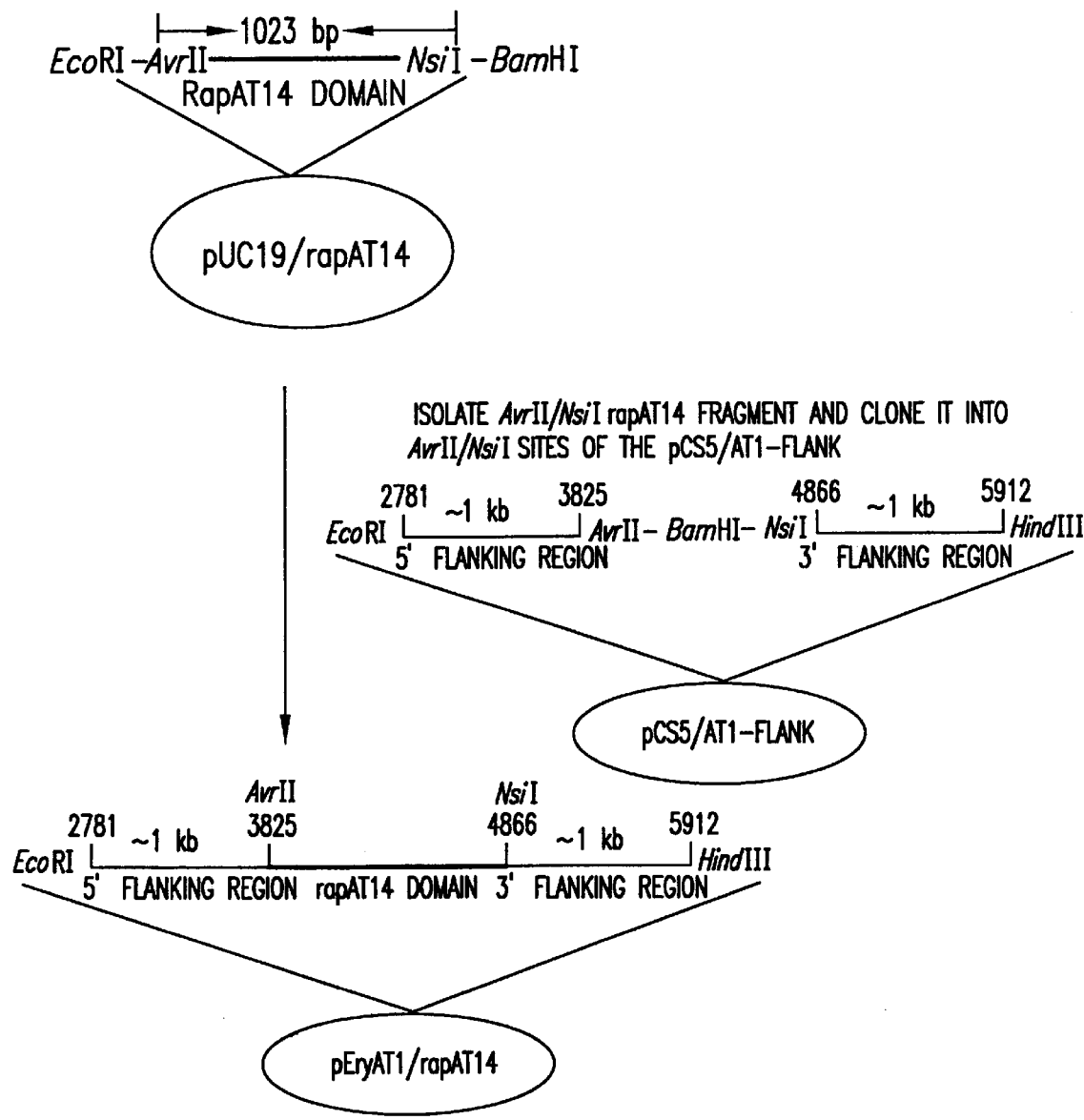
FIG. 24 is a flow diagram depicting construction of pEryAT1/rapAT14.

EXAMPLE 10
Construction of Plasmid pEryAT1/venAT pEryAT1/venAT was constructed using standard methods of recombinant DNA technology according to the schematic outlines of FIGS. 23 and 24. Two PCR oligonucleotides (SEQ ID NO:15 and SEQ ID NO:16) were designed to subclone the 1.03 kb DNA fragment that encodes the venAT domain (FIG. 19) from the S. venezuelae PKS cluster and to introduce two unique restriction sites, AvrII and NsiI, for cassette cloning (described in Example 2). This necessitated nucleotide changes (shown in bold in FIG. 19) at the beginning and near the end of the venAT sequence (underlined nucleotides are the wild-type sequence). In addition, two other restriction sites, EcoRI and BamHI, were also introduced at the 5' ends of the N-terminal and C-terminal oligonucleotides, respectively, for convenient subcloning of the PCR-generated product. The approximately 1 kb venAT-encoding DNA was PCR amplified from cosmid pVen17 template DNA (Example 2) using Vent$_R$® DNA Polymerase (New England Biolabs). A typical PCR reaction contained 10 μL ThermoPol Buffer, 10 μL formamide, 10 μL of 20% glycerol, 55 μL water, 100 pmole of each primer, and approximately 0.2 μg DNA. The sample was heated to 99° C. for 2 minutes, and then allowed to cool to 80° C. for 2 minutes, at which time 16 μL of a 1.25 mM mixture of dATP, dCTP, dGTP, and dTTP and 2 units of Vent DNA polymerase were added. A temperature cycle of 35 seconds at 96.5° C. and 2 minutes 15 seconds at 72° C. was then repeated 30 times, followed by a 3 minute incubation at 72° C. The desired PCR fragment was then isolated from low melting agarose by standard procedures. The PCR product was ligated to HindIII digested pUC18 and transformed into E. coli DH5α ((GIBCO BRL) according to the manufacturer's instructions. Clones were selected on LB plates containing 150 μg/mL ampicillin and 50 μL of a 2% solution of X-gal for blue/white selection. Clones were confirmed by restriction analysis and the fidelity of the insert was confirmed by DNA sequencing. The final construct was named pUC18/venAT.

Figure 20:
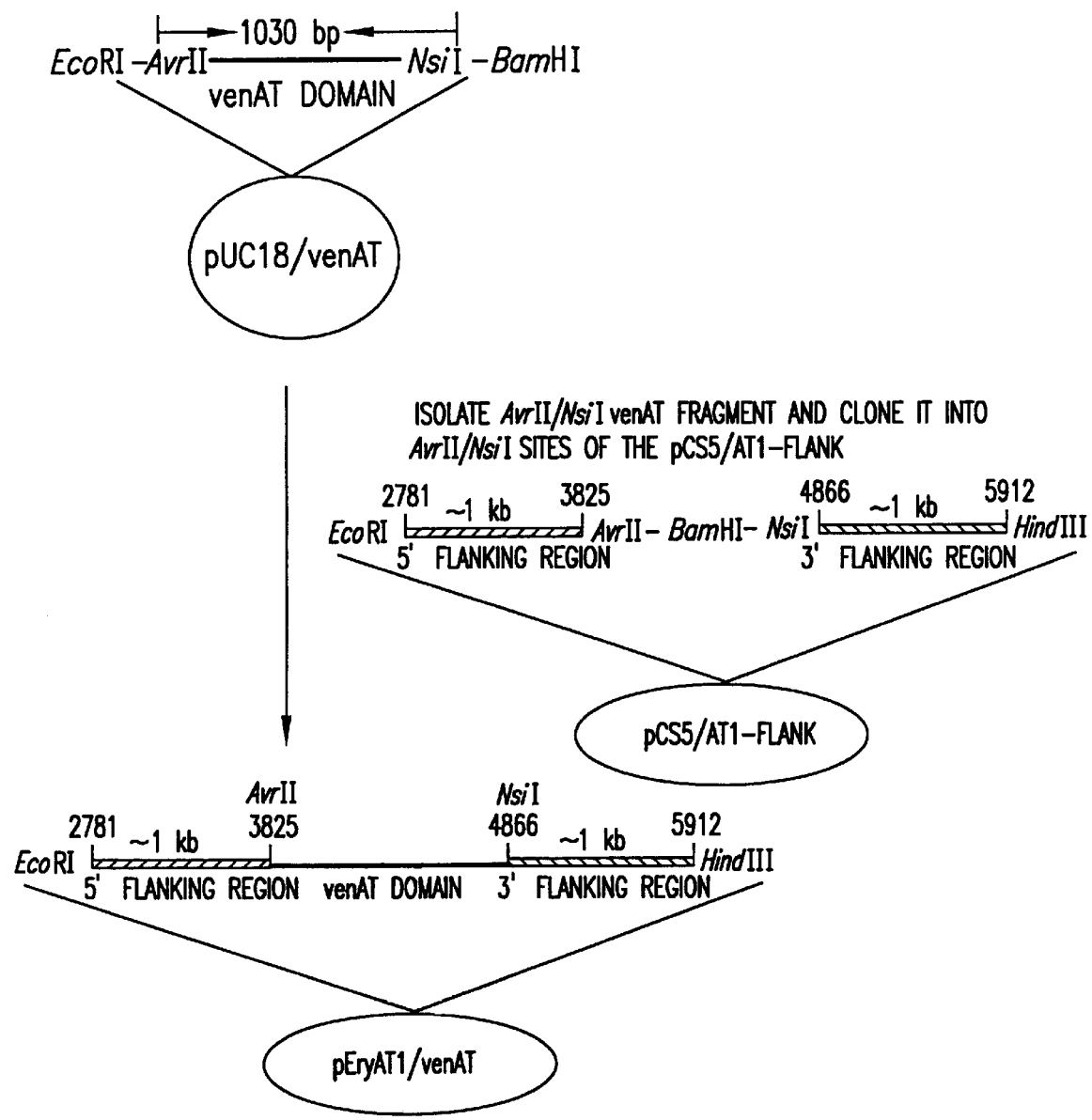
FIG. 20 is a flow diagram depicting construction of pEryAT1/venAT.

The final step in the construction of pEryAT1/venAT was to ligate the 1 kb venAT fragment having AvrII and NsiI ends to pCS5/AT1-flank (Example 3) cut with the same enzymes to give the gene replacement/integration plasmid pEryAT1/venAT (FIG. 20). All ligations were transformed into the intermediate host E. coli DH5α and clones selected as previously described.

EXAMPLE 11
Construction of Sac. erythraea ER720 EryAT1/venAT

A 12-desmethyl-12-deoxyerythromycin A producing microorganism was prepared by replacing the methylmalonyl acyltransferase domain of module 1 of the erythromycin PKS (EryAT1) of Sac. erythraea ER720 with a newly discovered malonyl acyltransferase domain (venAT) from S. venezuelae ATCC 15439. This was accomplished with the recombinant plasmid, pEryAT1/venAT, prepared as in Example 10. Transformation of ER720 and resolution of the integration event were carried out as described in Example 4 using 10 µL of DNA solution consisting of 3 µL of pEryAT1/venAT DNA at about 1 µg/mL in 7 µL of $P_M$ buffer. One thiostrepton resistant colony was isolated and was inoculated into SGGP containing thiostrepton (10 µg/mL) to isolate chromosomal DNA for Southern analysis. Integration of the plasmid DNA into the ER720 chromosome was further confirmed by Southern hybridization (data not shown). Hybridization was at 65° C. and the stringency wash was with 0.1×SSC at 65° C.

Figure 21:
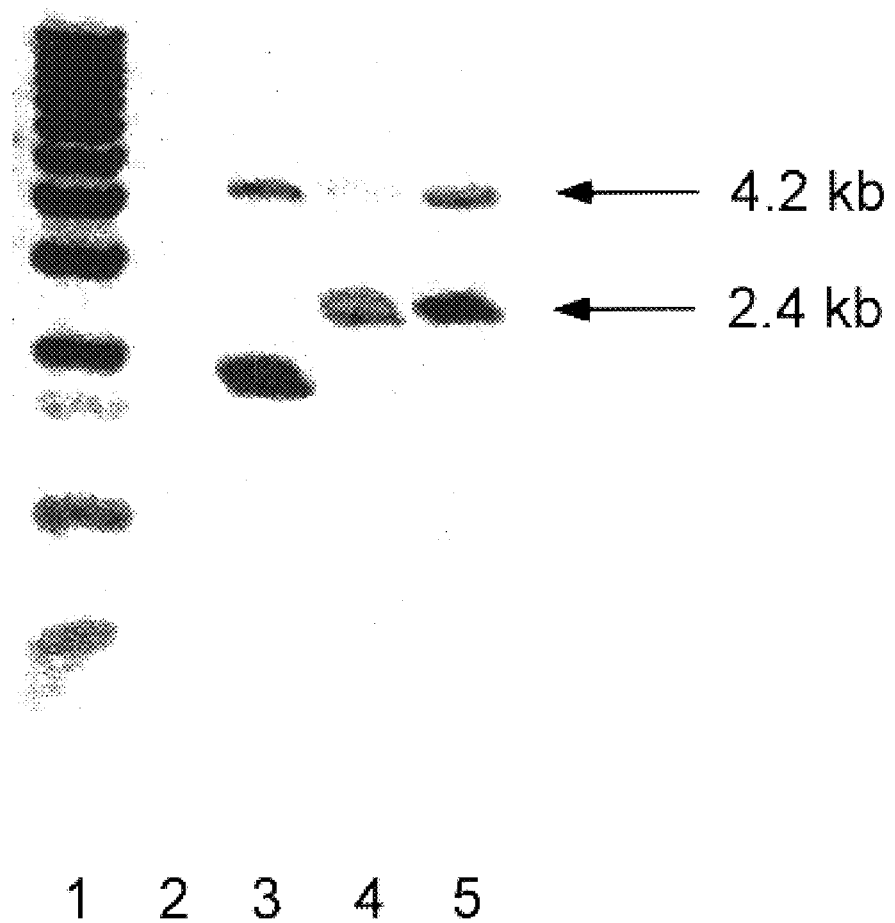
FIG. 21 is a computer generated PhosphorImage of a Southern analysis of chromosomal DNA from *Sac. erythraea* ER720 EryAT1/venAT resolvants, cut with PvuII and probed with a venAT sequence. As seen in lanes 4 and 5, the probe hybridized with fragments of 4.2 and 2.4 kb, indicating that venAT had replaced EryAT1 in these resolvants. Lane 1: molecular weight markers (1 kb ladder): lane 2: chromosomal DNA from a wild-type *Sac. erythraea* ER720: lane 3: chromosomal DNA from a *Sac. erythraea* ER720 EryAT1/venAT integrant; lane 4: chromosomal DNA from *Sac. erythraea* ER720 EryAT1/venAT resolvant clone #C.1: lane 5: chromosomal DNA from *Sac. erythraea* ER720 EryAT1/venAT resolvant clone #C.4.

The confirmed integrant was grown in SGGP without antibiotic for four days and then diluted 1000 fold into fresh medium and grown for 4 more days. Cells were then plated onto non-selective R3M plates for sporulation. Spores were plated on R3M plates to obtain individual colonies. which were then screened for sensitivity to thiostrepton, indicating loss of the plasmnid sequence from the chromosome. Four thiostrepton sensitive colonies were selected and 2 of these were confirmed by Southern hybridization, using conditions described above, to have the EryAT1 replaced by venAT (FIG. 21). The strain was named Sac. erythraea ER720 EryAT1/venAT.

EXAMPLE 12
Analysis of Compounds Produced by Sac. erythraea ER720 EryAT1/venAT Compounds produced by the recombinant Sac. erythraea strain, ER720 EryAT1/venAT. whose construction is described in Example 11, were characterized by TLC, bioautography, and mass spectrometry.

Figure 22:
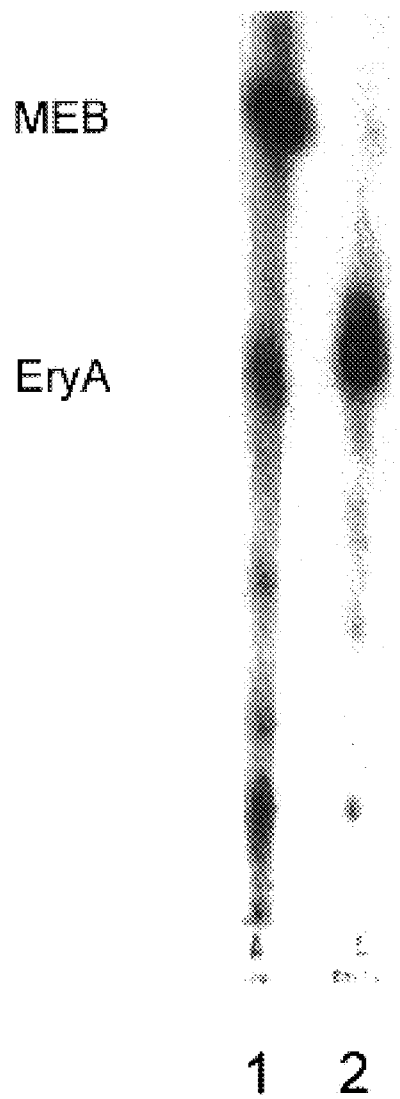
FIG. 22 is a computer reproduction of a TLC plate on which the products produced by *Sac. erythraea* ER720 EryAT1/venAT were run. Lane 1: erythromycin A standard (EryA; 5 µg) and 3-α-mycarosylerythronolide B (MEB; 10 µg); lane 2: compounds produced by *Sac. erythraea* ER720 EryAT1/venAT resolvant clone #C.4.

For TLC analysis cells were grown in either SGGP or SCM medium (20 g Soytone, 15 g Soluble Starch, 10.5 g MOPS, 1.5 g Yeast Extract and 0.1 g $CaCl_2$ per liter of distilled $H_2O$) for 4–5 days at 30° C. The culture (1.5 µL) was centrifuged for 1 minute in a microfuge to remove cells. One mL of the resulting supernatant was removed to another microfuge tube and the pH adjusted to 9.0 by the addition of 6 µL of $NH_4OH$. Then 0.5 mL of ethyl acetate was added, the tube was vortexed for 10 sec and then centrifuged for approximately 5 min to achieve phase separation. The organic phase was removed to another tube, and the aqueous phase was re-extracted with 0.5 mL of ethyl acetate. The second organic phase was combined with the first and dried in a Speed Vac. The residue was taken up in 10 µL of ethyl acetate and the entire sample was spotted onto a Merck 60F-254 silica gel TLC plate. The plate was run in isopropyl ether:methanol:$NH_4OH$ (75:35:2). Erythromycin derivatives were visualized by spraying the plates with anisaldehyde:sulfuric acid:ethanol (1:1:9). Using this reagent, a novel compound predicted to be 12-desmethyl-12-deoxyerythromycin A, appeared as a blue spot running slightly faster than erythromycin A (FIG. 22).

To detect biological activity, a TLC-bioautography assay was performed. In this assay, one µL of an extract prepared as above was spotted onto a TLC plate which was run as described above. The plate was then air-dried, placed face down on top of 100 mL of antibiotic medium 11 (DIEFCO-BACTO) containing Staphylococcus aureus as an indicator strain in a sterile bio-assay dish (245×245×25 mm) and incubated overnight at 37° C. As with the positive controls, a clear zone of inhibition developed around the sample spot indicating that the novel compound was bioactive.

To determine whether the novel spot seen on TLC had the molecular mass corresponding to the predicted 12-desmethyl-12-deoxyerythromycin A, an ethyl acetate extract was further analyzed by mass spectrometry. The mass spec samples were isolated by TLC basically as described above except that plates were not sprayed with anisaldehyde. The region of the novel spot was instead scraped from the TLC plate and the silica resin re-extracted with ethyl acetate-methanol (2:1) and then twice with ethyl acetate. The combined solvent phases were then dried in a Speed Vac. Mass spectrometric analysis revealed the novel compound to have a mass of 704, which corresponds to the molecular ion plus a proton ($M+H^+$) of 12-desmethyl-12-deoxyerythromycin A.

EXAMPLE 13
Construction of Plasmid pUC19/rapAT14

Two PCR oligonucleotides (SEQ ID NO:17 and SEQ ID NO:18) were designed to subclone the 1023 bp rapAT14-encoding DNA fragment from the rapamycin biosynthetic gene cluster (GenBank Accession #: X86780) and to introduce two unique restriction sites, AvrII and NsiI, for cassette cloning (described in Example 2). This necessitated nucleotide changes (shown in bold in FIG. 23) at the beginning and near the end of the rapAT14 sequence. (In FIG. 23, the underlined nucleotides are the wild-type sequence.) In addition, two other restriction sites, EcoRI and HindIII, were also introduced at the 5' ends of the N-terminal and C-terminal oligonucleotides, respectively, for convenient subcloning of the PCR-generated product. The approximately 1 kb rapAT14-encoding DNA was amplified by PCR using chromosomal DNA from Streptomyces hygroscopicus ATCC 29253 as template. The PCR conditions were as follows: The 100 µL reaction mixture contains 10 µL of 10× Thermopol Buffer (New England Biolabs), 2% glycerol, 10% formamide, 100 pmoles of each oligo, 100–200 ng of template DNA and water to 84 µL. The sample was then heated to 99° C. for two minutes followed by cooling to 80° C. for two minutes at which time 16 µL of a dNTP solution (1.25 mM dATP and dTTP, 1.5 mM dCTP and dGTP) and 1 µL of Vent$_R$® DNA Polymerase (New England Biolabs) was added. Cycling was as follows: 30 cycles at 96.5° C./35 sec, 65° C./1 min and 72° C./1.5 min followed by one cycle at 72° C. for 3 min. The entire reaction was then run on a 1.2% low-melting agarose gel and the desired fragment was isolated by melting the appropriate gel slice at 65° C., adding 3 volumes of TE buffer, extracting 2× with phenol and once with chloroform, and ethanol precipitating the aqueous phase. The isolated DNA was ligated directly into HincII digested pUC19. The ligation mixture was transformed into E. coli DH5α (GIBCO BRL) according to the manufacturer's instructions and transformants were selected on LB plates containing 150 µg/mL ampicillin and 50 µL of a 2% solution of X-gal for blue/white selection. Clones were confirmed by restriction analysis and the fidelity of the insert was confirmed by DNA sequencing. The final plasmid construct was named pUC19/rapAT14.

EXAMPLE 14
Construction of Plasmid pEryAT1/rapAT14 pEryAT1/rapAT14 was constructed using standard methods of recombinant DNA technology according to the schematic outlines of FIG. 24. To make a gene-replacement-vector specific for the eryAT1 domain, the two DNA regions immediately adjacent to eryAT1 were cloned and positioned adjacent to the DNA encoding the rapAT14 domain in order to allow homologous recombination to occur. The strategy and protocol for constructing the intermediate plasmid containing the flanking regions, pCS5/AT1-flank, are described in Example 3 and FIG. 9. To insert the rapAT14 fragment between the flanking regions, pUC19/rapAT14 (from Example 13) was digested with NsiI and AvrII and the resulting 1 kb fragment was isolated from a 0.8% agarose gel with Prep-A-Gene. pCS5/AT1-flank was also digested with these enzymes and the linearized plasmid was isolated from 0.8% agarose gel. The two fragments were ligated, transformed into the intermediate host *E. coli* DH5α and ampicillin resistant clones were selected as previously described. Insertion of the rapAT14 fragment between the ery flanking regions was confirmed by restriction analysis and the resulting plasmllid was called pEryAT1/rapAT14.

EXAMPLE 15
Construction of *Sac. erythraea* ER720 EryAT1/rapAT14

An example of a 12-desmethyl-12-deoxyerythromycin A producing microorganism was prepared by replacing the methylmalonyl acyltransferase domain of module 1 of the erythromycin PKS (EryAT1) of *Sac. erythraea* ER720 with the acyltransferase domain from module 14 of the rapamycin PKS from *S. hygroscopicus* ATCC 29253. This was accomplished with the recombinant plasrnid, pEryAT1/rapAT14, prepared as described in Example 14. Transformation of *Sac. erythraea* ER720 and resolution of the integration event were carried out according to the following method. *Sac. erythraea* ER720 cells were grown in 50 mL of SGGP medium (per 1 liter aqueous solution: 4 g peptone, 4 g yeast extract, 4 g casamino acids, 2 g glycine, 0.5 g $MgSO_4 \cdot 7 H_2O$, 10 g glucose 20 mL of 500 mM $KH_2PO_4$) for 3 days at 32° C. and then washed in 10 mL of 10.3% sucrose. The cells were resuspended in 10 mL of $P_M$ buffer containing 1 mg/mL lysozyme and incubated at 30° C. for 15–30 minutes until most of the mycelial fragments were converted into spherical protoplasts. ($P_M$ buffer per 1 liter aqueous solution: 200 g sucrose, 0.25 g $K_2SO_4$ in 890 mL $H_2O$, with the addition after sterilization of 100 mL 0.25 M TES, pH7.2, 2 mL trace elements solution (Hopwood, et al, 1985, Genetic Manipulation of Streptomyces A Laboratory Manual, The John Innes Foundation), 0.08 mL 2.5 M $CaCl_2$, 10 mL 0.5% $KH_2PO_4$, 2 mL 2.5M $MgCl_2$.) The protoplasts were washed once with $P_M$ and then resuspended in 3 mL of the same buffer.

Transformation was accomplished by centrifuging 200 µL of protoplasts for 15 seconds in a microfuge, decanting the supernatant, and resuspending the protoplasts in the $P_M$ remaining in the tube. Ten µL of DNA solution was added (3 µL of pEryAT1/rapAT14 DNA from Example 14 at about 1 µg/µL in 7 µL of $P_M$ buffer) and mixed with the protoplasts by gently tapping the tube. Two tenths of a milliliter of 25% PEG 8000 in T buffer (Hopwood, et al, 1985, Genetic Manipulation of Streptomyces A Laboratory Manual, The John Innes Institute) was then added, mixed by pipetting the solution 3 times and the suspension irnnediately spread on a dried R3M plate. The plate was incubated at 30° C. for 20 hours and overlaid with 2 mL of water containing 100 µg/mL thiostrepton, dried briefly and incubated 4 more days at 30° C.

To select stable transformants (integrants) colonies arising on the transformation plates were re-streaked onto R3M plates containing thiostrepton (20 µg/mL). Four colonies were confirmed to be thiostrepton resistant and were inoculated into 30 mL of SGGP contaminig thiostrepton (10 µg/mL). After growth for 3 days, one mL of each culture was extracted with ethyl acetate as described in Example 5, and run on a TLC plate to confirm that the strains were no longer making erythromycin A due to insertional inactivation by the integrating plasmid.

Figure 25:
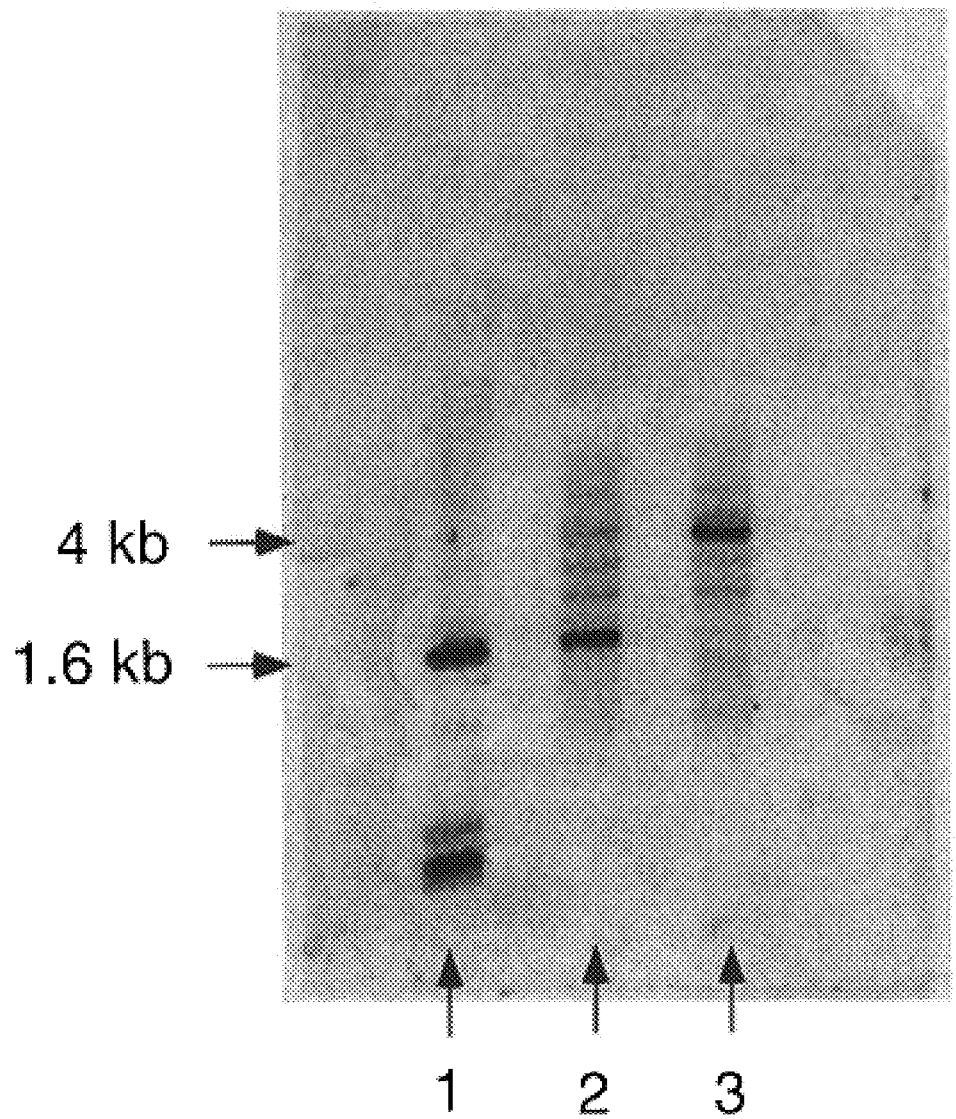
FIG. 25 is a computer generated PhosphorImage of a Southern analysis of chromosomal DNA from an *Sac. erythraea* ER720 EryAT1/rapAT14 resolvant, cut with StyI and probed with an EcoRI-HindIII fragment from pCS5AT1-flank. As shown in lane 2 the probe hybridized with a 1.6 kb fragment indicating that rapAT14 had replaced EryAT1 in the chromosome of this resolvant. Lane 1: molecular weight markers (1 kb ladder); lane 2: chromosomal DNA from *Sac. erythraea* ER720 EryAT1/rapAT14 resolvant clone #4-A(1); lane 3: chromosomal DNA from wild-type *Sac. erythraea* ER720.

Integrants #1 and #4 were grown in SGGP without antibiotic for four days and then plated onto non-selective R3M plates for sporulation. Spores were plated on R3M plates to obtain individual colonies, which were then screened for sensitivity to thiostrepton, indicating loss of the plasmid sequence from the chromosome. Six thiostrepton sensitive colonies were isolated from integrant #4 and one of these (4-A-1) was confirmed by Southern hybridization to have the EryAT1 replaced by the rapAT14 (FIG. 25). Hybridization was at 65° C. and the stringency wash was with 0.1×SSC at 65° C. The strain was named *Sac. erythraea* ER720 EryAT1/rapAT14.

EXAMPLE 16
Analysis of Compounds Produced by *Sac. erythraea* ER720 EryAT1/rapAT14

Figure 26:
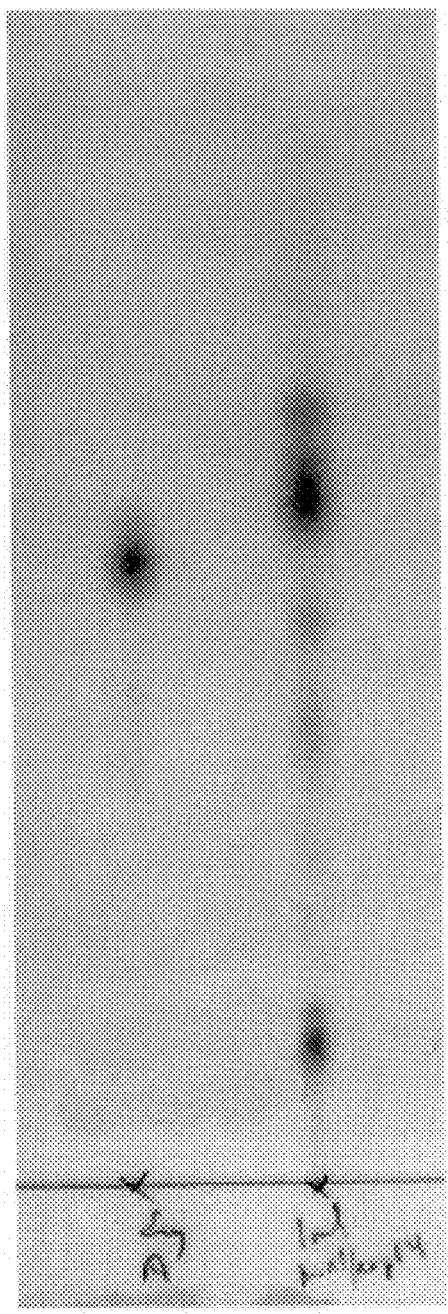
FIG. 26 is a computer reproduction of a TLC plate on which the products produced by *Sac. erythraea* ER720 EryAT1/rapAT14 were run Lane 1: erythromycin A standard (5 µg): lane 2: compounds produced by *Sac. erythraea* ER720 EryAT1/rapAT14 resolvant.

Compounds produced by the recombinant *Sac. erythraea* strain, ER720 EryAT1/rapAT14, whose construction is described in Example 15, were characterized by TLC and mass spectrometry. For TLC analysis strain 4A-1 was grown in SCM medium (20 g Soytone, 15 g Soluble Starch, 10.5 g MOPS, 1.5 g Yeast Extract and 0.1 g $CaCl_2$ per liter of distilled $H_2O$) for 4 days at 30° C. The culture (1.5 mL) was centrifuged for 1 minute in a microfuge to remove cells. One mL of the resulting supernatant was removed to another microfuge tube and the pH adjusted to 9 by the addition of 6 µL of $NH_4OH$. Then 0.5 µL of ethyl acetate was added, the tube was vortexed for 10 sec and then centrifuged for approximately 5 min to achieve phase separation. The organic phase was removed to another tube, and the aqueous phase was re-extracted with 0.5 mL of ethyl acetate. The second organic phase was combined with the first and dried in a Speed Vac. The residue was taken up in 13 µL of ethyl acetate and 10 µL was spotted onto a Merck 60F-254 silica gel TLC plate. The plate was run in isopropyl ether:methanol:$NH_4OH$ (75:35:2). Erythromycin derivatives were visualized by spraying the plates with anisaldehyde:sulfuric acid:ethanol (1:1:9). Using this reagent, a novel compound predicted to be 12-desmethyl-12-deoxyerythromycin A, appeared as a blue spot running slightly faster than erythromycin A (FIG. 26).

Figure 33:
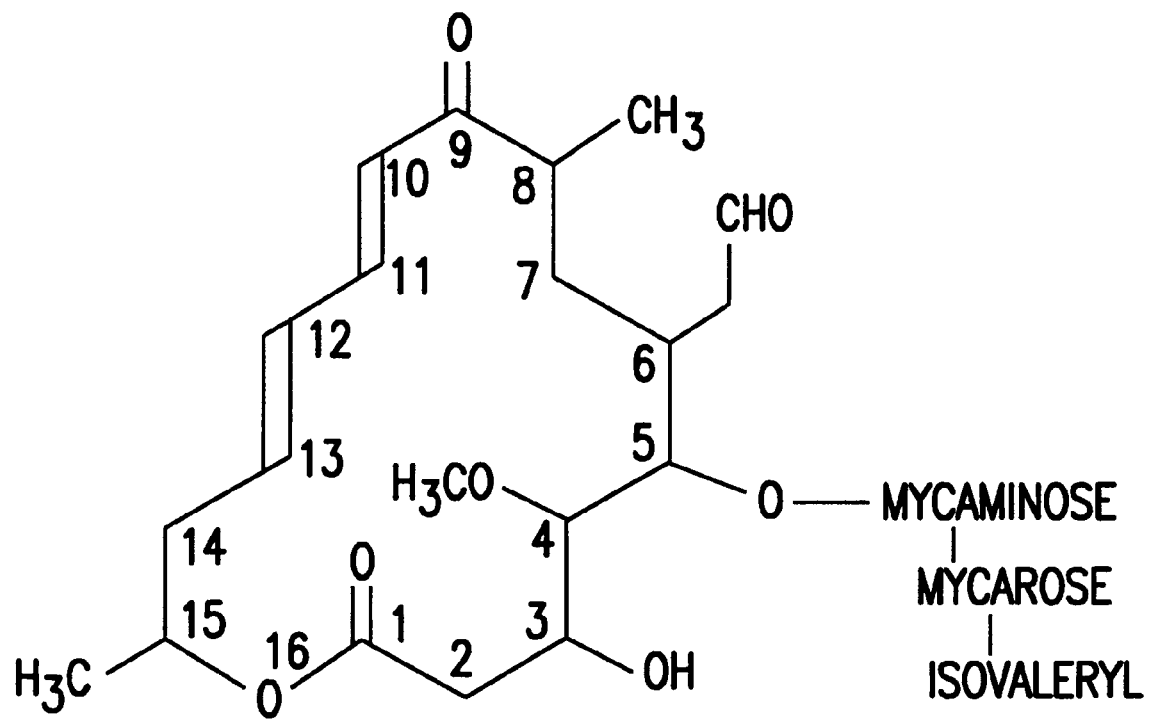
FIG. 33 is a diagram of the structure of the macrolide ring of niddamycin.

To determine whether the novel spot seen on TLC has the molecular mass corresponding to the predicted 12-desmethyl-12-deoxyerythromycin A, an ethyl acetate extract was further analyzed by Mass Spectrometry. *Sac. erythraea* ER720 EryAT1/rapAT14 was grown in SCM medium for 4 days. Ten mL of culture was centrifuged to remove mycelia and pH of the supernatant was adjusted to 9 with $NH_4OH$. The supernatant was then extracted twice with ethyl acetate and the organic phases pooled and dried. As shown in FIG. 33, mass spectrometric analysis of this crude ethyl acetate extract shows the mass of the novel spot to be 704, which corresponds to the molecular ion plus a proton (M+H$^+$) of 12-desmethyl-12-deoxyerythromycin A.

Figure 27:
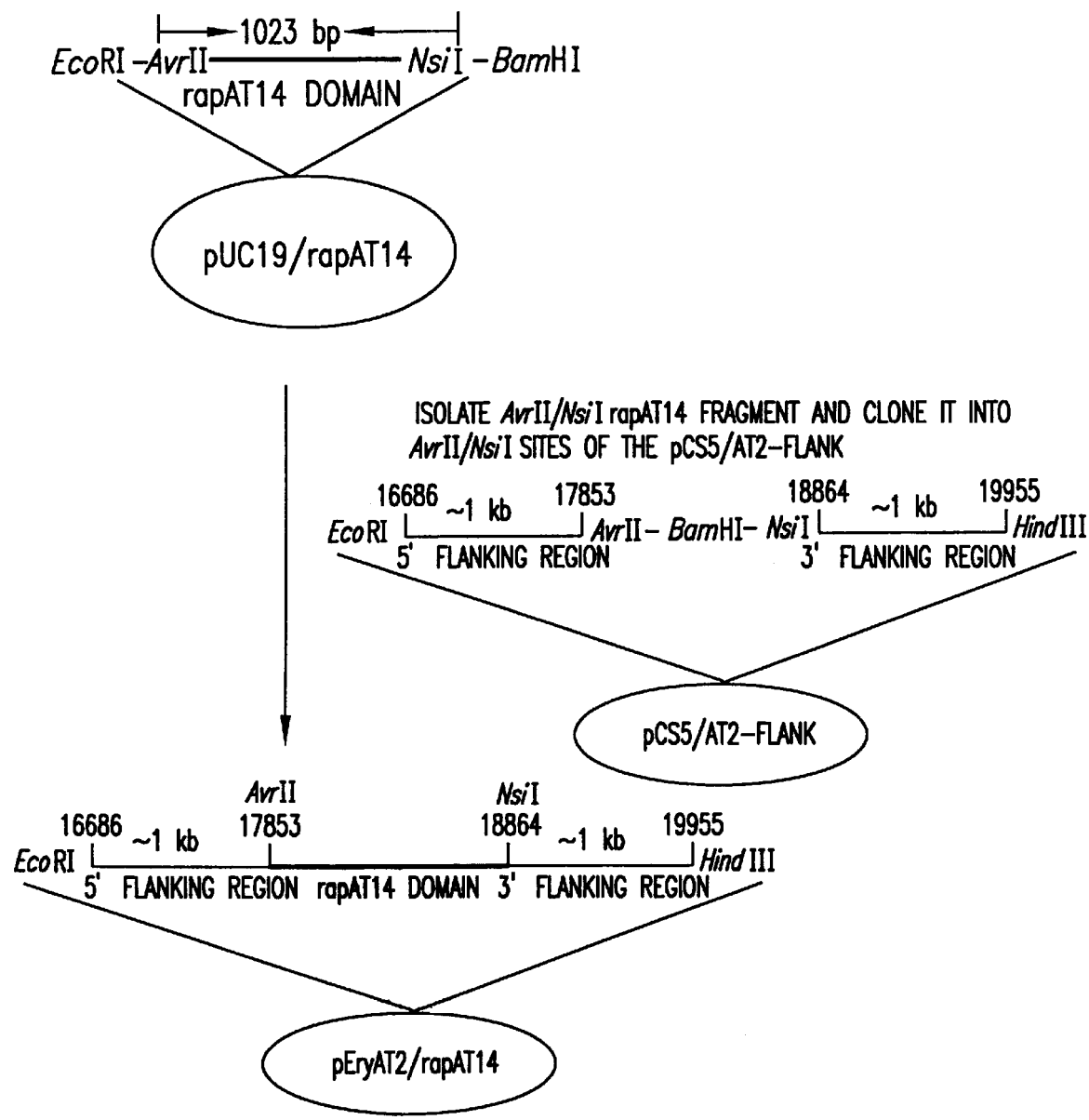
FIG. 27 is a flow diagram depicting construction of pEryAT2/rapAT14.

EXAMPLE 17
Construction of Plasmid pEryAT1/rapAT14 pEryAT2/rapAT14 was constructed using standard methods of recombinant DNA technology according to the schematic outlines of FIGS. 15 and 34. To make a gene-replacement-vector specific for the ery AT2 domain, the two DNA regions immediately adjacent to ery AT2 were cloned and positioned adjacent to the DNA encoding the rapAT14 domain in order to allow homologous recombination to occur. The strategy and protocol for constructing the intermediate plasmid containing the flanking regions, pCS5/AT2-flank, are described in Example 6 and FIG. 14. The final step in the construction of pEryAT2/rapAT14 was to ligate the 1 kb rapAT14-encoding DNA fragment having AvrII and NsiI ends to pCS5/AT2-flank (Example 6) cut with the same enzymes to give the gene replacement/integration plasmid pEryAT2/rapAT14 (FIG. 27). All ligations were transformed into the intermediate host *E. coli* DH5α and clones selected as previously described.

EXAMPLE 18
Construction of *Sac. erythraea* ER720 EryAT2/rapAT14

A 10-desmethylerythromycin A and 10-desmethyl-12-deoxyerythromycin A producing microorganism was prepared by replacing the DNA fragment encoding the methylmalonyl acyltransferase domain of module 2 of the erythromycin PKS (EryAT2) of *Sac. erythraea* ER720 with a DNA fragment encoding a malonyl acyltransferase domain (rapAT14) from *S. hygroscopicus* ATCC 29253. This was accomplished with the recombinant plasmid, pEryAT2/rapAT14, prepared as described in Example 17. Transformation of ER720 and resolution of the integration event were carried out as described in Example 4 using 10 $\mu$L of DNA solution consisting of 3 $\mu$L of pEryAT2/rapAT14 DNA at about 1 $\mu$g/$\mu$L in 7 $\mu$L of $P_M$ buffer. One thiostrepton resistant colony was isolated and was inoculated into SGGP containing thiostrepton (10 $\mu$g/mL) to isolate chromosomal DNA for Southern analysis. Integration of the plasmid DNA into the ER720 chromosome was further confirmed by Southern hybridization (data not shown). Hybridization was at 65° C. and the stringency wash was with 0.1×SSC at 65° C.

Figure 28:
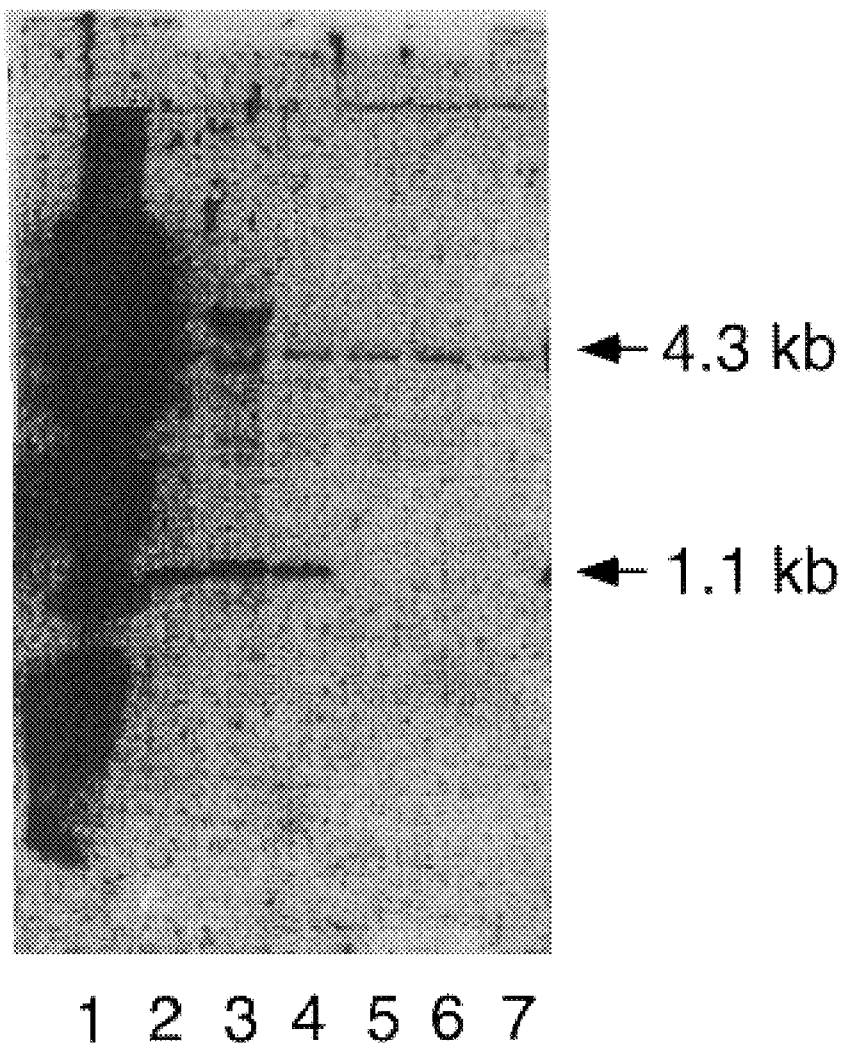
FIG. 28 is a computer generated PhosphorImage of a Southern analysis of chromosomal DNA from *Sac. erythraea* ER720 EryAT2/rapAT14 resolvants, cut with BspEI and probed with a fragment of 5'-flanking region of eryAT2. As shown in lanes 5, 6 and 7, the probe hybridized with a 4.3 kb fragment, indicating that rapAT14 had replaced EryAT2 in the chromosomes of these resolvants. Lane 1: molecular weight markers (1 kb ladder); lane 2: chromosomal DNA from wild-type *Sac. erythraea* ER720; lane 3: chromosomal DNA from *Sac. erythraea* ER720 resolvant to wild-type, clone #1.1; lane 4: chromosomal DNA from a *Sac. erythraea* ER720 EryAT2/rapAT14 integrant; lanes 5–7: chrormosomal DNA from *Sac. erythraea* ER720 EryAT2/rapAT14 resolvant clones #1.2, #1.3 and #1.4 respectively.

The confirmed integrant was grown in SGGP without antibiotic for four days and then diluted 1000 fold into fresh medium and grown for 4 more days. Protoplasts were then prepared and plated onto non-selective R3M plates to obtain individual colonies, which were then screened for sensitivity to thiostrepton, indicating loss of the plasmid sequence from the chromosome. Four thiostrepton sensitive colonies were selected and 3 of these were confirmed by Southern hybridization, using conditions described above, to have the EryAT2 replaced by rapAT14 (FIG. 28). The strain was named *Sac. erythraea* ER720 EryAT2/rapAT14.

EXAMPLE 19
Analysis of Compounds Produced by *Sac. erythraea* ER720 EryA2/rapAT14

Compounds produced by the recombinant *Sac. erythraea* strain, ER720 EryAT2/rapAT14, whose construction is described in Example 18, were characterized by TLC, bioassay, and mass spectrometry.

Figure 29:
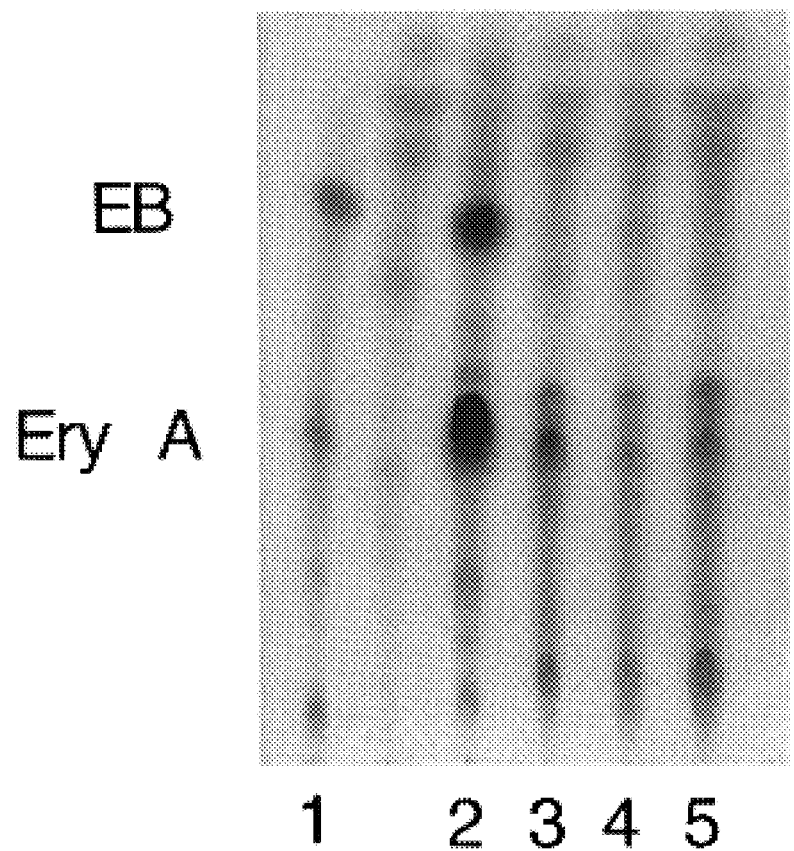
FIG. 29 is a computer reproduction of a TLC plate on which the products produced by *Sac. erythraea* ER720 EryAT2/rapAT14 were run. Lane 1: erythromycin A and erythronolide B (EryA and EB, respectively; 5 µg each); lane 2: compounds produced by wild-type *Sac. erythraea* ER720; lanes 3–5: compounds produced by *Sac. erythraea* ER720 EryAT2/rapAT14 resolvant clones #1.2, #1.3 and #1.4 respectively.

For TLC analysis cells were grown in either SGGP or SCM medium (20 g Soytone, 15 g Soluble Starch, 10.5 g MOPS, 1.5 g Yeast Extract and 0.1 g $CaCl_2$ per liter of distilled $H_2O$) for 4–5 days at 30° C. Culture (22 mL) was centrifuged for 5 minute to remove cells. The resulting supernatant was removed to another tube and the pH adjusted to 9.0 by the addition of 6$\mu$L/mL of $NH_4OH$. Then an equal volume of ethyl acetate was added, the liquid was mixed for 2 min. and then centrifuged for approximately 5 min. to achieve phase separation. The organic phase was removed to another tube, and the aqueous phase was re-extracted with half volume of ethyl acetate. The second organic phase was combined with the first and dried in a Speed Vac. The residue was taken up in 100 $\mu$L of ethyl acetate and one fourth of the sample was spotted onto a Merck 60F-254 silica gel TLC plate. The plate was run in isopropyl ether:methanol:$NH_4OH$ (75:35:2). Erythromycin derivatives were visualized by spraying the plates with anisaldehyde:sulfuric acid:ethanol (1:1:9). Using this reagent, two novel compounds predicted to be 10-desmethylerythromycin A and 10-desmethyl-12-deoxyerythromycin A, appeared as blue spots with the lower spot running slightly slower than erythromycin A and upper spot running slightly faster than erythromycin A (FIG. 29).

Figure 30:
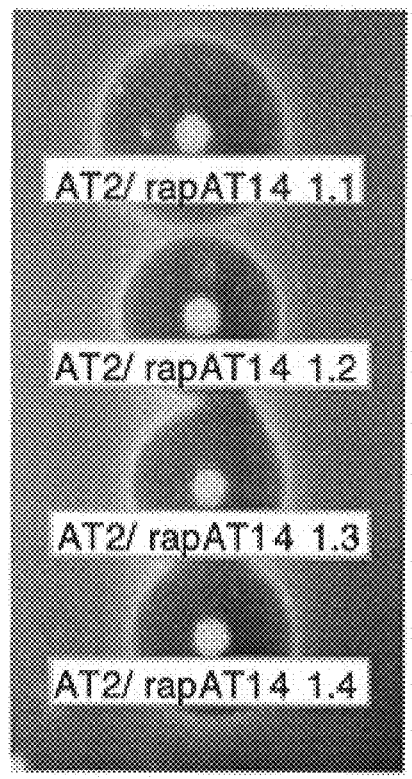
FIG. 30 is a computer reproduction of a bioassay of compounds made by *Sac. erythraea* ER720 EryAT2/rapAT14 resolvant clones #1.2, #1.3 and #1.4 and resolvant to wild-type clone #1.1.

To detect biological activity, a bioassay was performed. In this assay, another fourth of the extracted sample from above was spotted onto a disc. The disc was then air-dried and placed over a plate containing 50 mL of antibiotic medium 11 (DIFCO-BACTO) containing *Staphylococcus aureus* as an indicator strain. The inhibition zones were developed by overnight incubation of the plate at 37° C. As shown in FIG. 30, the novel compounds have bioactivity.

To determine whether the novel spots seen on TLC have the molecular mass corresponding to the predicted 10-desmethylerythromycin A and 10-desmethyl-12-deoxyerythromycin A, an ethyl acetate extract from another culture was further analyzed by mass spectrometry. The sample was a crude extract of a 20 mL culture grown for 4 days. Mass spectrometric analysis revealed the two novel compounds to have masses of 720 and 704, which correspond to the molecular ion plus a proton (M+H$_+$) of 10-desmethylerythromycin A and 10-desmethyl-12-deoxyerythromycin A, respectively.

EXAMPLE 20
Cloning of the ethylAT Domain from *Streptomyces caelestis*

A genomic library of *Streptomyces caelestis* NRRL-2821 (U.S. Pat. No. 3,218,239 issued Nov. 16, 1965) DNA was constructed in the bifunctional cosmid pNJ1 (Tuan, et al., *Gene*, 90: 21–29 (1990)). Cosmid vector was prepared by digesting 5 $\mu$g of pNJ1 with EcoRI, dephosphorylating with CIAP and then digesting with BglII to generate one arm and also digesting 5 $\mu$g of pNJ1 with HindIII, dephosphorylating with CIAP and then digesting with BglII to generate the other. Insert DNA was prepared by partially digesting approximately 5 $\mu$g of chromosomal *S. caelestis* NRRL-2821 DNA with SauIIIA according to the procedure outlined in Maniatis et al., supra. Digestion conditions were chosen which produced fragment sizes of approximately 40 kb. The ligation was performed by mixing approximately 1 $\mu$g of the digested chromosomal DNA with 0.5 $\mu$g of each cosmid arm. The ligation was incubated at 16° C. overnight. GigapackII XL (Stratagene®) was used for packaging 2 $\mu$L of the ligation mix according the manufacturer's instructions. Transformation was done in *E. coli* XL1-Blue MR cells (Stratagene®). Individual colonies were picked into thirty 96-well plates to give a 99.99% probability that the library represented all *S. caelestis* NRRL-2821 genomic sequences.

Figure 31:
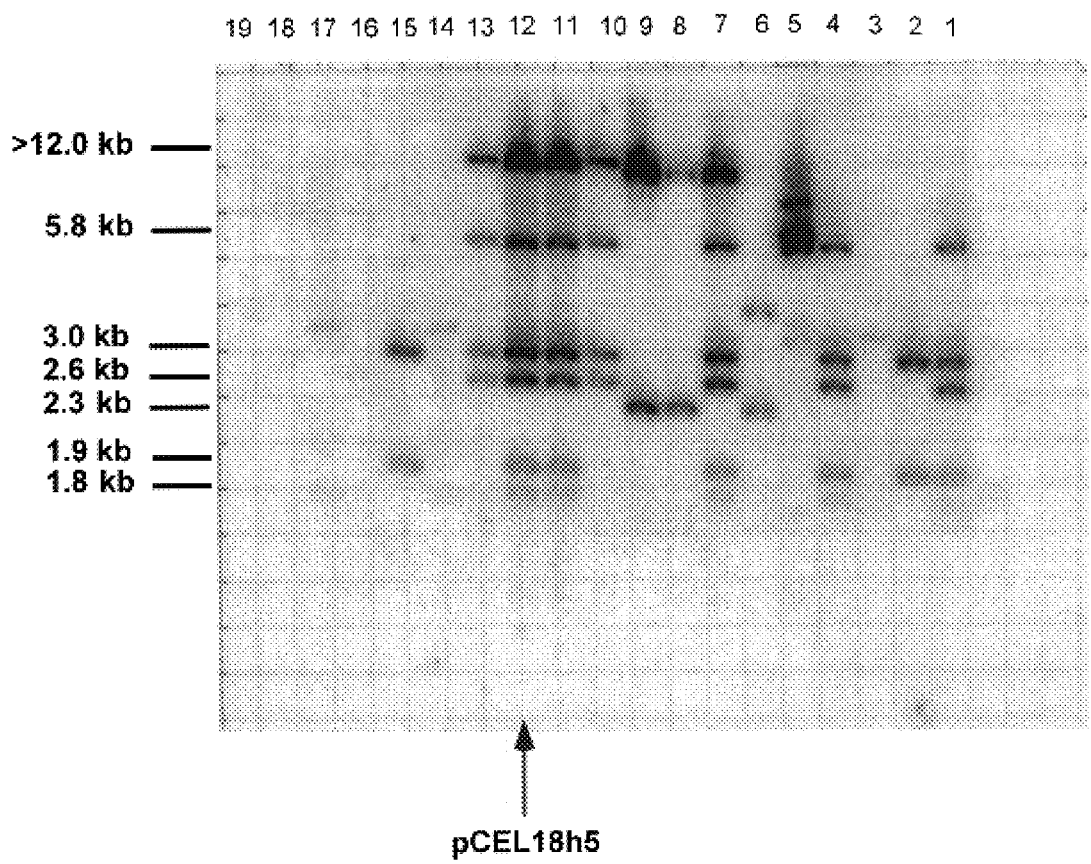
FIG. 31 is a computer generated PhosphorImage of a Southern analysis of a cosmid DNA library constructed from *Streptomyces caelestis* NRRL-2821 chromosomal DNA. Lanes 1–19: DNA prepared from 19 clones, digested with SstI and probed with a *Streptomyces caelestis* NRRL-2821 PKS specific probe.

The library was screened using a probe specific for the *S. caelestis* NRRL-2821 PKS region. The probe was generated by PCR amplification of *S. caelestis* NRRL-2821 genomic DNA using degenerate primers designed from consensus ketosynthase (KS) and acyltransferase (AT) sequences in the GenBank database. The KS specific oligo (SEQ ID NO:19) and the AT specific oligo (SEQ ID NO:20) generated a 900 bp PCR fragment. The PCR reaction contained 10 $\mu$L ThermoPol Buffer, 2 $\mu$L formamide, 25 $\mu$L of 20% glycerol, 3 $\mu$L 50 mM $MgCl_2$, 45 $\mu$L water, 50 pmole of each primer, and approximately 0.2 $\mu$g DNA. The sample was heated to 99° C. for 5 minutes, and then placed on ice, at which time a 10 $\mu$L cocktail consisting of 2 $\mu$L of a 10 mM mixture of dATP, dCTP, dGTP, and dTTP, 2 units of Vent DNA polymerase, and 7 $\mu$L of water was added. The sample was then transferred to a GeneAmp 9600 thermocycler (Perkin Elmer, Foster City, Calif.) and a temperature cycle of 1 minute at 95° C. 4 minutes at 50° C. and 4 minutes at 72° C. was repeated 30 times, followed by a 15 minute incubation at 72° C. The desired PCR fragment was then isolated from 1.0% low melting agarose by standard procedures. The KS/AT probe was made by labeling approximately 50 ng of the PCR fragment with $^{32}$P using the Megaprime DNA Labeling System (Amersham Life Science, Arlington Heights, Ill.). Library clones (2,880) were transferred from the 96-well plates to Hybond-N nylon filters (Amersham) and screened with the KS/AT probe according to procedures in Maniatis, et al., supra. Hybridization was performed at 65° C. and the final wash was in 0.1×SSC at 65° C. Nineteen of the clones hybridized strongly with the probe. These clones were then digested with SstI, run on a 1.0% agarose gel and transferred to Hybond-N nylon filters for Southern analysis using the KS/AT probe (FIG. 31). The cosmid identified as pCEL18h5 was chosen for further analysis since it contained the largest number of hybridizing restriction fragments.

The SstI fragments from cosmid pCEL18h5 were cloned into pGEM-3Zf (Promega, Madison, Wis.) and sequenced using the fmole DNA Cycle Sequencing System (Promega). The reactions were run on a Sequi-Gen II Sequencing Apparatus (Bio-Rad, Hercules, Calif.). Individual fragments were oriented relative to one another by sequencing off of cosmid pCEL18h5 using primers that hybridized to the 5' and 3' ends of the fragments to generate upstream and downstream sequence. These sequences were then matched with sequences from the individual fragments to place them in the proper order. A very large SstI fragment (>10 kb) was further digested with SmaI to generate smaller fragments for cloning and sequencing.

By searching the GenBank database with the sequences obtained it was possible to identify the various enzymatic motifs associated with the niddamycin PKS cluster and to group these motifs into modules (see FIG. 32) based on previous knowledge of Type I PKS organization. The C-6 position of the niddamycin macrolactone ring has an aldehyde derived from an ethyl side chain (FIG. 33). It was thus predicted that the AT of module 5 of the niddamycin cluster is responsible for incorporating this ethyl group into the growing chain. In addition, the carbon at C-7 of the molecule is completely saturated leading to the prediction that ER and DH motifs would also be present in module 5. These motifs were, in fact, found at the predicted region of the sequence. Furthermore, motifs for the preceding 4 modules were as predicted, with an inactive ketoreductase motif in module 4 which leaves a keto group at C-9 of the ring. Sequencing of that KR showed that the nucleotide binding site GXGXXG (SEQ ID NO:27) was mutated to DXTXXP (SEQ ID NO:28). The nucleotide sequence (SEQ ID NO:29) and corresponding amino acid sequence (SEQ ID NO:33) of the ethyl AT of module 5 are shown in FIG. 34 (top and bottom strands respectively).

A knockout experiment was also performed on this cluster, demonstrating that this sequence of DNA encodes the pathway for niddamycin biosynthesis (data not shown).

EXAMPLE 21

Construction of Plasmid pEAT4

Figure 35A:
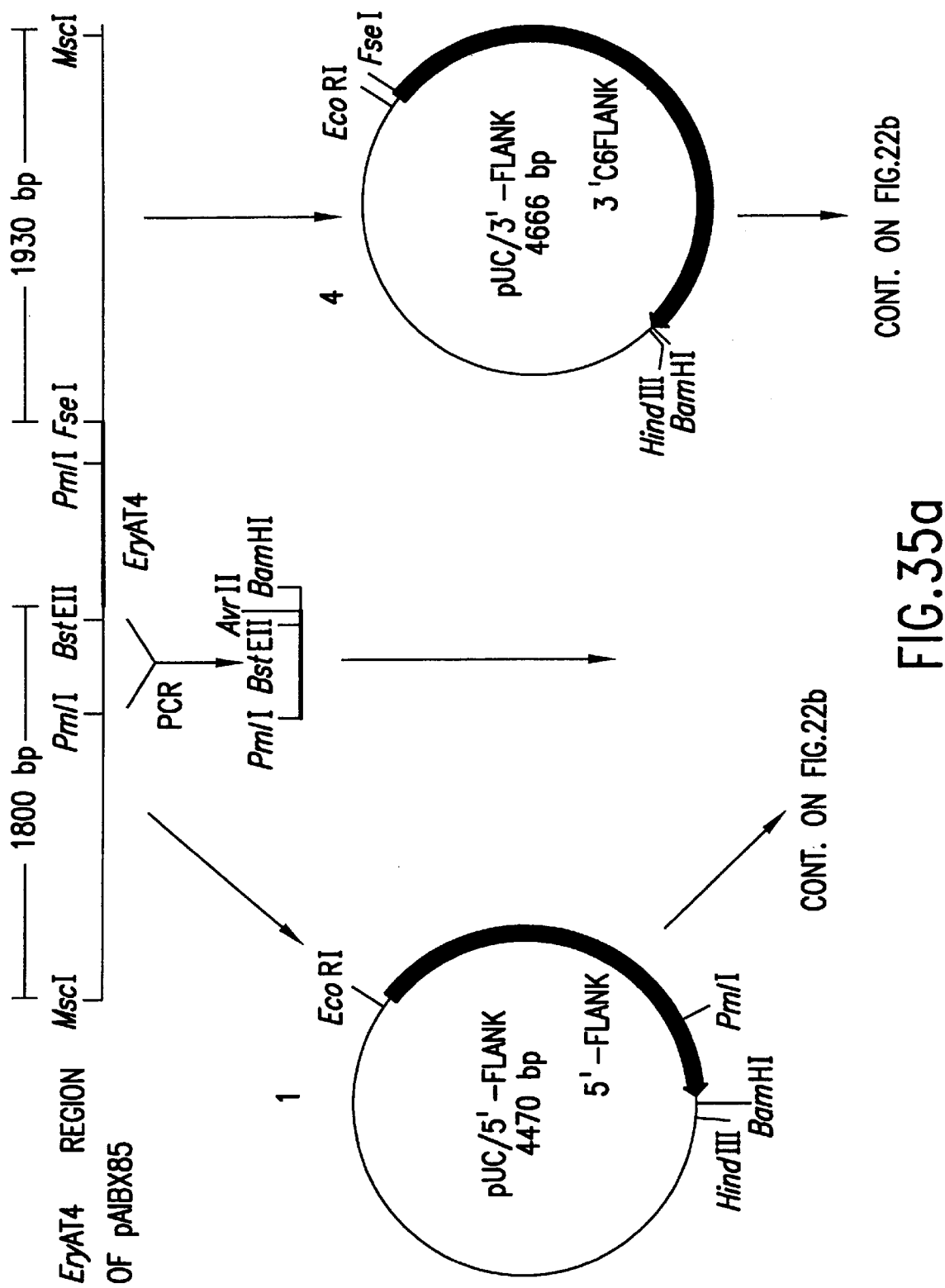
FIG. 35 is a flow diagram depicting the construction of pUC/ethAT/C-6.
Figure 35B:
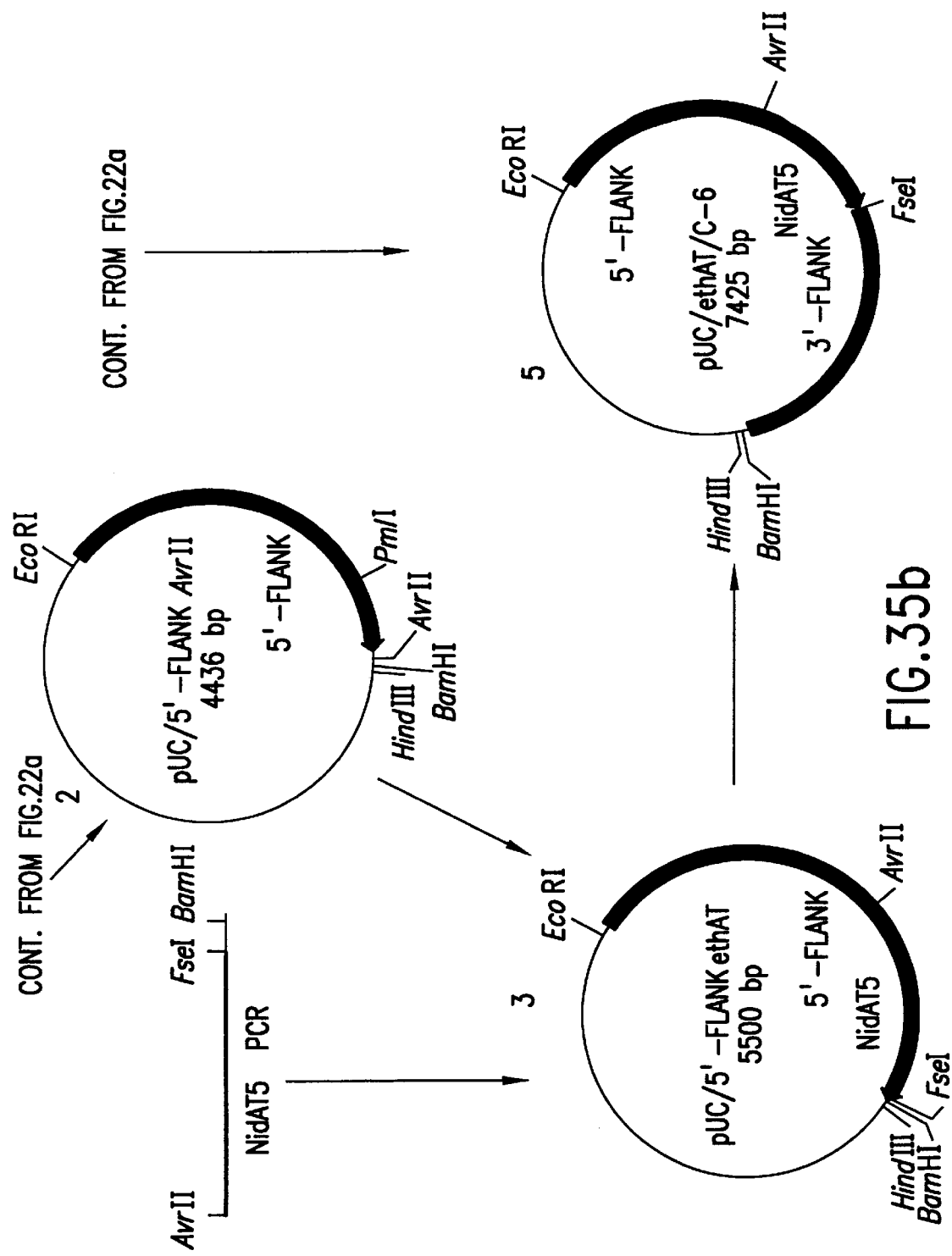

A multistep strategy was used to construct the plasmnid pUC/ethAT/C6 (FIG. 35), which consists of the DNA encoding the NidAT5 domain flanked by approximately 2.0 kb of sequence upstream and downstream from the eryAT4 encoding sequences, all contained in pUC19. EryAT4 flanking DNA was subcloned from pAIBX85. This plasmid is a pCS5 derivative containing 8.4 kb of *Sac. erythraea* DNA from an XhoI site to a BamHI site in the eryAII gene of the erythromycin PKS cluster. These sites correspond to bases 23211 and 31581, respectively, of GenBank accession number M63676. The EryAT4 5'-flanking DNA was isolated by digesting pAIBX85 with MscI and BstEII (corresponding to nucleotides 23,211 and 31,581, respectively). The resulting 1800 bp DNA fragment was treated with the Klenow Fragment of DNA Polymerase I, ligated into the SmaI site of pUC19, and transformed into *E. coli* DH5α. Clones were selected on LB plates containing 150 µg/mL ampicillin and 50 µL of a 2% solution of X-gal for blue/white selection. The clones were confirmed by restriction analysis, resulting in the intermediate vector pUC/5'-flank. For convenient cloning of the NidAT5-encoding sequences, an AvrII site was engineered at the 3' end of the 5' flanking DNA. This was accomplished by PCR amplification from the PmlI site of the 5' flanking DNA to the BstEII site with two oligonucleotides (SEQ ID NO:21 and SEQ ID NO:22). SEQ ID NO:22 incorporates an AvrII site and a BamHI site at the 3' end of the 5' flanking DNA. PCR conditions were as described in Example 20 using *Sac. erythraea* DNA as template with the following changes: Taq polymerase (GIBCO BRL) was used with the accompanying 10× buffer instead of Vent$_R$® DNA polymerase and cycling conditions were 96° C./30 sec, 55° C./30 sec, 72° C./30 sec for 25 cycles. The resulting 300 bp was then digested with the PmlI and BamHI gel purified from a 1.0% agarose gel with Prep-A-Gene, and ligated back into pUC/5'-flank digested with PmlI and BamHI to give pUC/5'-flank-AvrII. The ligation was transformed into DR5α and plated onto LB plates containing 150 µg/mL ampicillin. Clones were confirmed by restriction analysis and DNA sequencing.

In order to clone the NidAT5-encoding DNA fragment downstream of the 5' flanking DNA, an AvrII site was also engineered at the 5' end of the NidAT5-encoding DNA. As depicted in FIG. 36, an AvrII site could be engineered into the NidAT5 DNA without altering the amino acid sequence. Two PCR. oligonucleotides (SEQ ID NO:23 and SEQ ID NO:24) were designed to create an AvrII site at the 5' end and a BamHI site at the 3' end, respectively, of the NidAT5-encoding DNA. A convenient FseI site occurs naturally at the end of NidAT5-encoding sequence, so the resulting PCR fragment contains an FseI site just upstream of the PCR engineered BamHI site. SEQ ID NO:23 and SEQ ID NO:24 were used in a PCR reaction with the template p16–2.2. This plasmid is pUC19 containing a 2.2 kb SmaI fragment from module 5 of the niddamycin PKS cluster (see FIG. 32), which encompasses the sequences encoding NidAT5. The resulting 1.0 kb PCR fragment was digested with AvrII and BamHI, purified from a 1.0% agarose gel using Prep-A-Gene, and cloned into the AvrII/BamHI sites of pUC/5'-flank-AvrII. Clones were confirmed by restriction analysis and DNA sequencing, creating the intermediate plasmid pUC/5'-flank/ethAT.

The EryAT4 3'-flanking DNA was subcloned by digesting pAIBX85 with PmlI and MscI, corresponding to nucleotides 29,231 and 31,209, respectively, from the eryAII gene (GenBank accession number M63676). The DNA was gel purified on a 1.0% agarose gel using Prep-A-Gene and ligated into the SMaI site of pUC19. The ligation was transformed into DH5α and plated as described previously. Clones were confirmed by restriction analysis, resulting in the plasmid pUC/3'-flank.

Figure 37:
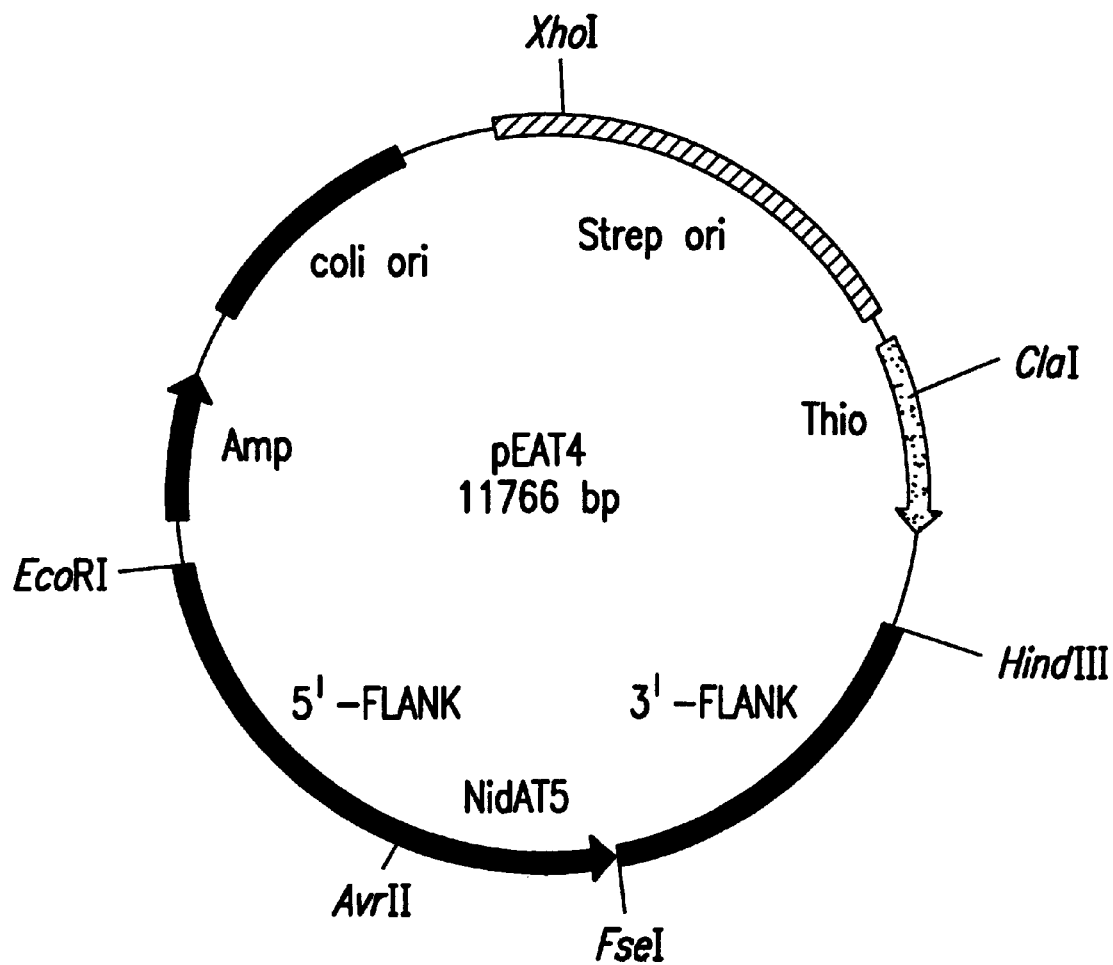
FIG. 37 is a diagram of the replacement plasmid pEAT4.

Attachment of the EryAT4 3'-flanking DNA to the NidAT5-encoding sequence was accomplished by digesting plasmid pUC/3'-flank with FseI and BamHI, gel purifying the fragment from a 1.0% agarose gel using Prep-A-Gene, and ligating it into pUC/5'-flank/ethAT that had been previously digested with FseI and BamHI. The ligation was transformed into DH5α as before and clones were analyzed by restriction analysis, resulting in the intermediate plasmid pUC/ethAT/C-6. The final step was to remove the NidAT5/ flanking DNA insert from pUC/ethAT/C-6 with EcoRI and HindIII and ligate it into the EcoRI/HindIII sites of pCS5, resulting in the gene replacement/integration plasmid pEAT4 (FIG. 37).

EXAMPLE 22
Construction of Sac. erythraea ER720 EAT4-46

An example of a 6-desmethyl-6-ethylerythromycin A producing microorganism was prepared by replacing the DNA fragment encoding the methylmalonyl acyltransferase domain in module 4 of the erythromycin PKS (EryAT4) of Sac. erythraea ER720 with a newly discovered DNA fragment encoding an ethylmalonyl acyltransferase domain (NidAT5) from S. caelestis NRRL-2821. This was accomplished using the recombinant plasmid pEAT4, prepared as described in Example 21. Transformation of Sac. erythraea ER720 and resolution of the integration event were carried out according to the procedures described in Example 4 using 10 μL of a DNA solution consisting of 3 μL of pEAT4 DNA from Example 21 at about 1 μg/μL in 7 μL of $P_M$ buffer. One colony was confirmed to be thiostrepton resistant and was inoculated into SGGP containing thiostrepton (10 μg/mL) to isolate chromosomal DNA for Southern analysis. Integration of the plasmid DNA into Sac. erythraea ER720 was confirmed by Southern analysis (data not shown). Hybridization was at 65° C. and the stringency wash was with 0.1×SSC at 65° C.

Figure 38:
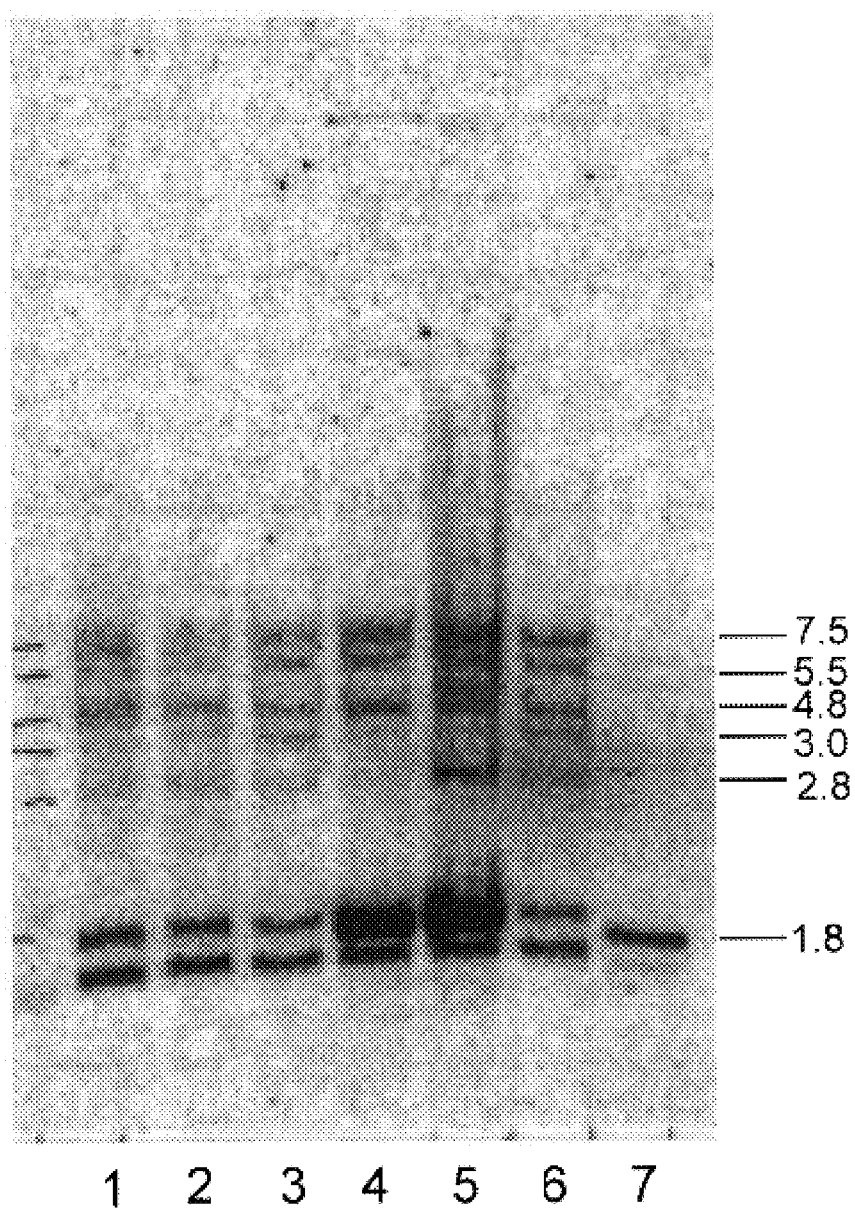
FIG. 38 is a computer generated PhosphorImage of a Southern analysis of chromosomal DNA from *Sac. erythraea* ER720 EAT4 resolvants digested with MluI and probed with a 900 bp DNA fragment spanning a KS/AT domain in *Streptomyces caelestis* NRRL-2821. Lane assignments are as follows: 1) wild type ER720; 2-7) resolvant clones. The resolvants with the NidAT5 domain in place of EryAT4 produced a strongly hybridizing 1.8 kb fragment (lanes 4, 5, and 7) which is missing in clones which resolved back to wild type (lanes 2, 3, and 6).

The confirmed integrant was then subcultured into 30 mL SGGP without antibiotic using 10 μL of the previous culture. After three days growth at 30° C. the strain was again subcultured into 30 mL of fresh SGGP as before and plated onto non-selective R3M plates for sporulation. Spores were plated on R3M plates to obtain individual colonies, which were then screened for sensitivity to thiostrepton, indicating loss of the plasmid sequence from the chromosome. Nine thiostrepton sensitive colonies were isolated and three of them were confirmed by Southern hybridization to have the EryAT4 replaced by NidAT5 (FIG. 38). Hybridization was at 65° C. and the stringency wash was with 0.1×SSC at 65° C. The strain was named Sac. erythraea ER720 EAT4-46, referred to as simply EAT4-46.

EXAMPLE 23
Analysis of Compounds Produced by EAT4-46

Compounds produced by strain EAT4-46, whose construction is described in Example 22, were characterized by TLC, bioautography and mass spectrometry.

The cells were grown in 30 mL of SCM for 45 days at 30° C. The culture was centrifuged for 10 minutes in a Sorval GLC-4 General Laboratory Centrifuge at setting 10 to remove cells. The resulting supernatant was adjusted to pH 9.0 by the addition of 180 μL of $NH_4OH$. Then 15 ml of ethyl acetate was added, the tube was vortexed for 30 seconds and then centrifuged for 10 minutes to achieve phase separation. The organic phase was removed to another tube, and the aqueous phase was re-extracted with 15 ml of ethyl acetate. The second organic phase was combined with the first and dried in a Speed-Vac. The residue was taken up in 30 μL of ethyl acetate and 10 μL was spotted onto a Merck 60F-254 silica gel TLC plate. The plate was run in a solvent containing isopropyl ether:methanol:$NH_4OH$ (75:35:2). Erythromycin derivatives were visualized by spraying the plates with anisaldehyde:sulfuric acid:ethanol (1:1:9). The results showed that EAT4-46 produced a compound that migrated with the same $r_f$ as erythromycin A produced by wild type Sac. erythraea ER720, except in much lower yield (data not shown).

To determine the molecular mass of the compound, an ethyl acetate extract was prepared from a 50 mL SCM culture of EAT4-46 as described above, using a proportionate amount of reagents. The resulting residue was taken up in 50 μL of ethyl acetate and run on a TLC plate as described previously, except that the plate was not sprayed with anisaldehyde. The compound of interest was isolated by scraping the silica resin in the vicinity of the spot and extracting the resin as described in Example 8. Mass spectrometric analysis revealed that the compound produced by the EAT4-46 strain had a mass of 734, which corresponds to the molecular ion plus a proton (M+H$^+$) of erythromycin A.

Figure 39:
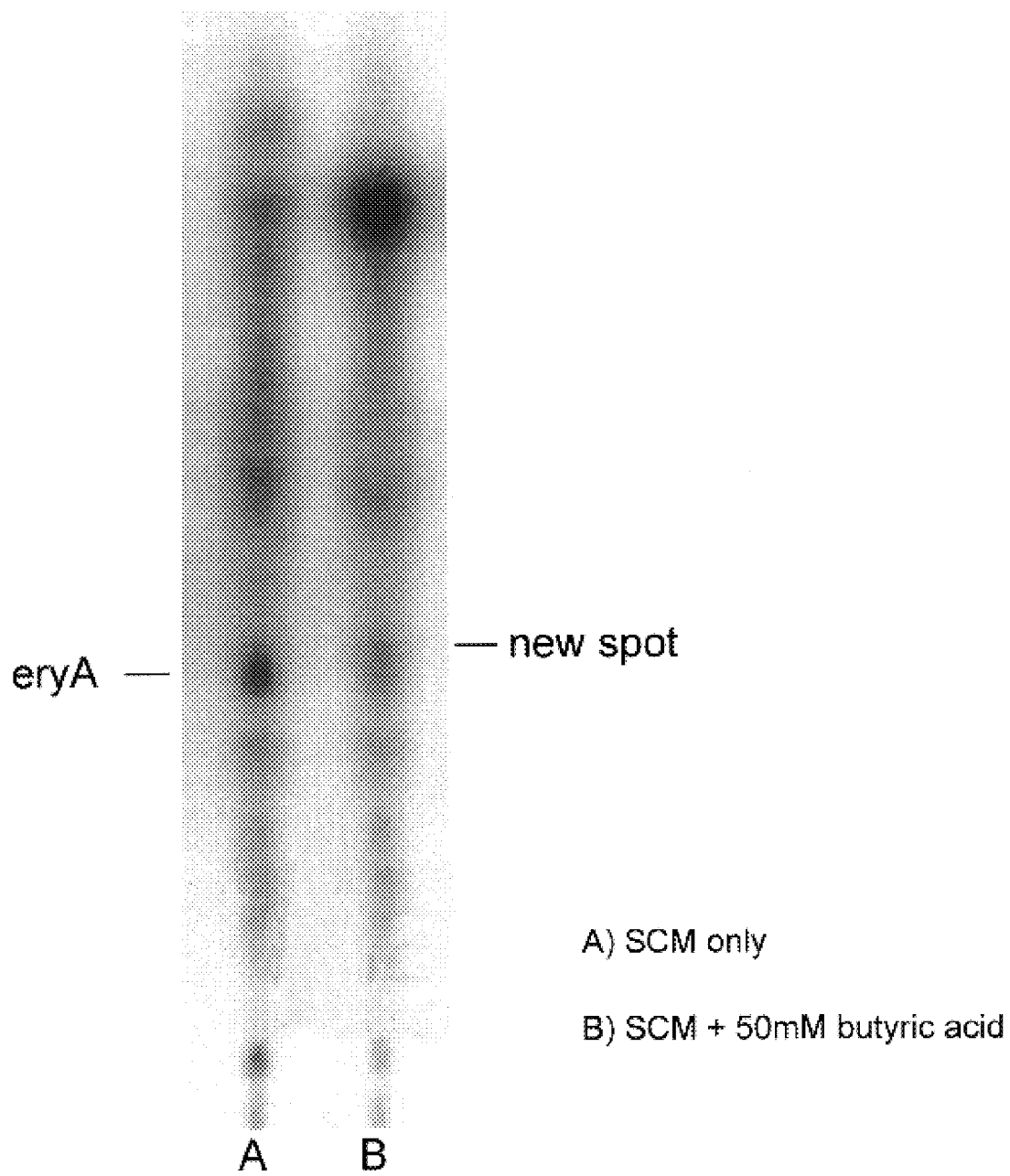
FIG. 39 is a computer reproduction of a TLC plate showing the products made by *Sac. erythraea* EAT4-46 after growing in SCM or SCM+50 mM butyric acid.

In an attempt to increase substrate pools for the NidAT5 ethylmalonyl AT construction, the EAT4-46 strain was grown in 100 mL of SCM media containing 50 mM butyric acid, pH 7.0. The culture was grown for 4 days at 30° C. and then centrifuged for 10 minutes in a Sorval GLC-4 Centrifuge to pellet the cells. The resulting supernatant was adjusted to pH 9.0 by the addition of 600 μL of $NH_4OH$ and extracted twice with ½ volumes of ethyl acetate as described previously. After drying in a Speed-Vac rotary concentrator, the extracted material was taken up in 100 μl of ethyl acetate and 10 μl was used for TLC analysis as described previously. Two spots running near eryA were observed in the butyric acid fed culture as opposed to only one spot in SCM media alone (FIG. 39). To determine the molecular mass of the two spots, most of the remainder of the extract was again subjected to TLC. and the compounds in the eryA region of the plate were isolated as described previously. Mass spectrometric analysis revealed that the two spots had molecular masses of 734 and 748. A molecular mass of 734 corresponds to the molecular ion plus a proton (M+H$^+$) of erythromycin A, whereas the species of molecular mass 748 is consistent with the molecular mass plus a proton (M+H$^+$) of ethylerythromycin A.

EXAMPLE 24
Clonino of the NidAT6 Domain from Streptomyces caelestis NRRL-2821

Figure 40:
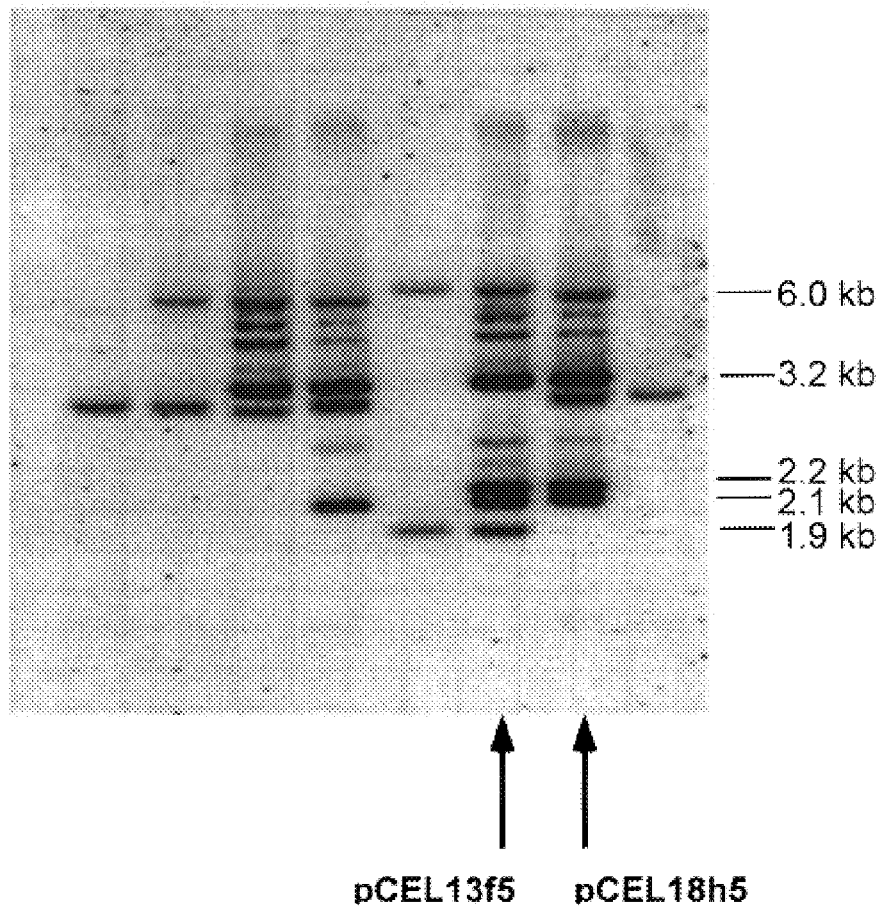
FIG. 40 is a computer generated PhosphorImage of a Southern analysis of clones from a cosmid DNA library constructed from *Streptomyces caelestis* NRRL-2821 chromosomal DNA. Clones were digested with SmaI and probed with a 900 bp DNA fragment spanning a KS/AT domain in *Streptomyces caelestis* NRRL-2821.

A genomic library of Streptomyces caelestis NRRL-2821 DNA was generated and screened with a probe specific for PKS genes as described in Example 20. From Southern analysis of SstI digests of the positive clones (FIG. 31), some clones were selected for further analysis. These clones were digested with SmaI and run on a 1% agarose gel for Southern hybridization with the PKS specific probe. The analysis revealed that a second cosmid, pCEL13f5, shared many hybridizing bands with pCEL18h5, but also contained two unique bands of 1.9 kb and 6.0 kb (FIG. 40). This cosmid was chosen for further analysis in order to determine the sequence of the remaining PKS genes in the niddamycin pathway. Cosmid pCEL$_{13}$f5 was digested with SstI and the fragments were ligated to pUC19. A large SstI fragment (>10 kb) was further digested with SmaI and ligated to pUC19. The ligations were transformed into DH5α cells and clones were selected on LB plates containing 150 μg/mL ampicillin and 50 μl of a 2% solution of X-gal for blue/white selection. DNA from clones containing the appropriate insert was isolated using the QIAprep Spin Plasmid Kit (QIAGEN Inc., Chatsworth, Calif.). Subclones were sequenced using the ABI PRISM Dye Terminator Cycle Sequencing Ready Reaction Kit (Perkin Elmer), and the reactions were run on a 4.75% acrylamide, 8.3 M urea gel in an Applied Biosystems 373 DNA Sequencing System.

Ordering of the inserts and motif identification was done as described in Example 20.

Figure 32:
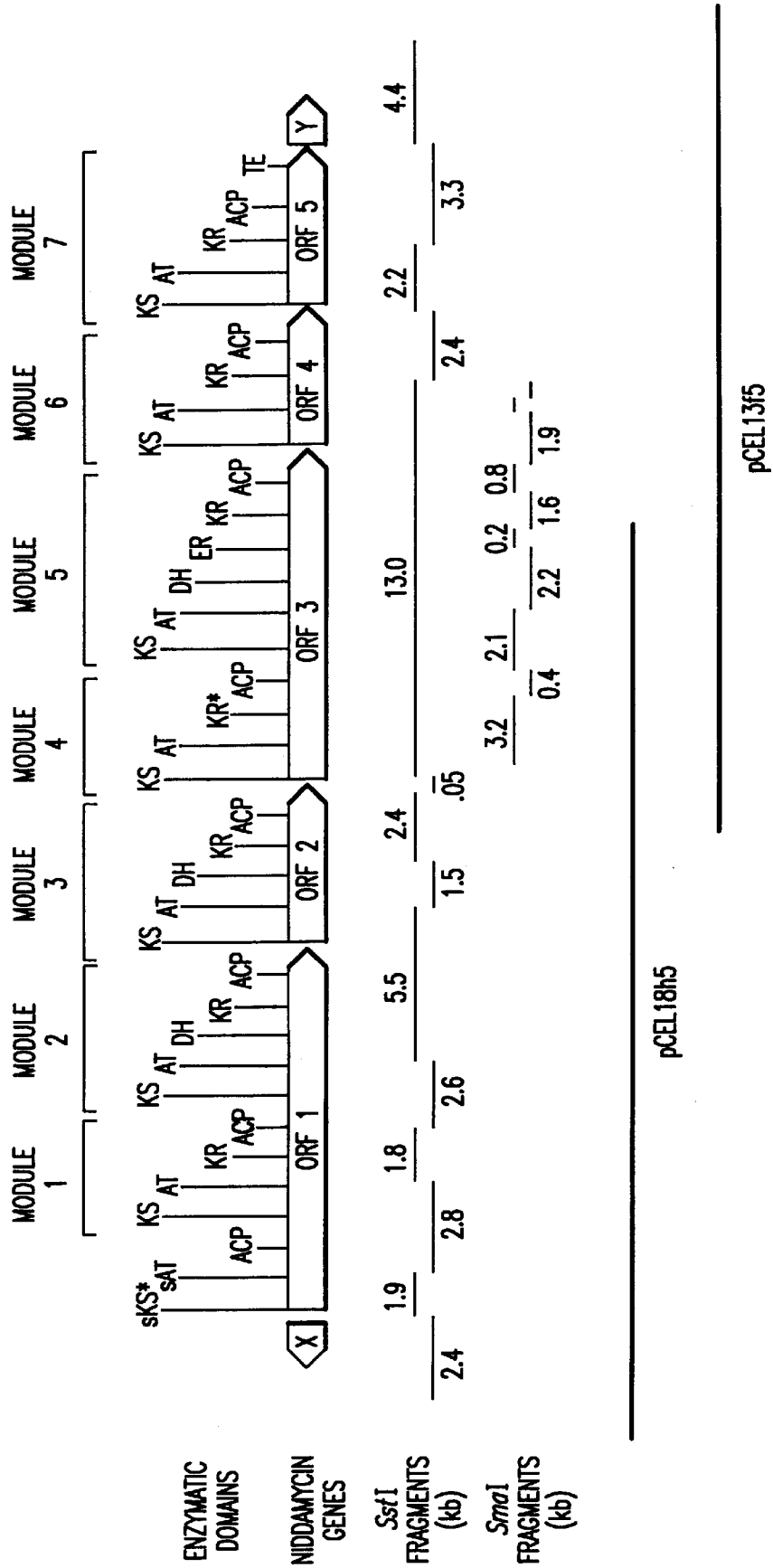
FIG. 32 is a schematic representation of the genetic organization of the PKS cluster from *Streptomyces caebestis* NRRL-2821.

The insert in cosmid pCEL13f5 was found to be approximately 25 kb in length, and the 5' end of the insert had about 10 kb of identical sequence with the 3' end of the insert in pCEL$_{18}$h5. Together, the two cosmids contain all of the PKS genes of the niddamycin pathway (FIG. 32). Based on the structure of niddamycin (FIG. 33), the AT contained in module 6 (NidAT6) may utilize hydroxymalonate (tartronate) in the biosynthesis of the C-3, C-4, and O-4 positions of the macrolactone ring of niddamycin. (S. Omura et al. (J. Antibiotics 36:611–613 (1983)) have suggested that glycolate may be incorporated in the biosynthesis of the C-3, C-4 and O-4 positions of leucomycin, a closely related 16-membered macrolide). The nucleotide sequence of NidAT6 (top strand, SEQ ID NO:30) and its corresponding amino acid sequence (lower strand, SEQ ID NO:34) are shown in FIG. 41. A comparison of the amino acid sequence of NidAT6 with other ATs in the Swissprot database shows that NidAT6 resembles methylmalonyl ATs (data not shown).

EXAMPLE 25
Construction of Plasmid pUC18/NidAT6

Two PCR oligonucleotides (SEQ ID NO:25 and SEQ ID NO:26) are designed to subclone the 1024 bp DNA fragment encoding the NidAT6 domain from the niddamycin PKS cluster and to introduce two unique restriction sites, AvrII and NsiI, for cassette cloning. This necessitates nucleotide changes, shown in bold in FIG. 42, at the beginning and near the end of the NidAT6-encoding DNA sequence. The changes shown also cause the replacement of a proline codon near the N-terminus of the NidAT6 domain with a valine codon, in order to increase the similarity of the domain junction sequence to that found naturally for some of the AT domains of the rapamycin PKS. (In FIG. 42. the underlined nucleotides are the wild-type sequence.) In addition, two other restriction sites, EcoRI and BglII, are also introduced at the 5' ends of the N-terminal and C-terminal oligonucleotides, respectively, for convenient subcloning of the PCR-generated product. The approximately 1 kb NidAT6 domain encoding DNA is amplified using methods described in Reagents and General Methods from Cosmid pCEL13f5. The PCR product is digested with EcoRI and BglII and subcloned into the EcoRI and BamHI sites of pUC18. The ligation mixture is transformed into E. coli DH5α (GIBCO BRL) according to the manufacturer's instructions and transformants are selected on LB plates containing 150 μg/mL ampicillin and 50 μL of a 2% solution of X-gal for blue/white selection. Clones are confirmed by restriction analysis and the fidelity of the insert is confirmed by DNA sequencing. The final plasmid construct is named pUC18/NidAT6.

Figure 43:
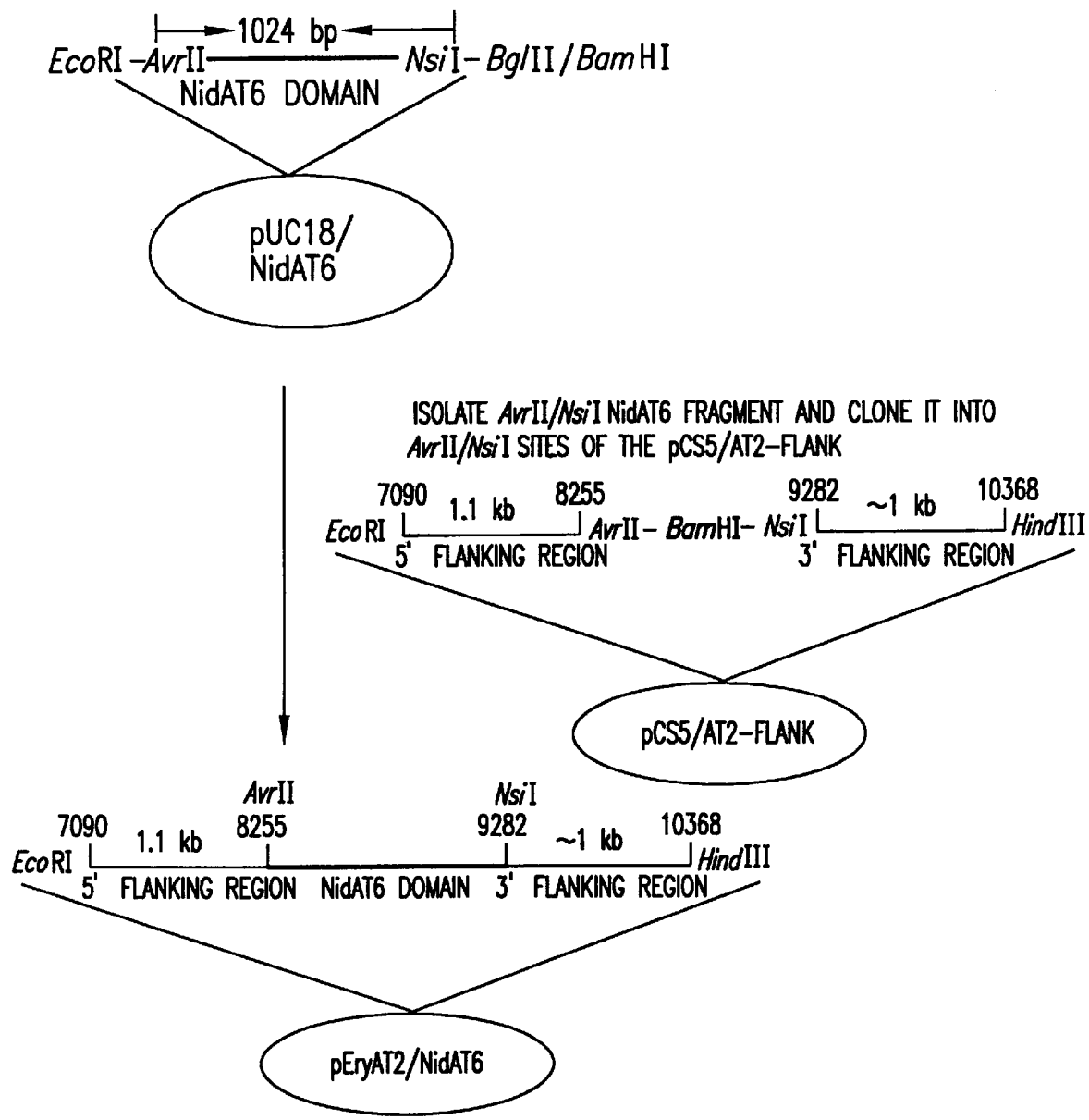
FIG. 43 is a flow diagram depicting construction of pEryAT2/NidAT6.

EXAMPLE 26
Construction of Plasmid pEryAT2/NidAT6 pEryAT2/NidAT6 is constructed using standard methods of recombinant DNA technology according to the schematic outlines of FIGS. 15 and 53. To make a gene-replacement-vector specific for the eryAT2 domain, the two DNA regions immediately adjacent to eryAT2 are cloned and positioned adjacent to the DNA encoding the NidAT6 domain in order to allow homologous recombination to occur. The strategy and protocol for constructing the intermediate plasmid containing the flanking regions, pCS5/AT2-flank, are described in Example 6 and FIG. 13. The final step in the construction of pEryAT2/NidAT6 is to ligate the 1 kb NidAT6-encoding DNA fragment having AvrII and NsiI ends to pCS5/AT2-flank (Example 6) cut with the same enzymes to give the gene replacement/integration plasmid pEryAT2/NidAT6 (FIG. 43). All ligation mixes are transformed into the intermediate host E. coli DH5α and clones are selected and characterized as described previously.

EXAMPLE 27
Construction of Sac. erythraea ER720 EryAT2/NidAT6

A 10-desmethyl-10-hydroxyerythromycin A and 12-deoxy-10-desmethyl-10-hydroxyerythromycin A producing microorganism is prepared by replacing the DNA fragment encoding the methylmalonyl acyltransferase domain of module 2 of the erythromycin PKS (EryAT2) of Sac. erythraea ER720 with a DNA fragment encoding a hydroxymalonyl acyltransferase domain (NidAT6) from S. caelestis NRRL-2821. This is accomplished with the recombinant plasmid, pEryAT2/NidAT6, prepared as described in Example 26. Transformation of ER720 and resolution of the integration event are carried out as described in Example 4 using 10 μL of DNA solution consisting of 3 μL of pEryAT2/NidAT6 DNA at about 1 μg/μl L in 7 μL of P$_M$ buffer. Thiostrepton resistant colonies are isolated and inoculated into SGGP containing thiostrepton (10 μg/mL) to isolate chromosomal DNA for Southern analysis. Integration of the plasmid DNA into the ER720 chromosome is further confirmed by Southern hybridization. Hybridization is at 65° C. and the stringency wash is with 0.1×SSC at 65° C.

Confirmed integrants are grown in SGGP without antibiotic for four days and then diluted 1000-fold into fresh medium and grown for 4 more days. Protoplasts are then prepared and plated onto non-selective R3M plates to obtain individual colonies, which are screened for sensitivity to thiostrepton, indicating loss of the plasmid sequence from the chromosome. Thiostrepton sensitive colonies are then selected and these are confirmed by Southern hybridization, using conditions described above, to have the EryAT2 replaced by NidAT6. The strain is designated Sac. erythraea ER720 EryAT2/NidAT6.

EXAMPLE 28
Analysis of Compounds Produced by Sac. erythraea ER720 EryAT2/NidAT6

Compounds produced by the recombinant Sac. erythraea strain, ER720 EryAT2/NidAT6, whose construction is described in Example 27, are characterized by TLC, bioassay, and mass spectrometry.

For TLC analysis cells are grown in either SGGP or SCM medium (20 g Soytone, 15 g Soluble Starch, 10.5 g MOPS, 1.5 g Yeast Extract and 0.1 g CaCl$_2$ per liter of distilled H$_2$O) for 4–5 days at 30° C. The culture is centrifuged for 5 min. to remove cells. The resulting supernatant is removed to another tube and the pH adjusted to 9.0 by the addition of 6 μL/mL of NH$_4$OH. Then an equal volume of ethyl acetate is added, the liquid is mixed for 2 min. and then centrifuged for approximately 5 min. to achieve phase separation. The organic phase is removed to another tube, and the aqueous phase is re-extracted with a half volume of ethyl acetate. The second organic phase is combined with the first and dried in a Speed Vac. The residue is taken up in approximately 25 μL of ethyl acetate and 15 μL are spotted onto a Merck 60F-254 silica gel TLC plate. The plate is run in isopropyl ether:methanol:NH$_4$OH (75:35:2). Erythromycin derivatives are visualized by spraying the plates with anisaldehyde:sulfuric acid:ethanol (1:1:9). Using this reagent, two novel compounds predicted to be 10-desmethyl-10-hydroxyerythromycin A and 12-deoxy-10-desmethyl-10-hydroxyerythromycin A, are expected to appear as blue spots running slightly slower than erythromycin A.

To determine whether the novel spots seen on TLC have the molecular mass corresponding to the predicted 10-desmethyl-10-hydroxyerythromycin A and 12-deoxy-10-desmethyl-10-hydroxyerythromycin A, the remaining extract is further analyzed by mass spectrometry. The two novel compounds are predicted to have masses of 736 and 720, which correspond to the molecular ion plus a proton (M+H$^+$) of 10-desmethyl-10-hydroxyerythromycin A and 12-deoxy-10-desmethyl-10-hydroxyerythromycin A, respectively.

What is claimed is:
1. A compound of the formula:

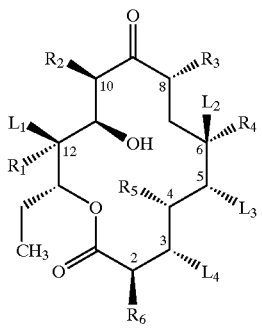

wherein
$R_1$, $R_2$, $R_3$, $R_4$, $R_5$, and $R_6$ are independently selected from Q wherein Q is selected from the group consisting of (a) —H, (b) —Me, (c) —Et, and (d) —OH;
$L_1$ and $L_2$ are independently —H or —OH;
$L_3$ is D-desosamine or —OH; and
$L_4$ is L-mycarose, L-cladinose or —OH
with the proviso that when $R_1$–$R_5$ are —Me, $R_6$ is other than —H or —Me.

2. The compound of claim 1 wherein Q is selected from the group consisting of (a), (b), and (c) and $L_1$, $L_2$, $L_3$ and $L_4$ are as defined therein.

3. The compound of claim 1 wherein Q is selected from the group consisting of (a), (b), and (d) and $L_1$, $L_2$, $L_3$ and $L_4$ are as defined therein.

4. The compound of claim 1 wherein Q is selected from the group consisting of (a), (c), and (d) and $L_1$, $L_2$, $L_3$ and $L_4$ are as defined therein.

5. The compound of claim 1 wherein Q is selected from the group consisting of (b), (c), and (d) and $L_1$, $L_2$, $L_3$ and $L_4$ are as defined therein.

6. The compound of claim 1 wherein Q is selected from the group consisting of (a) and (b) and $L_1$, $L_2$, $L_3$ and $L_4$ are as defined therein.

7. The compound of claim 1 wherein Q is selected from the group consisting of (a) and (c) and $L_1$, $L_2$, $L_3$ and $L_4$ are as defined therein.

8. The compound of claim 1 wherein Q is selected from the group consisting of (a) and (d) and $L_1$, $L_2$, $L_3$ and $L_4$ are as defined therein.

9. The compound of claim 1 wherein Q is selected from the group consisting of (b) and (c) and $L_1$, $L_2$, $L_3$ and $L_4$ are as defined therein.

10. The compound of claim 1 wherein Q is selected from the group consisting of (b) and (d) and $L_1$, $L_2$, $L_3$ and $L_4$ are as defined therein.

11. The compound of claim 1 wherein Q is selected from the group consisting of (c) and (d) and $L_1$, $L_2$, $L_3$ and $L_4$ are as defined therein.

12. The compound of claim 1 wherein Q is (a) and $L_1$, $L_2$, $L_3$ and $L_4$ are as defined therein.

13. The compound of claim 1 wherein Q is (c) and $L_1$, $L_2$, $L_3$ and $L_4$ are as defined therein.

14. The compound of claim 1 wherein Q is (d) and $L_1$, $L_2$, $L_3$ and $L_4$ are as defined therein.

15. The compound of claim 1 wherein
(a) $R_6$ and $R_1$ are —H and $R_2$, $R_3$, $R_4$ and $R_5$ are —Me,
(b) $R_5$ and $R_1$ are —H and $R_2$, $R_3$, $R_4$ and $R_6$ are —Me,
(c) $R_4$ and $R_1$ are —H and $R_2$, $R_3$, $R_5$ and $R_6$ are —Me,
(d) $R_3$ and $R_1$ are —H and $R_2$, $R_4$, $R_5$ and $R_6$ are —Me,
(e) $R_2$ and $R_1$ are —H and $R_3$, $R_4$, $R_5$ and $R_6$ are —Me,
(f) $R_6$ and $R_2$ are —H and $R_1$, $R_3$, $R_4$ and $R_5$ are —Me,
(g) $R_5$ and $R_2$ are —H and $R_1$, $R_3$, $R_4$ and $R_6$ are —Me,
(h) $R_4$ and $R_2$ are —H and $R_1$, $R_3$, $R_5$ and $R_6$ are —Me,
(i) $R_3$ and $R_2$ are —H and $R_1$, $R_4$, $R_5$ and $R_6$ are —Me,
(j) $R_6$ and $R_3$ are —H and $R_1$, $R_2$, $R_4$ and $R_5$ are —Me,
(k) $R_5$ and $R_3$ are —H and $R_1$, $R_2$, $R_4$ and $R_6$ are —Me,
(l) $R_4$ and $R_3$ are —H and $R_1$, $R_2$, $R_5$ and $R_6$ are —Me,
(m) $R_6$ and $R_4$ are —H and $R_1$, $R_2$, $R_3$ and $R_5$ are —Me,
(n) $R_5$ and $R_4$ are —H and $R_1$, $R_2$, $R_3$ and $R_6$ are —Me,
(o) $R_6$ and $R_5$ are —H and $R_1$, $R_2$, $R_3$ and $R_4$ are —Me, and
$L_1$, $L_2$, $L_3$ and $L_4$ are as defined therein.

16. The compound of claim 15 wherein (a)–(o) are as defined therein, $L_1$ and $L_2$ are —OH, $L_3$ is D-desosamine and $L_4$ is L-cladinose.

17. The compound of claim 1 wherein
(a) $R_6$, $R_2$ and $R_1$ are —H and $R_3$, $R_4$ and $R_5$ are —Me,
(b) $R_5$, $R_2$ and $R_1$ are —H and $R_3$, $R_4$ and $R_6$ are —Me,
(c) $R_4$, $R_2$ and $R_1$ are —H and $R_3$, $R_5$ and $R_6$ are —Me,
(d) $R_3$, $R_2$ and $R_1$ are —H and $R_4$, $R_5$ and $R_6$ are —Me,
(e) $R_6$, $R_3$ and $R_1$ are —H and $R_2$, $R_4$ and $R_5$ are —Me,
(f) $R_5$, $R_3$ and $R_1$ are —H and $R_2$, $R_4$ and $R_6$ are —Me,
(g) $R_4$, $R_3$ and $R_1$ are —H and $R_2$, $R_5$ and $R_6$ are —Me,
(h) $R_6$, $R_4$ and $R_1$ are —H and $R_2$, $R_3$ and $R_5$ are —Me,
(i) $R_5$, $R_4$ and $R_1$ are —H and $R_2$, $R_3$ and $R_6$ are —Me,
(j) $R_6$, $R_5$ and $R_1$ are —H and $R_2$, $R_3$ and $R_4$ are —Me,
(k) $R_6$, $R_3$ and $R_2$ are —H and $R_1$, $R_4$ and $R_5$ are —Me,
(l) $R_5$, $R_3$ and $R_2$ are —H and $R_1$, $R_4$ and $R_6$ are —Me,
(m) $R_4$, $R_3$ and $R_2$ are —H and $R_1$, $R_5$ and $R_6$ are —Me,
(n) $R_6$, $R_4$ and $R_2$ are —H and $R_1$, $R_3$ and $R_5$ are —Me,
(o) $R_5$, $R_4$ and $R_2$ are —H and $R_1$, $R_3$ and $R_6$ are —Me,
(p) $R_6$, $R_5$ and $R_2$ are —H and $R_1$, $R_3$ and $R_4$ are —Me,
(q) $R_6$, $R_4$ and $R_3$ are —H and $R_1$, $R_2$ and $R_5$ are —Me,
(r) $R_5$, $R_4$ and $R_3$ are —H and $R_1$, $R_2$ and $R_6$ are —Me,
(s) $R_6$, $R_5$ and $R_3$ are —H and $R_1$, $R_2$ and $R_4$ are —Me, or
(t) $R_6$, $R_5$ and $R_4$ are —H and $R_1$, $R_2$ and $R_3$ are —Me, and
$L_1$, $L_2$, $L_3$ and $L_4$ are as defined therein.

18. The compound of claim 17 wherein (a)–(t) are as defined therein, $L_1$ and $L_2$ are —OH, $L_3$ is D-desosamine and $L_4$ is L-cladinose.

19. The compound of claim 1 wherein
(a) $R_6$, $R_3$, $R_2$ and $R_1$ are —H and $R_5$, and $R_4$ are —Me,
(b) $R_5$, $R_3$, $R_2$ and $R_1$ are —H and $R_6$, and $R_4$ are —Me,
(c) $R_4$, $R_3$, $R_2$ and $R_1$ are —H and $R_5$, and $R_6$ are —Me,
(d) $R_6$, $R_4$, $R_2$ and $R_1$ are —H and $R_3$, and $R_5$ are —Me,
(e) $R_5$, $R_4$, $R_2$ and $R_1$ are —H and $R_3$, and $R_6$ are —Me,
(f) $R_6$, $R_5$, $R_2$ and $R_1$ are —H and $R_3$, and $R_4$ are —Me,
(g) $R_6$, $R_4$, $R_3$ and $R_1$ are —H and $R_2$, and $R_5$ are —Me,
(h) $R_5$, $R_4$, $R_3$ and $R_1$ are —H and $R_2$, and $R_6$ are —Me,
(i) $R_6$, $R_5$, $R_4$ and $R_1$ are —H and $R_2$, and $R_3$ are —Me,
(j) $R_2$, $R_4$, $R_3$ and $R_1$ are —H and $R_5$, and $R_6$ are —Me,
(k) $R_6$, $R_4$, $R_3$ and $R_2$ are —H and $R_1$, and $R_5$ are —Me,
(l) $R_5$, $R_4$, $R_3$ and $R_2$ are —H and $R_1$, and $R_6$ are —Me,
(m) $R_6$, $R_5$, $R_3$ and $R_2$ are —H and $R_1$, and $R_4$ are —Me, or (n) $R_6$, $R_5$, $R_4$ and $R_3$ are —H and $R_1$, and $R_2$ are —Me, and $L_1$, $L_2$, $L_3$ and $L_4$ are as defined therein.

20. The compound of claim 19 wherein (a)–(n) are as defined therein, $L_1$ and $L_2$ are —OH, $L_3$ is D-desosamine and $L_4$ is L-cladinose.

21. The compound of claim 1 wherein (a) $R_5$, $R_4$, $R_3$, $R_2$ and $R_1$ are —H and $R_6$ is —Me, (b) $R_6$, $R_4$, $R_3$, $R_2$ and $R_1$ are —H and $R_5$ is —Me, (c) $R_6$, $R_5$, $R_3$, $R_2$ and $R_1$ are —H and $R_4$ is —Me, (d) $R_6$, $R_5$, $R_4$, $R_2$ and $R_1$ are —H and $R_3$ is —Me, (e) $R_6$, $R_5$, $R_4$, $R_3$ and $R_1$ are —H and $R_2$ is —Me, or (f) $R_6$, $R_5$, $R_4$, $R_3$ and $R_2$ are —H and $R_1$ is —Me, and $L_1$, $L_2$, $L_3$ and $L_4$ are as defined therein.

22. The compound of claim 21 wherein (a)–(f) are as defined therein, $L_1$ and $L_2$ are —OH, $L_3$ is D-desosamine and $L_4$ is L-cladinose.

23. The compound of claim 1 wherein $R_1$, $R_2$, $R_3$, $R_4$, $R_5$ and $R_6$ are —H and $L_1$, $L_2$, $L_3$ and $L_4$ are as defined therein.

24. The compound of claim 23 wherein $R_1$, $R_2$, $R_3$, $R_4$, $R_5$ and $R_6$ are as defined therein, $L_1$ and $L_2$ are —OH, $L_3$ is D-desosamine and $L_4$ is L-cladinose.

25. The compound of claim 1 selected from the group consisting of 6,10-didesmethyl-6-ethylerythromycin A; 10,12-didesmethyl-12-deoxy-12-ethylerythromycin A; 10,12-didesmethyl-12-deoxy-10-hydroxyerythromycin A: 6,10,12-tridesmethyl-6,12-diethylerythromycin A, and 6,10,12-tridesmethyl-6-deoxy-6,12-diethylerythromycin A.

26. The compound of claim 1 selected from the group consisting of 10-desmethylerythronolide B, 10-desmethyl-6-deoxyerythronolide B, 12-desmethylerythronolide B, 12-desmethyl-6-deoxyerythronolide B, 12-desmethyl-12-ethylerythronolide B, 6-desmethyl-6-deoxy-6-ethylerythronolide B, 10-desmethylerythromycin A, 10-desmethyl-6,12-dideoxyerythromycin A, 12-desmethylerythromycin A, 12-desmethyl-12-deoxyerythromycin A, 12-desmethyl-6,12-dideoxyerythromycin A, 6-desmethyl-6-ethylerythromycin A, 12-desmethyl-12-ethylerythromycin A, 12-desmethyl-12-deoxy-12-ethylerythromycin A, 10-desmethyl-10-hydroxyerythromycin A, 12-desmethyl-12-epihydroxyerythromycin A, 10,12-didesmethylerythromycin A, 10,12-didesmethyl-12-deoxyerythromycin A, and 10,12-didesmethyl-6,12-dideoxyerythromycin A.

27. The compound of claim 1 selected from the group consisting of 10-desmethylerythronolide B, 10-desmethyl-6-deoxyerythronolide B, 12-desmethylerythronolide B, 12-desmethyl-6-deoxyerythronolide B, 10-desmethylerythromycin A, 10-desmethyl-12-deoxyerythromycin A, 10-desmethyl-6,12-dideoxyerythromycin A, 12-desmethylerythromycin A, 12-desmethyl-12-deoxyerythromycin A, 12-desmethyl-6,12-dideoxyerythromycin A, 10,12-didesmethylerythromycin A, 10,12-didesmethyl-12-deoxyerythromycin A, and 10,12-didesmethyl-6,12-dideoxyerythromycin A.

28. A compound selected from the group consisting of 10-desmethylerythromycin A, 10-desmethyl-12-deoxyerythromycin A, and 12-desmethyl-12-deoxyerythromycin A.

29. The compound 6-desmethyl-6-ethylerythromycin A.

\* \* \* \* \*